(12) United States Patent
Fujiwara

(10) Patent No.: US 8,859,292 B2
(45) Date of Patent: *Oct. 14, 2014

(54) METHOD FOR MEASURING TEMPERATURE OF BIOLOGICAL SAMPLE, METHOD FOR MEASURING CONCENTRATION OF BIOLOGICAL SAMPLE, SENSOR CHIP AND BIOSENSOR SYSTEM

(75) Inventor: Masaki Fujiwara, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 561 days.

This patent is subject to a terminal disclaimer.

(21) Appl. No.: 13/144,790

(22) PCT Filed: Jan. 28, 2010

(86) PCT No.: PCT/JP2010/000522
§ 371 (c)(1),
(2), (4) Date: Jul. 15, 2011

(87) PCT Pub. No.: WO2010/087191
PCT Pub. Date: Aug. 5, 2010

(65) Prior Publication Data
US 2011/0272294 A1 Nov. 10, 2011

(30) Foreign Application Priority Data
Jan. 30, 2009 (JP) ................. 2009-020956

(51) Int. Cl.
*G01N 27/416* (2006.01)
*C12Q 1/54* (2006.01)
*G01N 27/327* (2006.01)

(52) U.S. Cl.
CPC ................ *G01N 27/3274* (2013.01)
USPC ............. 436/147; 436/63; 436/70; 436/95; 436/149; 436/150; 422/82.01; 422/82.02; 422/82.12; 422/503; 435/14; 204/403.01; 205/792

(58) Field of Classification Search
CPC ....... G01N 27/26; G01N 27/27; G01N 27/28; G01N 27/30; G01N 27/49; G01N 27/327; G01N 27/3274; G01N 27/3271; G01N 27/3272; G01N 27/3273; G01N 27/413; G01N 27/416; G01N 25/20
USPC ....... 436/63, 70, 95, 147, 149, 150; 422/68.1, 73, 82.01, 82.02, 82.12, 503; 435/14, 29; 204/403.01
See application file for complete search history.

(56) References Cited

U.S. PATENT DOCUMENTS

| 6,780,296 B1 | 8/2004 | Bhullar et al. |
| 6,911,131 B2 | 6/2005 | Miyazaki et al. |

(Continued)

FOREIGN PATENT DOCUMENTS

| CA | 2 328 750 A1 | 6/2001 |
| CA | 2 696 661 | 6/2001 |

(Continued)

OTHER PUBLICATIONS

International Search Report issued Mar. 23, 2010 in International (PCT) Application No. PCT/JP2010/000522.

(Continued)

*Primary Examiner* — Maureen Wallenhorst
(74) *Attorney, Agent, or Firm* — Wenderoth, Lind & Ponack, L.L.P.

(57) ABSTRACT

A sensor chip is configured to measure the temperature of a blood sample and includes a capillary section and an electrode unit. The capillary section allows the blood sample to be introduced therein. The electrode unit is configured to measure the temperature of the blood sample and includes a working electrode and a counter electrode. The working electrode and the counter electrode respectively include a reaction reagent layer containing an electrolyte. Further, the electrode unit is configured to receive a predetermined voltage to be applied in measuring the temperature of the blood sample for allowing a result of the measurement to be less affected by increase and reduction in a glucose concentration and the like.

27 Claims, 138 Drawing Sheets

GLUCOSE MEASUREMENT → WORKING ELECTRODE A – COUNTER ELECTRODE B
ANALYTE DETECTION → WORKING ELECTRODE C – COUNTER ELECTRODE B
TEMPERATURE MEASUREMENT → WORKING ELECTRODE A – COUNTER ELECTRODE B

(56) References Cited

U.S. PATENT DOCUMENTS

| | | |
|---|---|---|
| 7,232,510 B2 | 6/2007 | Miyazaki et al. |
| 7,494,816 B2 | 2/2009 | Burke et al. |
| 7,510,643 B2 | 3/2009 | Bhullar et al. |
| 7,648,617 B2 | 1/2010 | Miyazaki et al. |
| 7,655,456 B2 | 2/2010 | Oshiman et al. |
| 7,850,839 B2 | 12/2010 | Miyazaki et al. |
| 7,867,369 B2 | 1/2011 | Bhullar et al. |
| 8,097,147 B2 | 1/2012 | Miyazaki et al. |
| 8,101,063 B2 | 1/2012 | Miyazaki et al. |
| 8,298,400 B2 | 10/2012 | Miyazaki et al. |
| 8,506,775 B2 | 8/2013 | Surridge et al. |
| 2002/0179442 A1 | 12/2002 | Miyazaki et al. |
| 2003/0159945 A1 | 8/2003 | Miyazaki et al. |
| 2004/0157338 A1 | 8/2004 | Burke et al. |
| 2004/0238357 A1 | 12/2004 | Bhullar et al. |
| 2005/0019219 A1 | 1/2005 | Oshiman et al. |
| 2005/0023137 A1 | 2/2005 | Bhullar et al. |
| 2005/0023152 A1 | 2/2005 | Surridge et al. |
| 2005/0194251 A1 | 9/2005 | Miyazaki et al. |
| 2006/0175206 A1 | 8/2006 | Miyazaki et al. |
| 2006/0175207 A1 | 8/2006 | Miyazaki et al. |
| 2008/0110754 A1 | 5/2008 | Miyazaki et al. |
| 2010/0006432 A1 | 1/2010 | Miyazaki et al. |
| 2010/0252454 A1 | 10/2010 | Miyazaki et al. |
| 2010/0320097 A1 | 12/2010 | Miyazaki et al. |
| 2011/0027816 A1* | 2/2011 | Fujiwara ................. 435/25 |
| 2011/0132776 A1 | 6/2011 | Miyazaki et al. |
| 2011/0132777 A1 | 6/2011 | Miyazaki et al. |
| 2011/0168575 A1* | 7/2011 | Lica et al. .............. 205/782 |
| 2011/0180404 A1 | 7/2011 | Miyazaki et al. |
| 2011/0203942 A1* | 8/2011 | Uchiyama .............. 205/782 |
| 2012/0043227 A1 | 2/2012 | Miyazaki et al. |
| 2013/0020208 A1 | 1/2013 | Miyazaki et al. |

FOREIGN PATENT DOCUMENTS

| | | |
|---|---|---|
| CA | 2 529 668 | 12/2004 |
| CA | 2 328 750 C | 7/2010 |
| CN | 1397017 | 2/2003 |
| CN | 1839313 | 9/2006 |
| EP | 1 114 994 | 7/2001 |
| EP | 1 197 749 | 4/2002 |
| EP | 1 467 201 | 10/2004 |
| JP | 9-250996 | 9/1997 |
| JP | 2001-235444 | 8/2001 |
| JP | 2003-42995 | 2/2003 |
| JP | 2003-156469 | 5/2003 |
| JP | 2005-265629 | 9/2005 |
| JP | 2007-33458 | 2/2007 |
| JP | 2007-524818 | 8/2007 |
| JP | 4374020 | 9/2009 |
| WO | 03/062812 | 7/2003 |
| WO | 2004/113896 | 12/2004 |
| WO | 2004/113910 | 12/2004 |
| WO | 2005/012900 | 2/2005 |

OTHER PUBLICATIONS

Chinese Office Action issued Aug. 29, 2013 in corresponding Chinese Application No. 201080003817.4.

Supplementary European Search Report issued May 3, 2013 in corresponding European Application No. EP 10 73 5663.

* cited by examiner

| | REAGENT CONCENTRATION |
|---|---|
| CMC (HE-1500F) | 0.05 wt% |
| H2O | |
| POTASSIUM FERRICYANIDE | 1.7 wt% |
| TAURINE | 1.0 wt% |
| MALTITOL | 0.1 wt% |
| ENZYME (FAD-GDH) | 1.5 U/CELL |

FIG. 4

FIG. 7
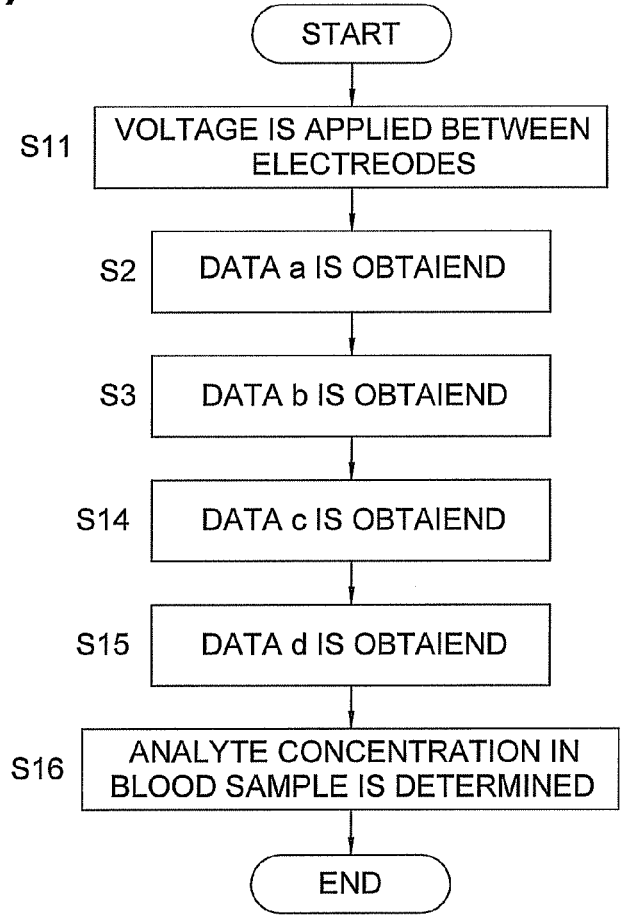
(a)
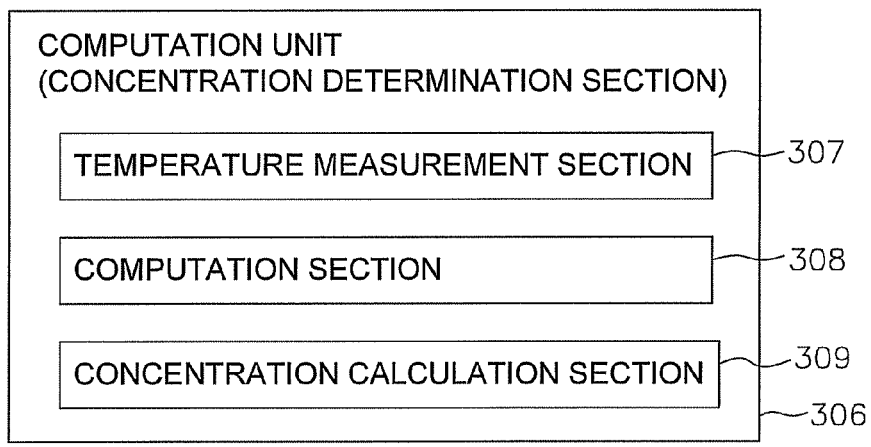
(b)

FIG. 8
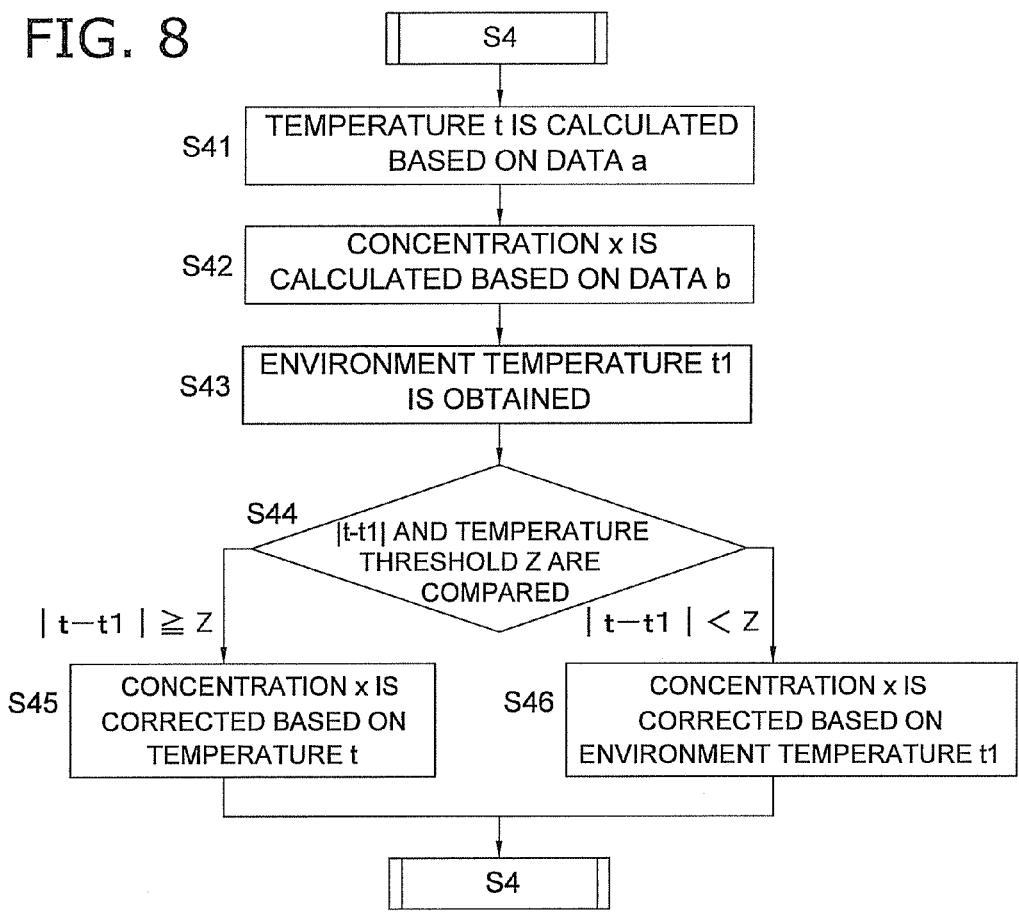
(a)
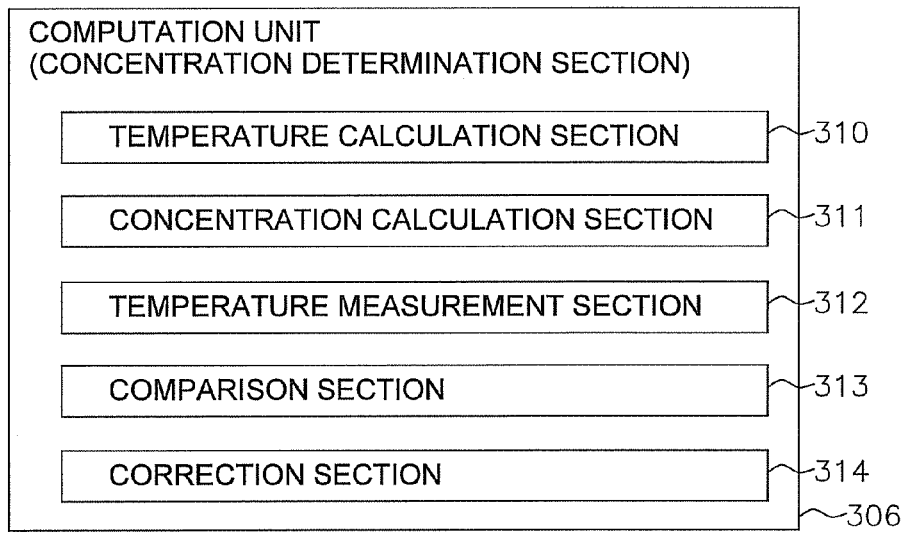
(b)

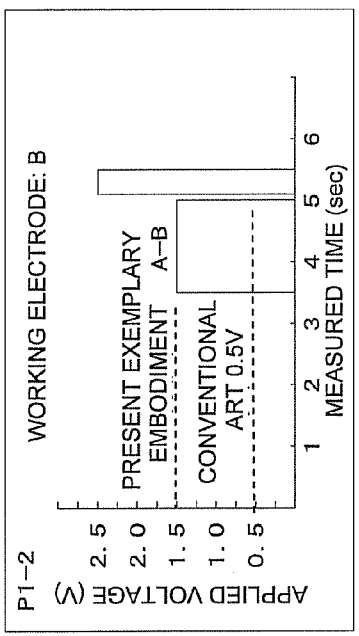
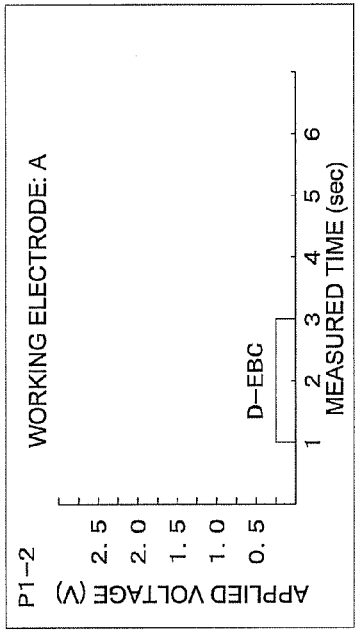
FIG. 10

FIG. 15
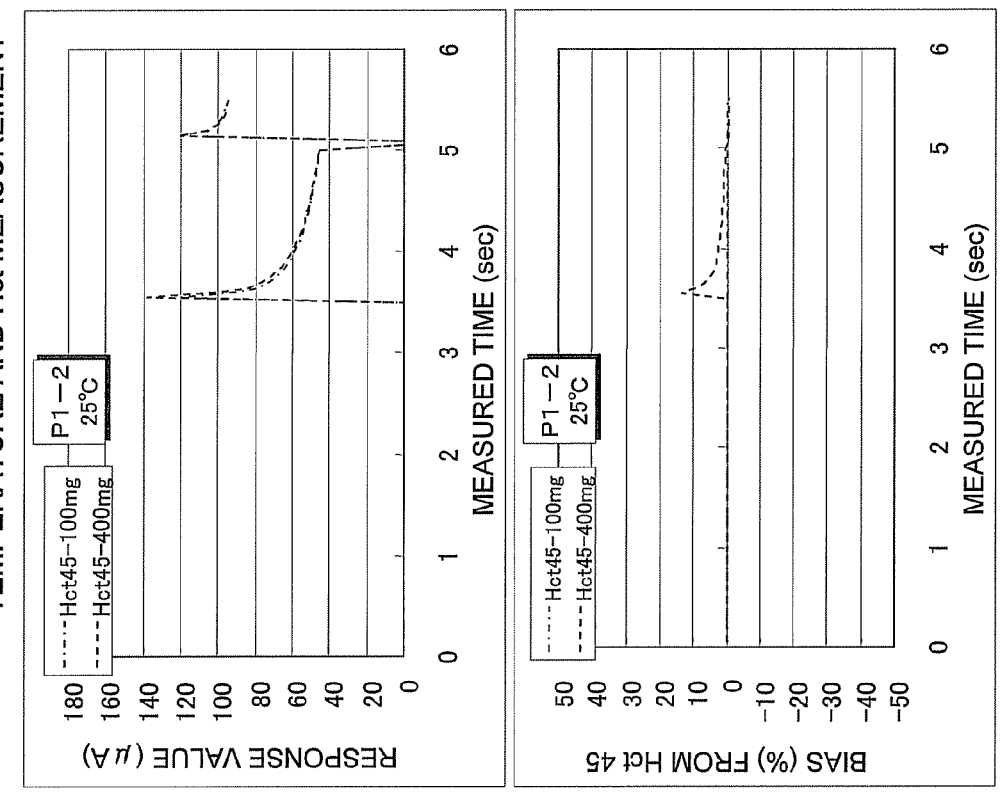
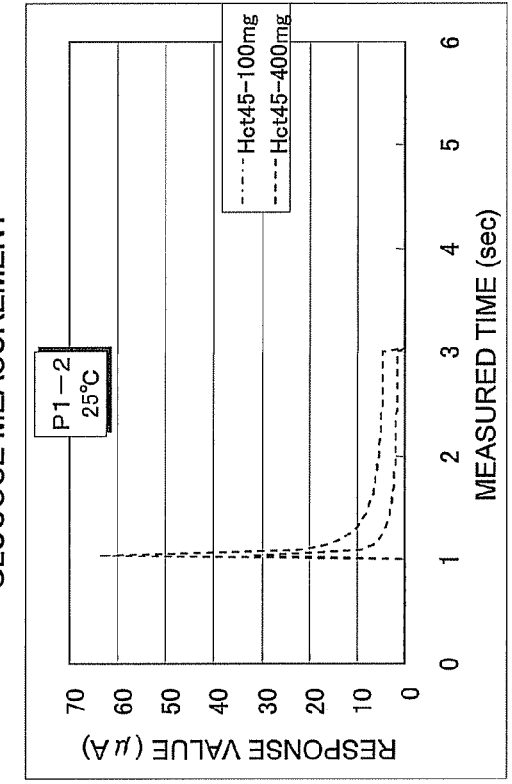
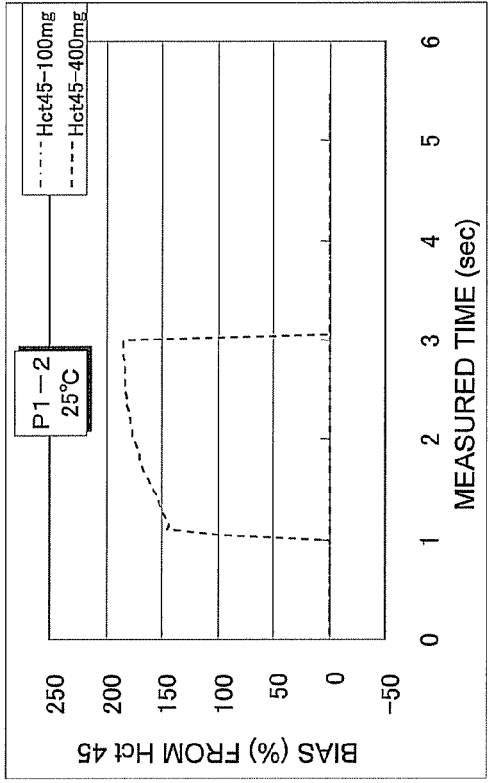

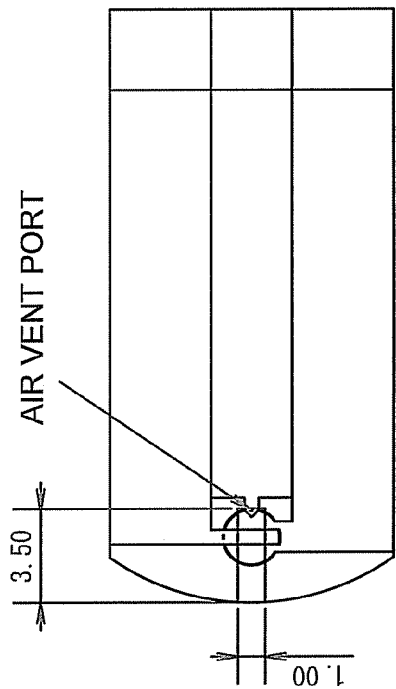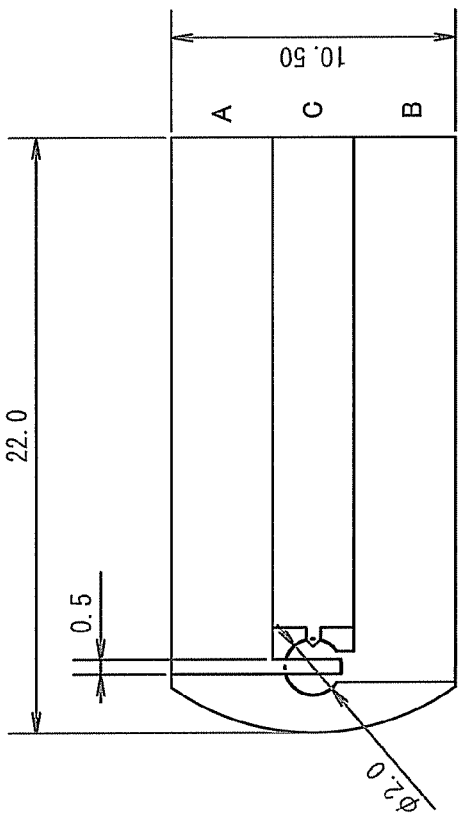
FIG. 17

FIG. 91
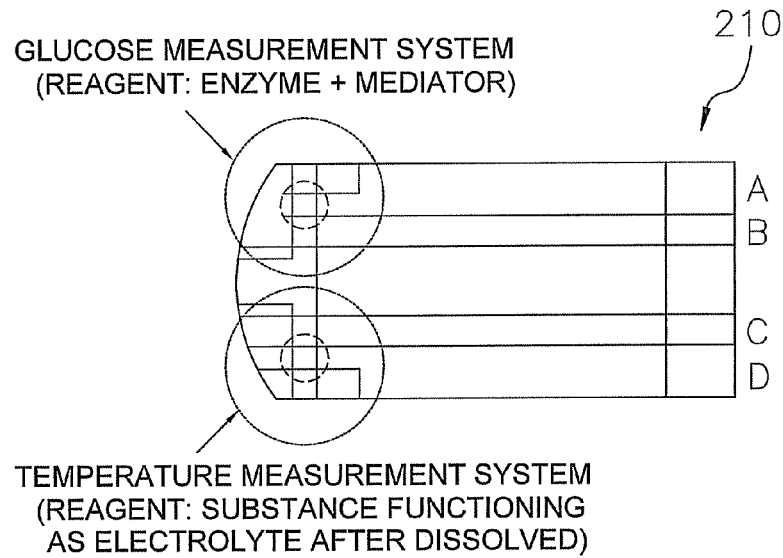
(a)
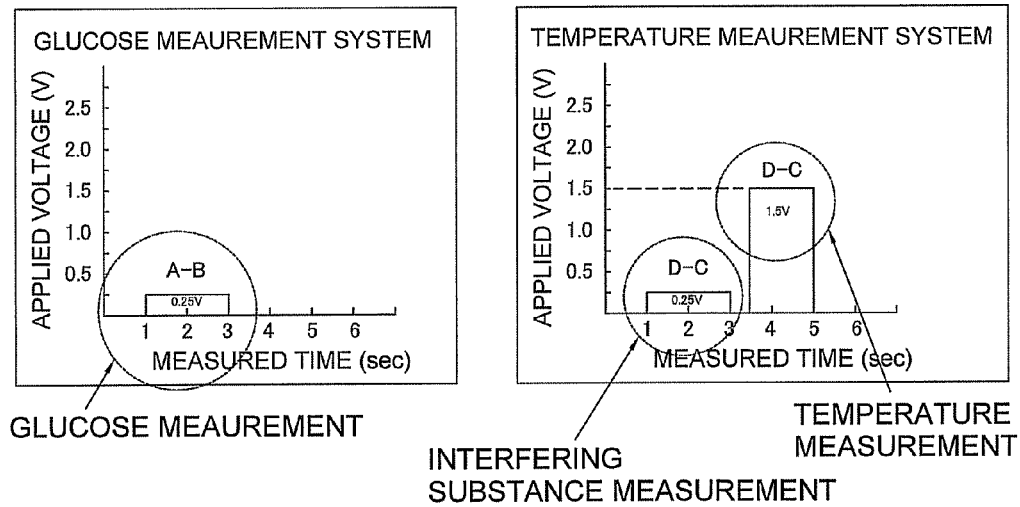
(b)          (c)

<REAGENT ARRANGEMENT ON WORKING ELECTRODE>

<REAGENT ARRANGEMENT ON COUNTER ELECTRODE (ELECTRODE B)>

FIG. 96
<2 ELECTRODES>
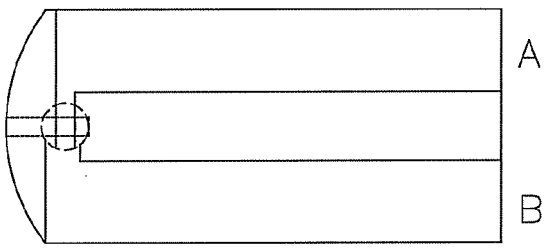
(a)
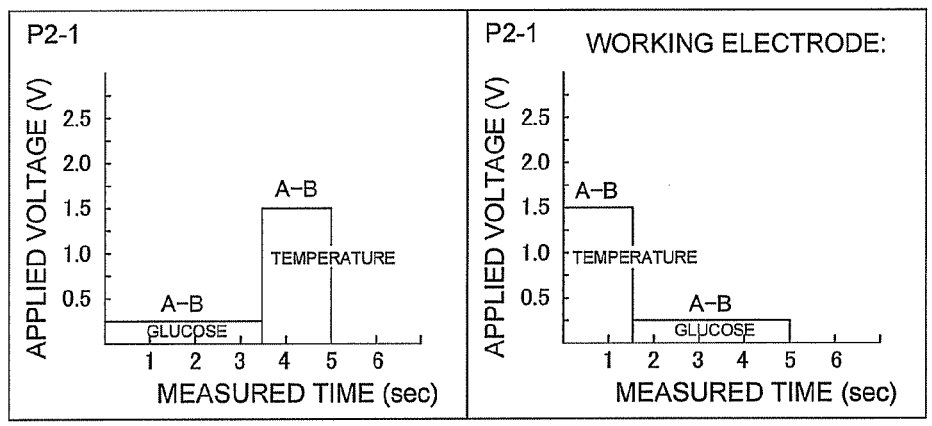
(b)　　　　　　　　(c)
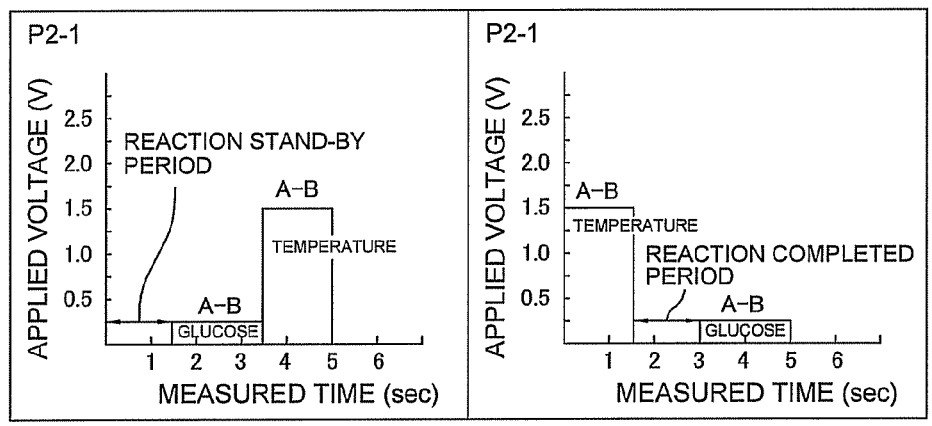
(d)　　　　　　　　(e)

FIG. 104

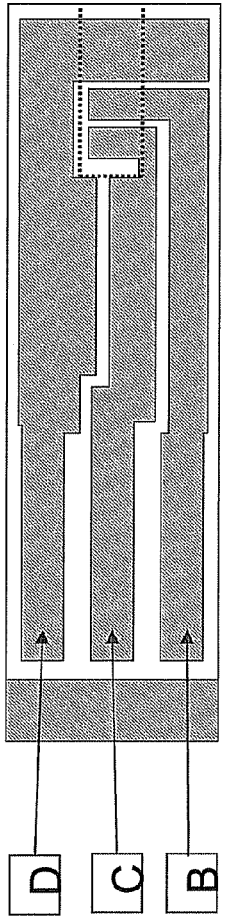

| ASSIGNED ORDER | ASSIGNED WORKING ELECTRODE | | ASSIGNED COUNTER ELECTRODE | | | | | | | APPLIED VOLTAGE (V) | DEPOSITING CURRENT (μA) | TIME (sec) | SUMMATION TIME (sec) |
|---|---|---|---|---|---|---|---|---|---|---|---|---|---|
| | | | COUNTER ELECTRODE 1 | COUNTER ELECTRODE 2 | COUNTER ELECTRODE 3 | COUNTER ELECTRODE 4 | COUNTER ELECTRODE 5 | COUNTER ELECTRODE 6 | COUNTER ELECTRODE 7 | | | | |
| T | WORKING ELECTRODE 1 | C | D | | | | | | | 500 | 0.05 | | |
| | WORKING ELECTRODE 2 | | | | | | | | | | | | |
| S | WORKING ELECTRODE 1 | | | | | | | | | | | 1.0 | 1.0 |
| | WORKING ELECTRODE 2 | | | | | | | | | | | | |
| S | WORKING ELECTRODE 1 | B | D | | | | | | | 500 | | 2.0 | 3.0 |
| | WORKING ELECTRODE 2 | | | | | | | | | | | | |
| S | WORKING ELECTRODE 1 | | | | | | | | | | | 0.1 | 3.1 |
| | WORKING ELECTRODE 2 | | | | | | | | | | | | |
| S | WORKING ELECTRODE 1 | | | | | | | | | 500~2000 | | 3.0 | 6.1 |
| | WORKING ELECTRODE 2 | B | D | | | | | | | | | | |

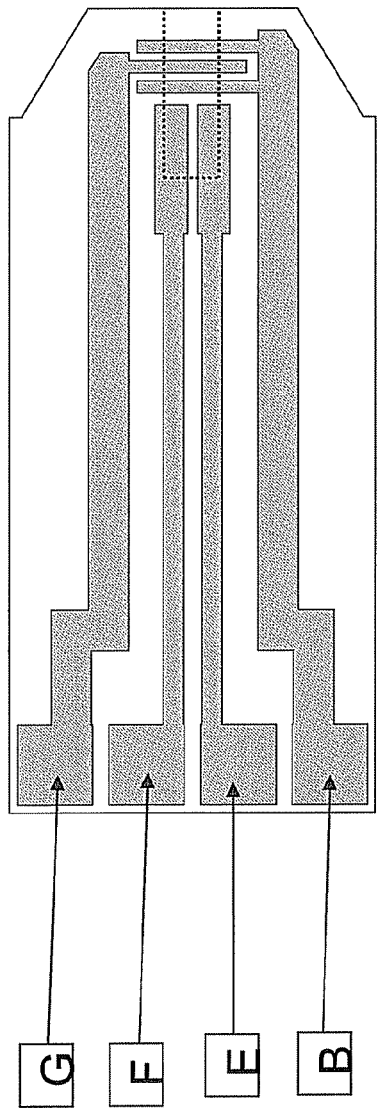

FIG. 110

| ASSIGNED ORDER | ASSIGNED WORKING ELECTRODE | | ASSIGNED COUNTER ELECTRODE | | | | | | | APPLIED VOLTAGE (V) | DEPOSITING CURRENT (μA) | TIME (sec) | SUMMATION TIME (sec) |
|---|---|---|---|---|---|---|---|---|---|---|---|---|---|
| | | | COUNTER ELECTRODE 1 | COUNTER ELECTRODE 2 | COUNTER ELECTRODE 3 | COUNTER ELECTRODE 4 | COUNTER ELECTRODE 5 | COUNTER ELECTRODE 6 | COUNTER ELECTRODE 7 | | | | |
| T | WORKING ELECTRODE 1 | E | F | | | | | | | 500 | 0.05 | | |
| | WORKING ELECTRODE 2 | | | | | | | | | | | | |
| S | WORKING ELECTRODE 1 | | | | | | | | | | | 1.0 | 1.0 |
| | WORKING ELECTRODE 2 | | | | | | | | | | | | |
| S | WORKING ELECTRODE 1 | G | B | | | | | | | 500 | | 2.0 | 3.0 |
| | WORKING ELECTRODE 2 | | | | | | | | | | | | |
| S | WORKING ELECTRODE 1 | | | | | | | | | | | 0.1 | 3.1 |
| | WORKING ELECTRODE 2 | | | | | | | | | | | | |
| S | WORKING ELECTRODE 1 | G | B | | | | | | | 500~2000 | | 3.0 | 6.1 |
| | WORKING ELECTRODE 2 | | | | | | | | | | | | |

METHOD FOR MEASURING TEMPERATURE OF BIOLOGICAL SAMPLE, METHOD FOR MEASURING CONCENTRATION OF BIOLOGICAL SAMPLE, SENSOR CHIP AND BIOSENSOR SYSTEM

TECHNICAL FIELD

The present invention relates to a method of measuring the temperature of a biological sample and a method of measuring the concentration of a biological sample, both of which are achieved using a sensor chip configured to measure the temperature, the concentration and the like of a biological sample, and further relates to a sensor chip and a biosensor system.

BACKGROUND ART

The portable biosensor systems have been used for measuring the concentration of an analyte contained in a blood sample (e.g., the concentration of glucose contained in blood, i.e., a blood glucose level). The portable biosensor systems are normally equipped with a measuring instrument including a computation unit and a sensor chip detachably attached to the measuring instrument. The analyte concentration is calculated based on the amount of an oxidant or reductant to be generated in the course of an enzyme cycling reaction mediated by an oxidoreductase for which the analyte serves as a substrate. The speed of the enzyme cycling reaction depends on the temperature of an on-going reaction (reaction temperature). Therefore, it is desirable to correct the analyte concentration based on the reaction temperature.

For example, the reaction temperature is measured by a temperature sensor disposed in the measuring instrument (Patent Literature 1). However, the inner temperature of the measuring instrument is measured in a biosensor system described in Patent Literature 1. In other words, the reaction temperature to be measured does not accurately reflect the temperature of the blood sample. Therefore, errors may be produced in measuring the analyte concentration.

Patent Literatures 2 to 4 describe biosensor systems intended to enhance accuracy of measuring the reaction temperature. The biosensor systems described in Patent Literatures 2 and 3 include a thermal conductive member in the vicinity of a blood sample holder of a sensor chip. A temperature sensor, disposed in a measuring instrument, is configured to detect the blood sample temperature to be transferred through the thermal conductive member. In the biosensor systems described in Patent Literatures 2 and 3, a resin plate is disposed between the thermal conductive member and the blood sample holder. Therefore, the thermal conductive member is prevented from making contact with the blood sample. In the biosensor system described in Patent Literature 4, a temperature sensor and a thermal conductive member are disposed on a sensor chip attachment section of a measuring instrument. The blood sample temperature is transferred to the temperature sensor through the thermal conductive member.

CITATION LIST

Patent Literature

Patent Literature 1: Japan Laid-open Patent Application Publication No. JP-A-2003-156469
Patent Literature 2: Japan Laid-open Patent Application Publication No. JP-A-2001-235444
Patent Literature 3: Japan Laid-open Patent Application Publication No. JP-A-2003-042995
Patent Literature 4: International Patent Application Publication No. WO/2003/062812.

SUMMARY

Technical Problem

When a user moves between two places with a large temperature difference (e.g., from outdoor to indoor in a winter/summer season) while bringing a biosensor system with him/her, a measuring instrument cannot cope with such an acute change in an environmental temperature. Therefore, the measuring instrument indicates a temperature higher/lower than the actual temperature of the destination environment for a while. When the measuring instrument is moved from an environment at 40° C. or 10° C. to an environment at 25° C., for instance, it takes about 30 minutes for the measuring instrument to finally indicate the destination environment temperature as 25° C. (Patent Literature 1). It is not easy to completely exclude the effect of temperature on the measuring instrument in measuring the reaction temperature with use of the temperature sensor of the measuring instrument. Therefore, errors still tend to be produced in measuring the analyte concentration in the biosensor systems described in Patent Literatures 2 to 4 when a sudden temperature change occurs in an environment where the sensor is used. Further in the biosensor systems described in Patent Literatures 2 to 4, the temperature of the blood sample is thermally transferred to the temperature sensor through the resin plate and the thermal conductive member. The reaction temperature to be measured does not still accurately reflect the actual blood sample temperature.

An object of the present invention is to provide a temperature measurement method and a concentration measurement method for enhancing accuracy in measuring the concentration of an analyte contained in a blood sample.

Another object of the present invention is to provide: a biosensor system configured to measure the temperature of a blood sample and inhibit occurrence of measurement errors due to a usage environmental temperature; and a sensor chip for temperature and concentration measurement use suitable for the biosensor system.

Solution to Problem

A biological sample temperature measurement method according to an aspect of the present invention is configured to measure a temperature of a biological sample in a sensor chip including: a temperature electrode unit formed by a working electrode and a counter electrode, each of which includes a regent containing an electrolyte; and a capillary allowing the biological sample to be introduced therein. The temperature measurement method includes a taking-in step and a temperature measurement step. In the taking-in step, a predetermined amount of the biological sample is taken in from an entirety of the biological sample introduced into the capillary. In the temperature measurement step, the temperature of the biological sample is measured by applying a predetermined voltage to the temperature electrode unit when the temperature of the biological sample is measured for allowing a result of the measurement to be less affected by increase and reduction in an analyte contained in the biological sample.

A biological sample concentration measurement method according to an aspect of the present invention is configured to measure a concentration of an analyte contained in a biological sample in a sensor chip including: an electrode unit formed by a working electrode and a counter electrode, each of which includes a reagent containing an electrolyte; and a capillary allowing the biological sample to be introduced therein. The biological sample concentration measurement method includes a taking-in step, a temperature measurement step and a concentration measurement step. In the taking-in step, a predetermined amount of the biological sample is taken in from an entirety of the biological sample introduced into the capillary. In the temperature measurement step, a temperature of the biological sample is measured by applying a predetermined voltage to the electrode unit when the temperature of the biological sample is measured for allowing a result of the measurement to be less affected by increase and reduction in an amount of the analyte contained in the biological sample. In the concentration measurement step, the concentration of the analyte contained in the biological sample is measured by applying a predetermined voltage to the electrode unit.

A sensor chip according to an aspect of the present invention is configured to measure a temperature of a biological sample. The sensor chip includes a capillary and a temperature electrode unit. The capillary allows the biological sample to be introduced therein. The temperature electrode unit is configured to measure the temperature of the biological sample. The temperature electrode unit includes a working electrode and a counter electrode, each of which includes a reagent containing an electrolyte. The temperature electrode unit is configured to receive a predetermined voltage to be applied in measuring the temperature of the biological sample for allowing a result of the measurement to be less affected by an analyte contained in the biological sample.

A measuring instrument according to an aspect of the present invention is configured to apply a voltage to a sensor chip including an electrode formed by a working electrode and a counter electrode, each of which includes a reagent containing an electrolyte. The measuring instrument includes an insertion section, a voltage application section and a temperature measurement section. The insertion section allows the sensor chip to be loaded therein. The voltage application section is configured to apply a predetermined voltage to the electrode unit of the sensor chip loaded into the insertion section for inhibiting the effect of an analyte contained in the biological sample. The temperature measurement section is configured to measure a temperature of the biological sample based on an output value of the voltage applied by the voltage application section.

A biosensor system according to an aspect of the present invention includes the aforementioned sensor chip, a measuring instrument, a voltage application section, a first temperature measurement section and an analyte measurement section. The measuring instrument includes a control circuit configured to control application of a predetermined voltage to the temperature electrode unit of the sensor chip for a predetermined period of time. The voltage application section is configured to apply the predetermined voltage to the temperature electrode unit for the predetermined period of time under the control of the control circuit. The first temperature measurement section is configured to measure the temperature of the biological sample based on a magnitude of an electric current flowing through the temperature electrode unit making contact with the biological sample. The analyte measurement section is configured to measure the concentration of the analyte based on a magnitude of an electric current to be generated in the biological sample as a result of an electrochemical reaction where the analyte contained in the biological sample serves as a substrate.

BRIEF DESCRIPTION OF DRAWINGS

FIG. 4 is an exploratory table representing an example of a reagent to be used in the biosensor system illustrated in FIG. 1

FIG. 7 includes a flowchart (a) representing a method of measuring the concentration of an analyte contained in a blood sample in a biosensor system according to another exemplary embodiment of the present invention and a functional block diagram (b) of a component included in the biosensor system.

FIG. 8 includes a flowchart (a) representing a method of measuring the concentration of an analyte contained in a blood sample in a biosensor system according to yet another exemplary embodiment of the present invention and a functional block diagram (b) of a component included in the biosensor system.

FIG. 10 includes exploratory diagrams of an exemplary pattern of applying a voltage to the sensor chip illustrated in FIG. 9 in an exemplary embodiment 1.

FIG. 15 includes charts representing the results of examining the effect of variation in a glucose concentration on the response current value in the exemplary embodiment 1.

FIG. 17 includes plan views illustrating a configuration of a sensor chip according to another exemplary embodiment of the present invention.

FIG. 91 includes a plan view (a) of a configuration of a sensor chip according to another exemplary embodiment of the present invention, a chart (b) representing an exemplary pattern of applying a voltage to electrodes in a glucose measurement system, and a chart (c) representing an exemplary pattern of applying a voltage to electrode in a temperature measurement system.

FIG. 96 includes a plan view (a) of a configuration of a sensor chip according to yet another exemplary embodiment of the present invention and charts (b) to (e) representing an exemplary pattern of applying a voltage to electrodes in a glucose measurement system and a temperature measurement system.

FIG. 104 includes an explanatory diagram representing a configuration of a sensor chip according to yet another exemplary embodiment of the present invention and an en explanatory table representing an exemplary pattern of applying a voltage to the sensor chip.

FIG. 110 includes an explanatory diagram representing a configuration of a sensor chip according to yet another exemplary embodiment of the present invention and an en explanatory table representing an exemplary pattern of applying a voltage to the sensor chip.

Figure 116:
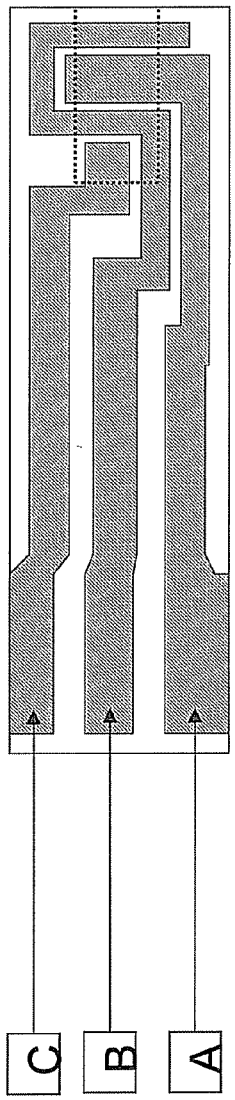
FIG. 116 includes an explanatory diagram representing a configuration of a sensor chip according to yet another exemplary embodiment of the present invention and an en explanatory table representing an exemplary pattern of applying a voltage to the sensor chip.
Figure 120:
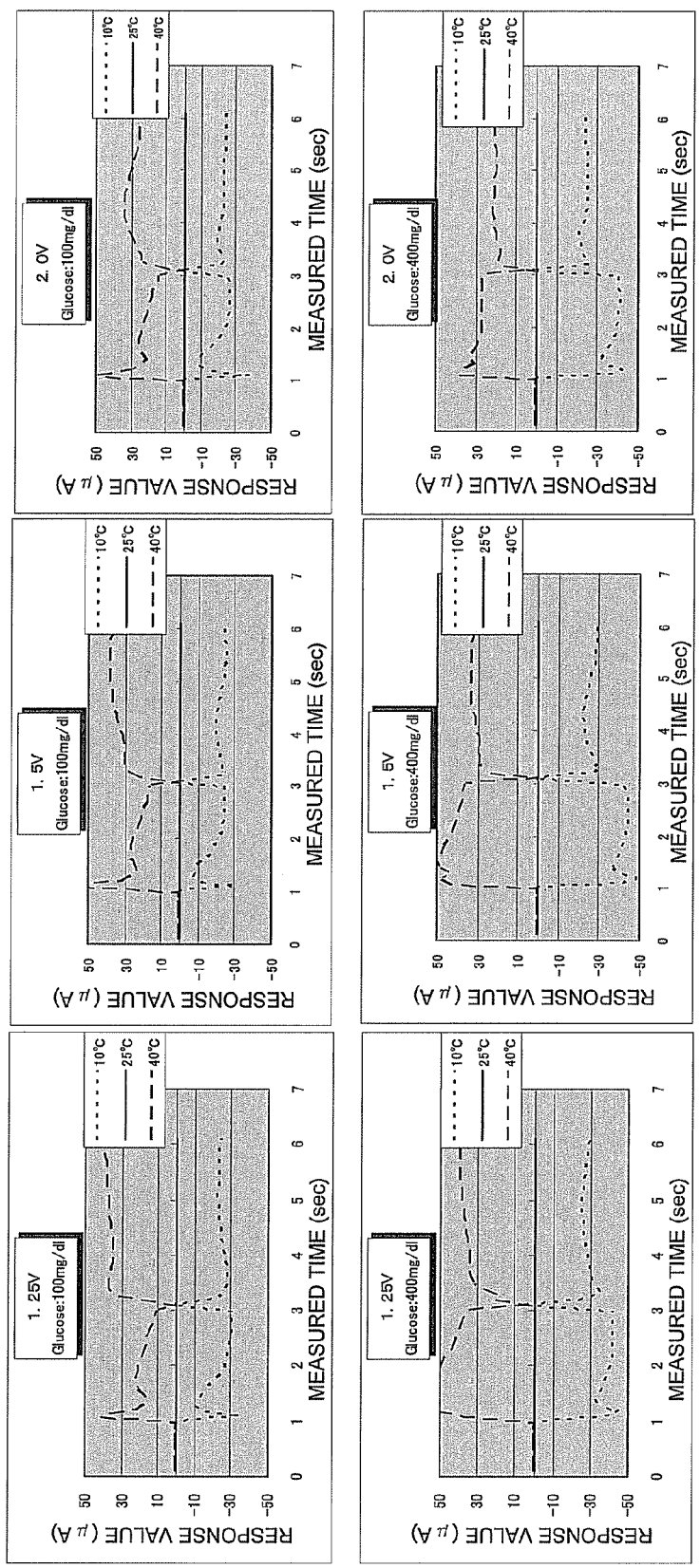

FIG. 120 includes charts representing a comprehensive result of examining the effect of variat ion in the temperature on the response current value in applying voltage of 1.25 to 2.0 V to the sensor chip illustrated in FIG. 116.

Figure 121:
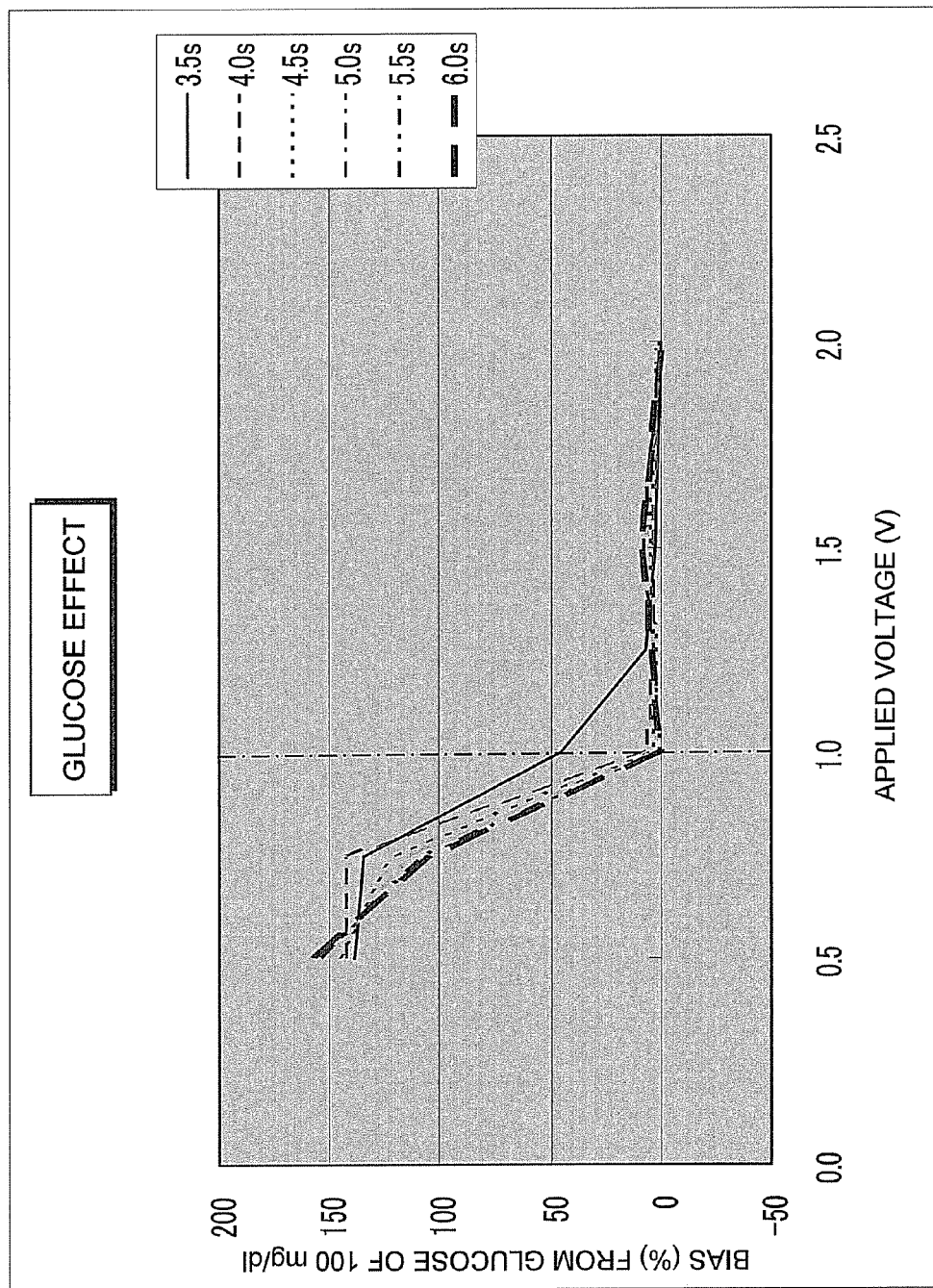

FIG. 121 is an explanatory chart comprehensively representing the magnitude of the applied voltage and the effect of the glucose concentration in the sensor chip illustrated in FIG. 116.

Figure 122:
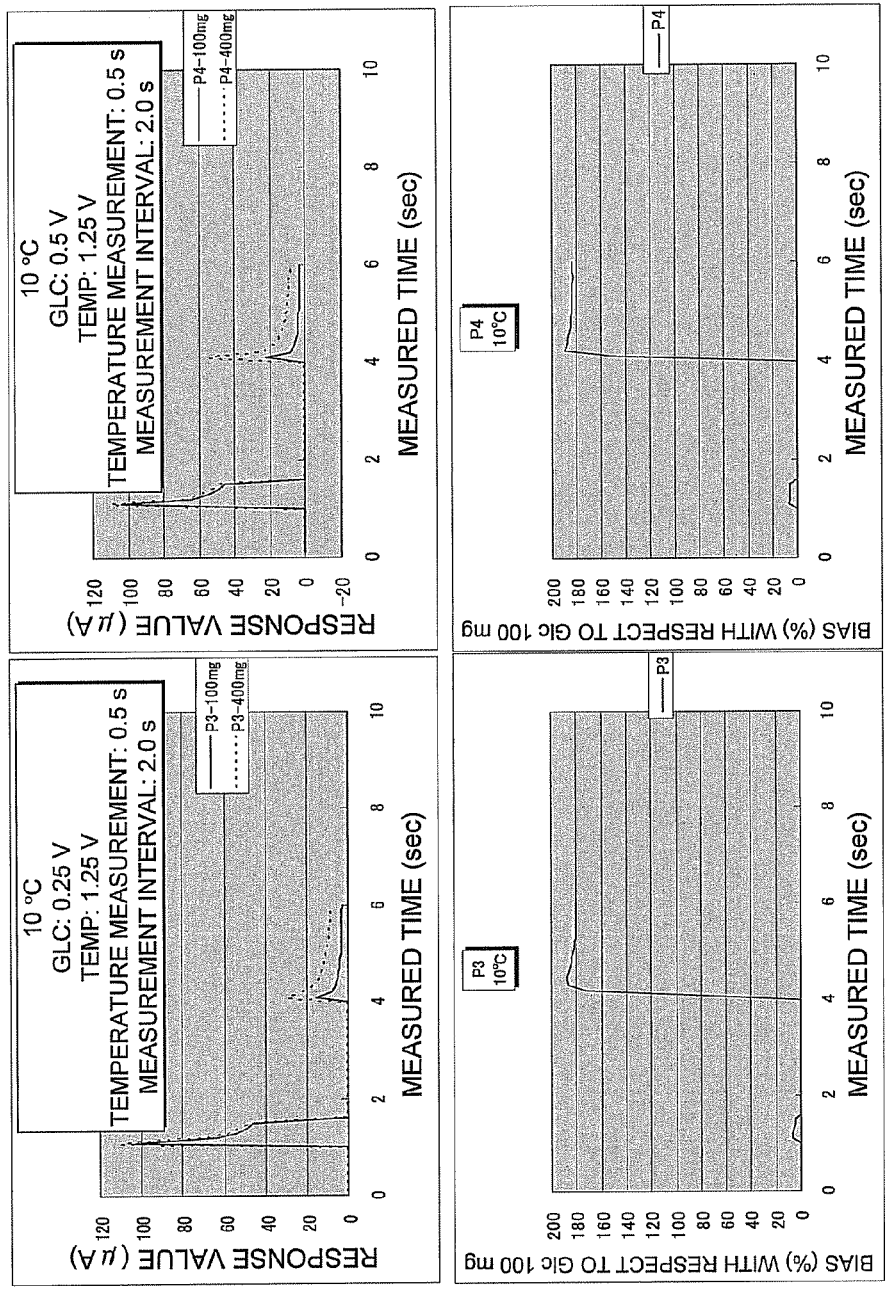

FIG. 122 includes charts representing the results of examining the response current value by applying a predetermined voltage to respective electrodes firstly in a glucose concentration measurement and secondly in a temperature measurement when a blood sample at 10° C. is used in yet another exemplary embodiment of the present invention.

Figure 123:
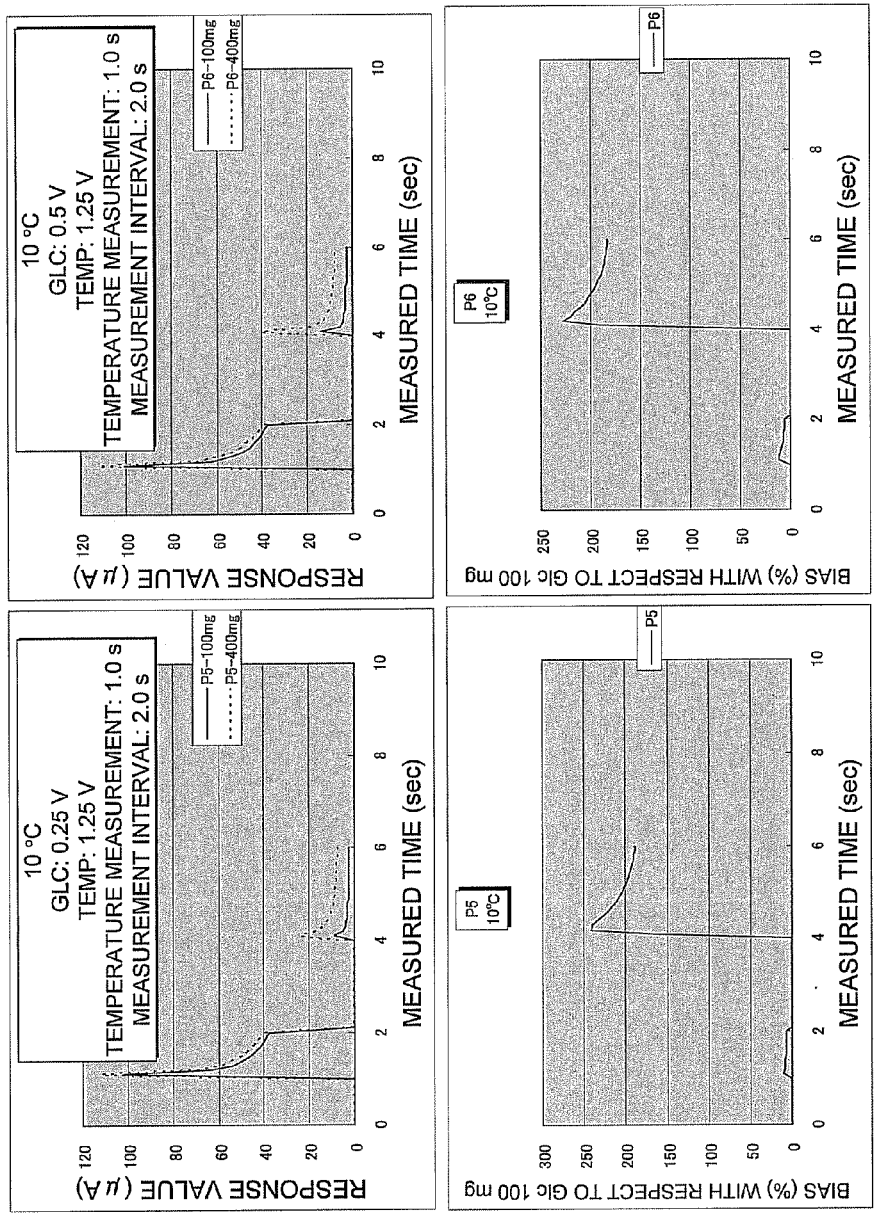

FIG. 123 includes charts representing the results of examining the response current value when the voltage application condition (voltage application time period) represented in the charts of FIG. 122 is changed.

Figure 124:
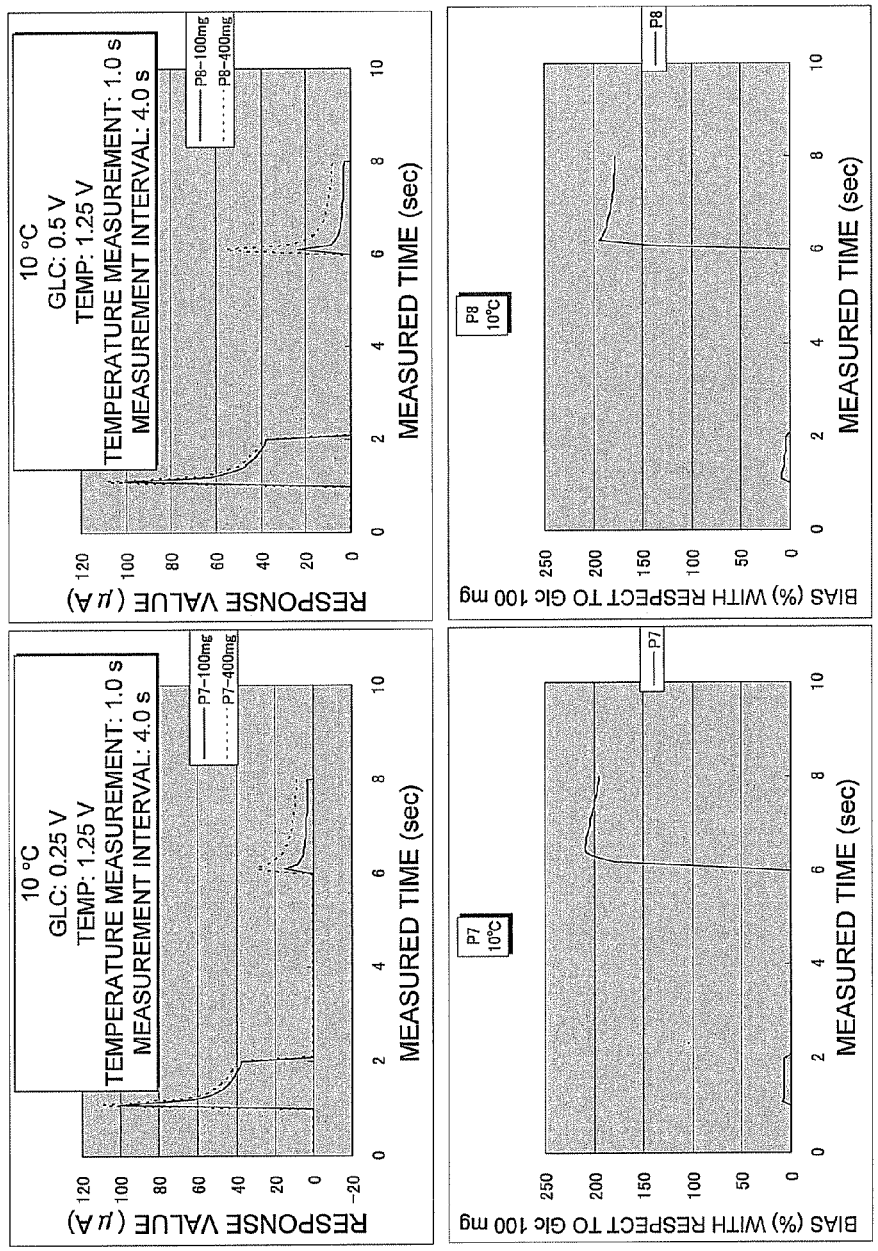

FIG. 124 includes charts representing the results of examining the response current value when the voltage application condition (voltage application interval) represented in the charts of FIG. 122 is changed.

Figure 125:
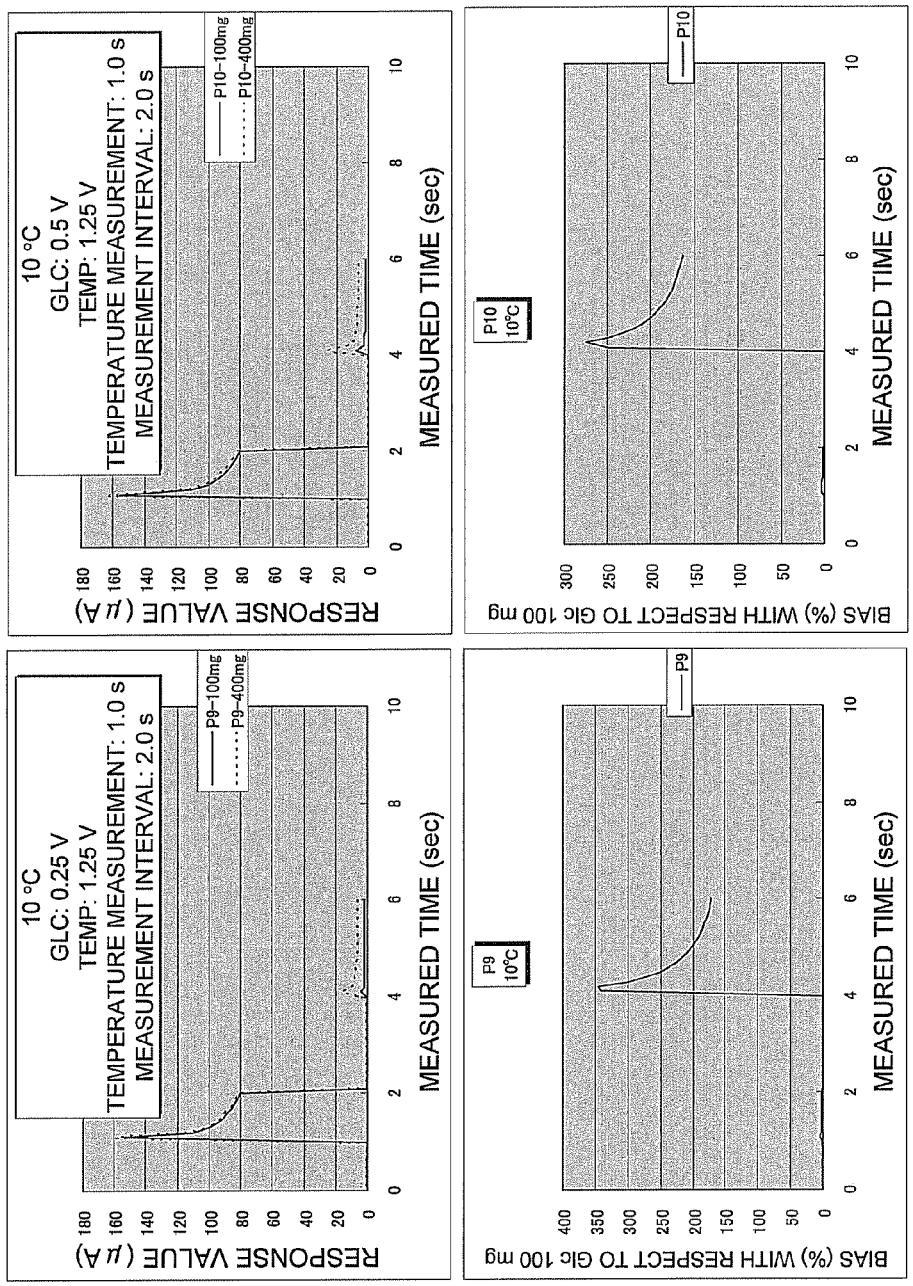

FIG. 125 includes charts representing the results of examining the response current value when the voltage application condition (temperature measurement voltage) represented in the charts of FIG. 122 is changed.

Figure 126:
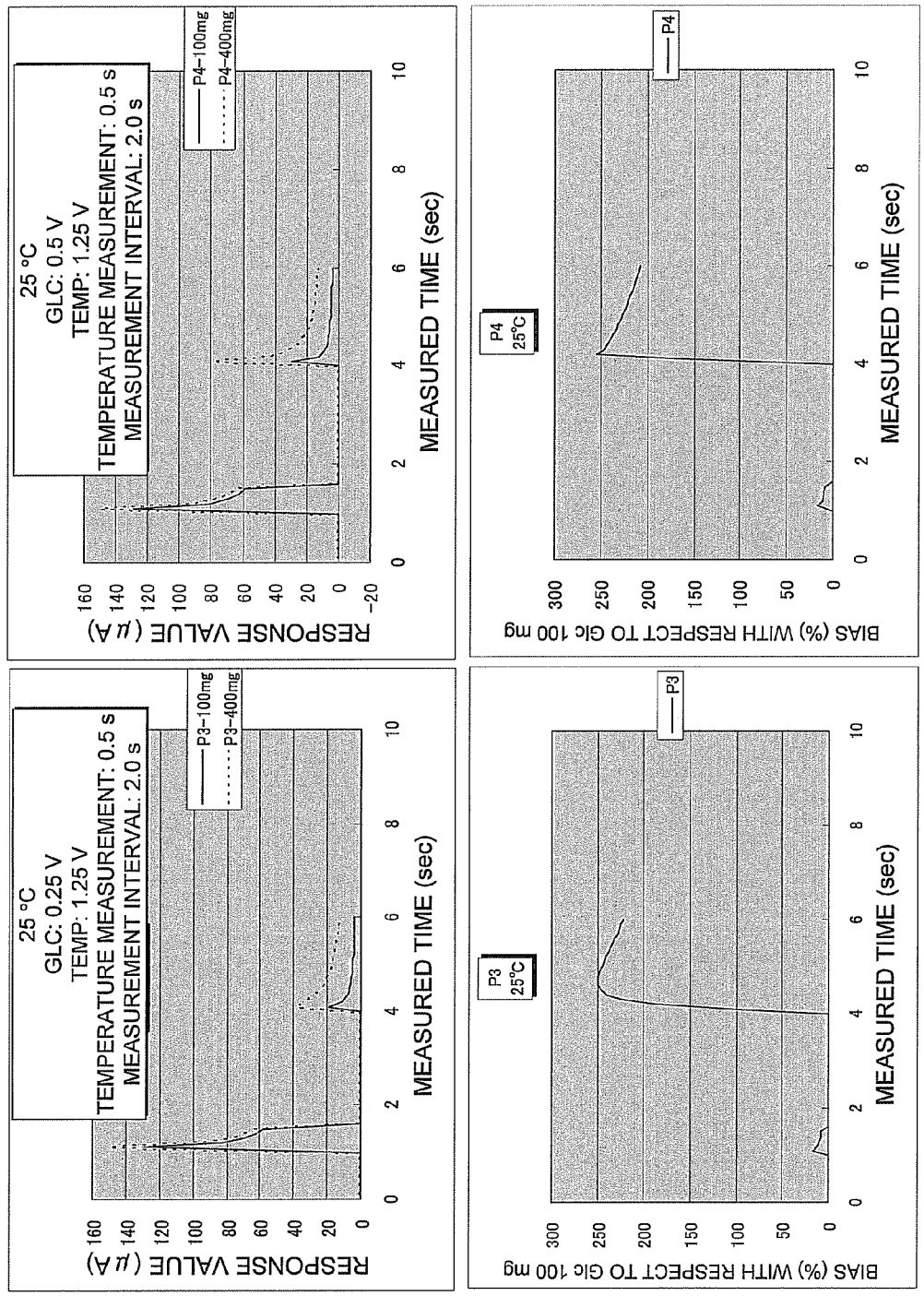

FIG. 126 includes charts representing the results of examining the response current value by applying a predetermined voltage to respective electrodes firstly in a glucose concentration measurement and secondly in a temperature measurement when a blood sample at 25° C. is used in yet another exemplary embodiment of the present invention.

Figure 127:
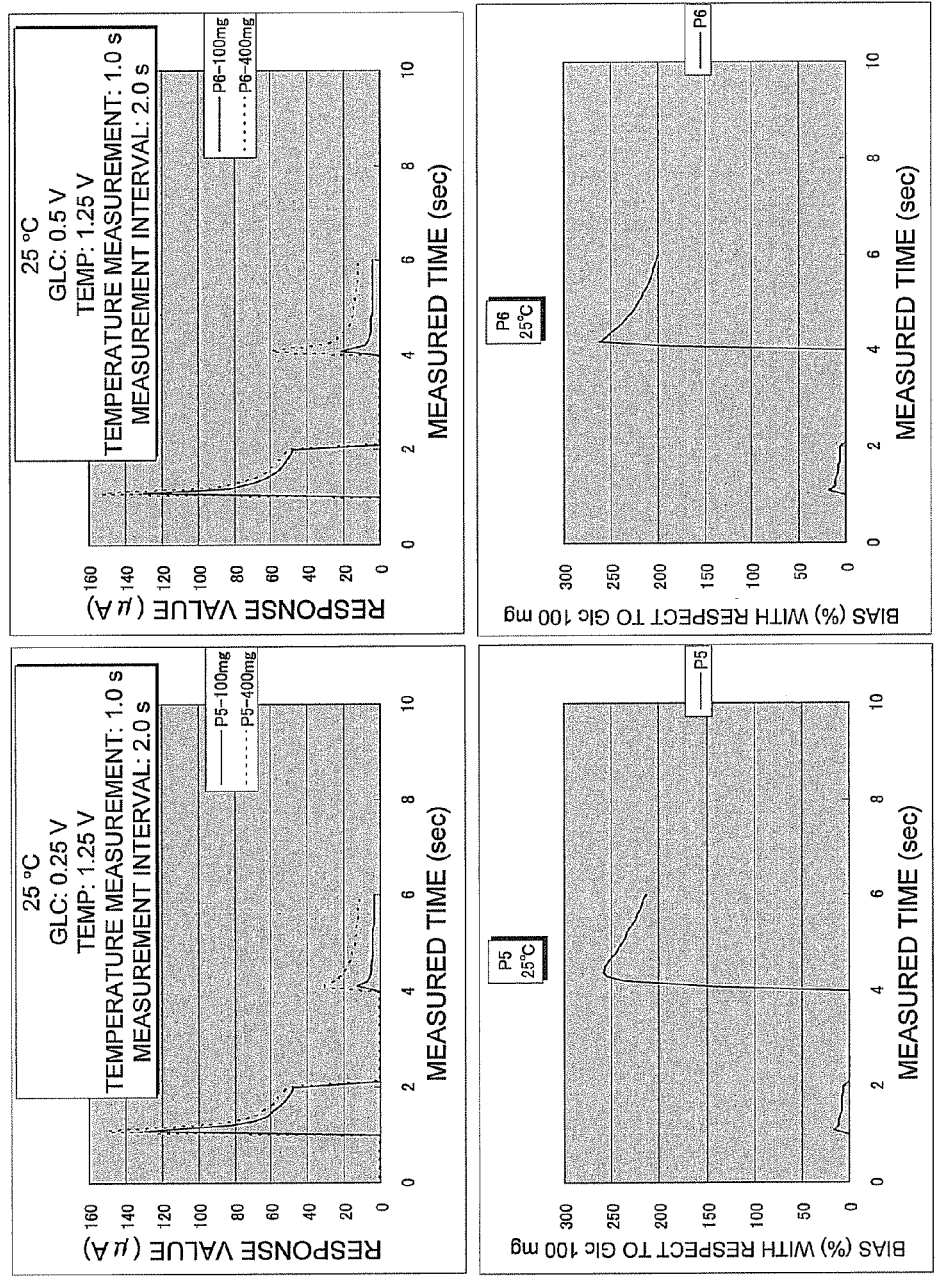

FIG. 127 includes charts representing the results of examining the response current value when the voltage application condition (voltage application time period) represented in the charts of FIG. 126 is changed.

Figure 128:
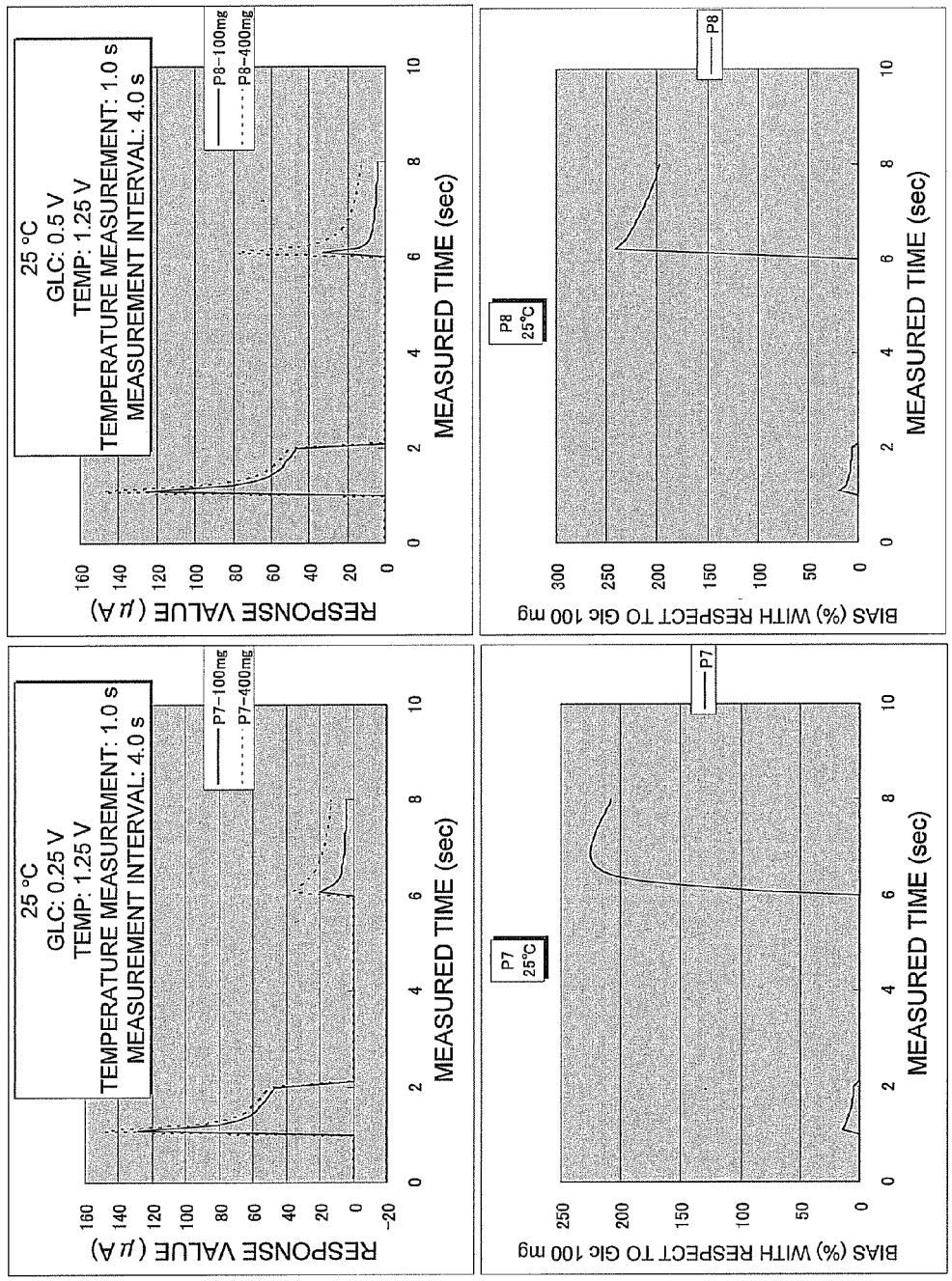

FIG. 128 includes charts representing the results of examining the response current value when the voltage application condition (voltage application interval) represented in the charts of FIG. 126 is changed.

Figure 129:
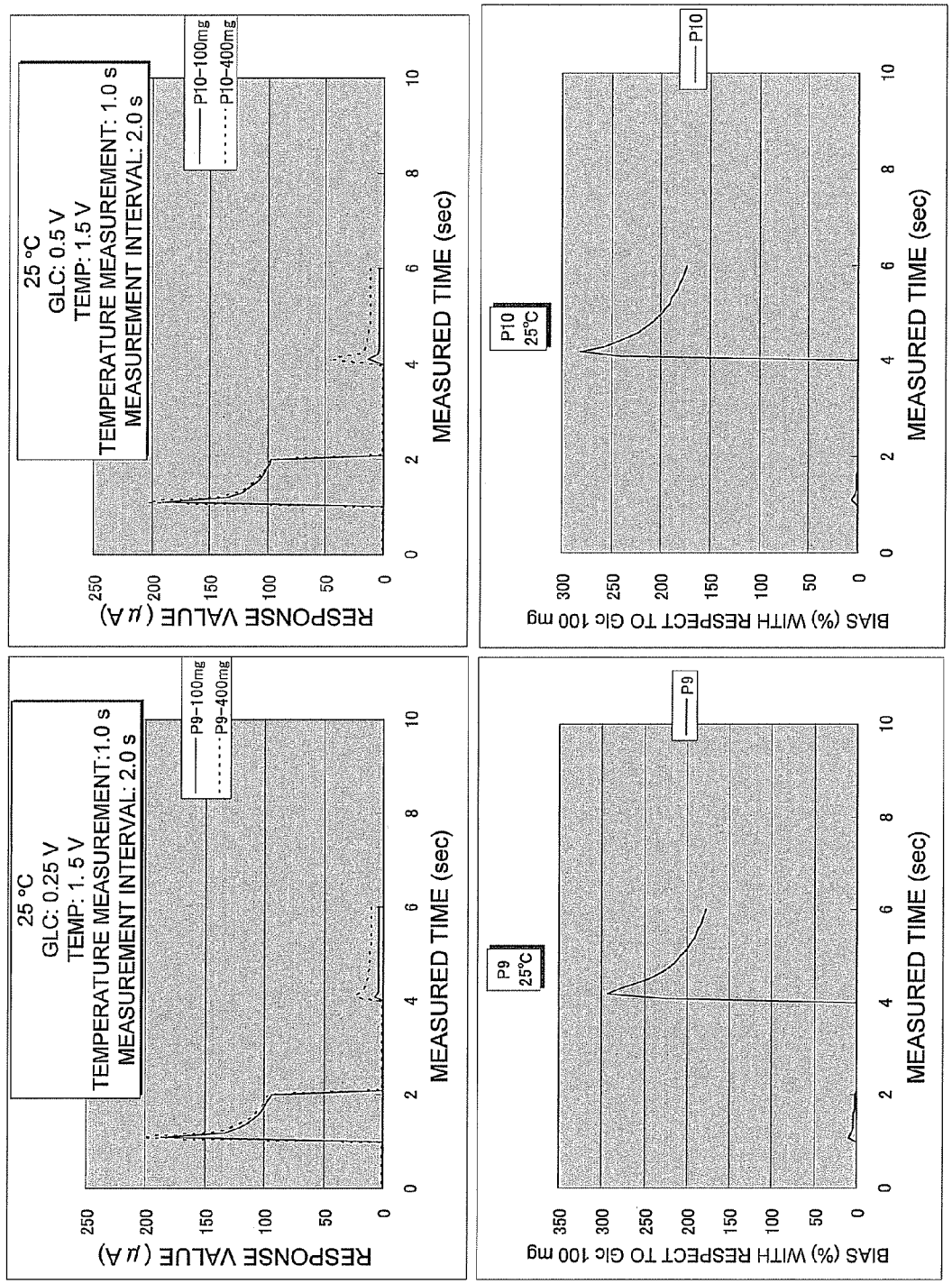

FIG. 129 includes charts representing the results of examining the response current value when the voltage application condition (temperature measurement voltage) represented in the charts of FIG. 126 is changed.

Figure 130:
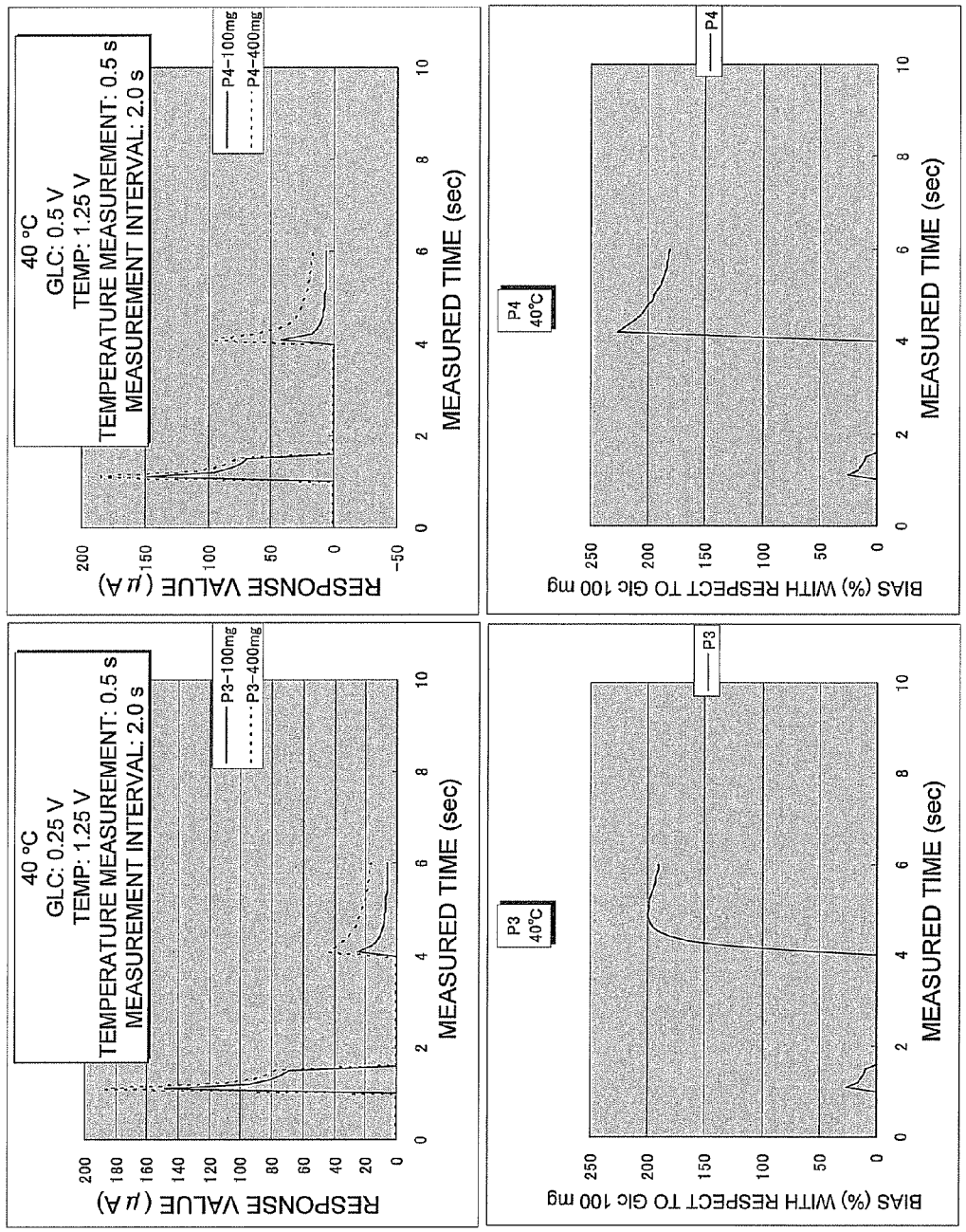

FIG. 130 includes charts representing the results of examining the response current value by applying a predetermined voltage to respective electrodes firstly in a glucose concentration measurement and secondly in a temperature measurement when a blood sample at 40° C. is used in yet another exemplary embodiment of the present invention.

Figure 131:
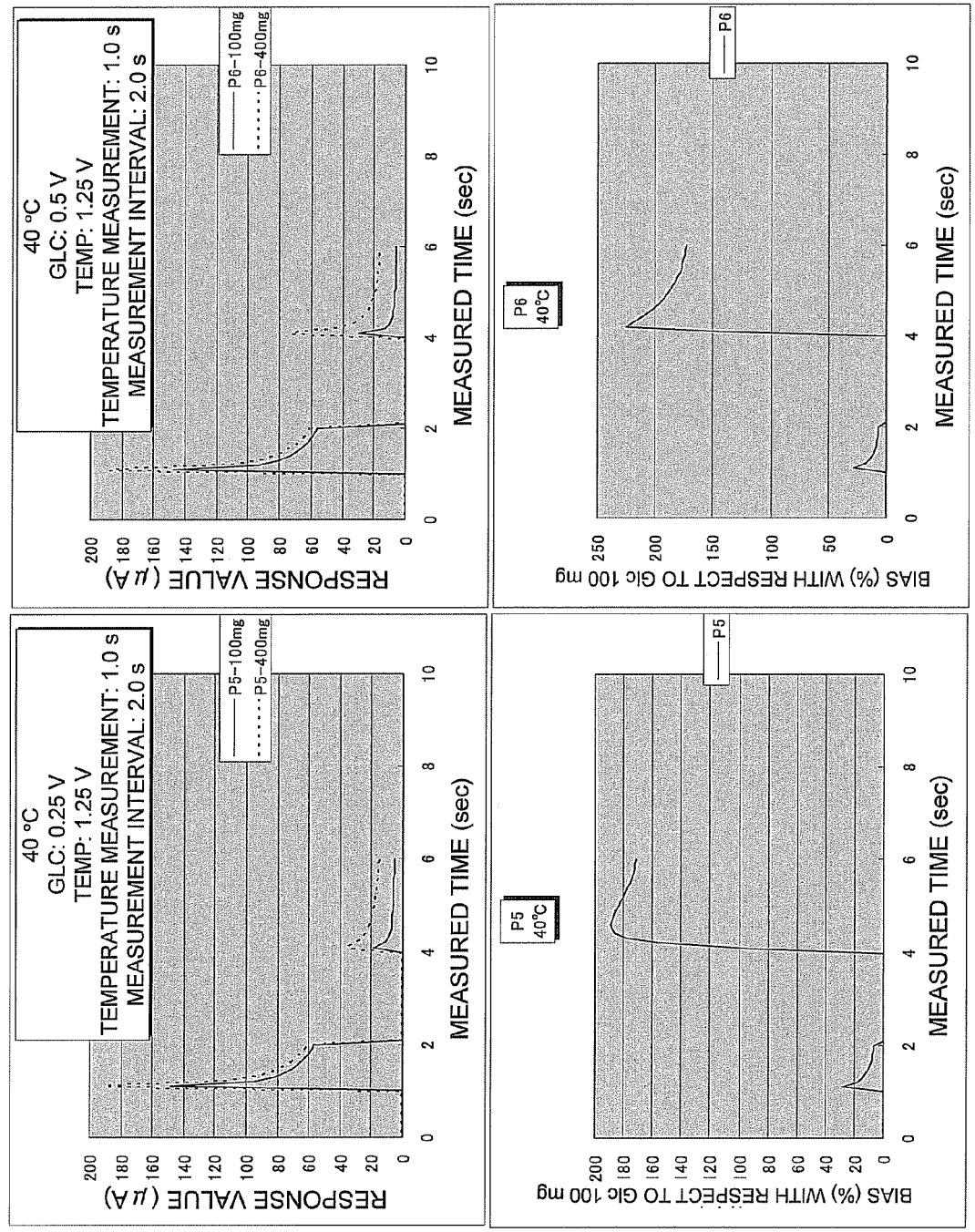

FIG. 131 includes charts representing the results of examining the response current value when the voltage application condition (voltage application time period) represented in the charts of FIG. 130 is changed.

Figure 132:
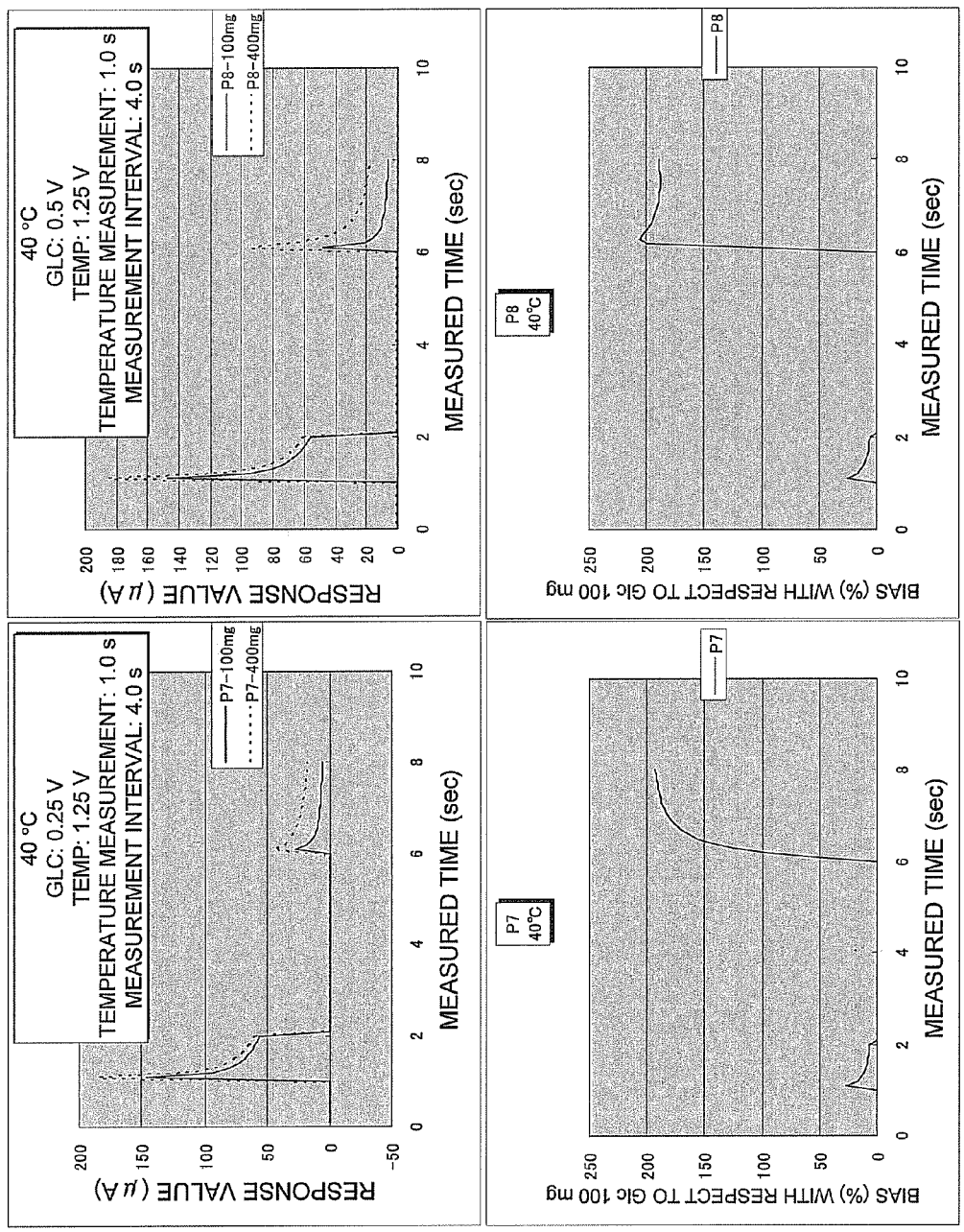

FIG. 132 includes charts representing the results of examining the response current value when the voltage application condition (voltage application interval) represented in the charts of FIG. 130 is changed.

Figure 133:
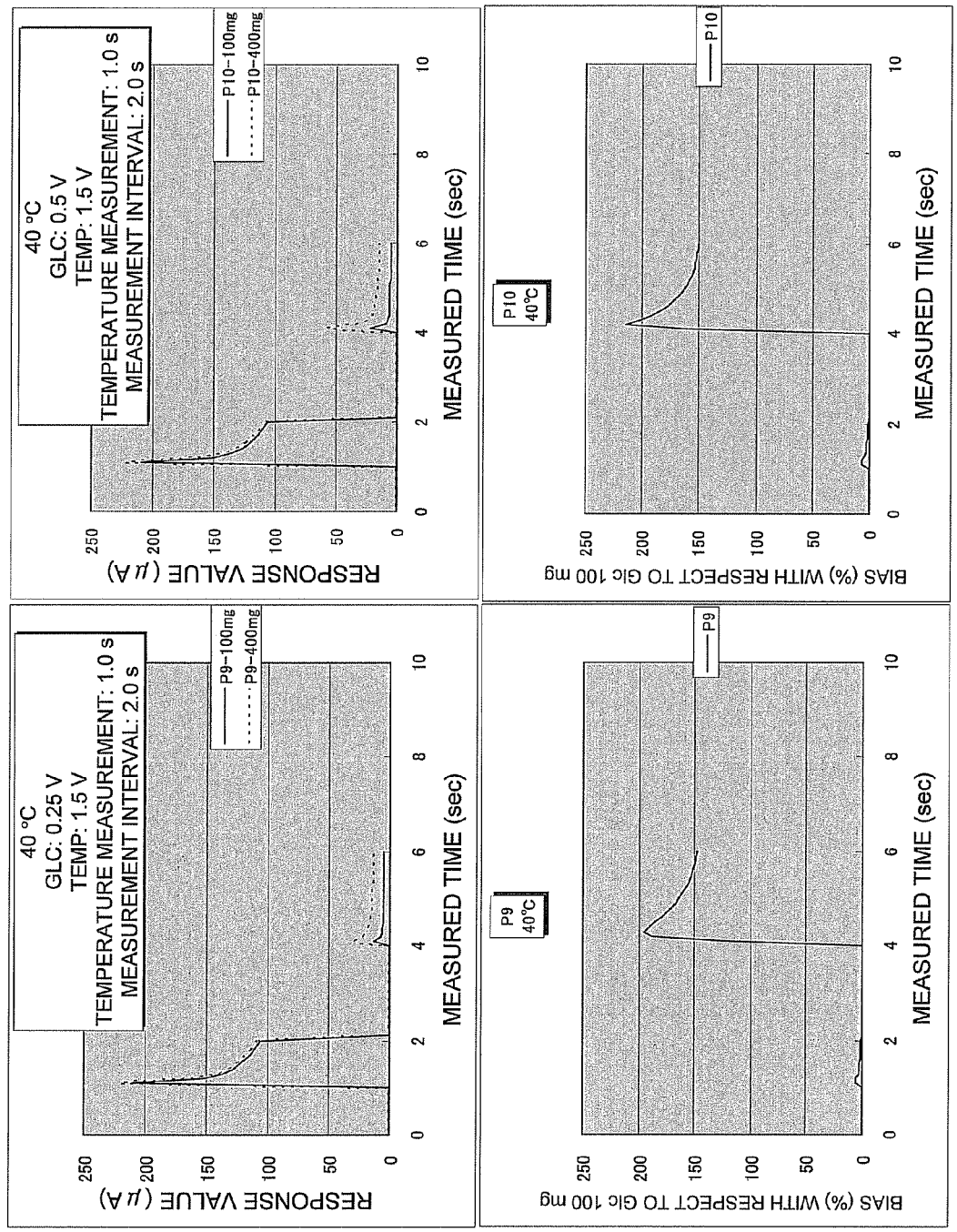

FIG. 133 includes charts representing the results of examining the response current value when the voltage application condition (temperature measurement voltage) represented in the charts of FIG. 130 is changed.

Figure 134:
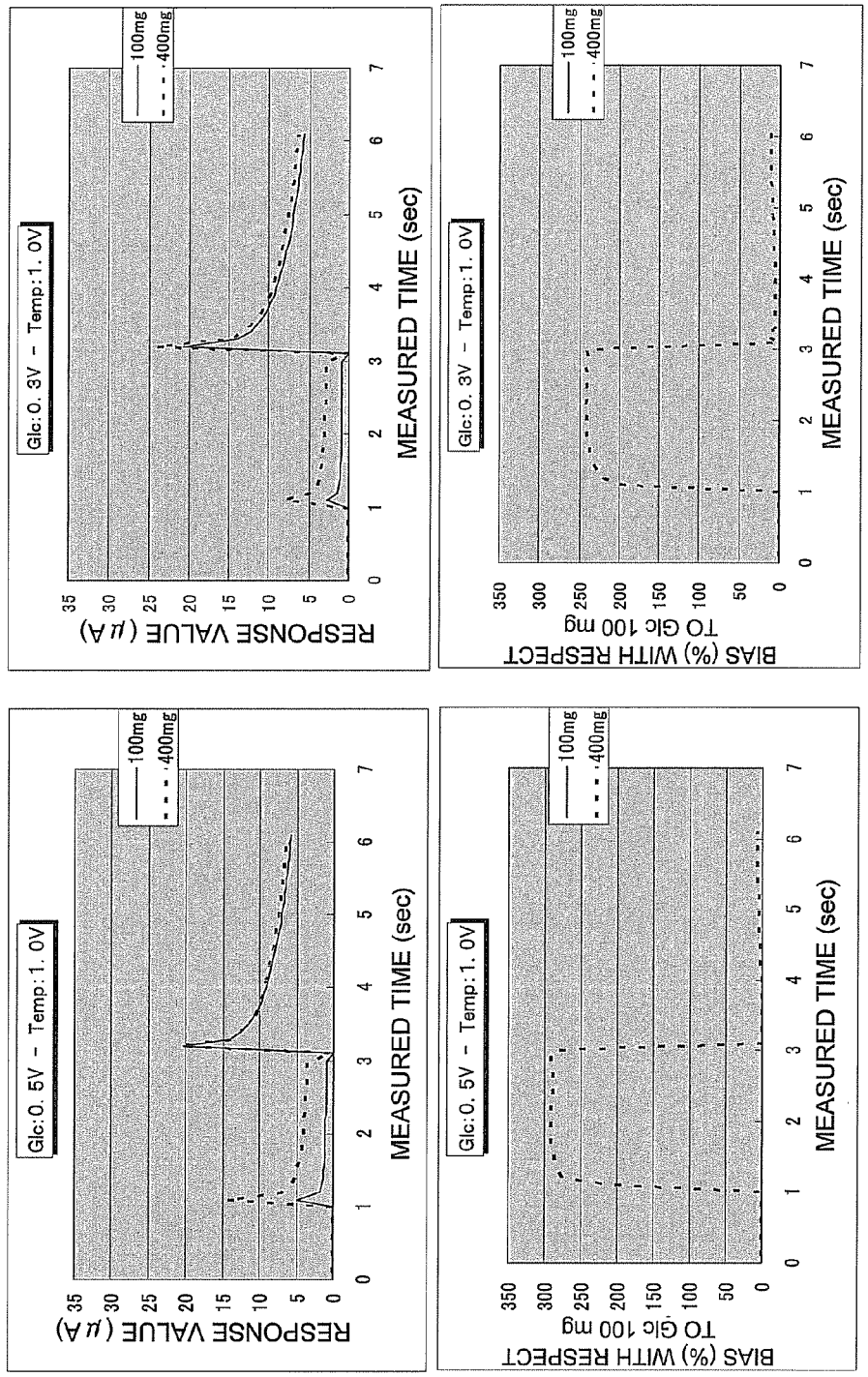

FIG. 134 includes charts representing the results of examining the response current value when the applied voltage in measuring the glucose concentration is changed in yet another exemplary embodiment of the present invention.

Figure 135:
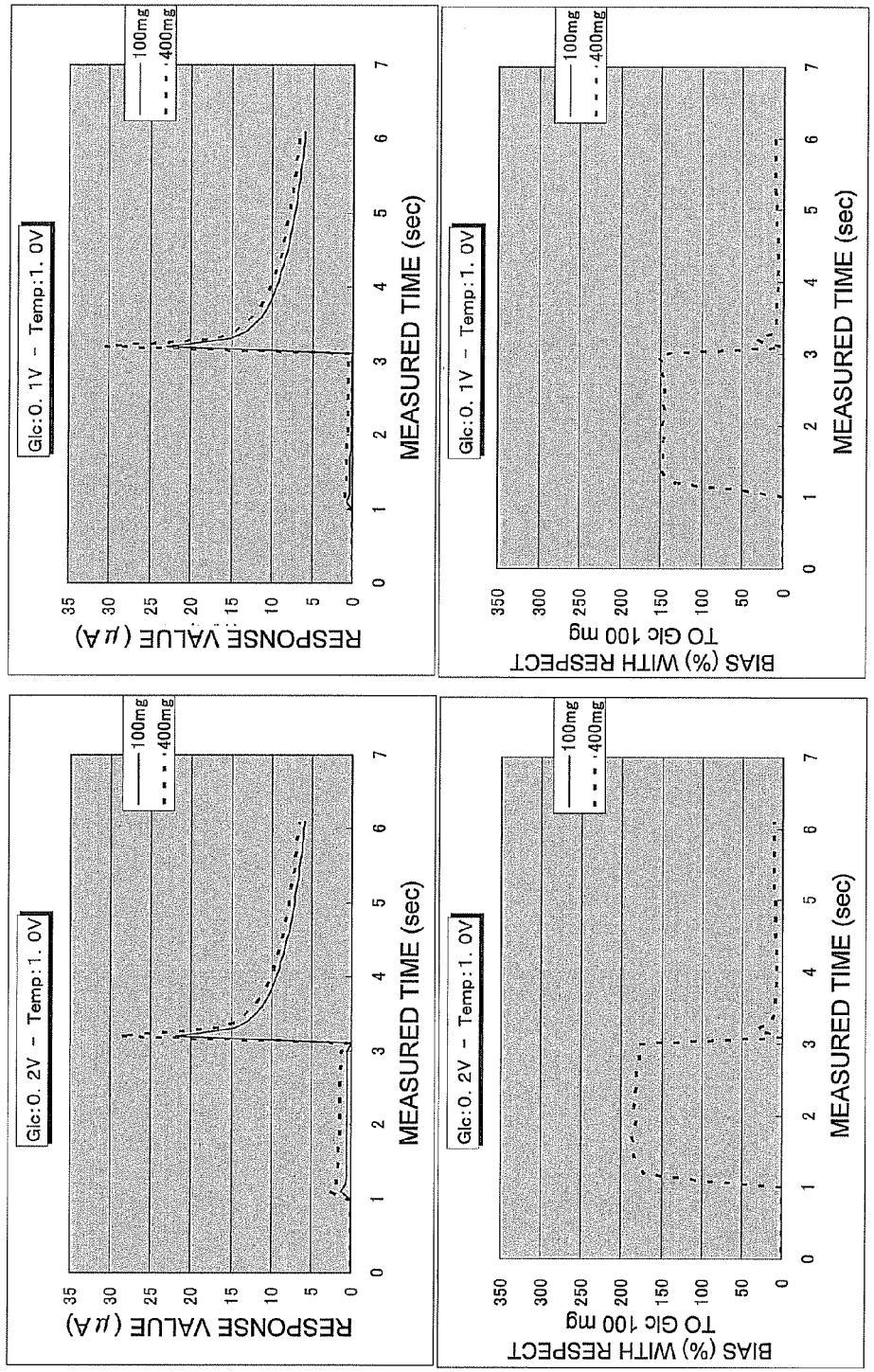

FIG. 135 includes charts representing the results of examining the response current value when the applied voltage represented in FIG. 134 is further reduced.

Figure 136:
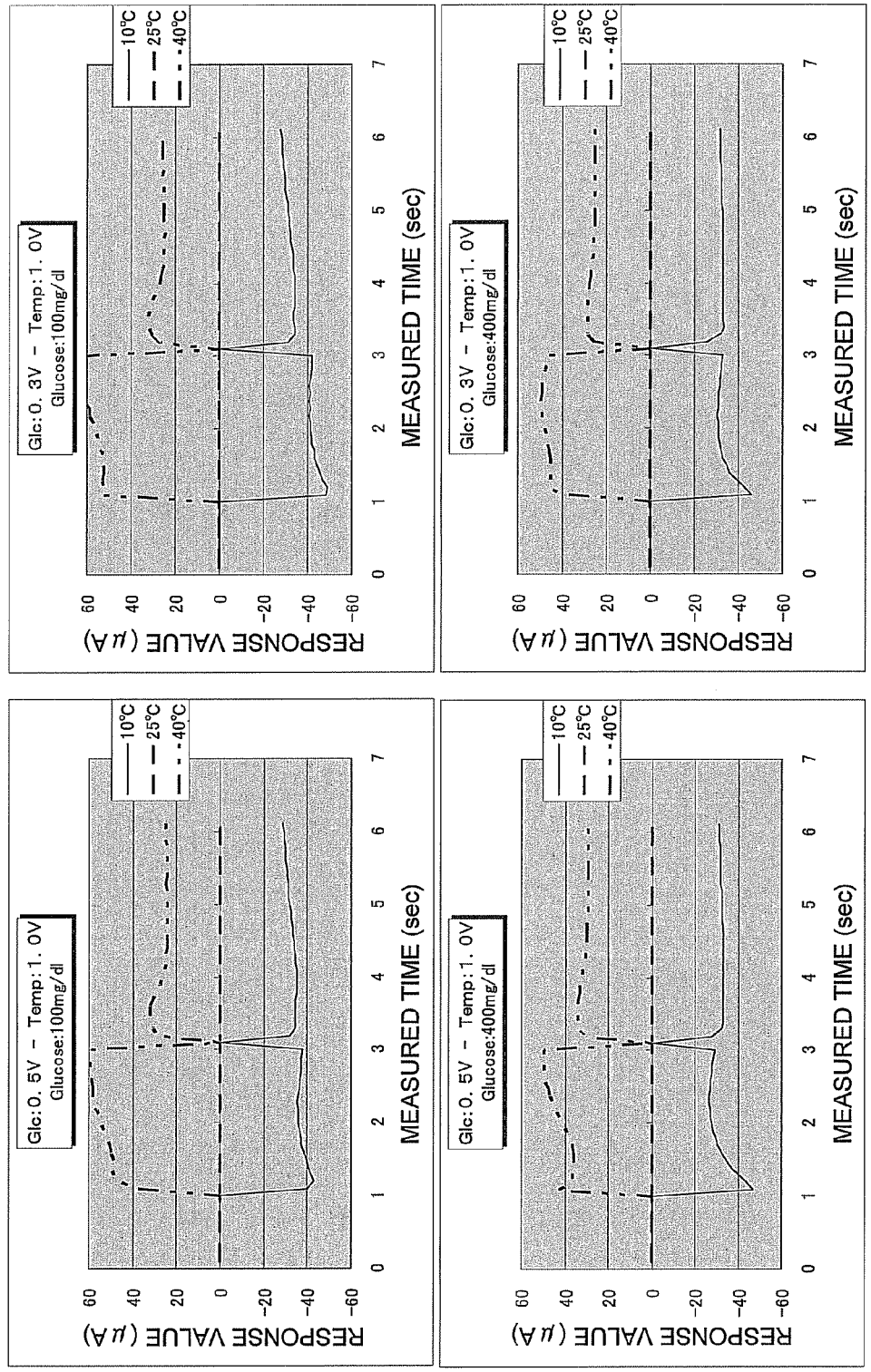
Figure 137:
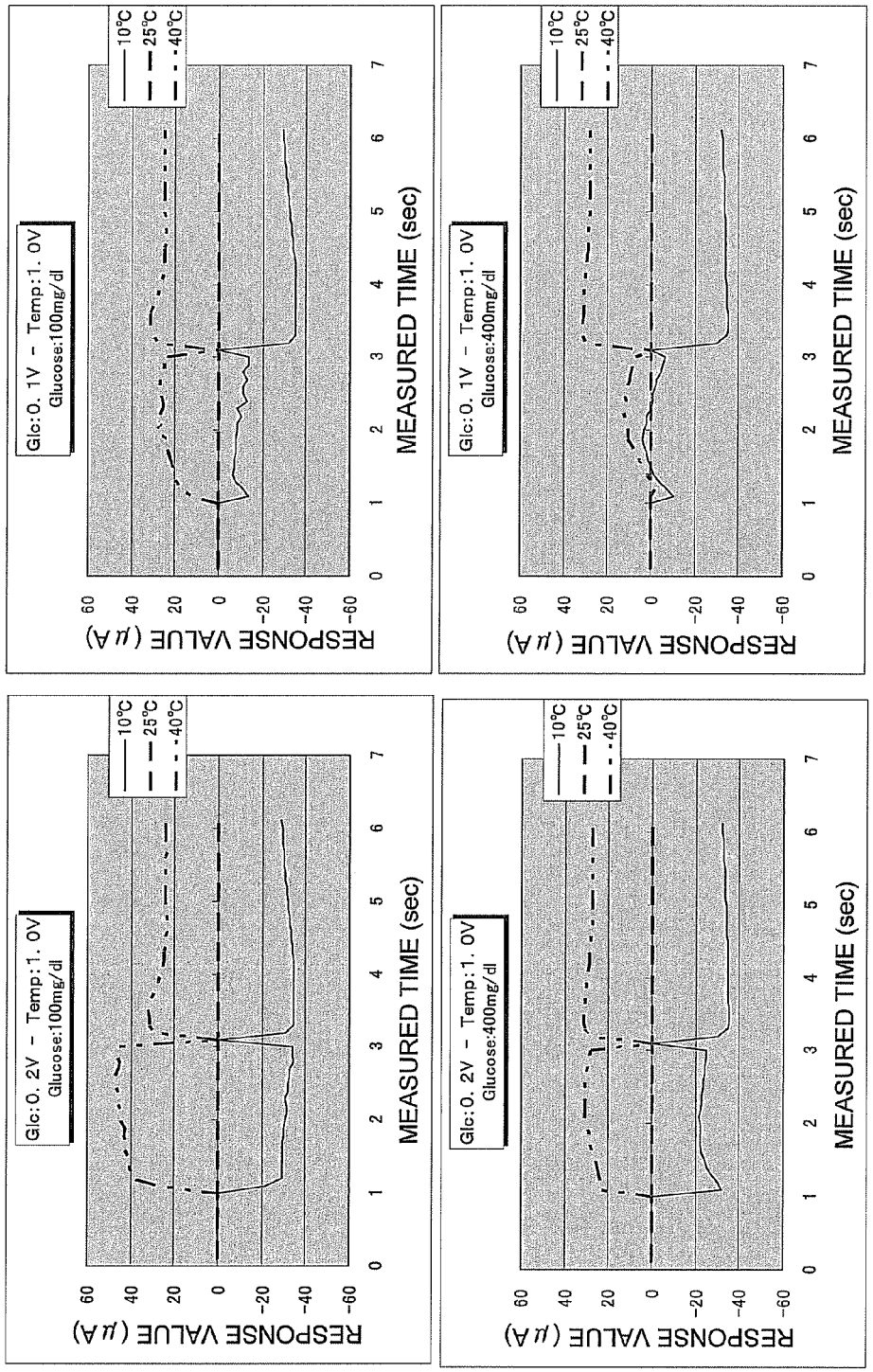
Figure 138:
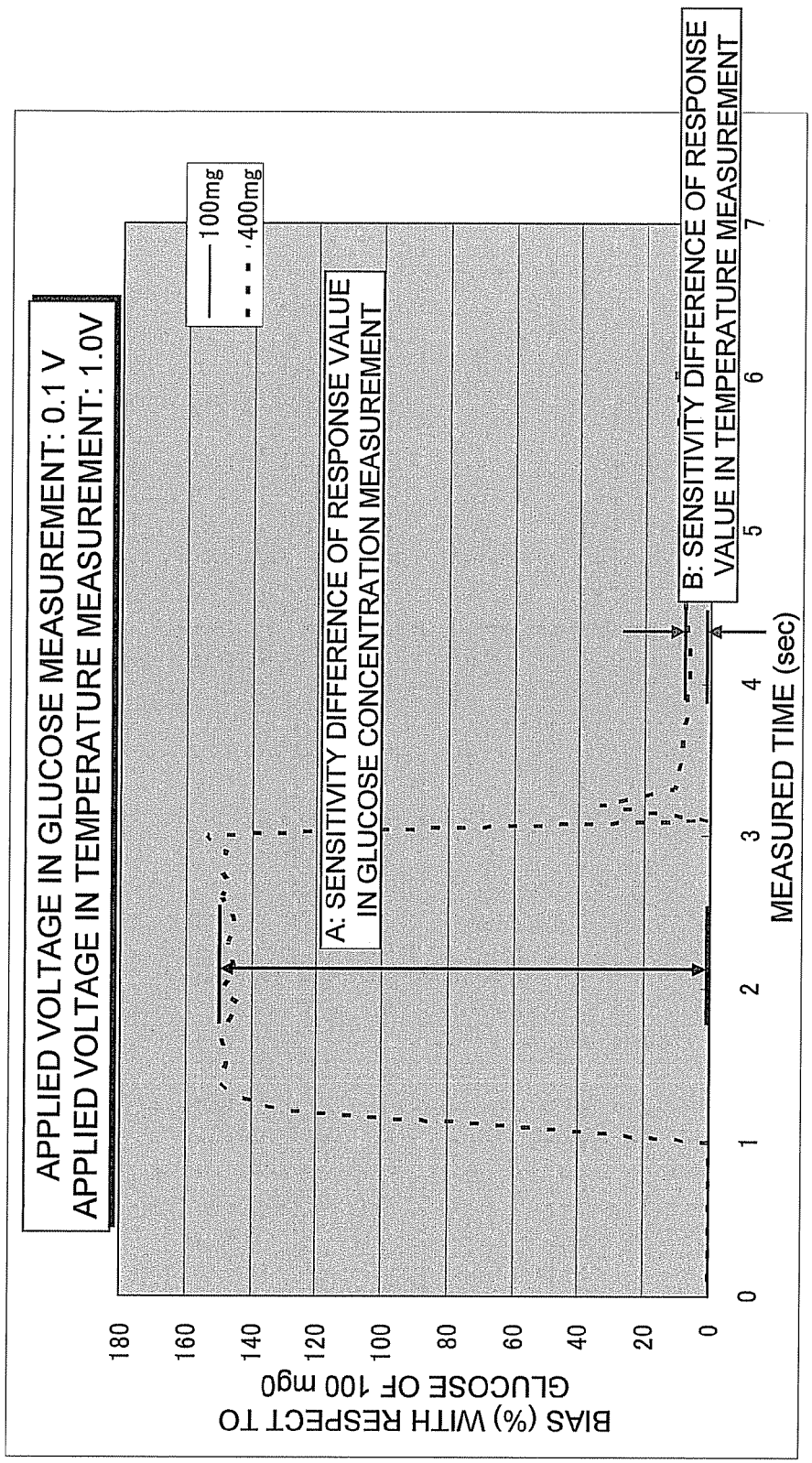

FIG. 136 includes charts corresponding to the charts of FIG. 134 and representing comprehensive results of examining the effect of variation in the temperature on the response current value in applying voltages of 0.5 and 0.3 V FIG. 137 includes charts corresponding to the charts of FIG. 135 and representing comprehensive results of examining the effect of variation in the temperature on the response current value in applying voltages of 0.2 and 0.1 V FIG. 138 is a chart representing a sensitivity difference of the response current value in a glucose concentration measurement and a sensitivity difference of the response current value in a temperature measurement when the glucose concentration is changed based on the measured results represented in FIGS. 134 to 137.

DESCRIPTION OF EMBODIMENTS

A biosensor system 100 using a sensor chip 200 according to an exemplary embodiment of the present invention will be hereinafter explained with reference to FIGS. 1 to 7 (b).

<Entire Configuration of Biosensor System 100>

Figure 1:
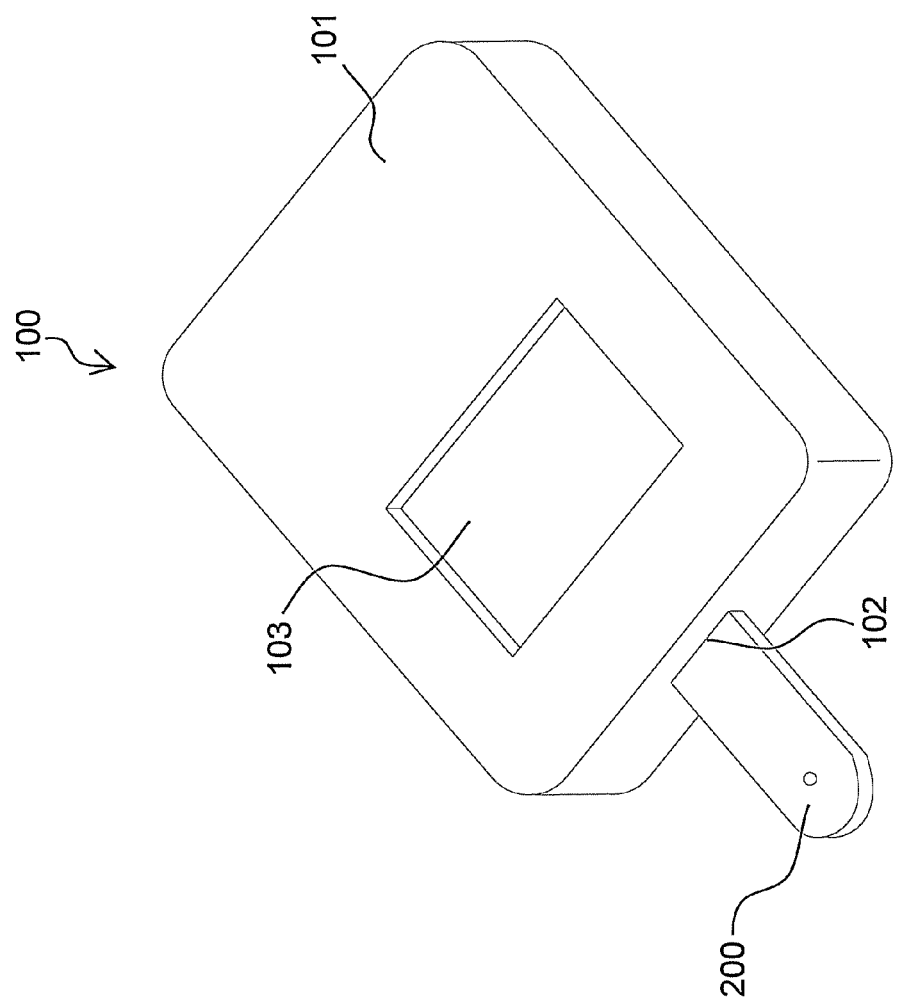
FIG. 1 is a perspective configuration view of a biosensor system according to an exemplary embodiment of the present invention.

The biosensor system 100 according to the present exemplary embodiment mainly includes a sensor configured to measure the temperature of a blood sample (i.e., a biological sample) and the concentration of an analyte contained in the blood sample. As illustrated in FIG. 1, the biosensor system 100 includes a measuring instrument 101 having a roughly rectangular cuboid shape and the sensor chip 200.

It should be noted that substances excluding blood cells (e.g., glucose, albumin, lactic acid, bilirubin and cholesterol) can be used as the analyte contained in the blood sample in the present exemplary embodiment. It is herein possible to use an oxidoreductase for which a target analyte serves as a substrate. Examples of the oxidoreductase include glucose oxidase, glucose dehydrogenase, lactate oxidase, lactate dehydrogenase, bilirubin oxidase and cholesterol oxidase. The amount of the oxidoreductase contained in a reaction reagent layer can be set to be in a range of 0.01 to 100 U (units), preferably in a range of 0.05 to 10 U, and more preferably in a range of 0.1 to 5 U.

The measuring instrument 101 includes an attachment port 102 as a rectangular slit on a lateral surface thereof. The sensor chip 200 is detachably connected to the attachment port 102. A display unit 103 is configured to display a measured result and is disposed in a roughly center part of one of the main surfaces of the measuring instrument 101. It should be noted that the configuration of the measuring instrument 101 will be hereinafter explained in detail.

(Sensor Chip 200)

Figure 2:
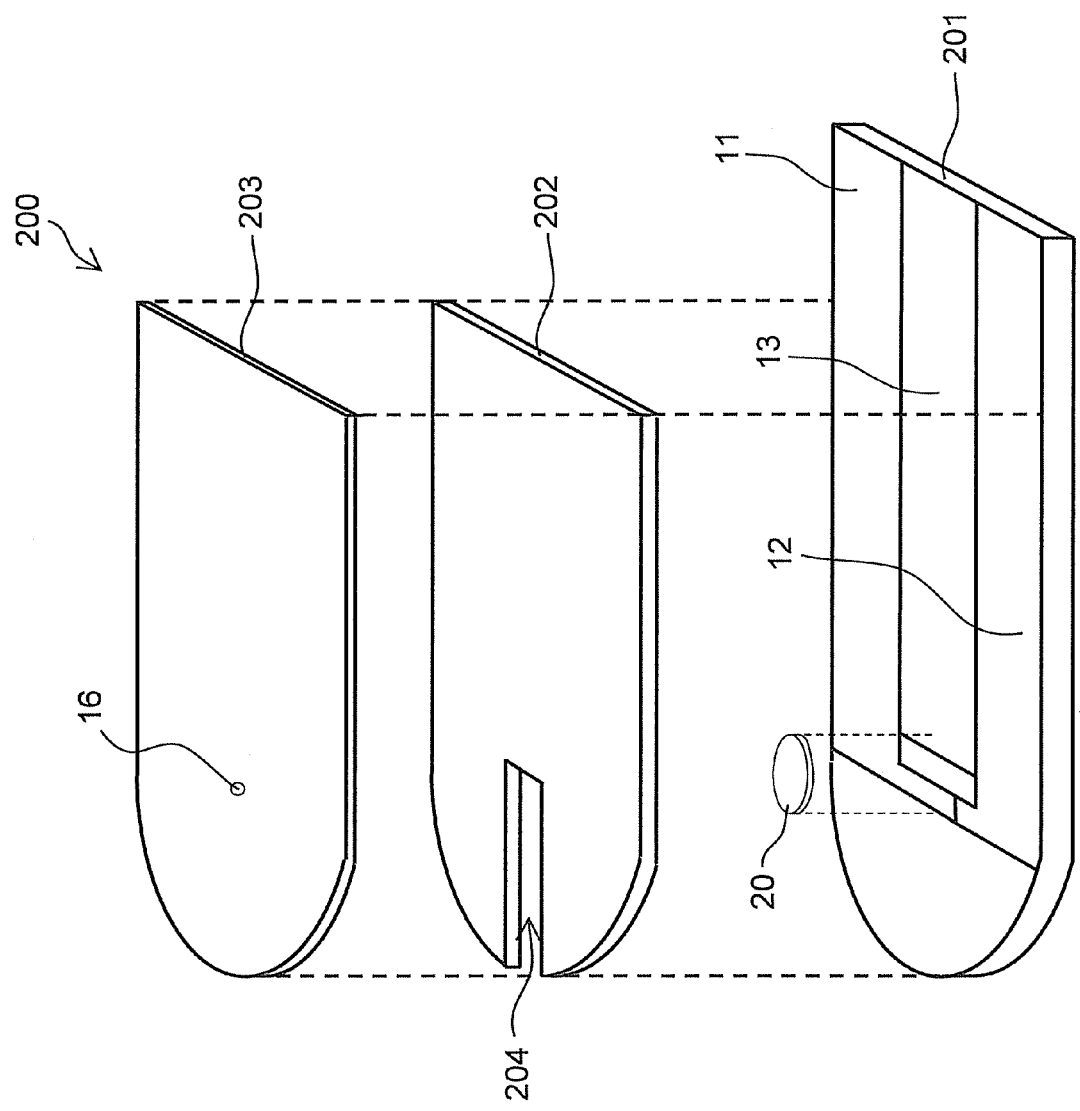
FIG. 2 is an exploded perspective view of a sensor chip included in the biosensor system illustrated in FIG. 1.
Figure 3:
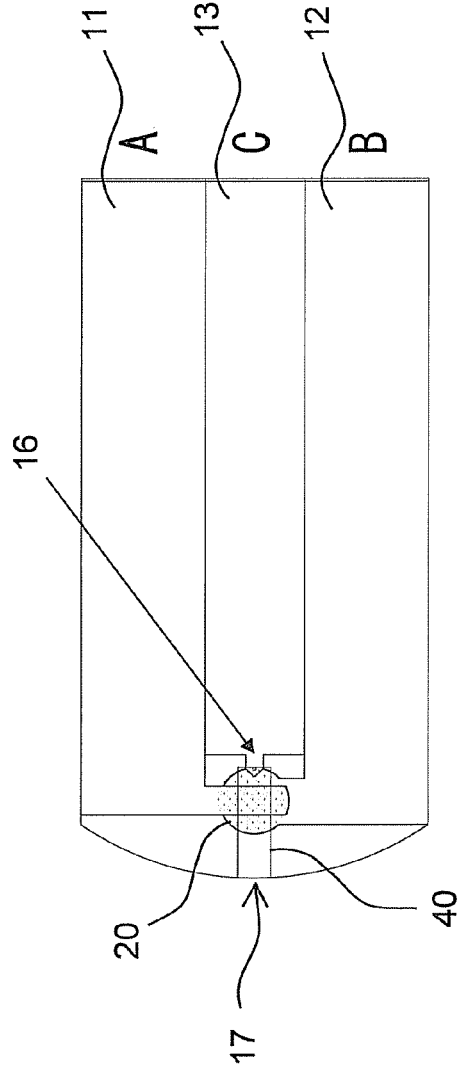
FIG. 3 is a plan view of the sensor chip illustrated in FIG. 2.

The sensor chip 200 is a disposable sensor chip to be discarded after a single use and is structured as illustrated in FIGS. 2 and 3. Specifically, a cover 203 is disposed on a part of an insulator substrate 201 through a spacer 202 with a rectangular notch 204 excluding on one end (a right end in FIG. 2) of the insulator substrate 201.

For example, the insulator substrate 201, the spacer 202 and the cover 203 are integrally formed by means of bonding, thermal welding or the like.

As the materials of the insulator substrate 201, the spacer 202 and the cover 203, any material can be selected from the group consisting of polyethylene terephthalate, polycarbonate, polyimide, polyethylene, polypropylene, polystyrene, polyvinyl chloride, polyoxymethylene, monomer cast nylon, polybutylene terephthalate, resins such as methacrylic resin and ABS resin, and further glass.

The notch 204 of the spacer 202 serves as a capillary section 40 (see FIG. 3) holding a blood sample in the integrated structure of the aforementioned members. The capillary section 40 has an elongated shape along the longitudinal direction of the sensor chip 200. The capillary section 40 is communicated with the outside at one end (i.e., a left end in FIGS. 2 and 3) of the spacer 202. In other words, the capillary section 40 is communicated with a blood sample inlet 17 opened to the outside of the sensor chip 200. A blood sample of roughly 5 μl or less is herein introduced into the capillary section 40.

The insulator substrate 201 includes three electrodes 11, 12 and 13 and a reaction reagent layer 20 on the surface thereof. Each of the electrodes 11, 12 and 13 is partially faced to the capillary section 40, while the reaction reagent layer 20 preliminarily includes a reaction reagent containing an electrolyte.

The reaction reagent layer 20 is disposed on the electrodes 11, 12 and 13.

Further, the cover 203 includes an air vent port 16. The air vent port 16 is configured to be faced to the rear portion of the notch 204 forming the capillary section 40 (i.e., a portion disposed on the opposite side of the biological sample inlet 17).

When introduced into the capillary section 40, the biological sample (i.e., the blood sample) flows through a detection section formed by the electrodes 11, 12 and 13 and the reaction reagent layer 20 at a controlled rate by means of a capillary phenomenon. Therefore, the blood sample as the biological sample is reliably deposited and measurement thereof is further stabilized.

Further, the inner surface of the capillary section 40 may be formed by a hydrophilic processing or made of a hydrophilic material. Accordingly, the blood sample as the biological sample will be further easily and reliably deposited (i.e., taken in).

The electrodes 11, 12 and 13 are opposed to each other. As illustrated in FIG. 3, a predetermined direct-current voltage (of 0.25 V, for instance) is applied for roughly 15 seconds or less to the electrode 11 as a working electrode A and the electrode 12 as a counter electrode B in measuring the concentration of glucose contained in the blood sample to be described. Further, a predetermined direct-current voltage is applied to the electrode 13 as the working electrode A and the electrode 12 as the counter electrode B in detecting an analyte. Yet further, a predetermined voltage is applied only for roughly 15 seconds or less to the electrode 11 as the working electrode A and the electrode 12 as the counter electrode B in measuring the temperature of the blood sample similarly to the glucose concentration measurement. Simply put, in the present exemplary embodiment, the electrodes 11 and 12 are used as a temperature electrode unit and an analysis electrode unit, whereas the electrodes 13 and 12 are used as an analyte detection electrode unit.

A direct-current voltage of 1 V or greater (e.g., 1.5 V) is herein applied to the electrodes 11 and 12 (the temperature electrode unit, the analysis electrode unit, a first temperature measurement section, an analyte measurement section) in measuring the temperature of the blood sample. The voltage of 1.5 V is herein set to be higher than a voltage (of 0.25 to 0.5 V) to be applied in measuring the concentration of glucose or the like. This aims at an accurate measurement of the blood sample temperature by inhibiting the effect of increase and reduction in the amount of glucose and hematocrit contained in the blood sample on the blood sample temperature.

In measuring the temperature, datum a related to the blood sample temperature is obtained based on the amount of electric current flowing through the temperature electrode unit (i.e., the electrodes 11 and 12). The material, undergoing electrochemical reactions on the temperature electrode unit, may be mainly water and may be alternatively a hemocyte component (e.g., erythrocytes and leucocytes) as long as it is a component contained in the blood sample. In measuring the analyte concentration, datum b, related to the concentration of the analyte contained in the blood sample, is obtained based on the amount of electric current flowing through the analysis electrode unit (i.e., the electrodes 11 and 12). The material, undergoing electrochemical reactions on the analysis electrode unit, may be mainly an electron mediator having received/donated electrons from/to the oxidoreductase. In the biosensor system 100 of the present exemplary embodiment, the analyte concentration is calculated by correcting the datum b related to the analyte concentration in the blood sample using the datum a related to the blood sample temperature.

In detecting the analyte, a voltage is applied between the electrode 12 and the electrode 13 disposed in the vicinity of the rear end of the capillary section 40. Accordingly, it is possible to easily detect the blood sample introduced into the rear part of the capillary section 40.

Further, each of the electrodes 11, 12 and 13 is coupled to a wire lead (not illustrated in the figures). One end of each wire lead is exposed to the outside of the sensor chip 200 at the end of the insulator substrate 201 that is not covered with the spacer 202 and the cover 203 for applying a voltage to each electrode correspondingly coupled to each wire lead.

The electrodes 11, 12 and 13 are herein formed on the insulator substrate 201 while being opposed in a two-dimensional arrangement. However, the electrodes 11, 12 and 13 may be disposed in a three-dimensional arrangement.

For example, the electrode 12 may be disposed under the cover 203 (see FIG. 2) while being opposed to the capillary section 40, whereas the electrode 11 and 13 may be disposed on the insulator substrate 201.

The reaction reagent layer 20 is a layer to which a reagent containing an electrolyte has been preliminarily applied. The reaction reagent layer 20 is formed for covering a part of the insulator substrate 201 where the electrodes 11, 12 and 13 are overlapped. The reaction reagent layer 20 contains an electron mediator and an oxidoreductase for which the analyte contained in the blood sample serves as a substrate. In the present exemplary embodiment, a reagent represented in FIG. 4 is used as the regent applied as the reaction reagent layer 20. The regent is obtained by dissolving CMC (HE-1500F) of 0.05 wt %, potassium ferricyanide of 1.7 wt %, taurine of 1.0 wt %, maltitol of 0.1 wt % and enzyme (FAD-GDH manufactured by Ikedatohka Industries Co., Ltd) of 1.5 U/cell in $H_2O$ (water). The reaction reagent layer 20 is formed by dropping the reagent of 0.9 mg on the electrodes 11, 12 and 13 of the sensor chip 200 and drying it out.

It should be noted that the reaction reagent layer 20 preferably contains an electron mediator having a function of receiving/donating electrons produced in enzyme reactions from/to the electrodes, such as potassium ferricyanide, p-benzoquinone, p-benzoquinone derivatives, oxidized phenazine methosulfate, methylene blue, ferricinium and ferricinium derivatives. The reaction reagent layer 20 may contain water-soluble polymer for enhancing formability of the reaction reagent layer. As the water-soluble polymer, at least one can be selected from the group consisting of carboxymethylcellulose and salts thereof, hydroxyethylcellulose, hydroxypropylcellulose, methylcellulose, ethylcellulose, ethylhydroxyethylcellulose, carboxyethylcellulose and salts thereof, polyvinyl alcohol, polyvinylpyrrolidone, polyamino acids such as polylysine, polystyrene sulfonate and salts thereof, gelatin and derivatives thereof, polyacrylic acid and salts thereof, polymethacrylic acid and salts thereof, starch and derivatives thereof, maleic anhydride polymer and salts thereof, and agarose gel and derivatives thereof.

The capillary section 40 includes the air vent port 16 on the end thereof disposed opposite to the tip thereof where the blood sample is deposited. When deposited on the blood sample inlet 17, the blood sample can be sucked into the capillary section 40 by means of a capillary phenomenon. Accordingly, the sucked blood sample can be filled to the predetermined position on the electrodes 11, 12 and 13 of the capillary section 40.

It should be noted that heretofore known conductive materials, such as palladium, platinum, gold, silver, titanium, copper, nickel and carbon, can be used as the materials of the electrodes 11, 12 and 13.

(Measuring Instrument 101)

Figure 5:
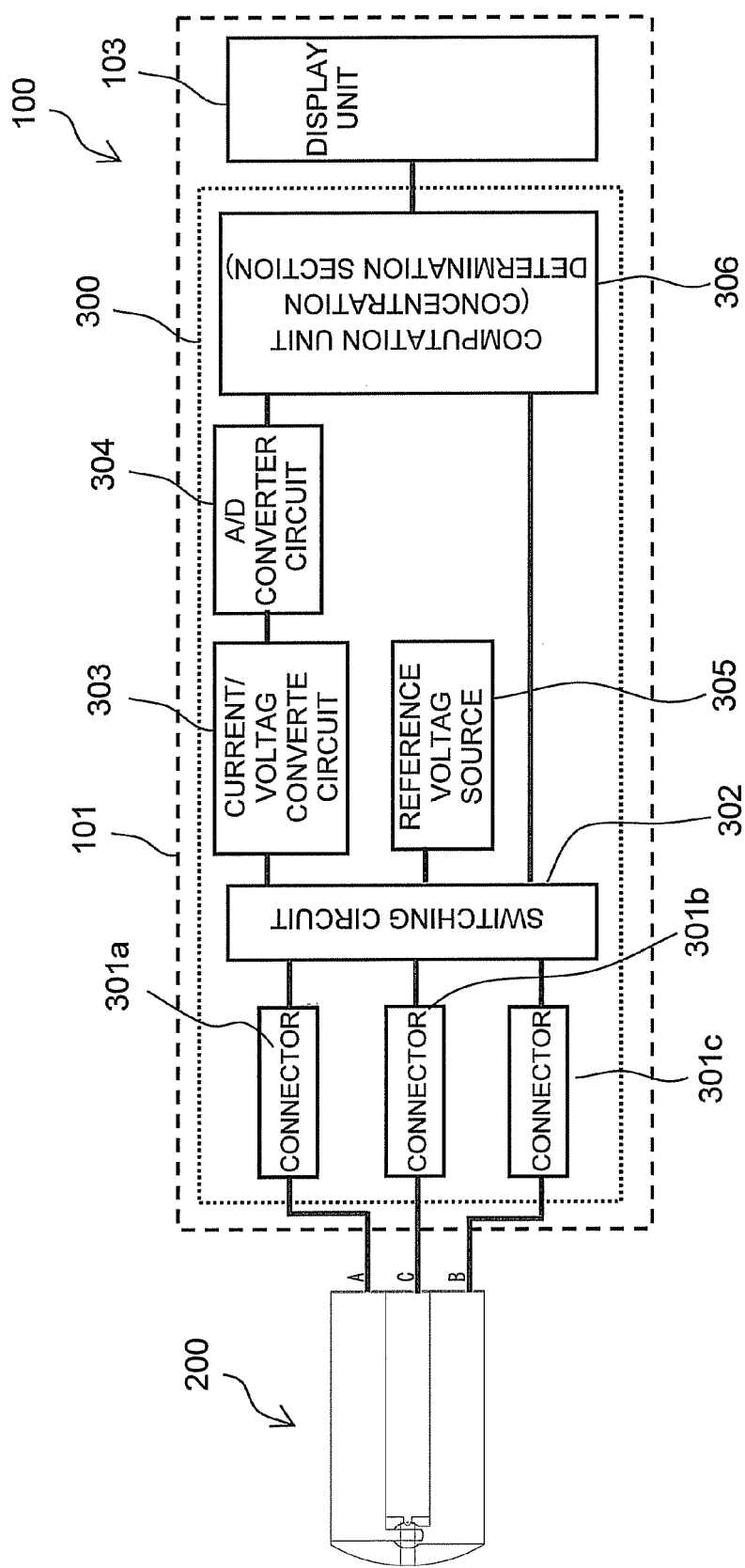
FIG. 5 is a diagram illustrating an exemplary configuration of a circuit provided in the biosensor system illustrated in FIG. 1 for measuring the concentration of an analyte contained in a blood sample.

As illustrated in FIG. 5, the measuring instrument 101 includes a control circuit 300 and the display unit 103. The control circuit 300 is configured to apply a voltage between at least two electrodes selected from the electrodes 11, 12 and 13 of the sensor chip 200 (see FIGS. 2 and 3). The display unit 103 is configured to display a measured result.

As illustrated in FIG. 5, the control circuit 300 includes three connectors 301a, 301b and 301c, a switching circuit 302, a current/voltage convertor circuit 303, an analogue/digital convertor circuit (hereinafter referred to as an A/D convertor circuit) 304, a reference voltage source (voltage application section) 305, and a computation unit (concentration determination section) 306. The control circuit 300 is configured to switch a potential to be applied to an electrode through the switching circuit 302 for using the electrode as either a positive electrode (i.e., an anode) or a negative electrode (i.e., a cathode).

The computation unit 306 includes a heretofore known central processing unit (CPU) and conversion tables for determining the concentration of the analyte contained in the blood sample based on the aforementioned data a and b. Further, the computation unit 306 is configured to correct the concentration of the analyte contained in the blood sample while with reference to conversion tables that correction coefficients are set based on environmental temperatures. More specifically, the analyte concentration is temporarily calculated with reference to a conversion table for temporal measurement, and a final analyte concentration is then determined by correcting the temporarily calculated analyte concentration with reference to a conversion table for temperature correction.

Excluding the aforementioned function as the concentration determination section, the computation unit 306 further includes a control function of switching the switching circuit 302, a function of receiving an input from the A/D convertor circuit 304, a function of controlling the voltage of the reference voltage source 305 as the voltage application section, a function of controlling the measurement procedure regarding either an application timing and an application time period or a switching timing of a temperature measurement and a concentration measurement, a function of outputting display data to the display unit 103, and a function of communicating with external devices. Further, the computation unit 306 is configured to entirely control the measuring instrument.

<Blood Sample Temperature Measurement and Analyte Concentration Measurement>

Figure 6:
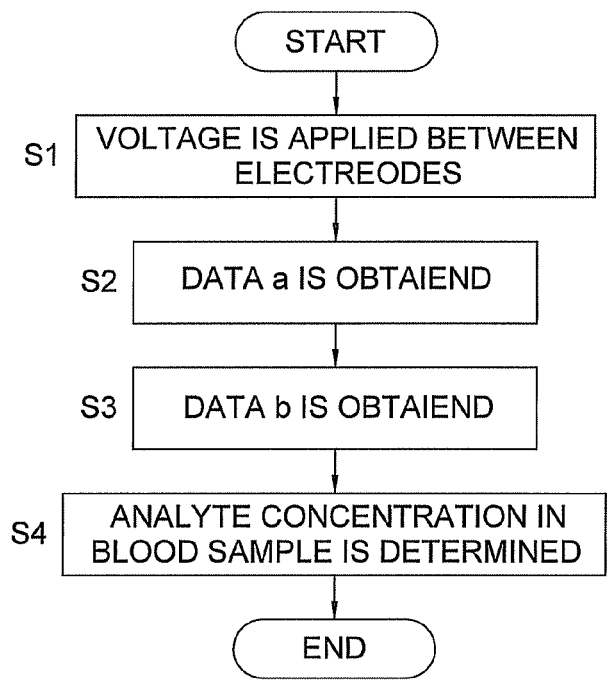
FIG. 6 is a flowchart representing the flow of a blood sample concentration measurement method in the biosensor system illustrated in FIG. 1.

In the present exemplary embodiment, for instance, the temperature of the blood sample and the concentration of the analyte contained in the blood sample are measured using the biosensor system 100 (see FIG. 1) as represented in FIG. 6.

First, in response to a command of the CPU of the computation unit 306 (see FIG. 5), the electrode 13 is connected to the current/voltage convertor circuit 303 (see FIG. 5) through the connector 301b, whereas the electrode 12 is connected to the reference voltage source 305 (see FIG. 5) through the connector 301c. Subsequently, a constant voltage is applied between the electrodes in response to a command of the CPU (Step S1). For example, the applied voltage is configured to be 0.01 to 2.0 V, preferably 0.1 to 1.0 V, and more preferably 0.2 to 0.5 V when the electrode 13 is set as a positive electrode (i.e., an anode) whereas the electrode 12 is set to be a negative electrode (i.e., a cathode). The voltage is configured to be applied until the blood sample is introduced into the rear part of the capillary section 40 since the sensor chip is inserted into the measuring instrument 101.

When the blood sample is introduced into the capillary section 40 from the blood sample inlet 17 of the sensor chip 200, an electric current flows between the electrode 13 and the electrode 12. It is herein detected that the capillary section 40 is filled with the blood sample by detecting increase in an electric current level per a unit time. The current/voltage convertor circuit 303 is configured to convert the current value into a voltage value, and the A/D converter circuit 304 is configured to convert the voltage value into a digital value. The obtained digital value is inputted into the CPU. Based on the digital value, the CPU is configured to detect that the blood sample is introduced into the rear part of the capillary section.

After introduction of the blood sample, reactions are produced between the enzyme and the analyte contained in the blood sample and between the enzyme and the electron mediator, for instance, in a time range of 0 to 60 seconds, preferably in a time range of 0 to 15 seconds, and more preferably in a time range of 0 to 5 seconds.

Next, the aforementioned datum a related to the blood sample temperature is obtained as follows (Step S2).

First, the switching circuit 302 is activated in response to a command of the aforementioned CPU. Accordingly, the electrode 11 is connected to the current/voltage convertor circuit 303 through the connector 301a, whereas the electrode 12 is connected to the reference voltage source 305 through the connector 301c. Subsequently, a constant voltage is applied between the electrodes in response to a command of the CPU. For example, the applied voltage is configured to be 1.0 to 5.0

V and preferably 1.0 to 3.0 V when the electrode 11 is set as a positive electrode (i.e., an anode) whereas the electrode 12 is set as a negative electrode (i.e., a cathode), as described below. It should be noted that the polarity of the electrode 11 and that of the electrode 12 may be reversed. Specifically, the voltage to be applied to the electrode 11 may be negative with respect to the voltage to be applied to the electrode 12. The aforementioned configuration is easily applied especially when the electrode 11 can be considered to be roughly equivalent to the electrode 12 in terms of an electric potential. The voltage application time period falls in a time range of 0.1 to 30 seconds, preferably a time range of 0.5 to 10 seconds, and more preferably a time range of 1 to 5 seconds. The current/voltage convertor circuit 303 is configured to conver the amount of electric current, flowing between the electrodes in response to the voltage application, into a voltage value in response to a signal outputted from the control circuit for instructing abtainment of the datum a. Subsequently, the A/D convertor circuit 304 is configured to convert the obtained voltage value into a digital value. The digital value is inputted into the CPU and is stored in a memory of the computation unit 306 as the datum a.

Next, the aforementioned datum b related to the concentration of the analyte contained in the blood sample is obtained as follows (Step S3).

First, the switching circuit 302 is activated in response to a command from the CPU. Accordingly, the electrode 11 is connected to the current/voltage convertor circuit 303 through the connector 301a, whereas the electrode 12 is connected to the reference voltage source 305 through the connector 301c. Subsequently, a measurement sequence is inputted in response to a command from the CPU. For example, the applied voltage is herein configured to be 0.05 to 1.0 V, preferably 0.1 to 0.8 V, and more preferably 0.2 to 0.5 V, for instance, when the electrode 11 is set as a positive electrode (i.e., an anode) whereas the electrode 12 is set as a negative electrode (i.e., a cathode). The voltage application time period falls in a range of 0.1 to 30 seconds, preferably a range of 0.1 to 15 seconds, and more preferably a range of 0.1 to 5 seconds. The current/voltage convertor circuit 303 is configured to convert the amount of an electric current flowing between the electrodes in response to the voltage application into a voltage value in response to a signal transmitted to a measurement section from the control circuit for instructing obtainment of the datum b. Subsequently, the A/D convertor circuit 304 is configured to convert the converted voltage value into a digital value. The digital value is inputted into the CPU and is stored in a memory of the computation unit 306 as the datum b.

It should be noted that the control circuit is preferably configured to transmit a signal to the measurement section for instructing obtainment of the datum b within a range of 0.5 to 5 seconds since the blood sample is introduced into the capillary section 40 of the sensor chip from the perspective of speeding up the analyte concentration measurement.

Alternatively, the datum b may be obtained earlier than the datum a. Prior to obtainment of the datum b, however, it takes considerable time for dissolution of the reagent, enzyme reactions, and reactions between the electron mediator and the enzyme. Therefore, the datum b is preferably obtained later than the datum a. Yet alternatively, the data a and b may be simultaneously obtained using a sensor chip equipped with two electrode systems. In this case, however, voltages are simultaneously applied to the electrode systems within a single solution system. Electric currents may accordingly interfere with each other. Therefore, it is preferable to separately obtain the data a and b.

It should be noted that a preferable applied voltage in the temperature measurement can be specified not only as a direct numeric value but also as numeric values such as a ratio of the applied voltage in the temperature measurement with respect to the applied voltage in the glucose concentration measurement and a electric potential difference. Similarly, a preferable applied voltage in the glucose concentration measurement can be specified as numeric values such as a ratio of the applied voltage in the glucose concentration measurement with respect to the applied voltage in the temperature measurement and an electric potential difference.

The present invention will be explained in more detail with the following exemplary embodiments.

(Exemplary Embodiment 1)

An exemplary embodiment of the present invention will be hereinafter explained with reference to FIGS. 9 and 10 and charts in FIGS. 11 to 16.

Figure 9:
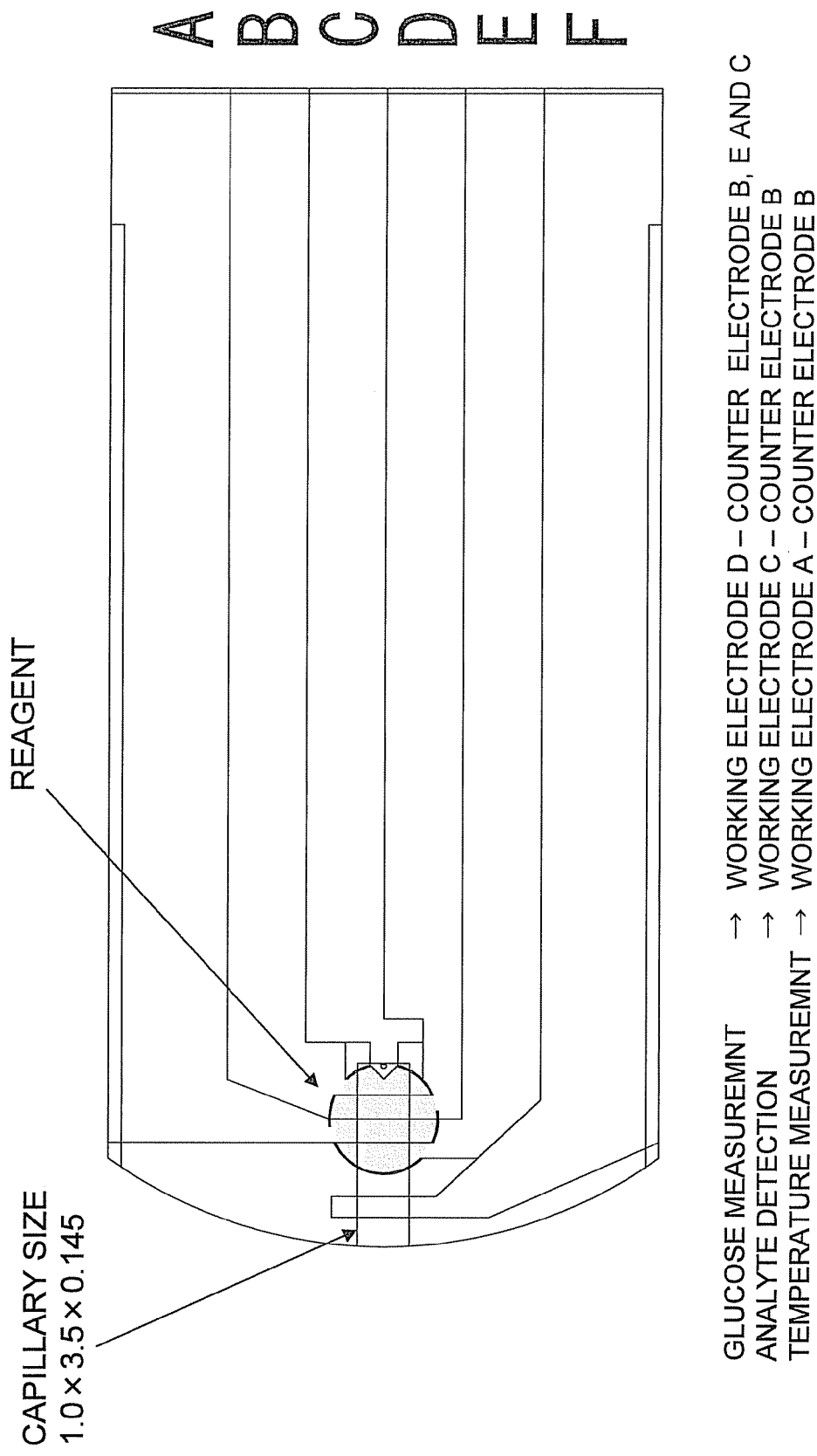
FIG. 9 is a plan view illustrating a configuration of a sensor chip according to an exemplary embodiment of the present invention.

In the present exemplary embodiment, an electric current value, detected in each electrode, was measured by changing conditions of a glucose concentration, a hematocrit (Hct) value and a blood glucose temperature, using a sensor chip that has a capillary size of 1.0×3.5×0.145 mm and includes six electrodes A to F as illustrated in FIG. 9.

Specifically, the combination of the electrode D (as the working electrode) and electrodes B, E and C (as the counter electrodes) was used for measuring the glucose concentration. The combination of the electrode C (as the working electrode) and the electrode B (as the counter electrode) was used for detecting the analyte. The combination of the electrode A (as the working electrode) and the electrode B (as the counter electrode) was used for measuring the blood sample temperature.

It should be noted that a reagent disposed on the electrodes are the same as the reagent (see FIG. 4) explained in the aforementioned exemplary embodiment.

As represented in FIG. 10, a predetermined voltage was herein applied to the respective electrodes A to F for a predetermined period of time in executing the respective measurements in the sensor chip having the electrode configuration illustrated in FIG. 9.

Specifically, a voltage of 0.25 V was herein firstly applied to the combination of the working electrode C and the counter electrode B in detecting the analyte. Next, a voltage of 0.25 V was applied to the combination of the working electrode D and the counter electrodes B, E and C as the analysis electrode unit in a measured time period from 1.0 second to 3.0 second in measuring the glucose concentration in the blood sample. Next, a voltage of 1.5 V was applied to the combination of the working electrode A and the counter electrode B as the temperature electrode unit in a measured time period from 3.5 second to 5.0 second in measuring the blood sample temperature. Next, a voltage of 2.5 V was applied to the combination of the working electrode F and the counter electrodes A, B, C, D and E in a measured time period from 5.0 second to 5.5 second in measuring the Hct value.

It should be noted that a high voltage of 1.5 V was applied in the present exemplary embodiment unlike a voltage of 0.25 to 0.5 V to be applied in measuring the glucose concentration and the like in the well-known sensor chips. The configuration was herein applied for using the sensor chip as a high-precision temperature sensor, compared to a reference example 1 to be described, through exclusion of the effects of increase and reduction in the glucose concentration and increase and reduction in the Hct value, i.e., through extraction of only the effect of the temperature. Further, the working electrodes were classified into two groups in executing the respective measurements as represented in FIG. 10. The configuration aims at preventing reduction in the detection ability of the glucose concentration to be measured at a low voltage (of 0.25 V) because a relatively high voltage of 1.5 to 2.5 V is applied in measuring the temperature and the Hct value.

Figure 11:
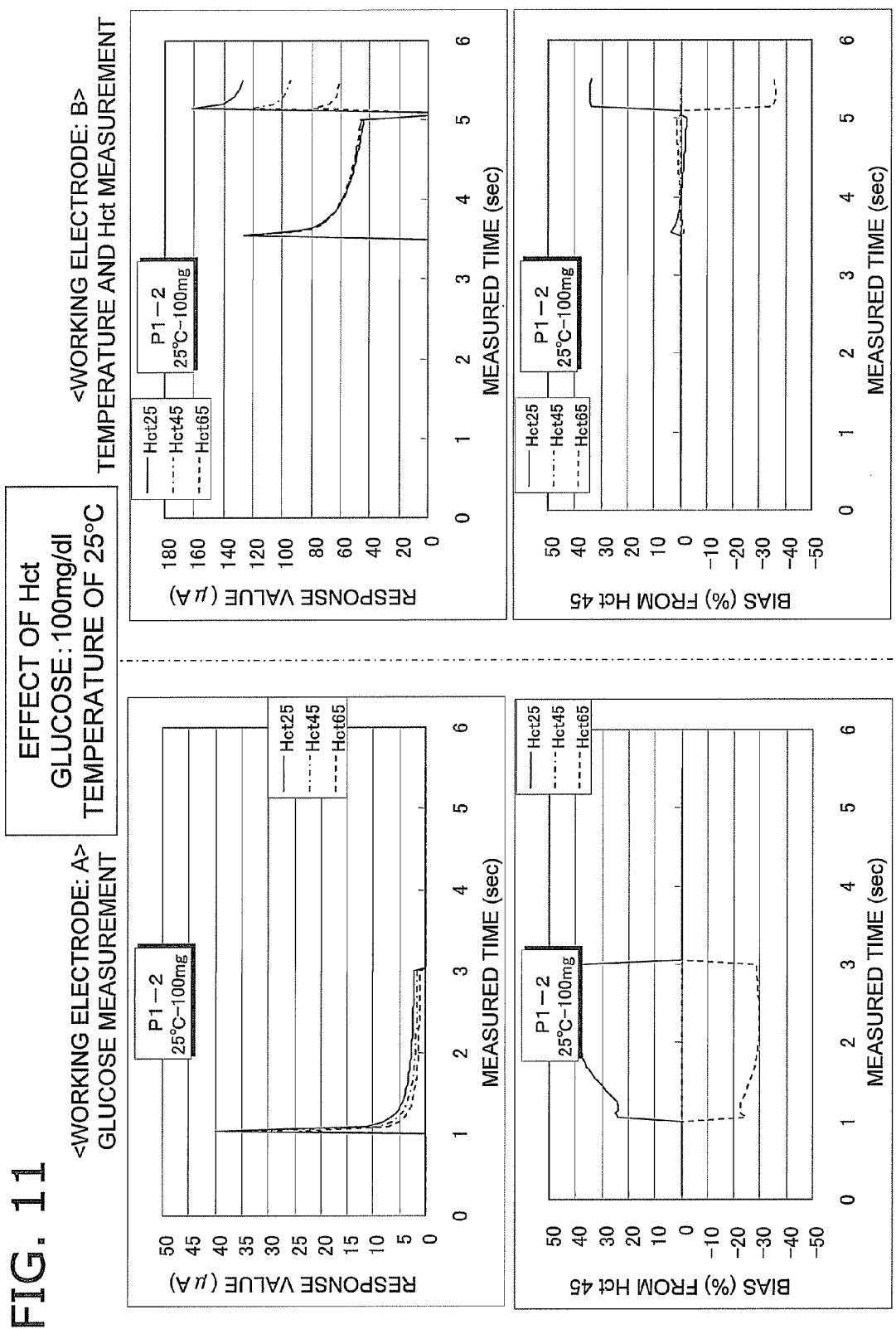
FIG. 11 includes charts representing the results of examining the effect of variation in an Hct value on a response current value in the exemplary embodiment 1.
Figure 12:
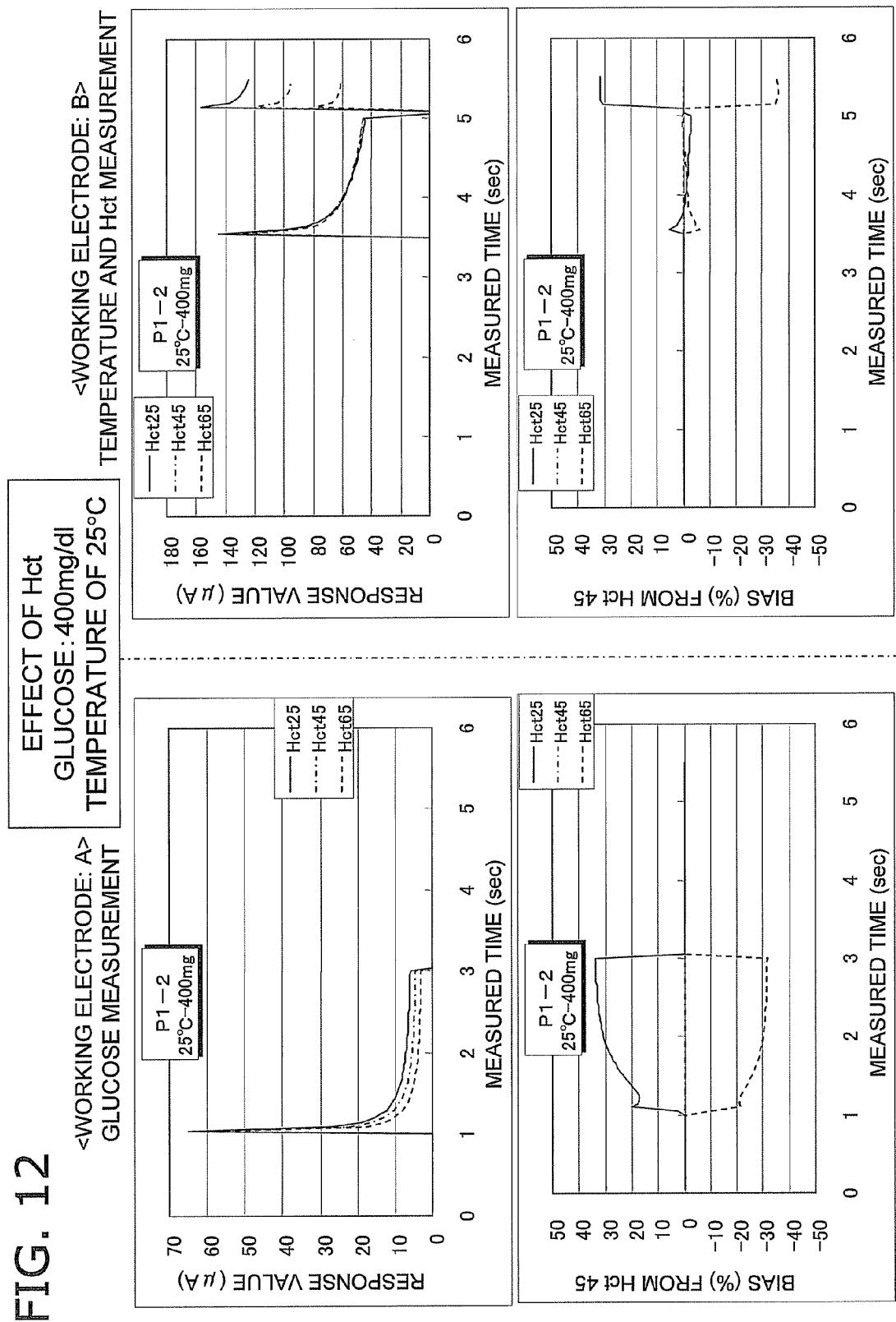
FIG. 12 includes charts representing the results of examining the effect of variation in the Hct value on the response current value in the exemplary embodiment 1.

FIGS. 11 and 12 represent the measured results of response current values in the respective electrodes when the glucose concentration and the temperature were set to be constant for examining the effect of increase and reduction in the Hct value on the response current value.

Specifically in FIG. 11, variation in the response current value was examined where the glucose concentration was set to be constant as 100 mg/dl and the temperature was set to be constant as 25° C. while the Hct value was set to be 25, 45 and 65. In FIG. 12, on the other hand, variation in the response current value was exampled where the glucose concentration was set to be constant as 400 mg/dl and the temperature was set to be constant as 25° C. while the Hct value was set to be 25, 45 and 65 similarly to the above.

As represented in the left upper chart of FIG. 11, it was consequently found that the response current value varied in accordance with the magnitude of the Hct value even when the glucose concentration was constant in measuring the glucose concentration. Further, as represented in the left lower chart of FIG. 11, it was found that deviations of response current values corresponding to Hct values of 25 and 65 from a response current value corresponding to an Hct value of 45 were plus/minus 30% or greater in measuring the glucose concentration.

On the other hand, as represented in the right upper chart of FIG. 11, it was found that almost no difference was produced among response current values at three Hct values in a measured time period from 3.5 second to 5.0 second for temperature measurement in measuring the temperature of the blood sample and the Hct value. Further, as represented in the right lower chart of FIG. 11, deviations of response current values corresponding to Hct values of 25 and 65 from a response current value corresponding to an Hct value of 45 were inhibited to be roughly 2 to 3% in measuring the temperature of the blood sample and the Hct value.

Likewise, as represented in the left upper and lower charts of FIG. 12 where the glucose concentration was set to be 400 mg/dl, it was found that a deviation of plus/minus 30% or greater was produced in measuring the glucose concentration. On the other hand, as represented in the right upper and lower charts of FIG. 12, it was found that deviation was inhibited to be roughly several % in measuring the temperature and the Hct value.

In the present exemplary embodiment, it was found from the measured results of response current represented in FIGS. 11 and 12 that the response current value varied in response to increase and reduction in the Hct value even when the glucose concentration was constant in applying a voltage for measuring the glucose concentration. It was also found that the response current value could be obtained without being affected by increase and reduction in the Hct value when a voltage of 1.5 V, higher than that to be applied in measuring the glucose concentration, to the electrodes functioning as the temperature electrode unit.

Figure 13:
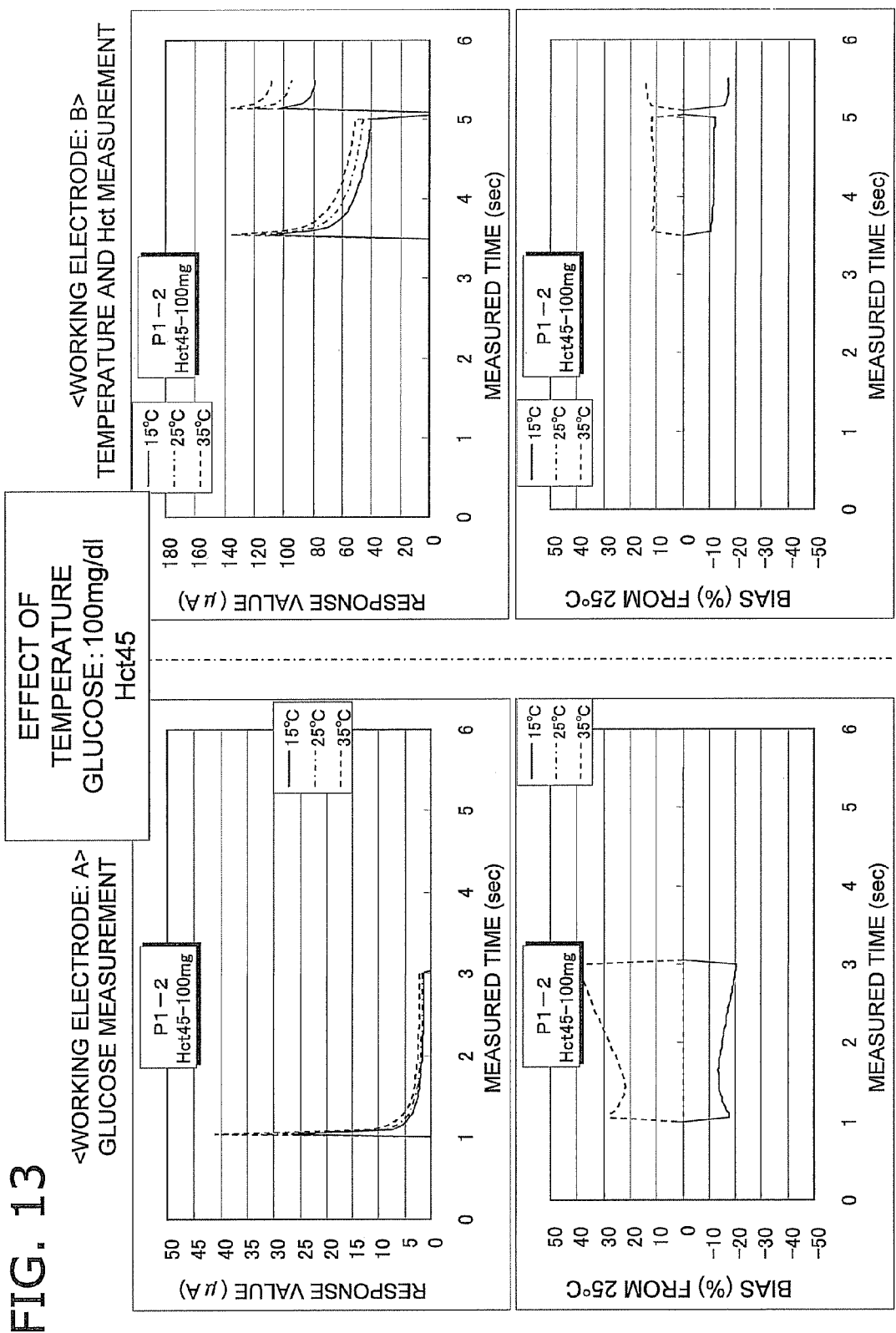
FIG. 13 includes charts representing the results of examining the effect of variation in a blood sample temperature on the response current value in the exemplary embodiment 1.
Figure 14:
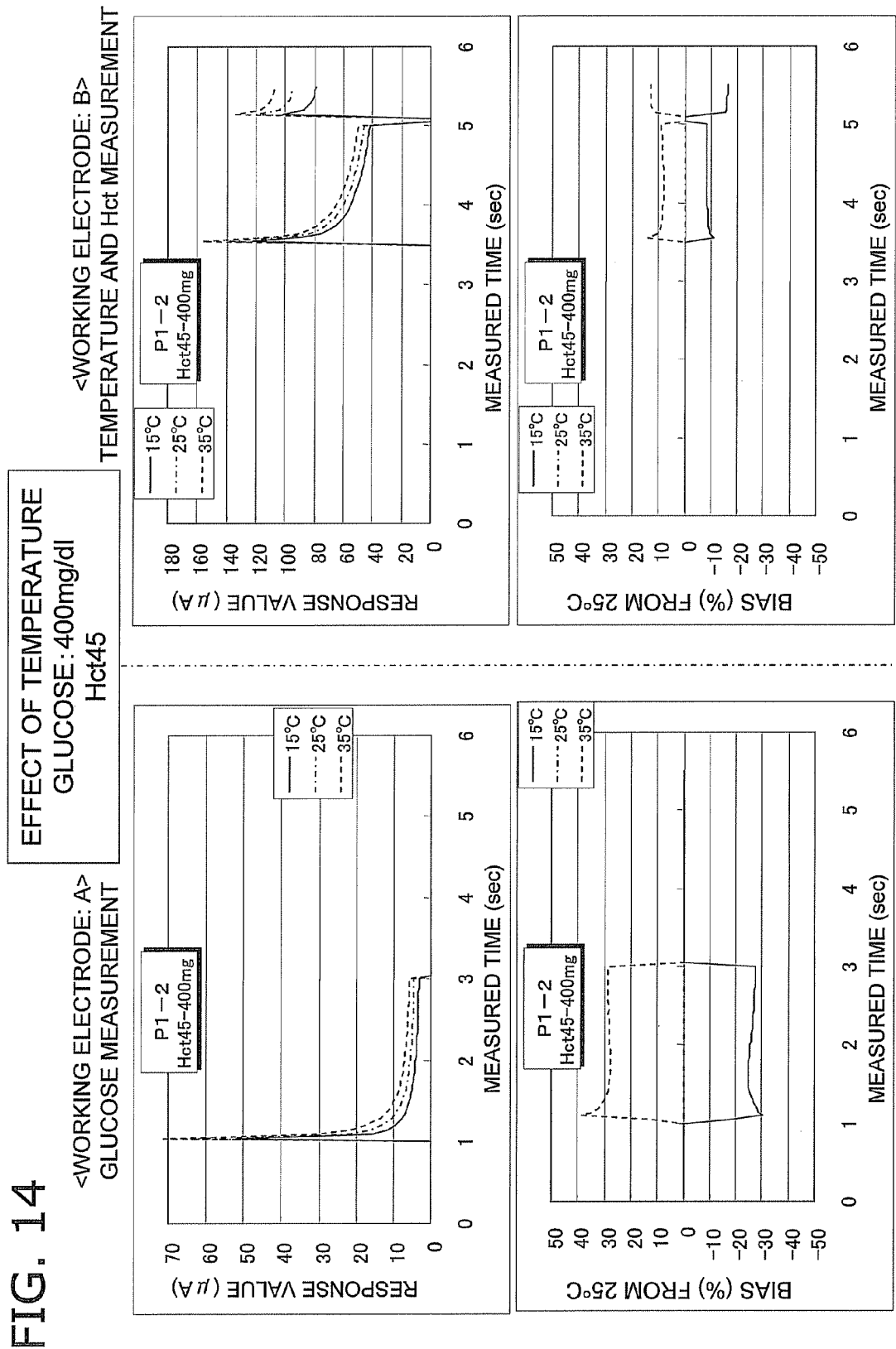
FIG. 14 includes charts representing the results of examining the effect of variation in the blood sample temperature on the response current value in the exemplary embodiment 1.

Next, FIGS. 13 and 14 represent the measured results of response current values in the respective electrodes where the glucose concentrations was set to be 100 mg/dl and 400 mg/dl while the Hct value was set to be constant as 45 for examining the effect of increase and reduction in the temperature on the detected current value.

Specifically in FIG. 13, variation in the response current value was examined where the glucose concentration was set to be constant as 100 mg/dl and the Hct value was set to be constant as 45 while the temperature was set to be 15° C., 25° C. and 35° C. In FIG. 14, on the other hand, variation in the response current value was examined where the glucose concentration was set to be constant as 40 mg/dl and the Hct value was set to be constant as 45 while the temperature was set to be 15° C., 25° C. and 35° C. similarly to the above.

As represented in the left upper chart of FIG. 13, it was consequently found that the response current value varied in accordance with the magnitude of the temperature even when the glucose concentration was constant in measuring the glucose concentration. Further, as represented in the left lower chart of FIG. 13, it was found that deviations of temperatures of 15° C. and 35° C. from a temperature of 25° C. fell in a range of roughly plus/minus 20% in measuring the glucose concentration.

On the other hand, as represented in the right upper chart of FIG. 13, it was found that differences were produced among response current values at three temperatures in a measured time period from 3.5 second to 5.0 second for temperature measurement in measuring the temperature and the Hct value. Further, as represented in the right lower chart of FIG. 13, it was found that deviations of temperatures of 15° C. and 35° C. from a temperature of 25° C. fell in a range of plus/minus 10% in measuring the temperature and the Hct value.

Likewise, as represented in the left upper and lower charts of FIG. 14 where the glucose concentration was set to be 400 mg/dl, it was found that a deviation of plus/minus 20% or greater was produced in measuring the glucose concentration. On the other hand, as represented in the right upper and lower charts of FIG. 14, it was found that deviation was produced in a range of roughly plus/minus 10% in measuring the temperature and the Hct value.

In the present exemplary embodiment, it was found from the measured results of response current represented in FIGS. 13 and 14 that the effect of increase and reduction in the temperature could be extracted as a response current value when a high voltage of 1.5 V was applied in measuring the temperature. Further, it was found that the response current value could be measured at a sensitivity of 1° C./1% in measuring the temperature.

FIG. 15 represents the measured results of response current values in the respective electrodes where the Hct value and the temperature were set to be constant for examining the effect of the glucose concentration.

Specifically in FIG. 15, variation in the response current value was examined where the constant Hct value was set to be constant as 45 and the temperature was set to be constant as 25° C. while the glucose concentrations was set to be 100 mg/dl and 400 mg/dl.

As represented in the left upper chart of FIG. 15, it was consequently found that a difference between glucose concentrations of 100 mg/dl and 400 mg/dl was detected as a response current value in measuring the glucose concentration. As represented in the lower left chart of FIG. 15, it was found that a glucose concentration of 400 mg/dl could be detected as a deviation of roughly plus 150 to 200% from a glucose concentration of 100 mg/dl.

Further, as represented in the right upper chart of FIG. 15, it was found that almost no difference was produced between response current values corresponding to two glucose concentrations in a measured period from 3.5 to 5.0 seconds for temperature measurement in measuring the temperature and the Hct value. Yet further, as represented in the right lower chart of FIG. 15, it was found that a deviation of a glucose concentration of 400 mg/dl from a glucose concentration of 100 mg/dl could be inhibited to roughly plus/minus several % in measuring the temperature and the Hct value.

In the present exemplary embodiment, it was found from the measured results of response current represented in FIG. 15 that the response current value could be detected for respective glucose concentration levels while being affected by increase and reduction in the glucose concentration. Further, it was found that the response current value could be extracted while being hardly affected by increase and reduction in the glucose concentration when a high voltage of 1.5 V was applied in measuring the temperature.

Figure 16:
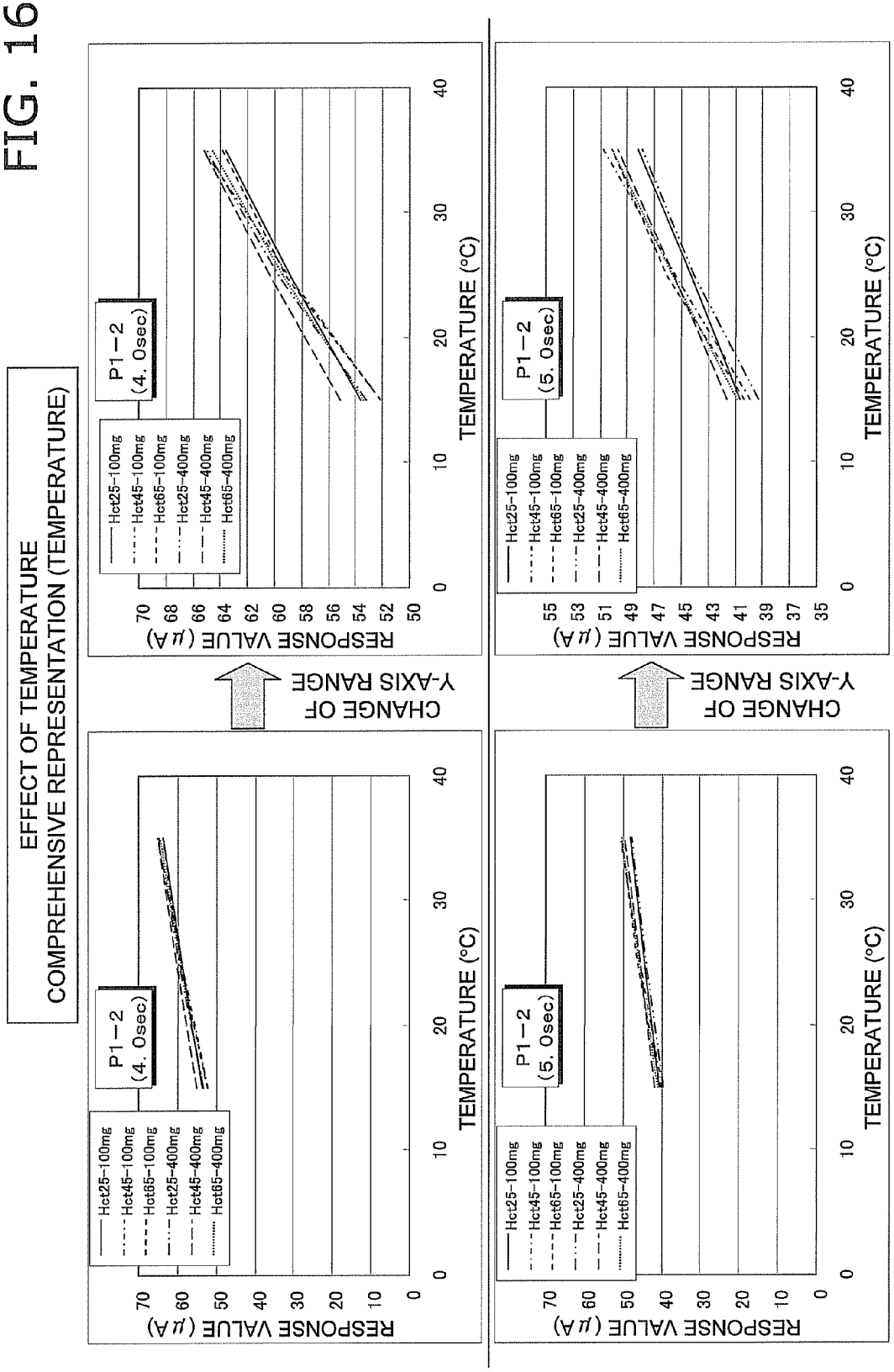
FIG. 16 includes charts representing a relation between variation in the blood sample temperature and variation in the response current value in the exemplary embodiment 1.

FIG. 16 comprehensively represents the measured results of response current values represented in FIGS. 11 to 14 and represents variation in the response current value (Axis Y) with respect to the temperature (Axis X) where the Hct value and the glucose concentration were changed.

Specifically, as represented in the upper charts of FIG. 16, it was found that the response current value roughly linearly varied in response to variation in the temperature at the timing of 4.0 second as a measured time point included in a voltage application time period from 3.5 second to 5.0 second for temperature measurement. Further, it was found that temperature could be measured in an accuracy range of roughly 24° C. to 27° C., for instance, when the response current value was 60 μA.

Further, as represented in the lower charts of FIG. 16, it was also found that the response current value roughly linearly varied in response to variation in the temperature at the timing of 5.0 second as a measured time point. Further, it was found that the temperature could be measured in an accuracy range of roughly 23° C. to 26° C. when the response current value was 45 μA.

It was found from the aforementioned measured results that the response current value, only depending on variation in the temperature, could be detected regardless of increase and reduction in the glucose concentration and increase and reduction in the Hct value by applying a predetermined voltage of roughly 1.5 V, which was higher than a voltage of 0.25 V to 0.5 V to be applied in measuring the glucose concentration, in measuring the temperature as configured in the present exemplary embodiment. Therefore, it was found that the sensor chip according to the present exemplary embodiment could be utilized as a high precision temperature sensor for directly measuring the temperature of the blood sample.

(Exemplary Embodiment 2)

Another exemplary embodiment of the present invention will be hereinafter explained with reference to FIGS. 17 and 18 and charts of FIGS. 19 and 88.

Simply put, in the present exemplary embodiment, the response current value was measured using the sensor chip having the electrode pattern illustrated in FIG. 17 in order to verify an appropriate range of voltage to be applied in the sensor chip of the present exemplary embodiment for measuring the temperature of the blood sample without the effects of increase and reduction in the glucose concentration and increase and reduction in the Hct value in the blood sample and the like.

Specifically, the sensor chip used in the present exemplary embodiment includes three electrodes A, B and C and has a size of 22.0 mm (as a longitudinal length)×10.50 mm (as a transverse length). The electrodes A and B are overlapped under the condition that the overlapped portion of the electrode A has a transverse length of 0.5 mm and the overlapped portion of the electrode B has a circular shape with a diameter of 2.0 mm Further, a capillary section with a size of 3.50 mm (as a longitudinal length)×1.00 mm (as a transverse length) is formed to be opposed to and overlapped with the electrodes A and B. Yet further, a Pb substrate for disposing the electrodes A, B and C thereon has a thickness of 188 μm. A spacer has a thickness of 100 μm. An upper cover has a thickness of 100 μm. The capillary section has a volume of 0.35 μL.

Figure 18:
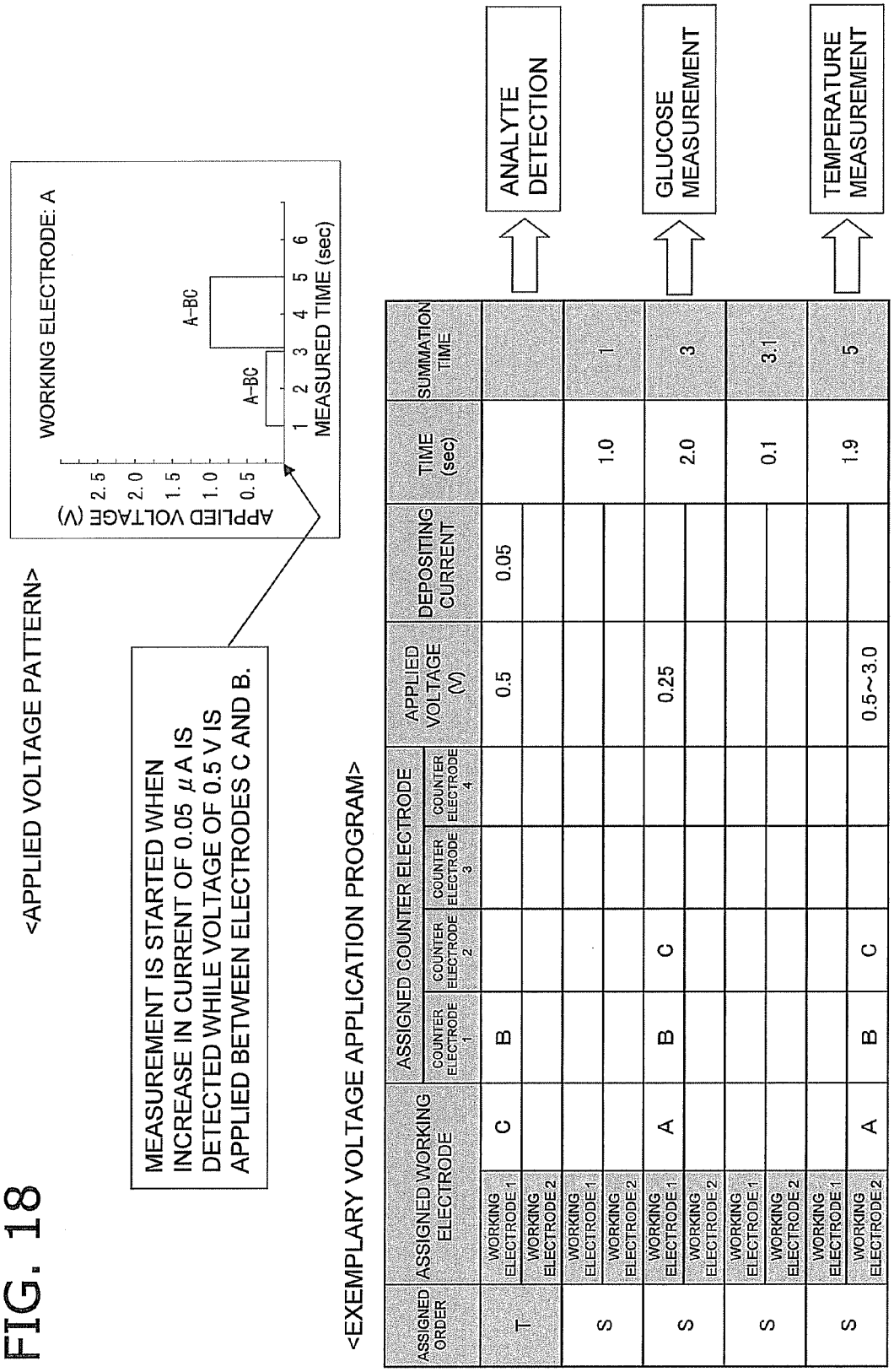
FIG. 18 includes explanatory diagrams representing an exemplary pattern of applying a voltage to the sensor chip illustrated in FIG. 17 in an exemplary embodiment 2.

Next, as represented in FIG. 18, the magnitude and the application time period of a voltage to be applied to the electrodes A, B and C were set as follows. Firstly, a voltage of 0.25 V was applied between the electrode A and the electrodes B and C for about two seconds in a measured time period from 1.0 second to 3.0 second in order to measure the glucose concentration. Subsequently, a voltage varying from 0.5 V to 3.0 V was applied between the electrode A and the electrodes B and C for about 1.9 seconds in a measured time period from 3.1 second to 5.0 second in order to measure the temperature. It should be noted that the measurement was started at the timing when increase in an electricity of 0.05 μA was detected during application of a voltage of 0.5 V between the electrode C and the electrode B.

The following explanation relates to the results of examining the effects of increase and reduction in the glucose concentration and increase and reduction in the Hct value on the temperature measurement when the applied voltage was changed from 0.5 V to 3.0 V.

<Applied Voltage of 0.5 V>

Measurements were herein executed for examining the effects of variation in the temperature (10° C., 25° C. and 40° C.) of the blood sample, variation in the Hct value (25, 45 and 65) and variation in the glucose concentration (100 mg/dl, 400 mg/dl) on the response current value when a voltage to be applied between the electrode A and the electrodes B and C was set to be 0.5 V.

Figure 19:
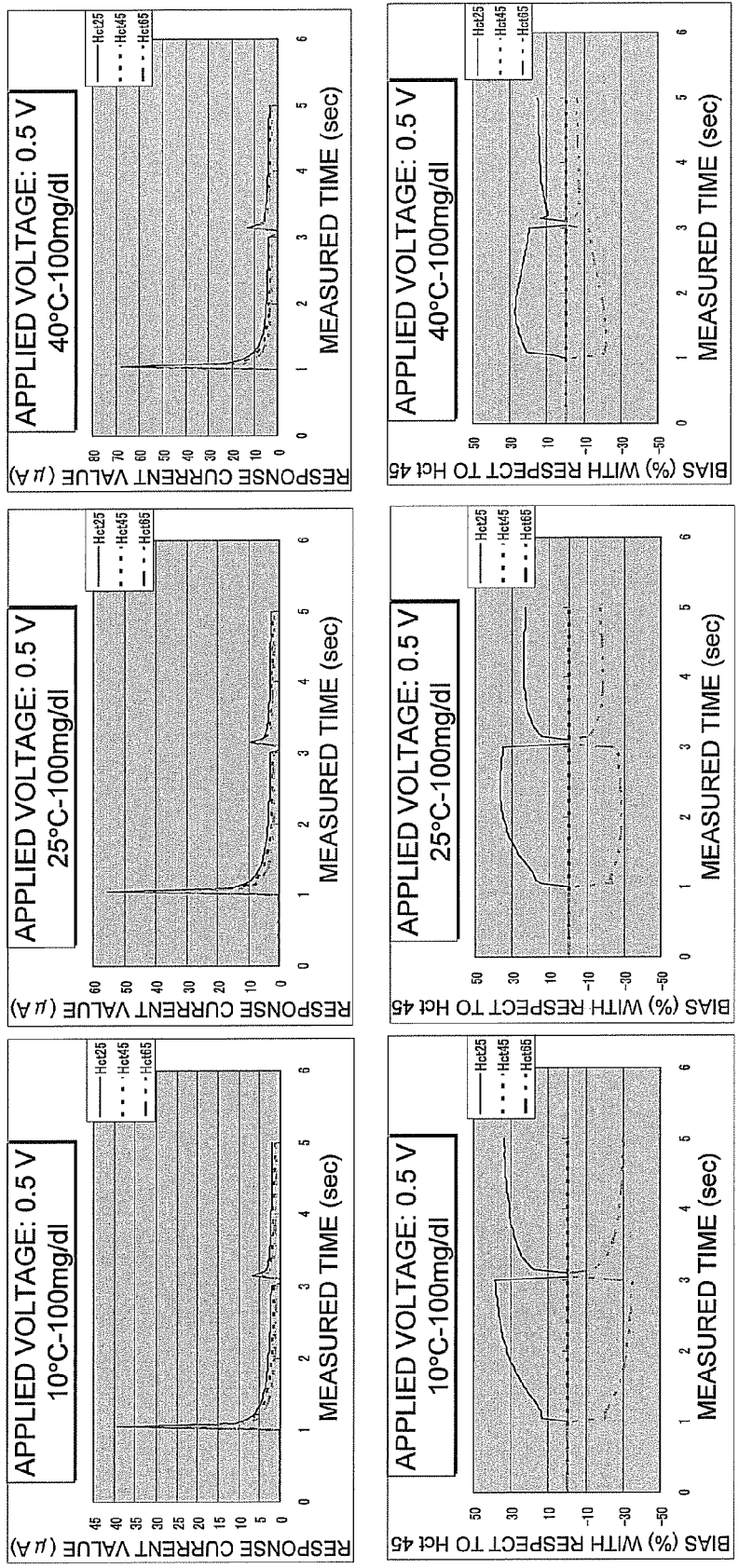
FIG. 19 includes charts representing the results of examining the effect of variation in the temperature and variation in the Hct value on the response current value in applying a voltage of 0.5 V in the exemplary embodiment 2.

In FIG. 19, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 19, each of the lower charts represents deviations of response current values corresponding to Hct values of 25 and 65 from a response current value corresponding to an Hct value of 45 in a corresponding one of the upper charts represented above the lower charts.

As represented in the charts of FIG. 19, it was consequently found that the response current value widely varied due to increase and reduction in the Hct value at the respective blood sample temperatures of 10° C., 25° C. and 40° C. in both measuring the glucose concentration and measuring the temperature.

Figure 20:
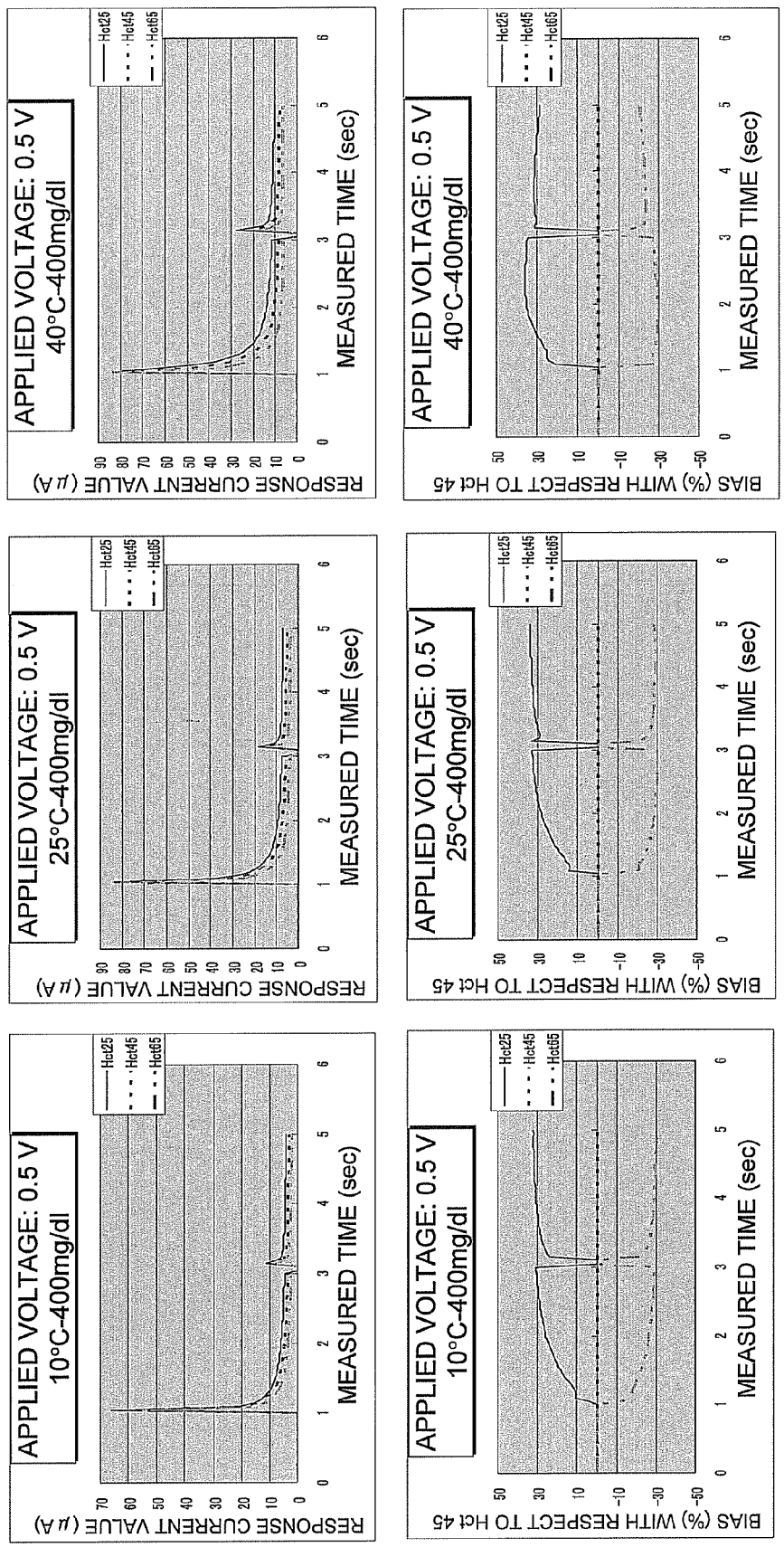
FIG. 20 includes charts representing the results of examining the effect of variation in the temperature and variation in the Hct value on the response current value in applying a voltage of 0.5 V in the exemplary embodiment 2.

FIG. 20 represents the measured results when the glucose concentration in FIG. 19 was changed from 100 mg/dl to 400 mg/dl.

Similarly to the aforementioned results, it was also found that the response current value widely varied due to increase and reduction in the Hct value at the respective blood sample temperatures of 10° C., 25° C. and 40° C. in both measuring the glucose concentration and measuring the temperature.

Figure 21:
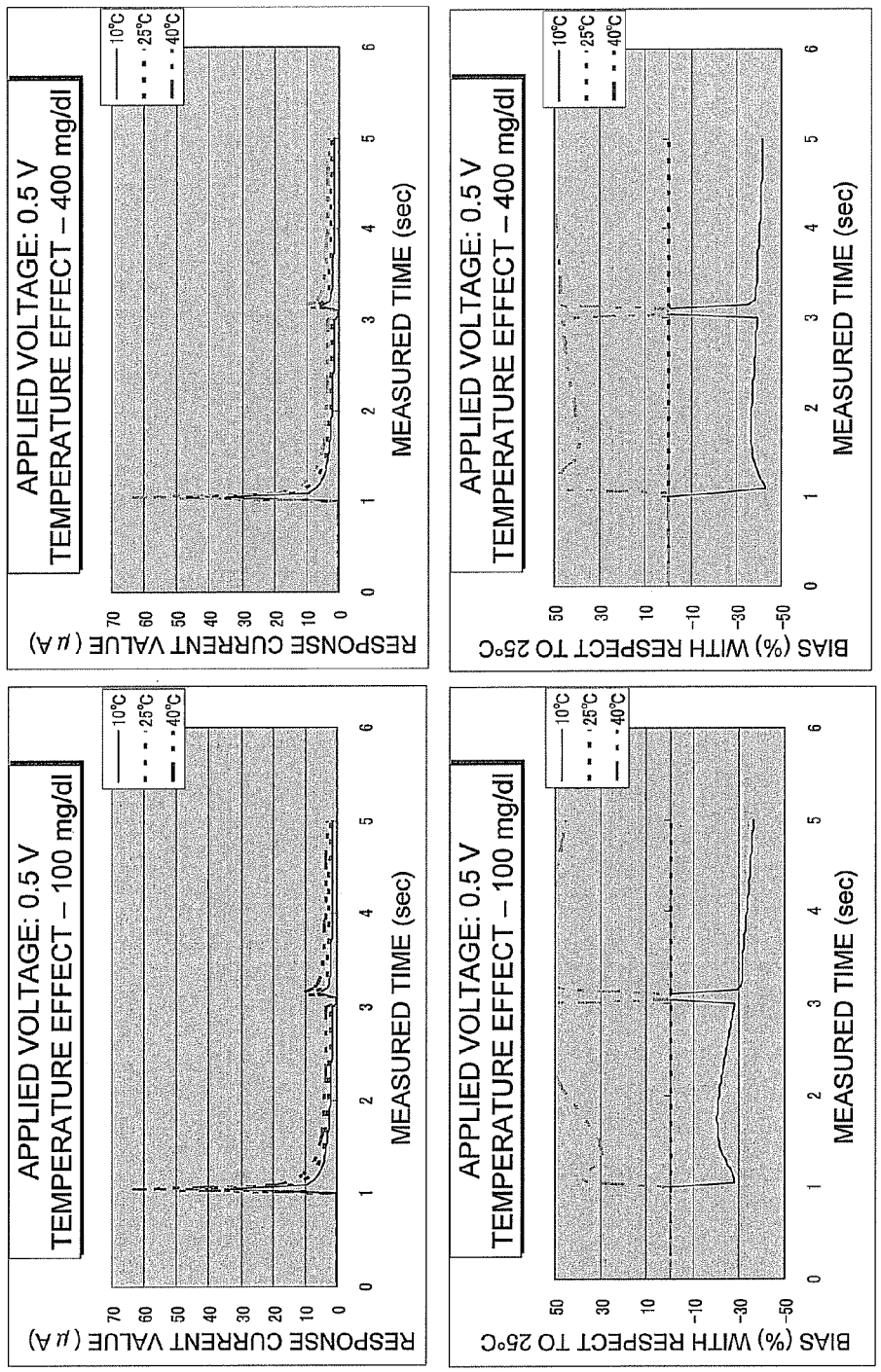
FIG. 21 includes charts representing a comprehensive result of examining the effect of variation in the temperature on the response current value in applying a voltage of 0.5 V in the exemplary embodiment 2.

FIG. 21 represents the measured results when the temperature conditions (10° C., 25° C. and 40° C.) were changed within each chart for easily understanding the effect of the blood sample temperature. It should be noted that the left upper and lower charts of FIG. 21 represent the measured results of response current values when the glucose concentration was set to be 100 mg/dl, whereas the right upper and lower charts of FIG. 21 represent the measured results of response current values when the glucose concentration was set to be 400 mg/dl.

It was consequently found that the response current value widely varied at both glucose concentrations of 100 mg/dl and 400 mg/dl in both measuring the temperature and measuring the glucose concentration when the blood sample temperature was changed.

Figure 22:
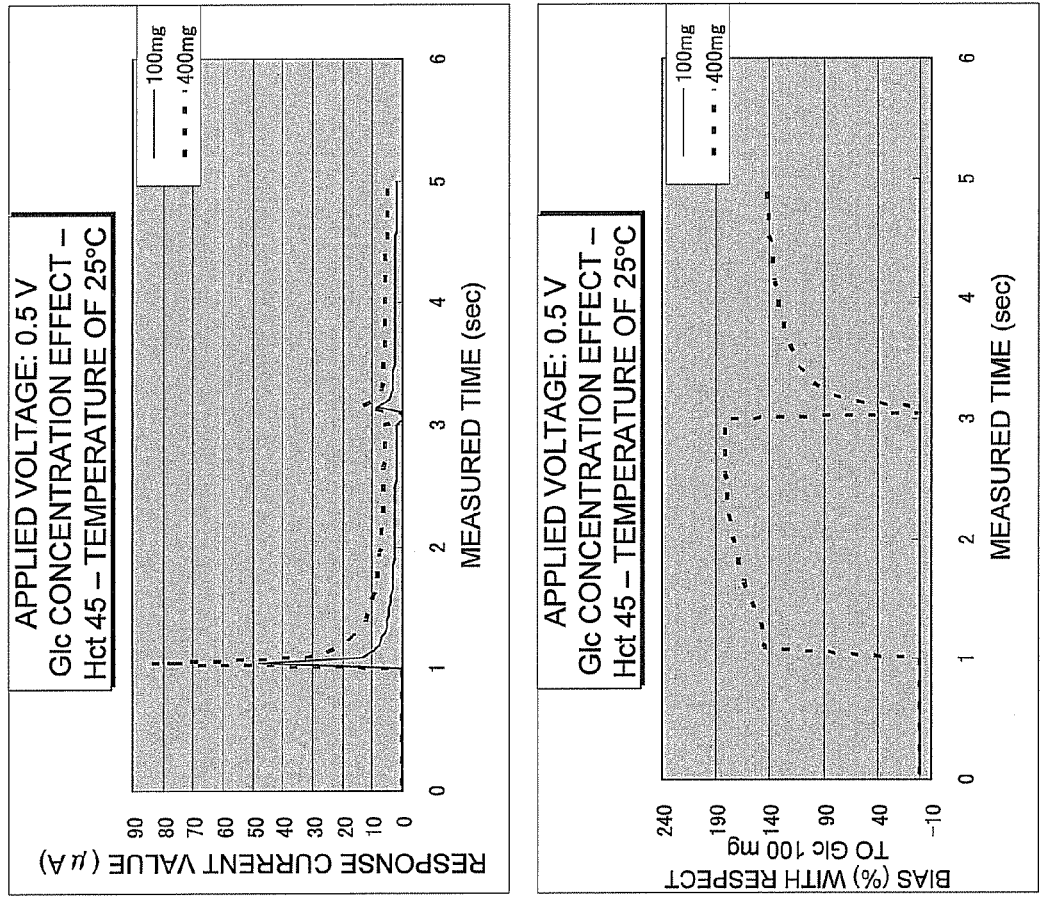
FIG. 22 includes charts representing a comprehensive result of examining the effect of variation in the glucose concentration on the response current value in applying a voltage of 0.5 V in the exemplary embodiment 2.

FIG. 22 represents the measured results when the glucose concentration was changed and set to be 100 mg/dl and 400 mg/dl in each chart for easily understanding the effect of the glucose concentration. It should be noted that the upper chart of FIG. 22 represents the measured results of response current values when the glucose concentration was set to be 100 mg/dl and 400 mg/dl, whereas the lower chart of FIG. 22 represents a deviation between response current values corresponding to glucose concentrations of 100 mg/dl and 400 mg/dl.

It was consequently found that the response current value widely varied in both measuring the glucose concentration and measuring the temperature when the glucose concentration was changed and set to be 100 mg/dl and 400 mg/dl.

It was found from the aforementioned results that the response current value was affected by variation in the glucose concentration, variation in the Hct value and variation in the temperature when the response current value was measured by applying a voltage of 0.5 V between the electrode A and the electrodes B and C and it was thereby impossible to extract only the effect of variation in the temperature.

<Applied Voltage of 0.7 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 0.7 V.

Figure 23:
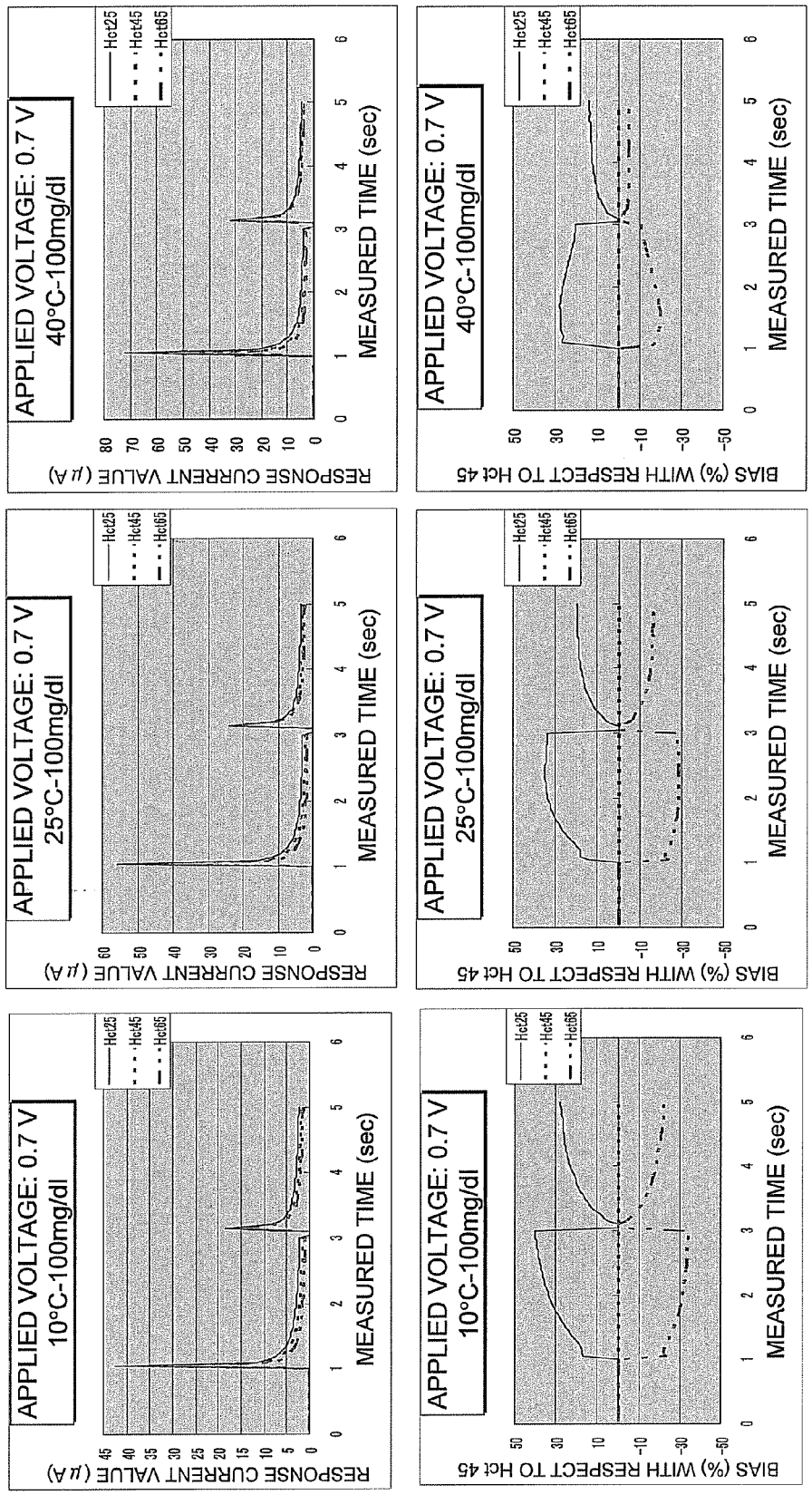
FIG. 23 includes charts representing the results of examining the effect of variation in the temperature and variation in the Hct value on the response current value in applying a voltage of 0.7 V in the exemplary embodiment 2.

In FIG. 23, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 23, each of the lower charts represents deviations of response current values corresponding to Hct values of 25 and 65 from a response current value corresponding to an Hct value of 45 in a corresponding one of the upper charts represented above the lower charts.

As represented in the charts of FIG. 23, it was consequently found that the response current value widely varied due to increase and reduction in the Hct value at the respective blood sample temperatures of 10° C., 25° C. and 40° C. in both measuring the glucose concentration and measuring the temperature.

Figure 24:
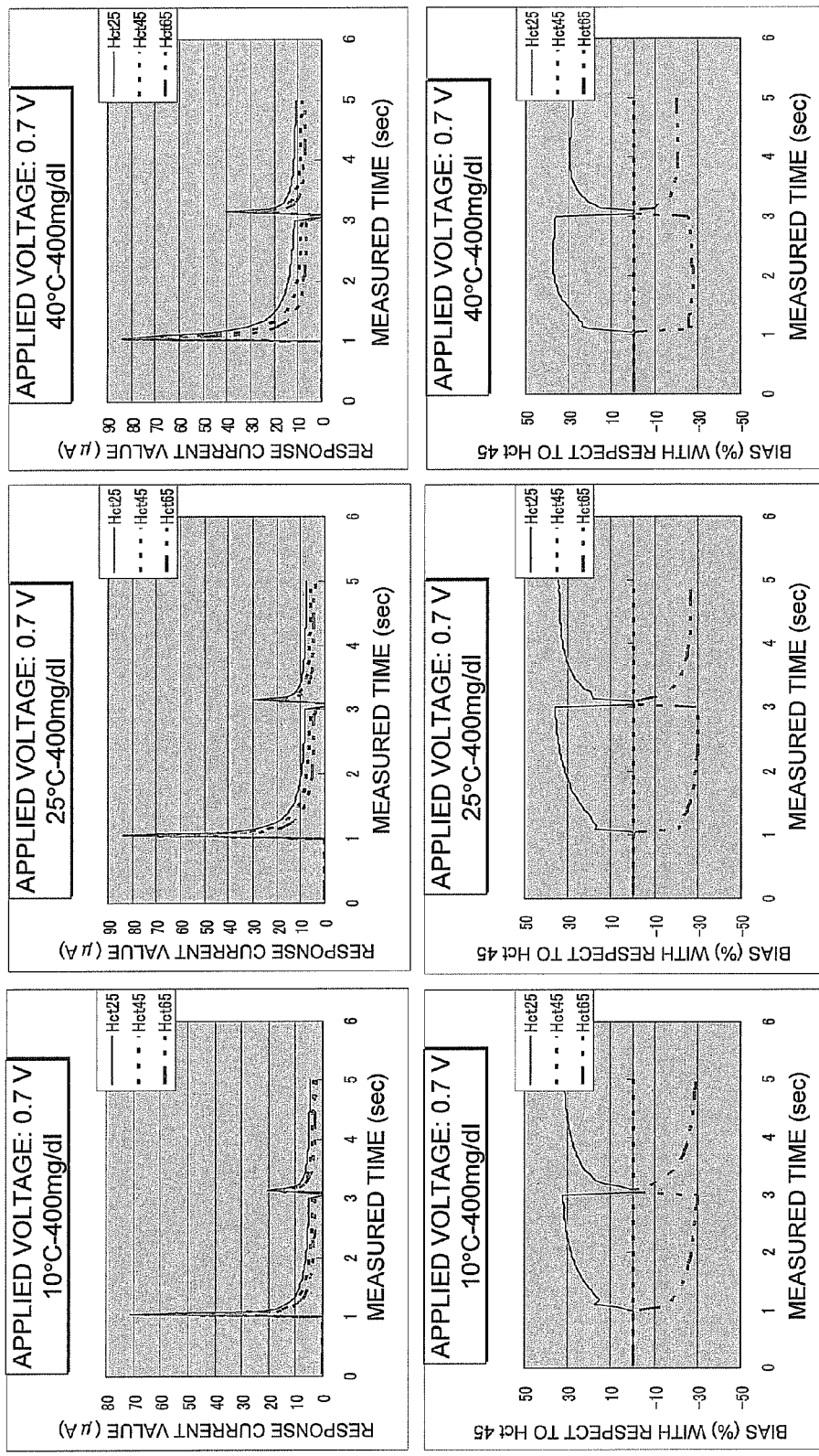
FIG. 24 includes charts representing the results of examining the effect of variation in the temperature and variation in the Hct value on the response current value in applying a voltage of 0.7 V in the exemplary embodiment 2.

FIG. 24 represents the measured results when the glucose concentration in FIG. 23 was changed from 100 mg/dl to 400 mg/dl.

Similarly to the aforementioned results, it was also found that the response current value widely varied due to increase and reduction in the Hct value at the respective blood sample temperatures of 10° C., 25° C. and 40° C. in both measuring the glucose concentration and measuring the temperature.

Figure 25:
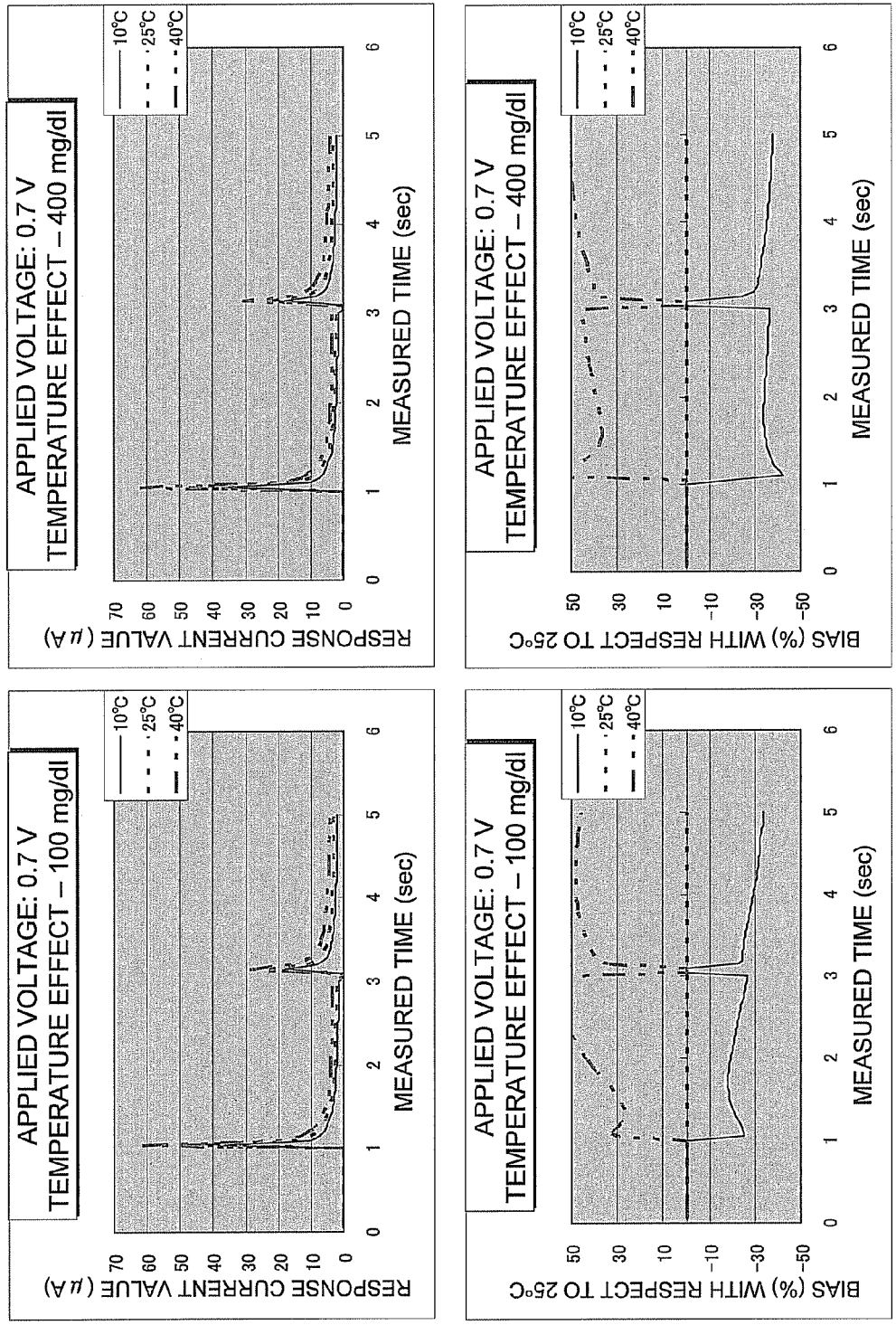
FIG. 25 includes charts representing a comprehensive result of examining the effect of variation in the temperature on the response current value in applying a voltage of 0.7 V in the exemplary embodiment 2.

FIG. 25 represents the measured results when the temperature conditions (10° C., 25° C. and 40° C.) were changed within each chart for easily understanding the effect of the blood sample temperature. It should be noted that the left upper and lower charts of FIG. 25 represent the measured results of response current values when the glucose concentration was set to be 100 mg/dl, whereas the right upper and lower charts of FIG. 25 represent the measured results of response current values when the glucose concentration was set to be 400 mg/dl.

It was consequently found that the response current value widely varied at both glucose concentrations of 100 mg/dl and 400 mg/dl in both measuring the temperature and measuring the glucose concentration when the blood sample temperature was changed.

Figure 26:
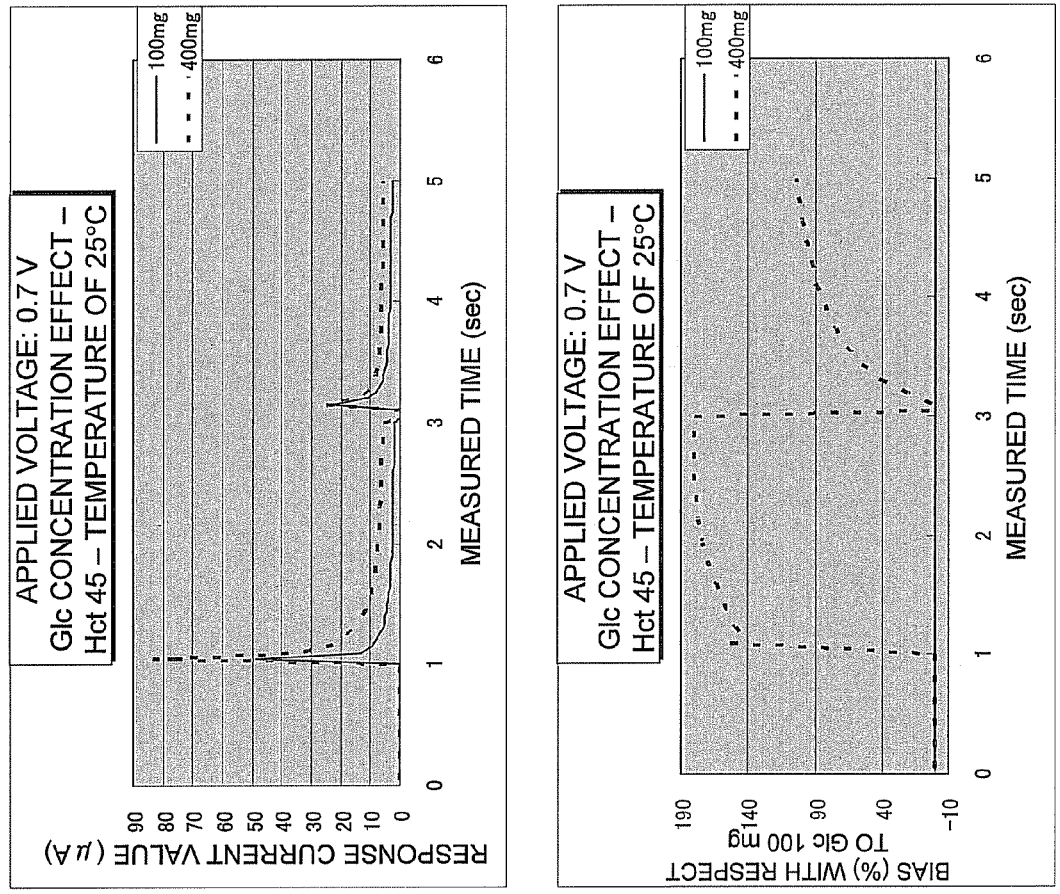
FIG. 26 includes charts representing a comprehensive result of examining the effect of variation in the glucose concentration on the response current value in applying a voltage of 0.7 V in the exemplary embodiment 2.

FIG. 26 represents the measured results when the glucose concentration was changed and set to be 100 mg/dl and 400 mg/dl in each chart for easily understanding the effect of the glucose concentration. It should be noted that the upper chart of FIG. 26 represents the measured results of response current values when the glucose concentration was set to be 100 mg/dl and 400 mg/dl, whereas the lower chart of FIG. 26 represents a deviation between response current values corresponding to glucose concentrations of 100 mg/dl and 400 mg/dl.

It was consequently found that the response current value widely varied in both measuring the glucose concentration and measuring the temperature when the glucose concentration was changed and set to be 100 mg/dl and 400 mg/dl.

It was found from the aforementioned results that the response current value was affected by variation in the glucose concentration, variation in the Hct value and variation in the temperature when the response current value was measured by applying a voltage of 0.7 V between the electrode A and the electrodes B and C and it was thereby impossible to extract only the effect of variation in the temperature.

<Applied Voltage of 0.8 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 0.8 V.

Figure 27:
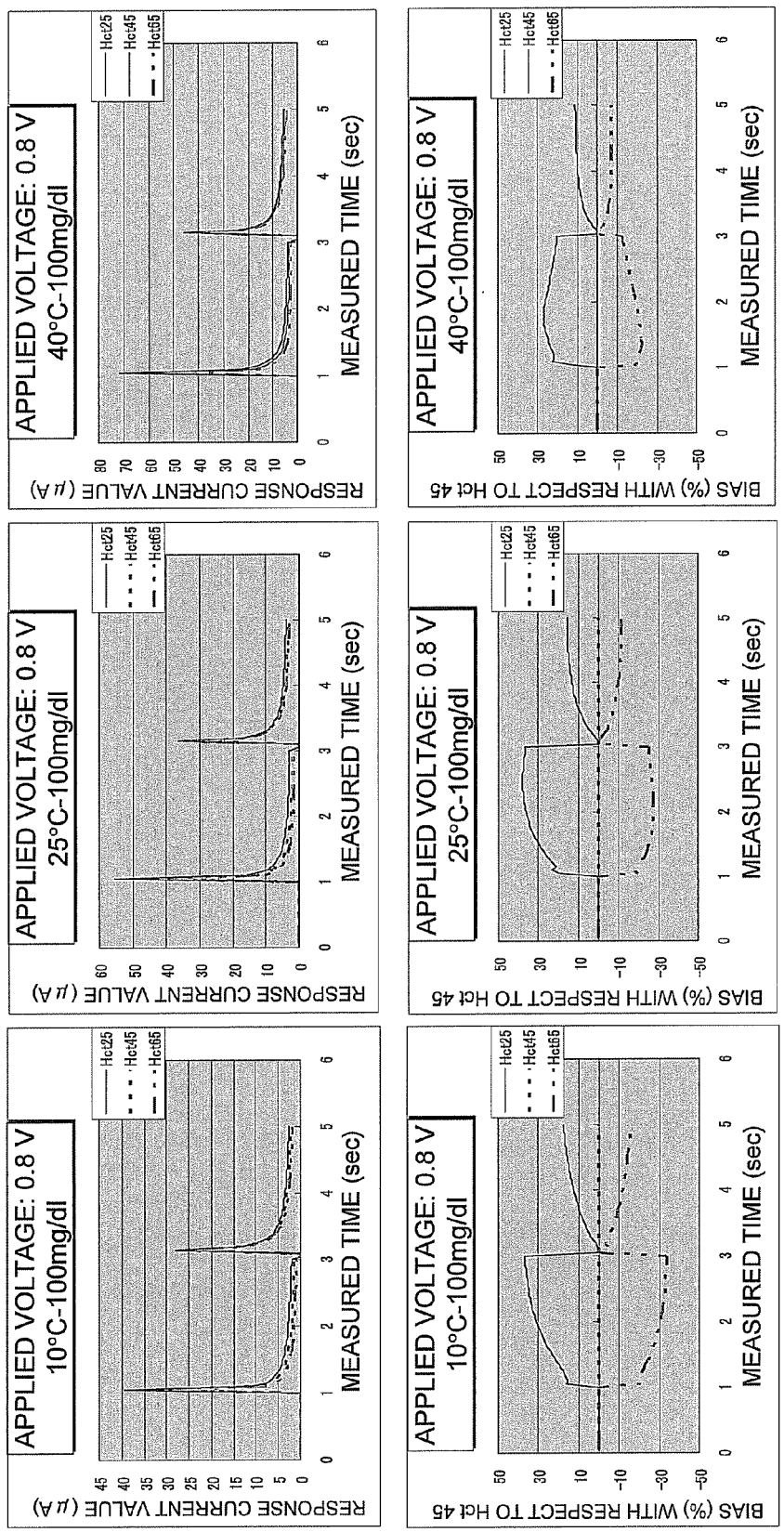
FIG. 27 includes charts representing the results of examining the effect of variation in the temperature and variation in the Hct value on the response current value in applying a voltage of 0.8 V in the exemplary embodiment 2.

In FIG. 27, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 27, each of the lower charts represents deviations of response current values corresponding to Hct values of 25 and 65 from a response current value corresponding to an Hct value of 45 in a corresponding one of the upper charts represented above the lower charts.

As represented in the charts of FIG. 27, it was consequently found that the response current value widely varied due to increase and reduction in the Hct value at the respective blood sample temperatures of 10° C., 25° C. and 40° C. in both measuring the glucose concentration and measuring the temperature.

Figure 28:
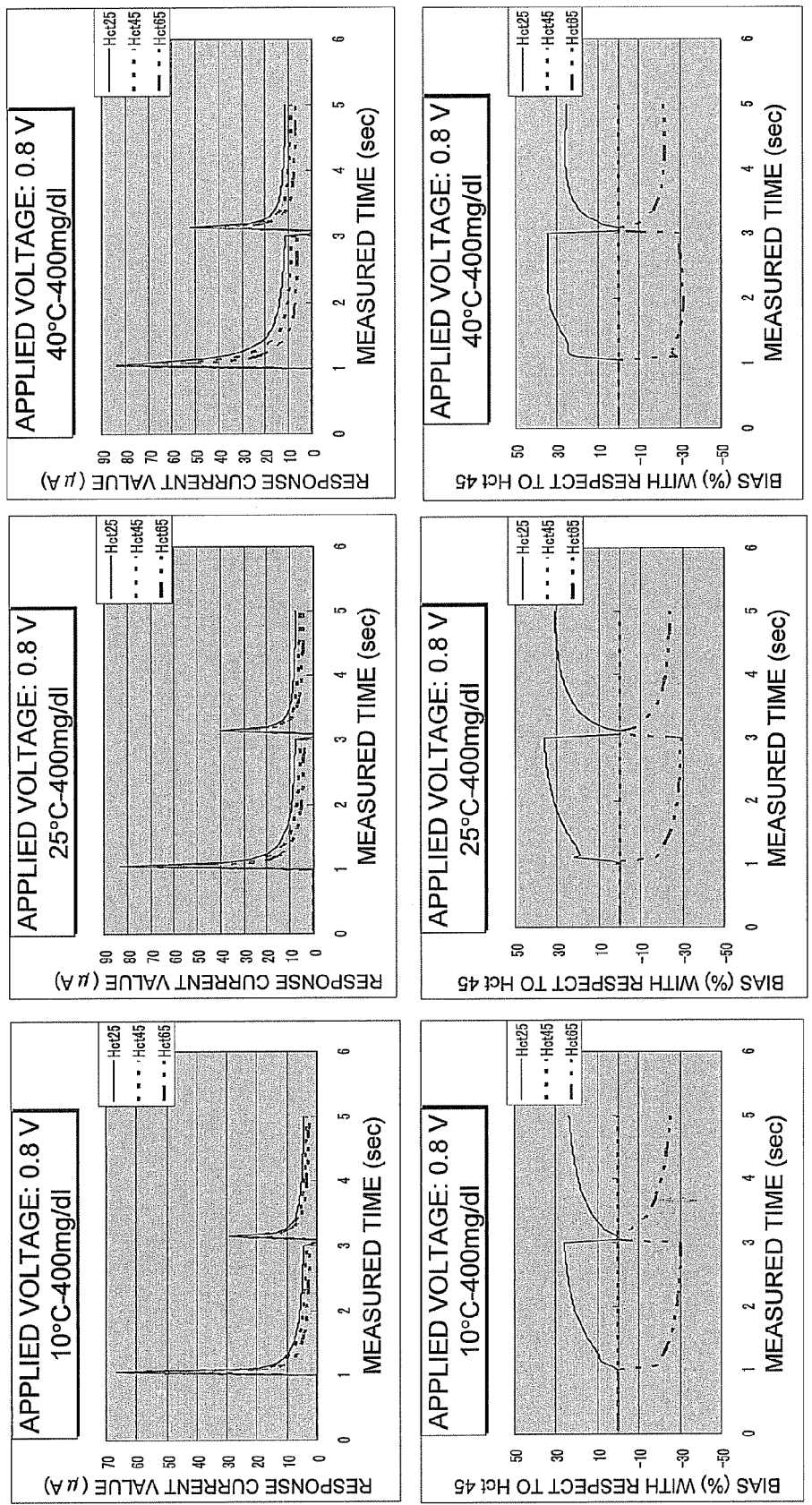
FIG. 28 includes charts representing the results of examining the effect of variation in the temperature and variation in the Hct value on the response current value in applying a voltage of 0.8 V in the exemplary embodiment 2.

FIG. 28 represents the measured results when the glucose concentration in FIG. 27 was changed from 100 mg/dl to 400 mg/dl.

Similarly to the aforementioned results, it was also found that the response current value widely varied due to increase and reduction in the Hct value at the respective blood sample temperatures of 10° C., 25° C. and 40° C. in both measuring the glucose concentration and measuring the temperature.

Figure 29:
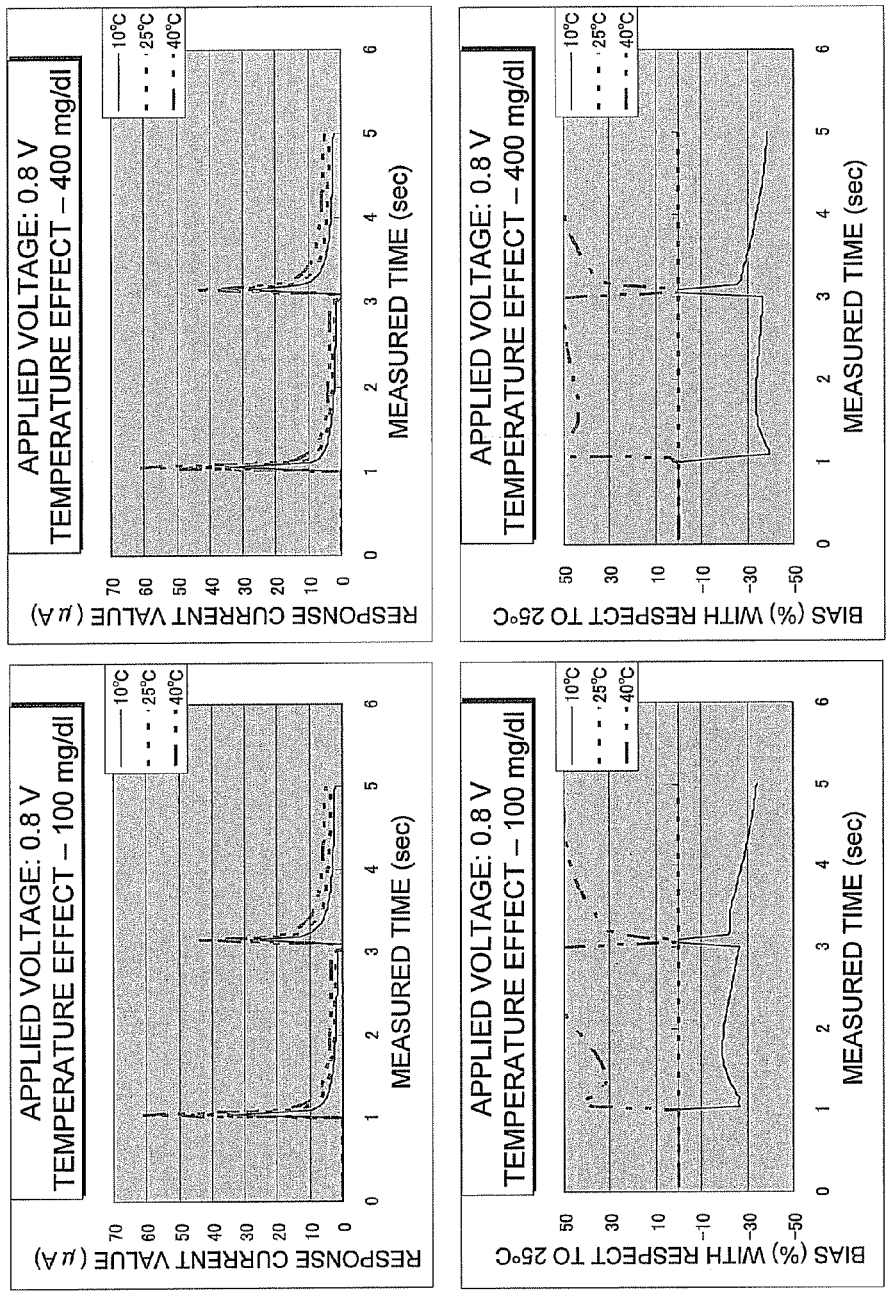
FIG. 29 includes charts representing a comprehensive result of examining the effect of variation in the temperature on the response current value in applying a voltage of 0.8 V in the exemplary embodiment 2.

FIG. 29 represents the measured results when the temperature conditions (10° C., 25° C. and 40° C.) were changed within each chart for easily understanding the effect of the blood sample temperature. It should be noted that the left upper and lower charts of FIG. 29 represent the measured results of response current values when the glucose concentration was set to be 100 mg/dl, whereas the right upper and lower charts of FIG. 29 represent the measured results of response current values when the glucose concentration was set to be 400 mg/dl.

It was consequently found that the response current value widely varied at both glucose concentrations of 100 mg/dl and 400 mg/dl in both measuring the temperature and measuring the glucose concentration when the blood sample temperature was changed.

Figure 30:
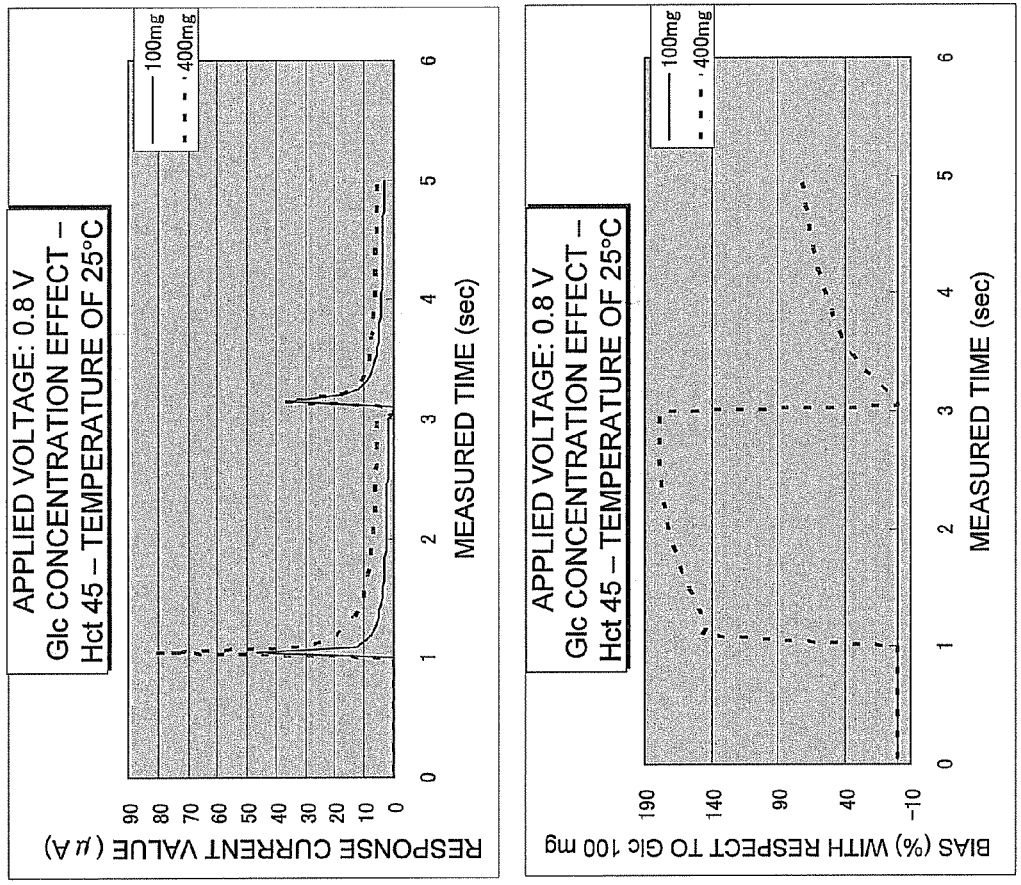
FIG. 30 includes charts representing a comprehensive result of examining the effect of variation in the glucose concentration on the response current value in applying a voltage of 0.8 V in the exemplary embodiment 2.

FIG. 30 represents the measured results when the glucose concentration was changed and set to be 100 mg/dl and 400 mg/dl in each chart for easily understanding the effect of the glucose concentration. It should be noted that the upper chart of FIG. 30 represents the measured results of response current values when the glucose concentration was set to be 100 mg/dl and 400 mg/dl, whereas the lower chart of FIG. 30 represents a deviation between response current values corresponding to glucose concentrations of 100 mg/dl and 400 mg/dl.

It was consequently found that the response current value widely varied in both measuring the glucose concentration and measuring the temperature when the glucose concentration was changed and set to be 100 mg/dl and 400 mg/dl.

It was found from the aforementioned results that the response current value was affected by variation in the glucose concentration, variation in the Hct value and variation in the temperature when the response current value was measured by applying a voltage of 0.8 V between the electrode A and the electrodes B and C and it was thereby impossible to extract only the effect of variation in the temperature.

<Applied Voltage of 0.9 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 0.9 V.

Figure 31:
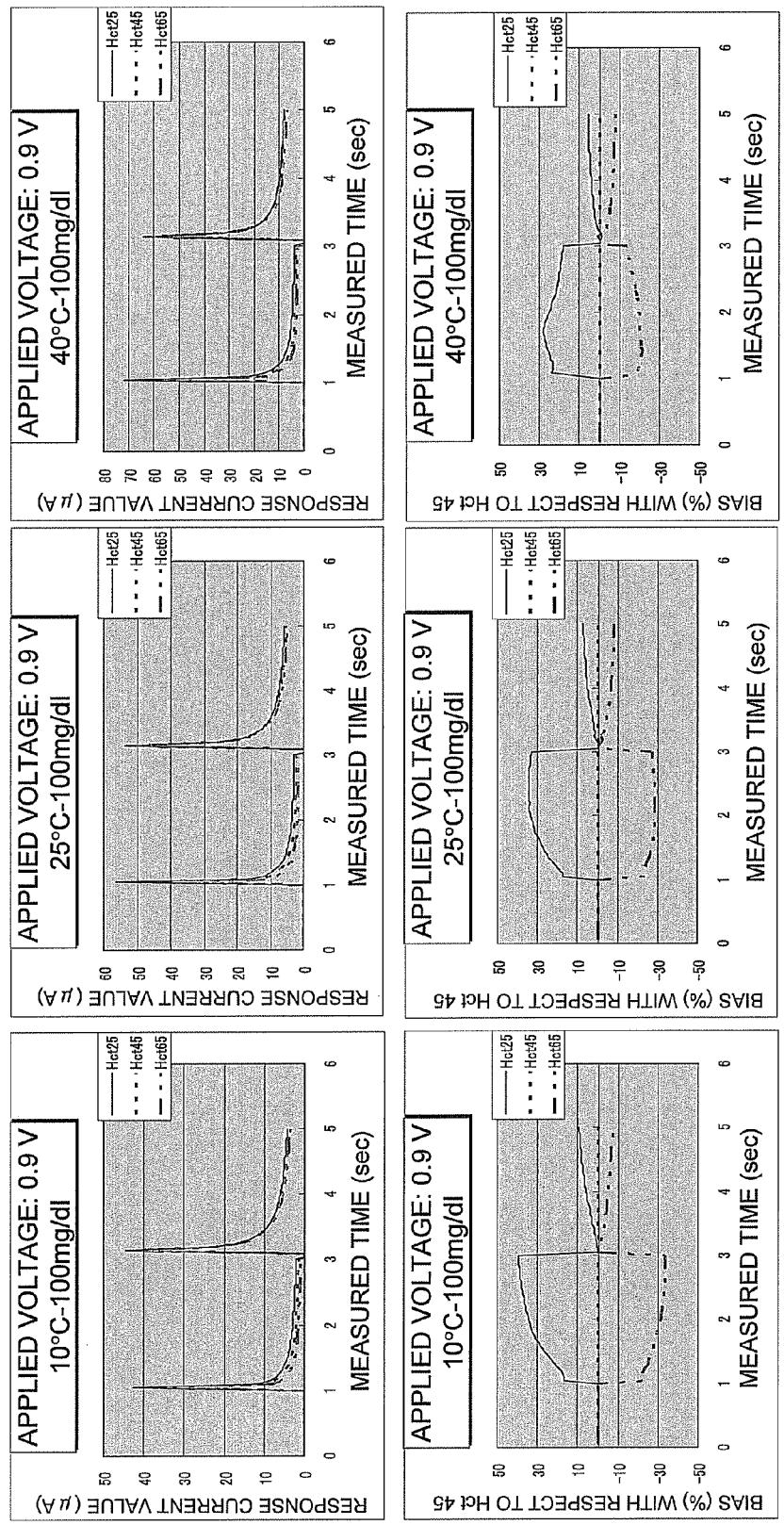
FIG. 31 includes charts representing the results of examining the effect of variation in the temperature and variation in the Hct value on the response current value in applying a voltage of 0.9 V in the exemplary embodiment 2.

In FIG. 31, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 31, each of the lower charts represents deviations of response current values corresponding to Hct values of 25 and 65 from a response current value corresponding to an Hct value of 45 in a corresponding one of the upper charts represented above the lower charts.

As represented in the charts of FIG. 31, it was consequently found that the response current value widely varied due to increase and reduction in the Hct value at the respective blood sample temperatures of 10° C., 25° C. and 40° C. in measuring the glucose concentration. On the other hand, it was found that deviations among response current values were still produced in a range of roughly plus/minus 10% in measuring the temperature even though the response current value was less affected by increase and reduction in the Hct value compared to the aforementioned results of applied voltages of 0.5 V to 0.8 V.

Figure 32:
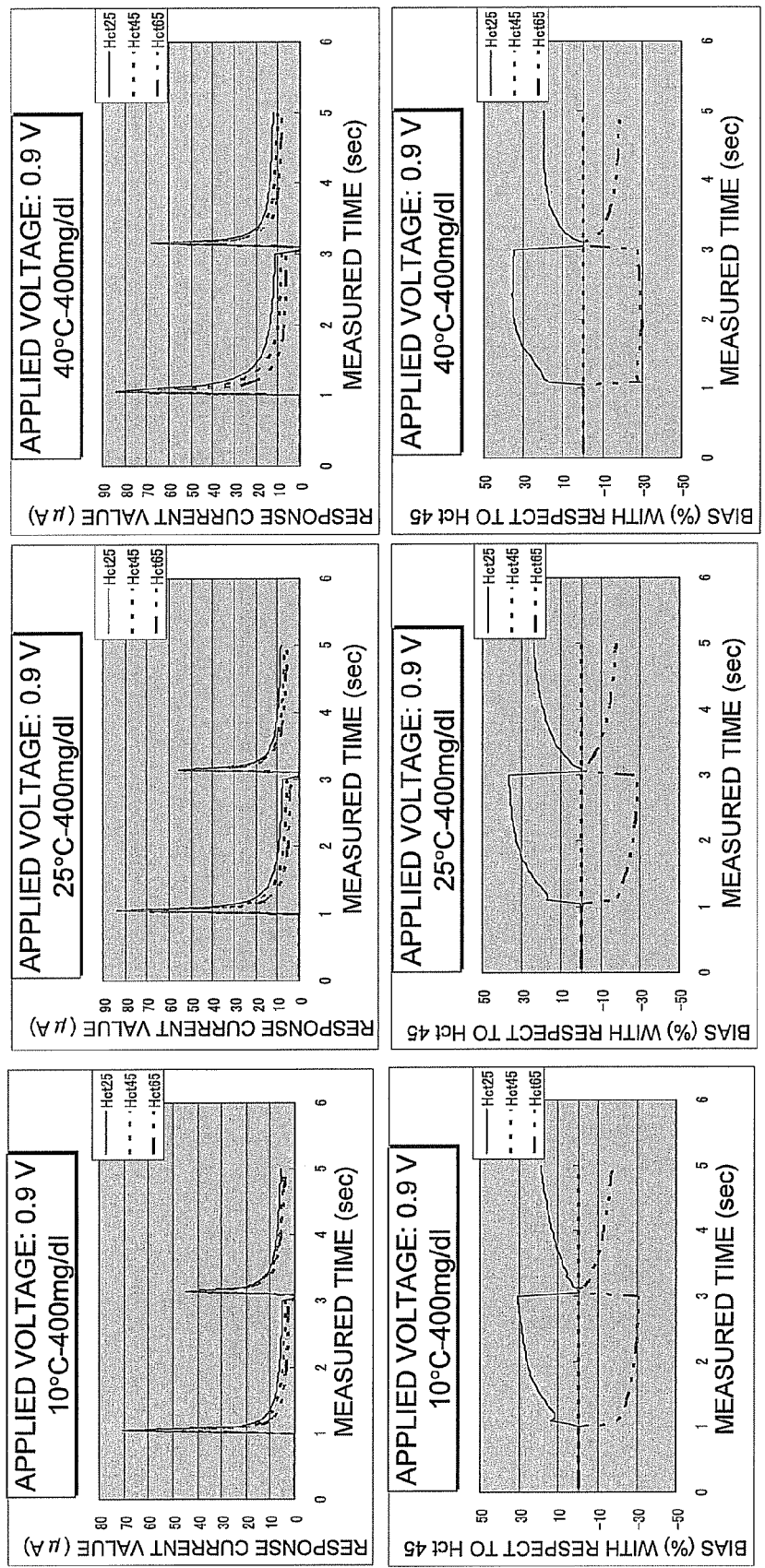
FIG. 32 includes charts representing the results of examining the effect of variation in the temperature and variation in the Hct value on the response current value in applying a voltage of 0.9 V in the exemplary embodiment 2.

FIG. 32 represents the measured results when the glucose concentration in FIG. 31 was changed from 100 mg/dl to 400 mg/dl.

Similarly to the aforementioned results, it was also found that the response current value widely varied due to increase and reduction in the Hct value at the respective blood sample temperatures of 10° C., 25° C. and 40° C. in both measuring the glucose concentration and measuring the temperature.

Figure 33:
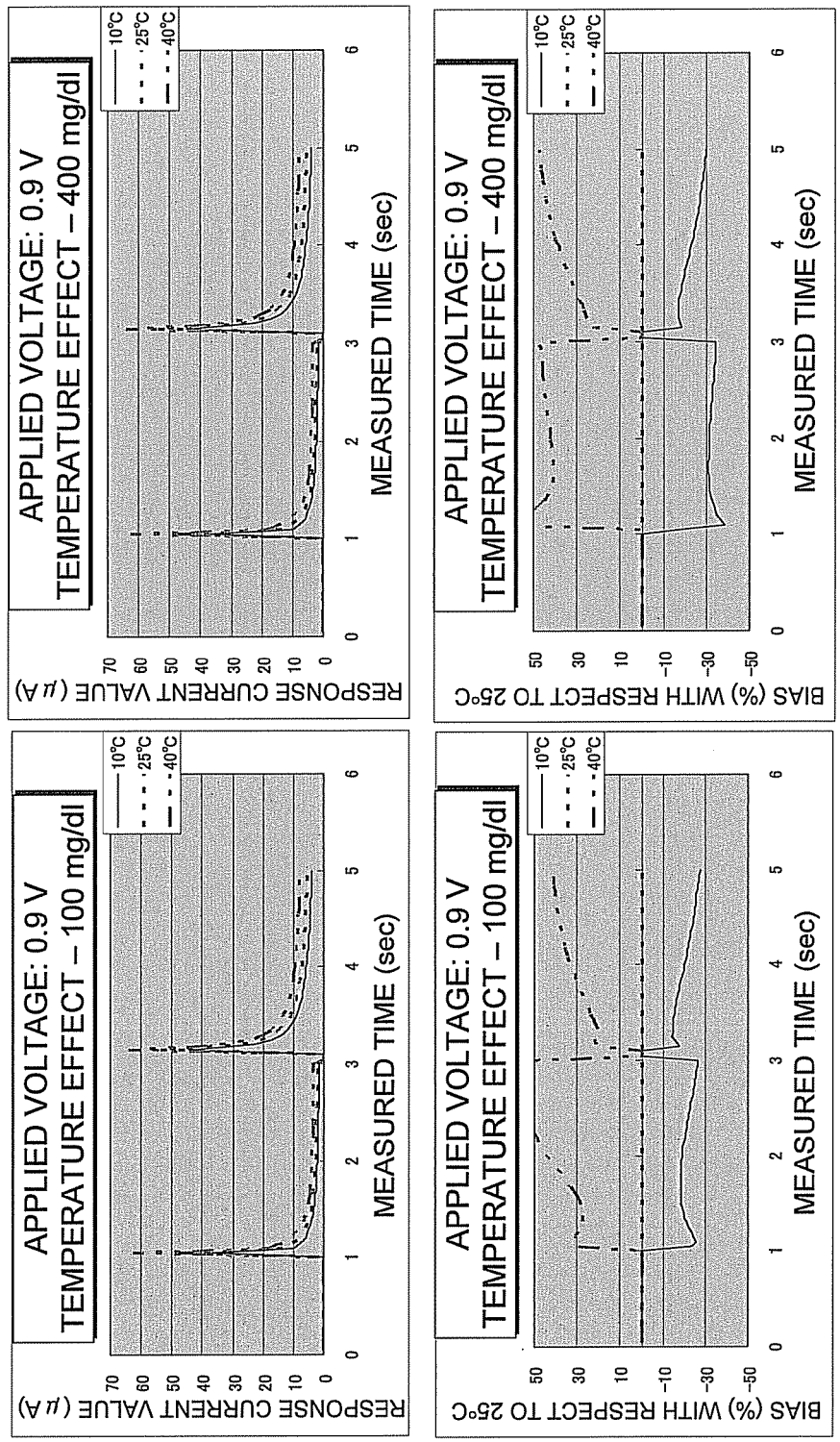
FIG. 33 includes charts representing a comprehensive result of examining the effect of variation in the temperature on the response current value in applying a voltage of 0.9 V in the exemplary embodiment 2.

FIG. 33 represents the measured results when the temperature conditions (10° C., 25° C. and 40° C.) were changed within each chart for easily understanding the effect of the blood sample temperature. It should be noted that the left upper and lower charts of FIG. 33 represent the measured results of response current values when the glucose concentration was set to be 100 mg/dl, whereas the right upper and lower charts of FIG. 33 represent the measured results of response current values when the glucose concentration was set to be 400 mg/dl.

It was consequently found that the response current value widely varied at both glucose concentrations of 100 mg/dl and 400 mg/dl in both measuring the temperature and measuring the glucose concentration when the blood sample temperature was changed.

Figure 34:
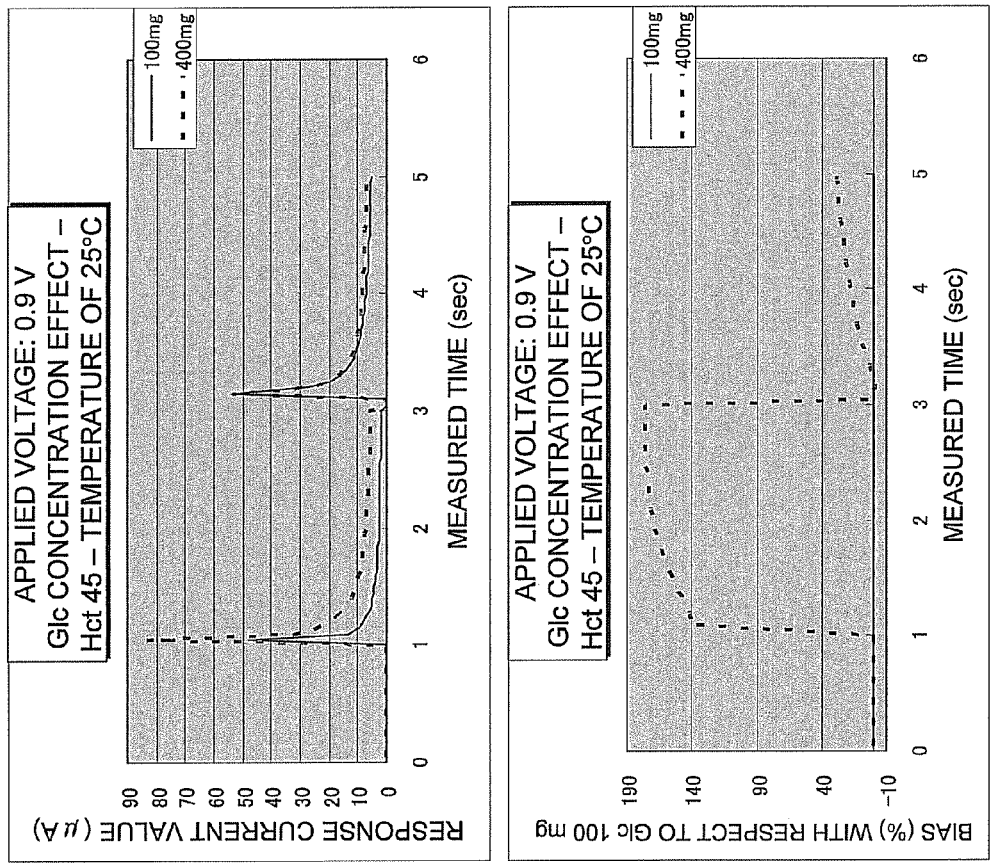
FIG. 34 includes charts representing a comprehensive result of examining the effect of variation in the glucose concentration on the response current value in applying a voltage of 0.9 V in the exemplary embodiment 2.

FIG. 34 represents the measured results when the glucose concentration was changed and set to be 100 mg/dl and 400 mg/dl in each chart for easily understanding the effect of the glucose concentration. It should be noted that the upper chart of FIG. 34 represents the measured results of response current values when the glucose concentration was set to be 100 mg/dl and 400 mg/dl, whereas the lower chart of FIG. 34 represents a deviation between response current values corresponding to glucose concentrations of 100 mg/dl and 400 mg/dl.

It was consequently found that the response current value widely varied in both measuring the glucose concentration and measuring the temperature when the glucose concentration was changed and set to be 100 mg/dl and 400 mg/dl.

It was found from the aforementioned results that the response current value was affected by variation in the glucose concentration, variation in the Hct value and variation in the temperature when the response current value was measured by applying a voltage of 0.9 V between the electrode A and the electrodes B and C and it was thereby impossible to extract only the effect of variation in the temperature.

<Applied Voltage of 1.0 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 1.0 V.

Figure 35:
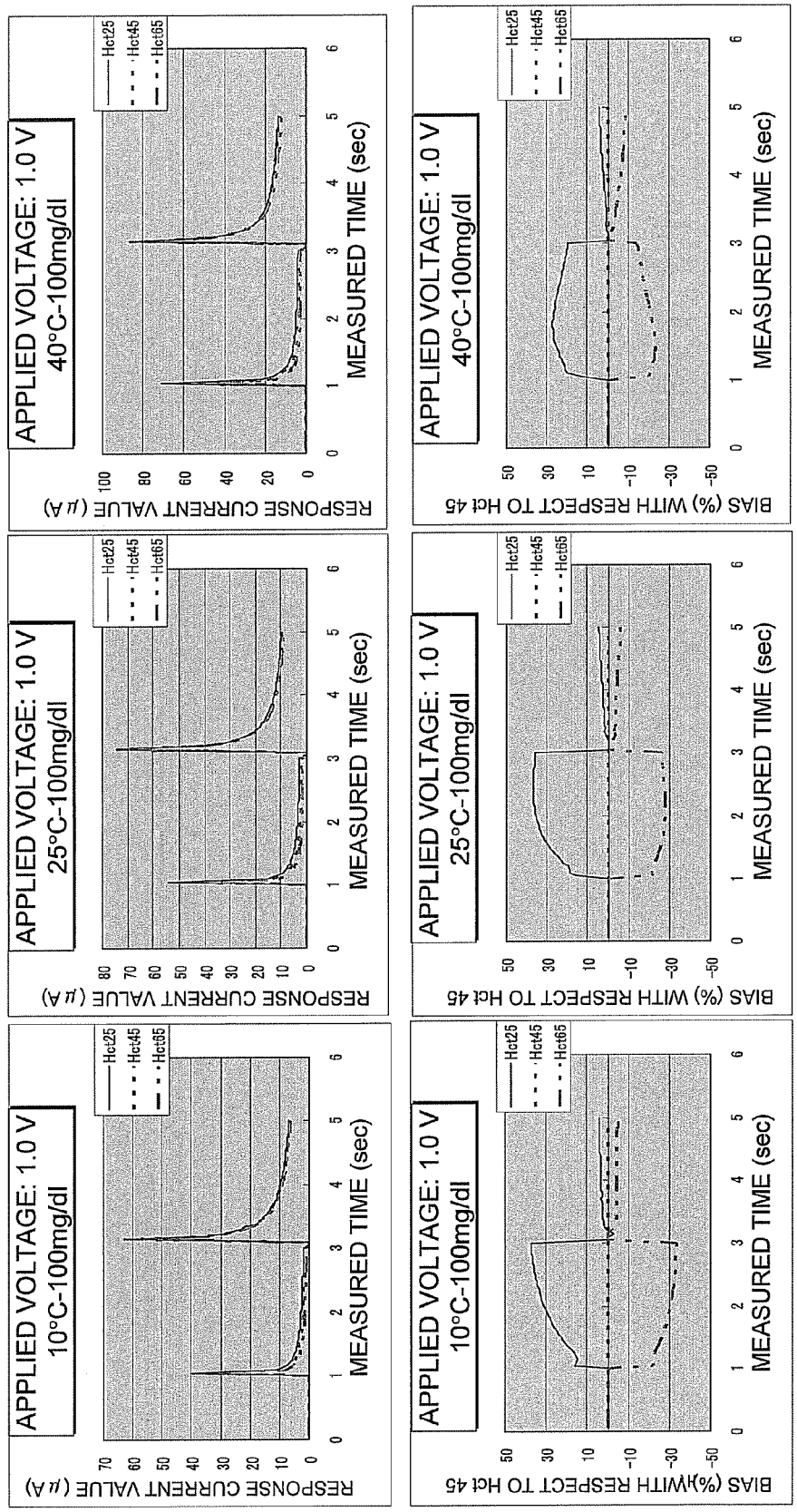
FIG. 35 includes charts representing the results of examining the effect of variation in the temperature and variation in the Hct value on the response current value in applying a voltage of 1.0 V in the exemplary embodiment 2.

In FIG. 35, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 35, each of the lower charts represents deviations of response current values corresponding to Hct values of 25 and 65 from a response current value corresponding to an Hct value of 45 in a corresponding one of the upper charts represented above the lower charts.

As represented in the charts of FIG. 35, it was consequently found that the response current value widely varied due to increase and reduction in the Hct value at the respective blood sample temperatures of 10° C., 25° C. and 40° C. in measuring the glucose concentration. On the other hand, it was found that deviations among response current values were still produced in a range of roughly plus/minus several % in measuring the temperature even though the response current value was less affected by increase and reduction in the Hct value.

Figure 36:
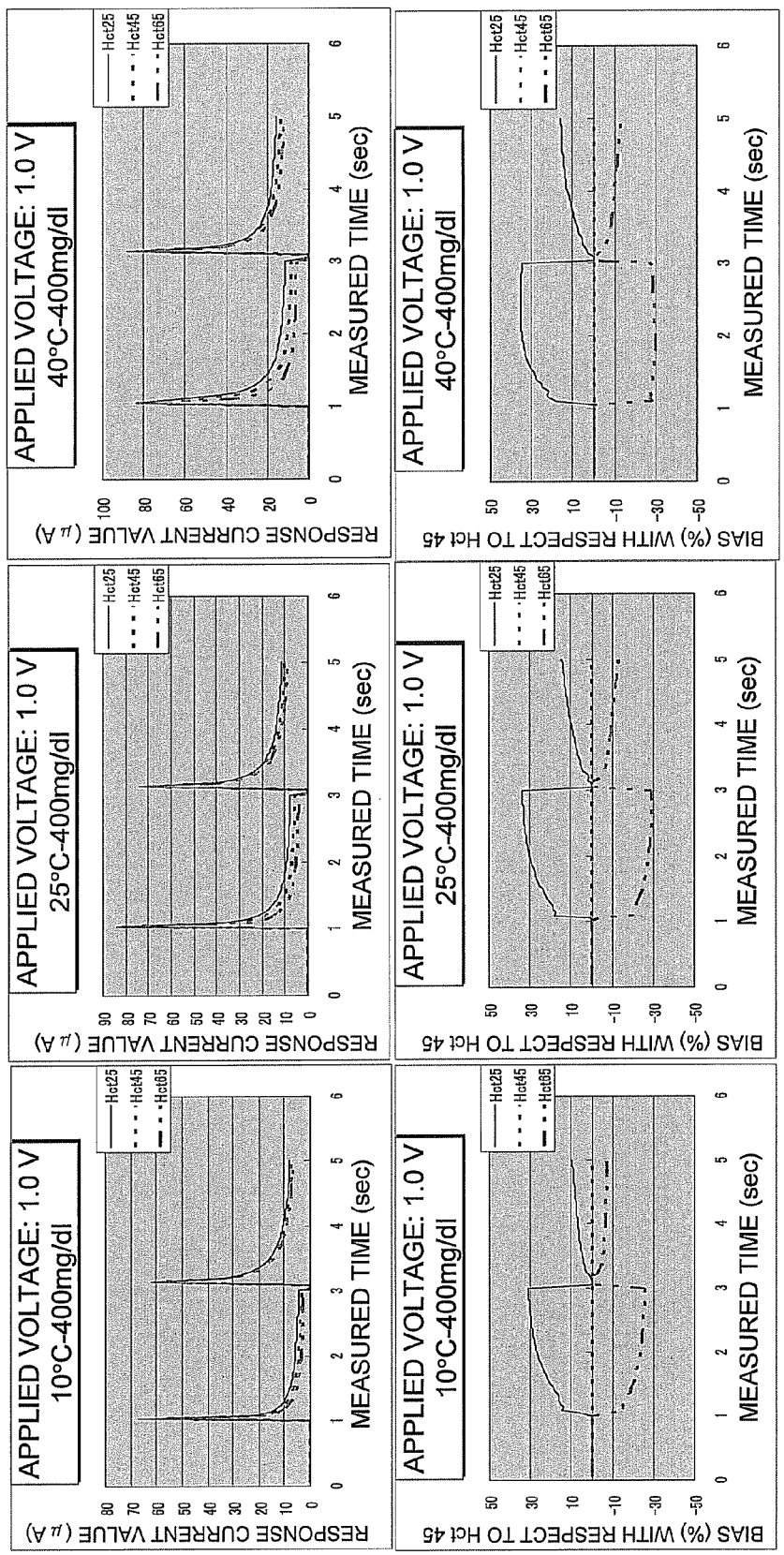
FIG. 36 includes charts representing the results of examining the effect of variation in the temperature and variation in the Hct value on the response current value in applying a voltage of 1.0 V in the exemplary embodiment 2.

FIG. 36 represents the measured results when the glucose concentration in FIG. 35 was changed from 100 mg/dl to 400 mg/dl.

Similarly to the aforementioned results, it was also found that the response current value widely varied due to increase and reduction in the Hct value at the respective blood sample temperatures of 10° C., 25° C. and 40° C. in both measuring the glucose concentration and measuring the temperature.

Figure 37:
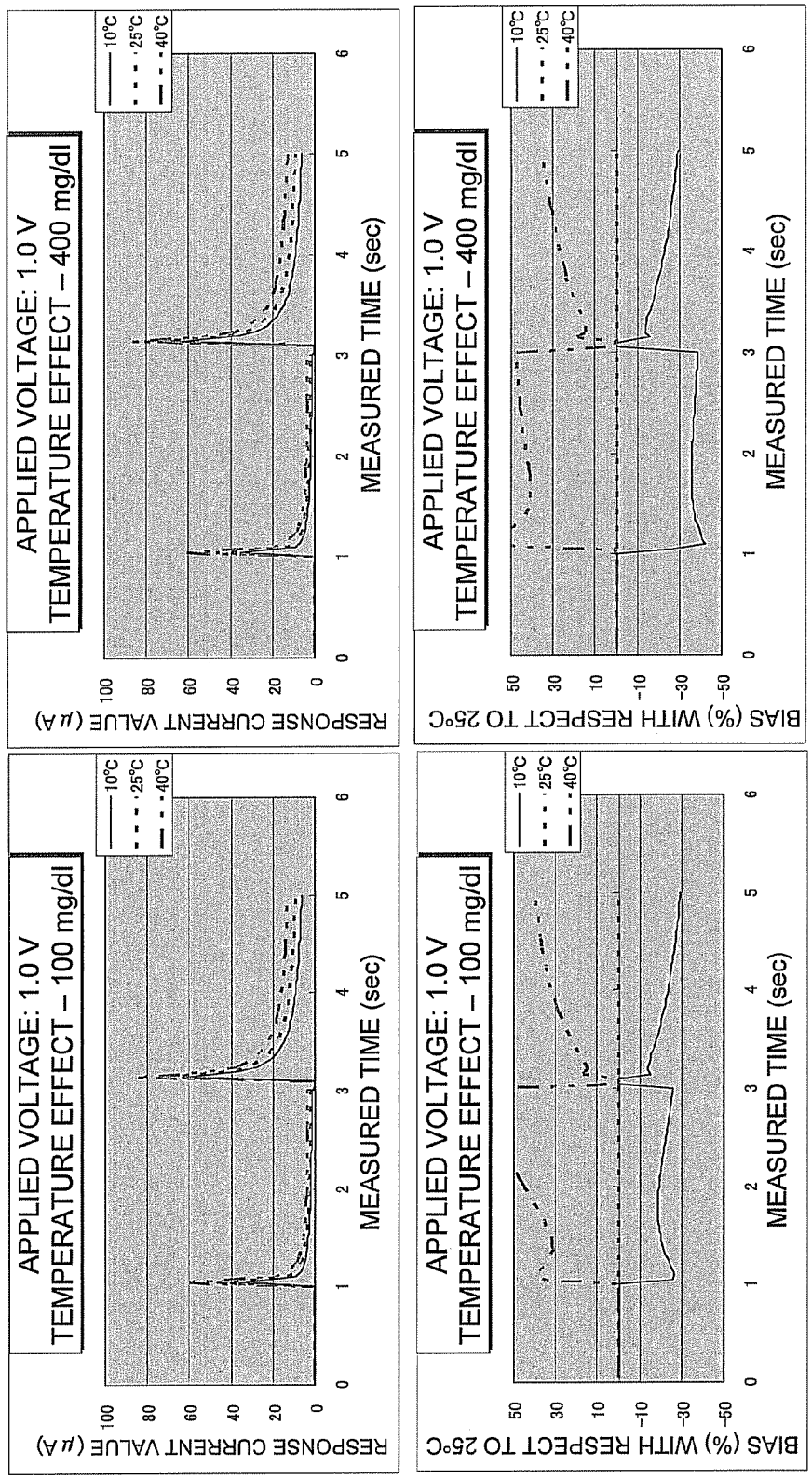
FIG. 37 includes charts representing a comprehensive result of examining the effect of variation in the temperature on the response current value in applying a voltage of 1.0 V in the exemplary embodiment 2.

FIG. 37 represents the measured results when the temperature conditions (10° C., 25° C. and 40° C.) were changed within each chart for easily understanding the effect of the blood sample temperature. It should be noted that the left upper and lower charts of FIG. 37 represent the measured results of response current values when the glucose concentration was set to be 100 mg/dl, whereas the right upper and lower charts of FIG. 37 represent the measured results of response current values when the glucose concentration was set to be 400 mg/dl.

It was consequently found that the response current value widely varied at both glucose concentrations of 100 mg/dl and 400 mg/dl in both measuring the temperature and measuring the glucose concentration when the blood sample temperature was changed.

Figure 38:
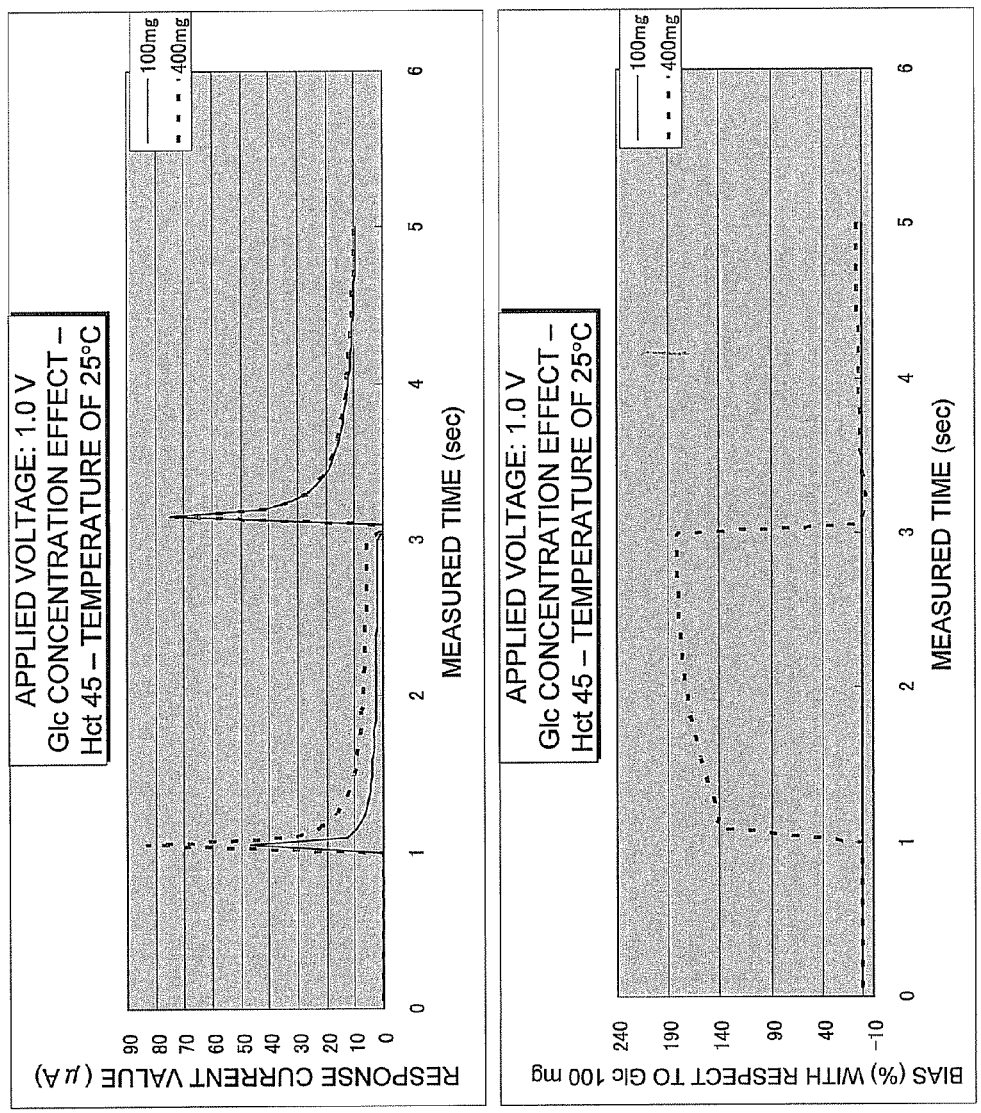
FIG. 38 includes charts representing a comprehensive result of examining the effect of variation in the glucose concentration on the response current value in applying a voltage of 1.0 V in the exemplary embodiment 2.

FIG. 38 represents the measured results when the glucose concentration was changed and set to be 100 mg/dl and 400 mg/dl in each chart for easily understanding the effect of the glucose concentration. It should be noted that the upper chart of FIG. 38 represents the measured results of response current values when the glucose concentration was set to be 100 mg/dl and 400 mg/dl, whereas the lower chart of FIG. 38 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature when the glucose concentration was changed and set to be 100 mg/dl and 400 mg/dl.

It was found from the aforementioned results that the response current value was affected by variation in the Hct value and variation in the temperature when the response current value was measured by applying a voltage of 1.0 V between the electrode A and the electrodes B and C and it was thereby impossible to extract only the effect of variation in the temperature. However, it was found from the results represented in FIG. 38 that the response current value was hardly affected by increase and reduction in the glucose concentration in measuring the temperature (i.e., in a measured time period from 3.0 second to 5.0 second) when a voltage of 1.0 V was applied between the electrode A and the electrodes B and C.

<Applied Voltage of 1.1 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 1.1 V.

Figure 39:
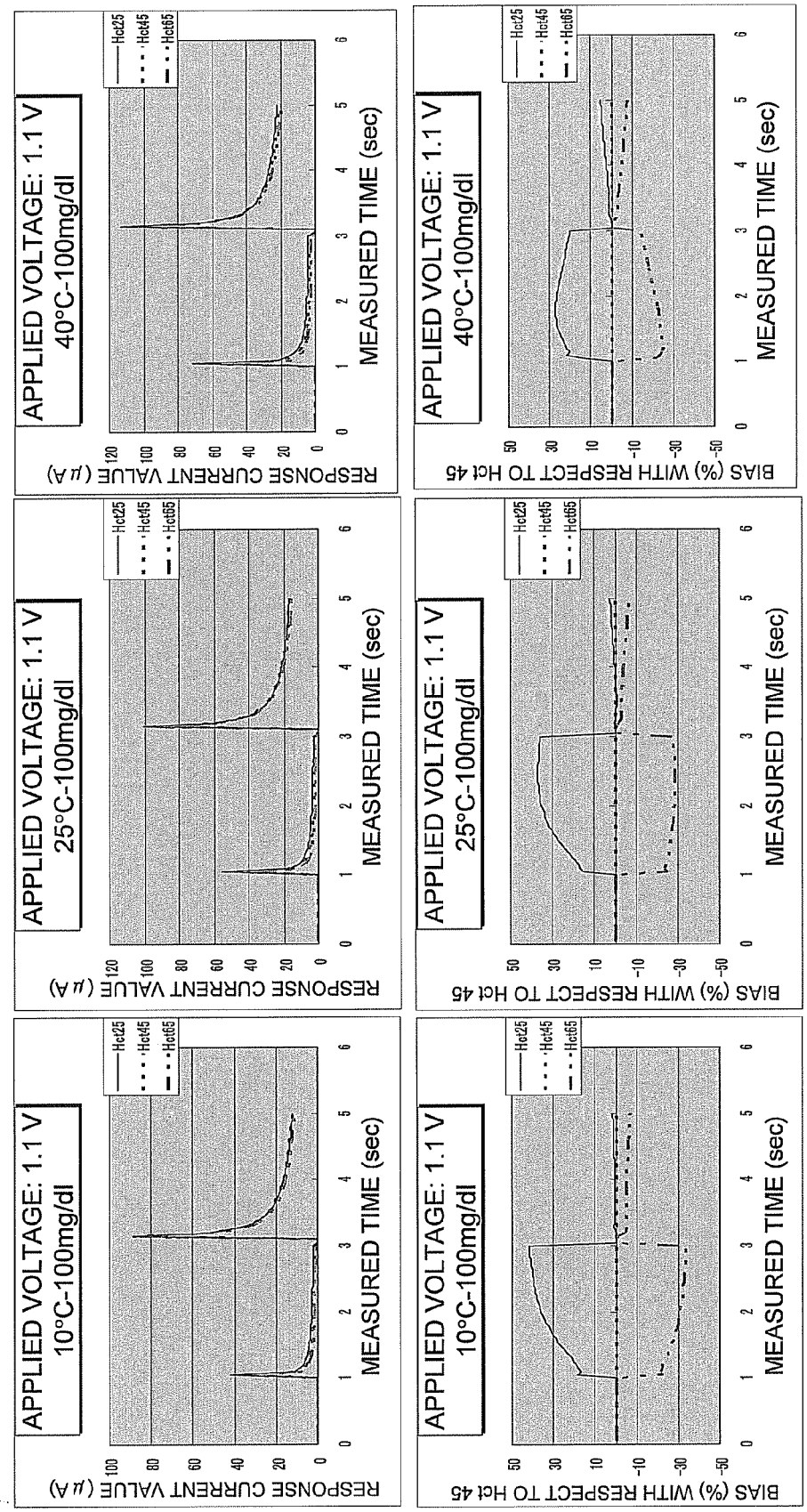
FIG. 39 includes charts representing the results of examining the effect of variation in the temperature and variation in the Hct value on the response current value in applying a voltage of 1.1 V in the exemplary embodiment 2.

In FIG. 39, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 39, each of the lower charts represents deviations of response current values corresponding to Hct values of 25 and 65 from a response current value corresponding to an Hct value of 45 in a corresponding one of the upper charts represented above the lower charts.

As represented in the charts of FIG. 39, it was consequently found that the response current value widely varied due to increase and reduction in the Hct value at the respective blood sample temperatures of 10° C., 25° C. and 40° C. in measuring the glucose concentration. On the other hand, it was found that deviations among response current values were still produced in a range of roughly plus/minus several % in measuring the temperature even though the response current value was less affected by increase and reduction in the Hct value.

Figure 40:
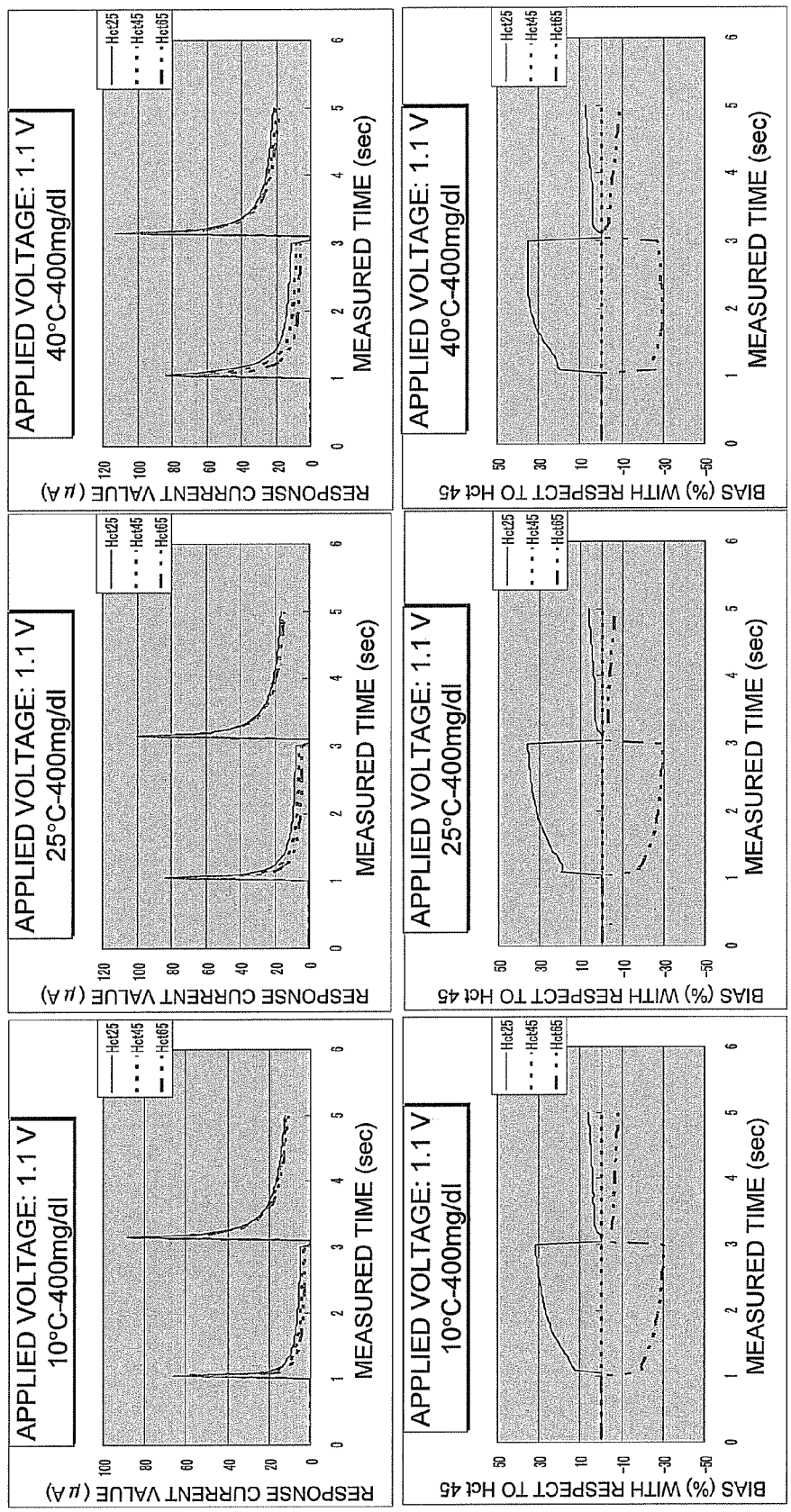
FIG. 40 includes charts representing the results of examining the effect of variation in the temperature and variation in the Hct value on the response current value in applying a voltage of 1.1 V in the exemplary embodiment 2.

FIG. 40 represents the measured results when the glucose concentration in FIG. 39 was changed from 100 mg/dl to 400 mg/dl.

Similarly to the aforementioned results, it was also found that the response current value varied due to increase and reduction in the Hct value at the respective blood sample temperatures of 10° C., 25° C. and 40° C. in both measuring the glucose concentration and measuring the temperature. It should be noted that deviations among response current values were inhibited to less than plus/minus 10% in measuring the temperature, compared to the aforementioned results of applied voltages of 0.5 V to 1.0 V.

Figure 41:
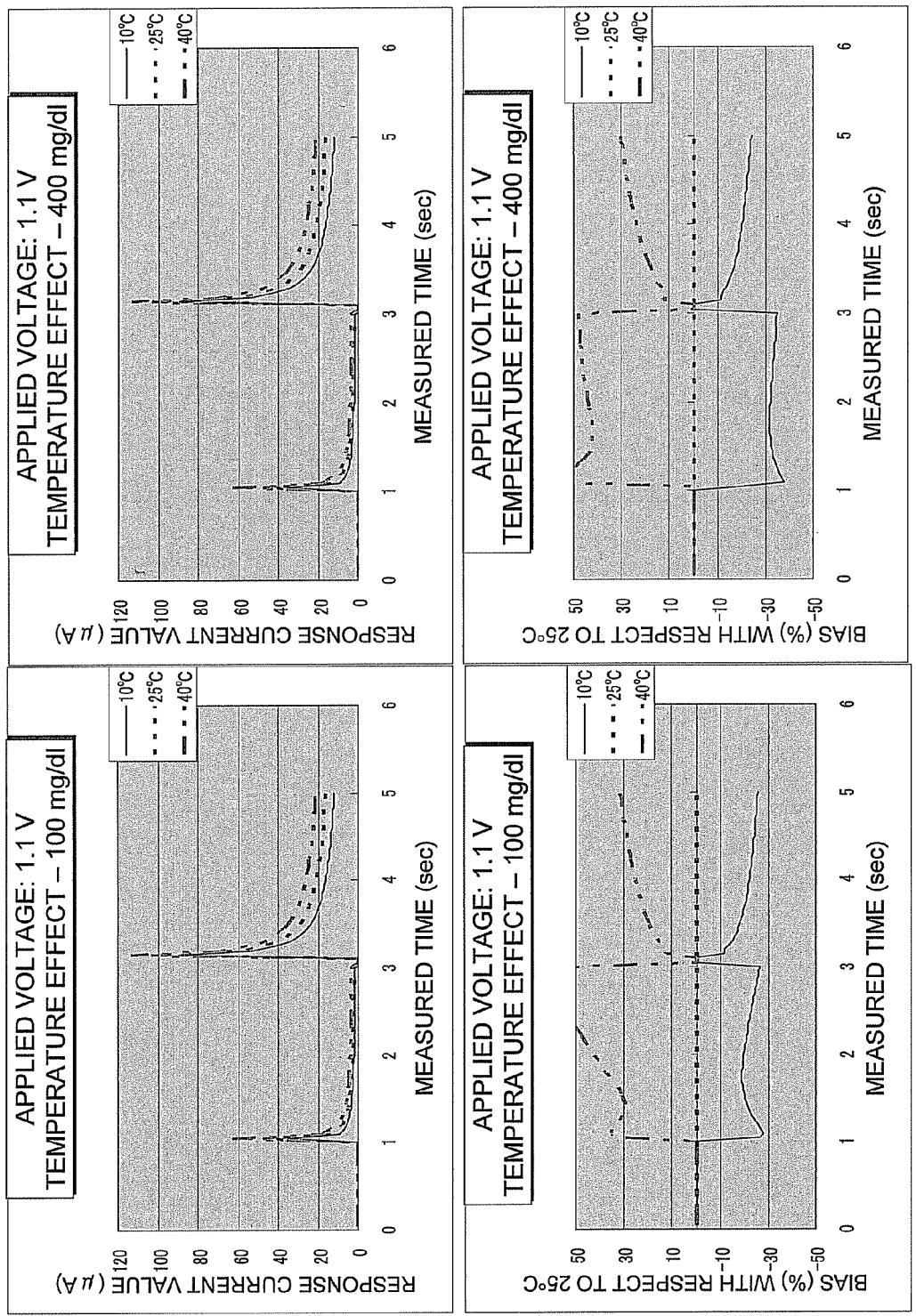
FIG. 41 includes charts representing a comprehensive result of examining the effect of variation in the temperature on the response current value in applying a voltage of 1.1 V in the exemplary embodiment 2.

FIG. 41 represents the measured results when the temperature conditions (10° C., 25° C. and 40° C.) were changed within each chart for easily understanding the effect of the blood sample temperature. It should be noted that the left upper and lower charts of FIG. 41 represent the measured results of response current values when the glucose concentration was set to be 100 mg/dl, whereas the right upper and lower charts of FIG. 41 represent the measured results of response current values when the glucose concentration was set to be 400 mg/dl.

It was consequently found that the response current value widely varied at both glucose concentrations of 100 mg/dl and 400 mg/dl in both measuring the temperature and measuring the glucose concentration when the blood sample temperature was changed.

Figure 42:
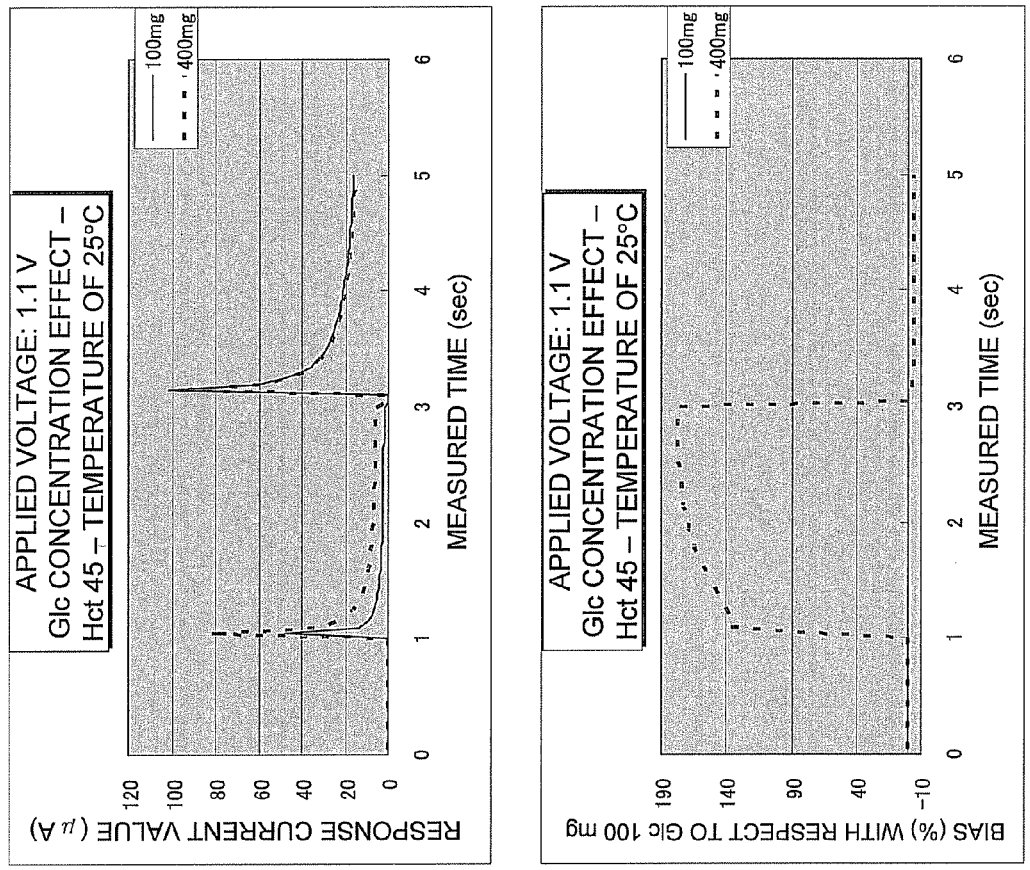
FIG. 42 includes charts representing a comprehensive result of examining the effect of variation in the glucose concentration on the response current value in applying a voltage of 1.1 V in the exemplary embodiment 2.

FIG. 42 represents the measured results when the glucose concentration was changed and set to be 100 mg/dl and 400 mg/dl in each chart for easily understanding the effect of the glucose concentration. It should be noted that the upper chart of FIG. 42 represents the measured results of response current values when the glucose concentration was set to be 100 mg/dl and 400 mg/dl, whereas the lower chart of FIG. 42 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature when the glucose concentration was changed and set to be 100 mg/dl and 400 mg/dl, similarly to the aforementioned result of an applied voltage of 1.0 V.

It was found from the aforementioned results that the response current value was affected by variation in the Hct value and variation in the temperature when the response current value was measured by applying a voltage of 1.1 V between the electrode A and the electrodes B and C and it was thereby impossible to extract only the effect of variation in the temperature. However, it was found from the results represented in FIG. 42 that the response current value was hardly affected by increase and reduction in the glucose concentration in measuring the temperature (i.e., in a measured time period from 3.0 second to 5.0 second) when a voltage of 1.1 V was applied between the electrode A and the electrodes B and C.

<Applied Voltage of 1.2 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 1.2 V.

Figure 43:
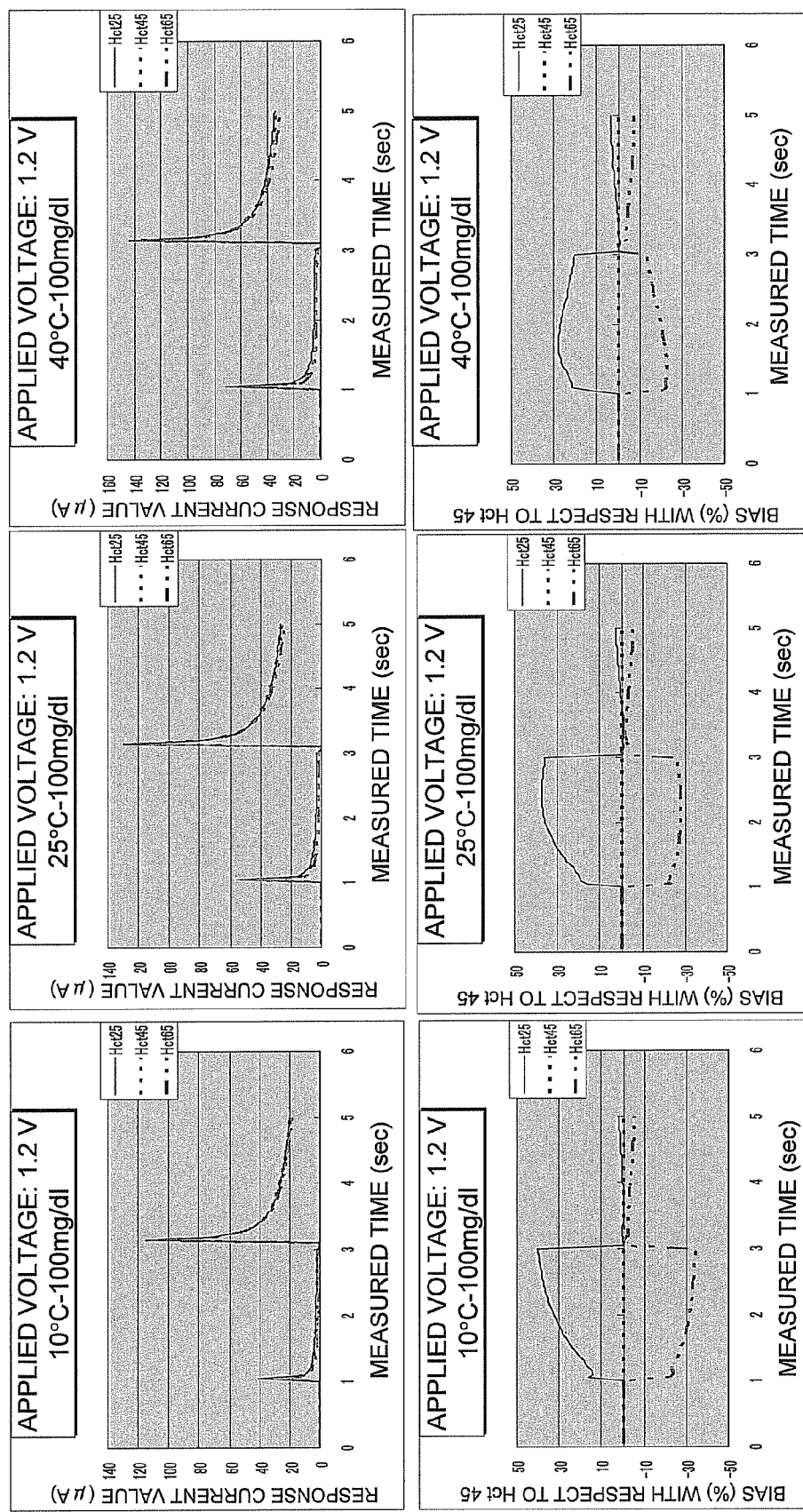
FIG. 43 includes charts representing the results of examining the effect of variation in the temperature and variation in the Hct value on the response current value in applying a voltage of 1.2 V in the exemplary embodiment 2.

In FIG. 43, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 43, each of the lower charts represents deviations of response current values corresponding to Hct values of 25 and 65 from a response current value corresponding to an Hct value of 45 in a corresponding one of the upper charts represented above the lower charts.

As represented in the charts of FIG. 43, it was consequently found that the response current value widely varied due to increase and reduction in the Hct value at the respective blood sample temperatures of 10° C., 25° C. and 40° C. in measuring the glucose concentration. On the other hand, it was found that deviations among response current values were still produced in a range of roughly plus/minus several % in measuring the temperature even though the response current value was less affected by increase and reduction in the Hct value.

Figure 44:
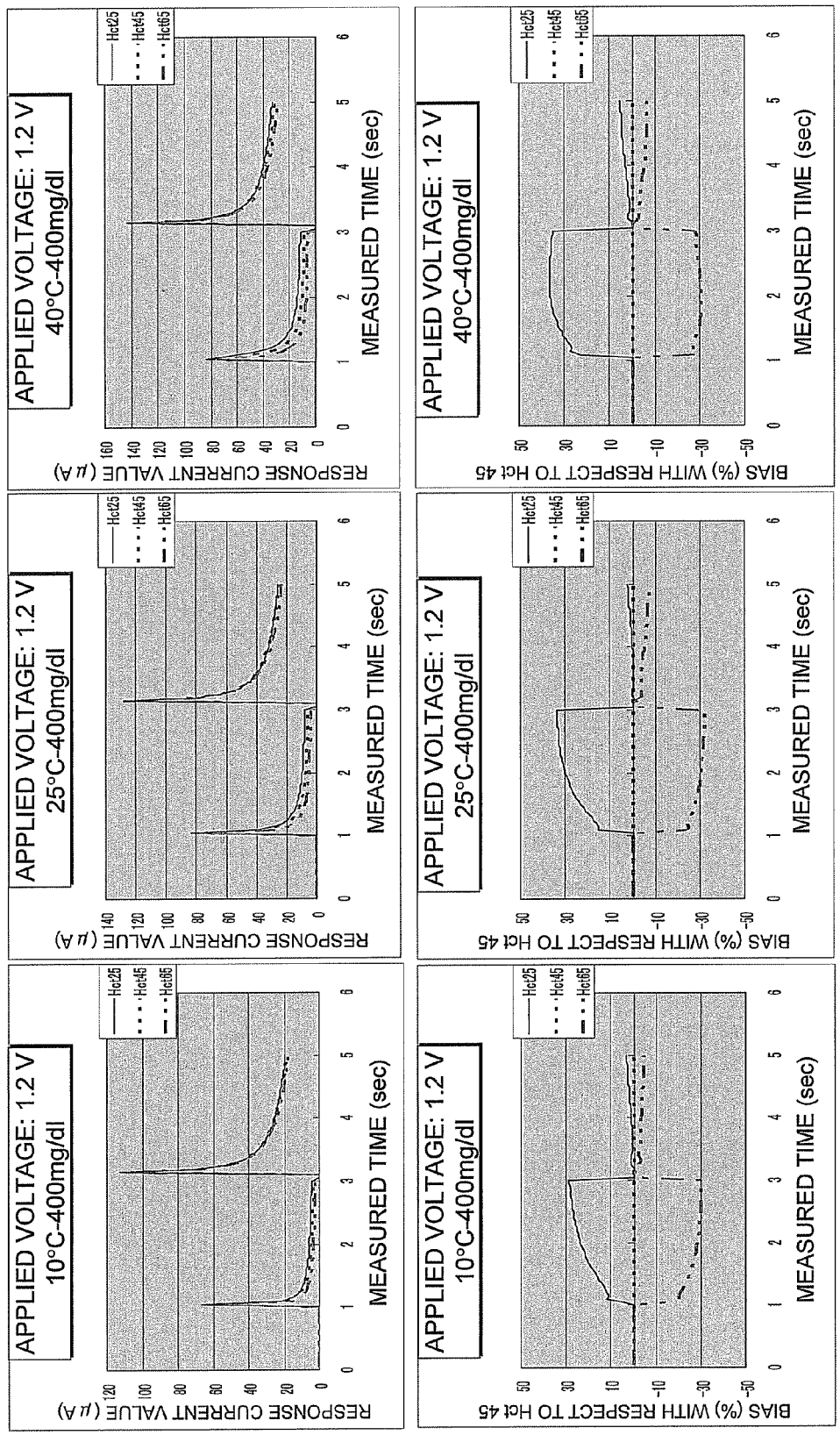
FIG. 44 includes charts representing the results of examining the effect of variation in the temperature and variation in the Hct value on the response current value in applying a voltage of 1.2 V in the exemplary embodiment 2.

FIG. 44 represents the measured results when the glucose concentration in FIG. 43 was changed from 100 mg/dl to 400 mg/dl.

Similarly to the aforementioned results, it was also found that the response current value widely varied due to increase and reduction in the Hct value at the respective blood sample temperatures of 10° C., 25° C. and 40° C. in both measuring the glucose concentration and measuring the temperature. However, it was found that deviations among response current values were inhibited to less than plus/minus several % in measuring the temperature compared to the aforementioned results of applied voltages of 0.5 V to 1.2 V.

Figure 45:
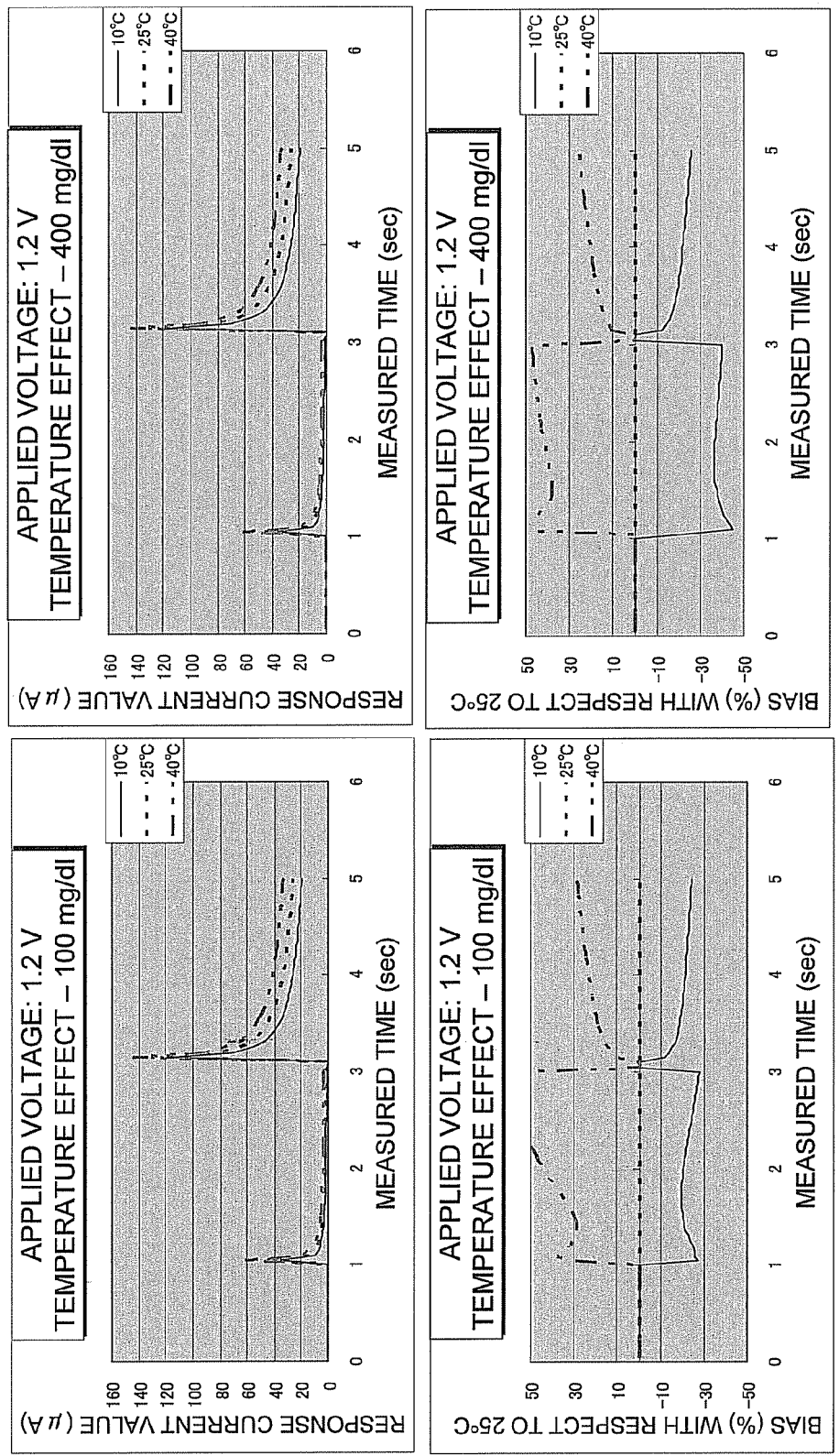
FIG. 45 includes charts representing a comprehensive result of examining the effect of variation in the temperature on the response current value in applying a voltage of 1.2 V in the exemplary embodiment 2.

FIG. 45 represents the measured results when the temperature conditions (10° C., 25° C. and 40° C.) were changed within each chart for easily understanding the effect of the blood sample temperature. It should be noted that the left upper and lower charts of FIG. 45 represent the measured results of response current values when the glucose concentration was set to be 100 mg/dl, whereas the right upper and lower charts of FIG. 45 represent the measured results of response current values when the glucose concentration was set to be 400 mg/dl.

It was consequently found that the response current value widely varied at both glucose concentrations of 100 mg/dl and 400 mg/dl in both measuring the temperature and measuring the glucose concentration when the blood sample temperature was changed.

Figure 46:
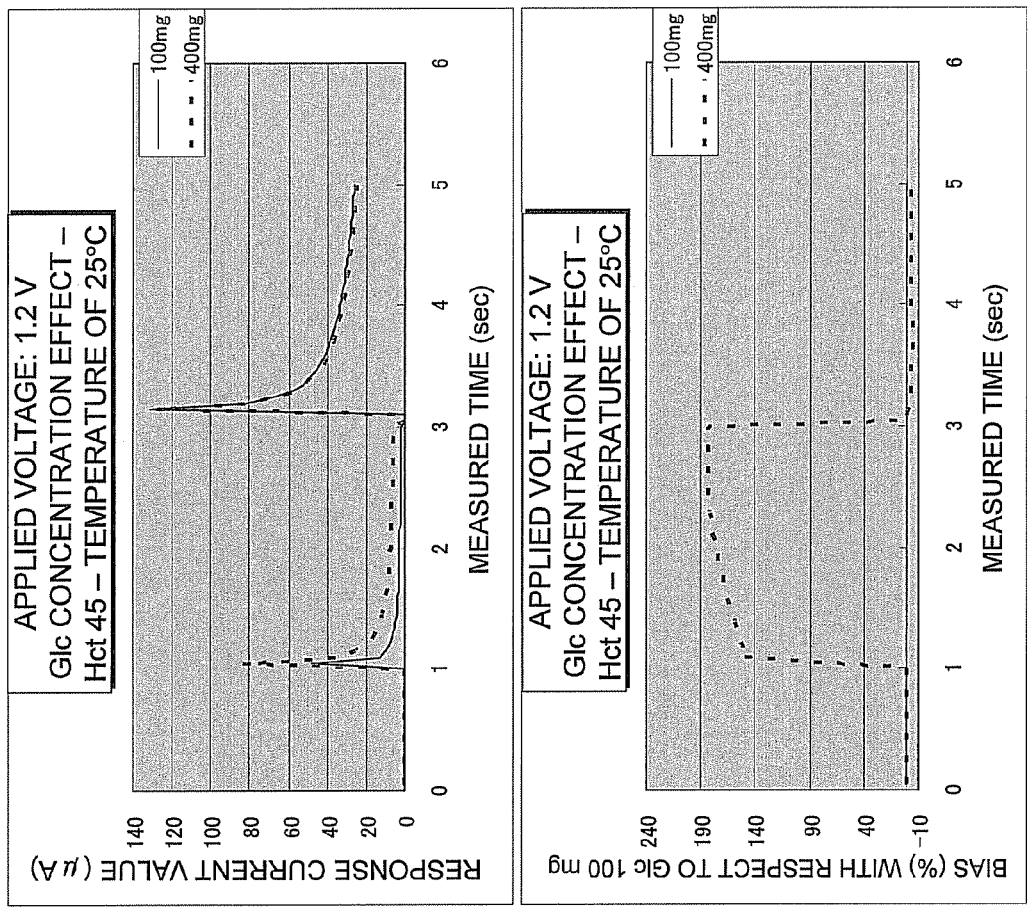
FIG. 46 includes charts representing a comprehensive result of examining the effect of variation in the glucose concentration on the response current value in applying a voltage of 1.2 V in the exemplary embodiment 2.

FIG. 46 represents the measured results when the glucose concentration was changed and set to be 100 mg/dl and 400 mg/dl in each chart for easily understanding the effect of the glucose concentration. It should be noted that the upper chart of FIG. 46 represents the measured results of response current values when the glucose concentration was set to be 100 mg/dl and 400 mg/dl, whereas the lower chart of FIG. 46 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature, similarly to the aforementioned results of applied voltages of 1.0 V and 1.1 V.

It was found from the aforementioned results that the response current value was affected by variation in the Hct value and variation in the temperature when the response current value was measured by applying a voltage of 1.2 V between the electrode A and the electrodes B and C and it was thereby impossible to extract only the effect of variation in the temperature. However, it was found from the results represented in FIG. 46 that the response current value was hardly affected by increase and reduction in the glucose concentration in measuring the temperature (i.e., in a measured time period from 3.0 second to 5.0 second) when a voltage of 1.2 V was applied between the electrode A and the electrodes B and C.

<Applied Voltage of 1.5 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 1.5 V.

Figure 47:
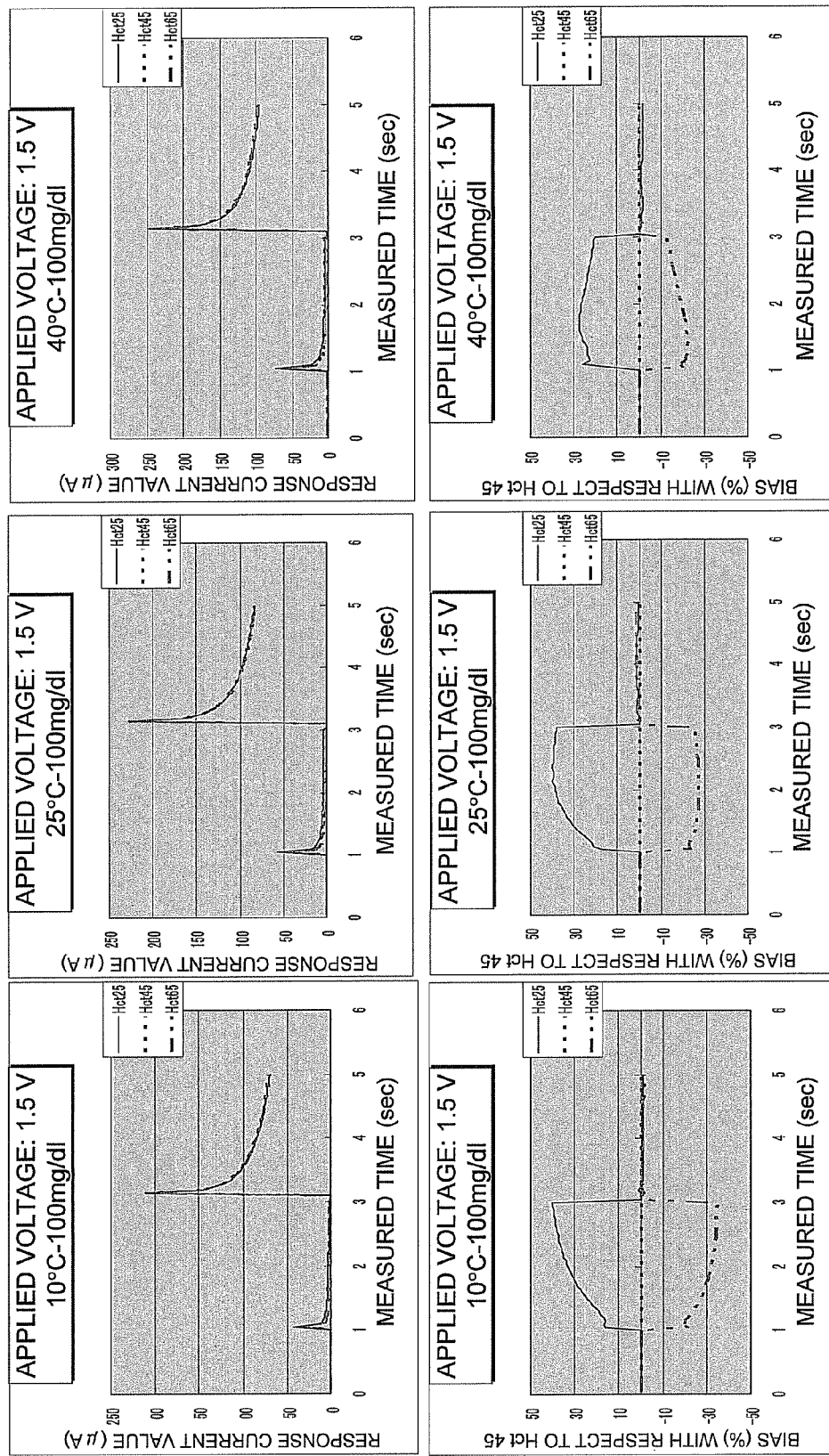
FIG. 47 includes charts representing the results of examining the effect of variation in the temperature and variation in the Hct value on the response current value in applying a voltage of 1.5 V in the exemplary embodiment 2.

In FIG. 47, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 47, each of the lower charts represents deviations of response current values corresponding to Hct values of 25 and 65 from a response current value corresponding to an Hct value of 45 in a corresponding one of the upper charts represented above the lower charts.

As represented in the charts of FIG. 47, it was consequently found that the response current value widely varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature.

Figure 48:
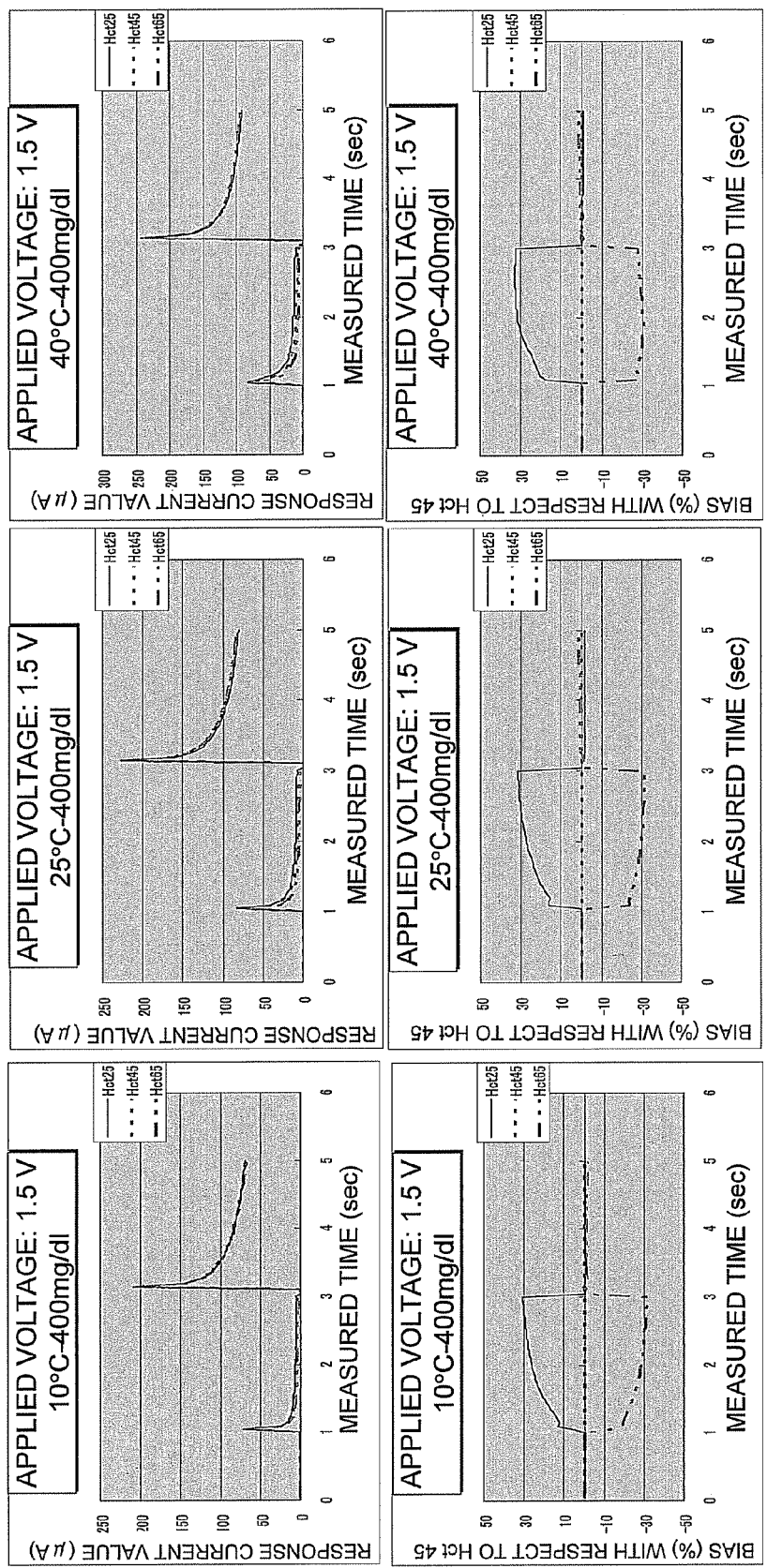
FIG. 48 includes charts representing the results of examining the effect of variation in the temperature and variation in the Hct value on the response current value in applying a voltage of 1.5 V in the exemplary embodiment 2.

FIG. 48 represents the measured results when the glucose concentration in FIG. 47 was changed from 100 mg/dl to 400 mg/dl.

Similarly to the aforementioned results, it was also found that the response current value varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature, similarly to the aforementioned result of a glucose concentration of 100 mg/dl represented in FIG. 47.

Figure 49:
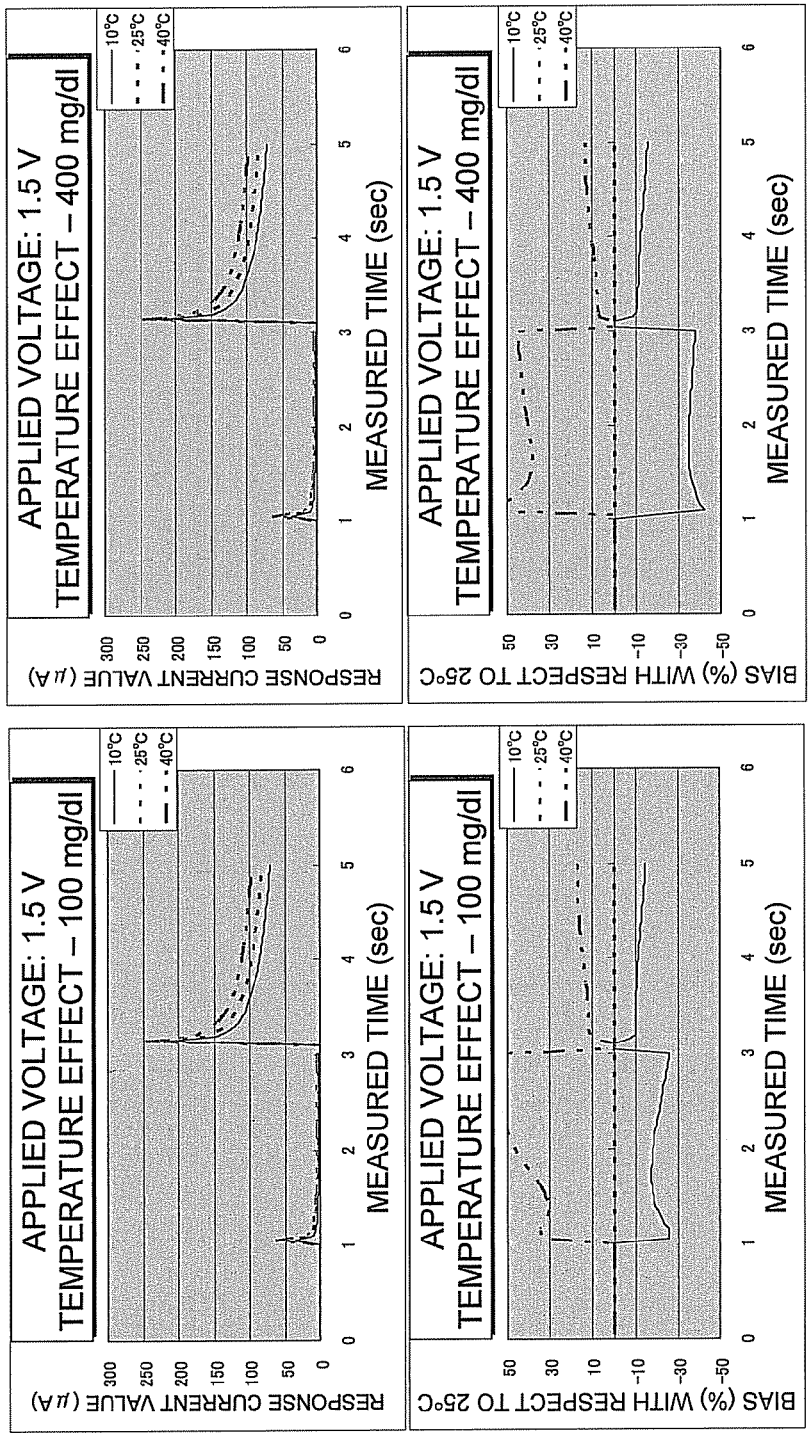
FIG. 49 includes charts representing a comprehensive result of examining the effect of variation in the temperature on the response current value in applying a voltage of 1.5 V in the exemplary embodiment 2.

FIG. 49 represents the measured results when the temperature conditions (10° C., 25° C. and 40° C.) were changed within each chart for easily understanding the effect of the blood sample temperature. It should be noted that the left upper and lower charts of FIG. 49 represent the measured results of response current values when the glucose concentration was set to be 100 mg/dl, whereas the right upper and lower charts of FIG. 49 represent the measured results of response current values when the glucose concentration was set to be 400 mg/dl.

It was consequently found that the response current value varied at both glucose concentrations of 100 mg/dl and 400 mg/dl in both measuring the temperature and measuring the glucose concentration when the blood sample temperature was changed. It was herein found that the response current value was changed at a sensitivity of roughly 1° C./1% when the blood sample temperature was changed. This indicates that the sensor chip of the present exemplary embodiment functions as a temperature sensor.

Figure 50:
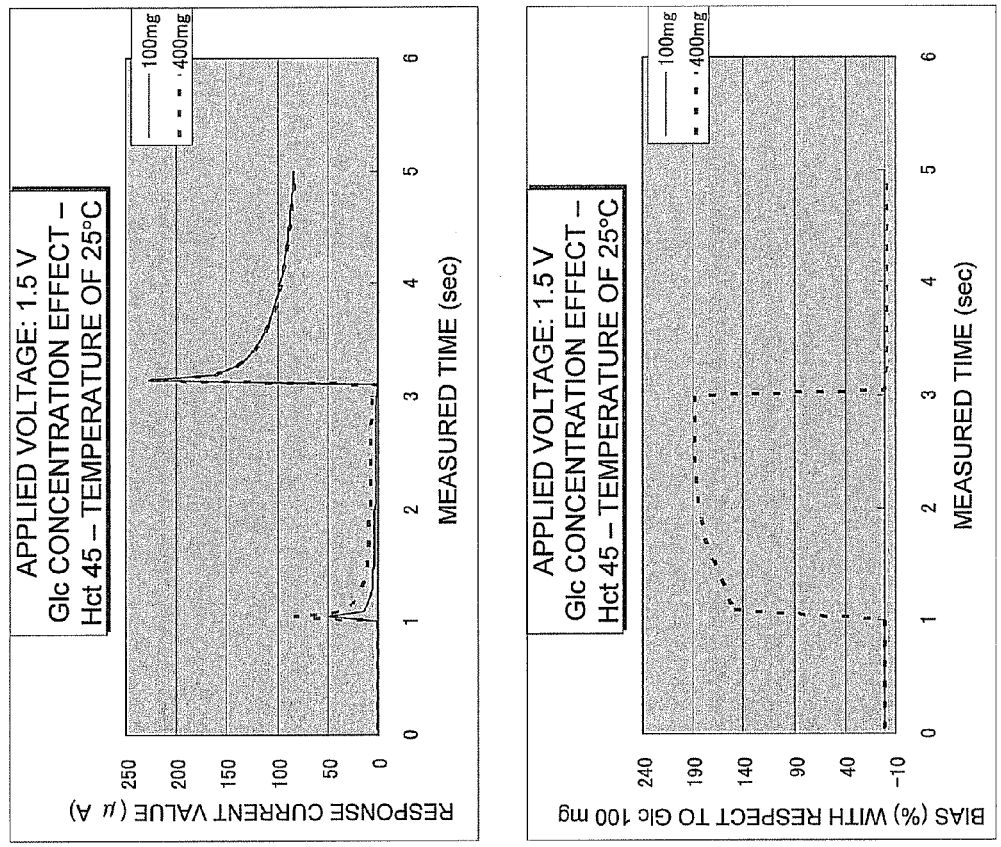
FIG. 50 includes charts representing a comprehensive result of examining the effect of variation in the glucose concentration on the response current value in applying a voltage of 1.5 V in the exemplary embodiment 2.

FIG. 50 represents the measured results when the glucose concentration was changed and set to be 100 mg/dl and 400 mg/dl in each chart for easily understanding the effect of the glucose concentration. It should be noted that the upper chart of FIG. 50 represents the measured results of response current values when the glucose concentration was set to be 100 mg/dl and 400 mg/dl, whereas the lower chart of FIG. 50 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature, similarly to the aforementioned results of applied voltages of 1.0 V to 1.2 V.

It was found from the aforementioned results that the response current value was not affected by variation in the glucose concentration and variation in the Hct value when the response current value was measured by applying a voltage of 1.5 V between the electrode A and the electrodes B and C and it was thereby possible to extract only the effect of variation in the temperature.

In the present exemplary embodiment, it is possible to exclude the effects of increase and reduction in the glucose concentration and increase and reduction in the Hct value by measuring the response current value through the application of a voltage of 1.5 V between the electrode A and the electrodes B and C. It is thereby possible to use the present sensor chip as a temperature sensor.

<Applied Voltage of 1.75 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 1.75 V.

Figure 51:
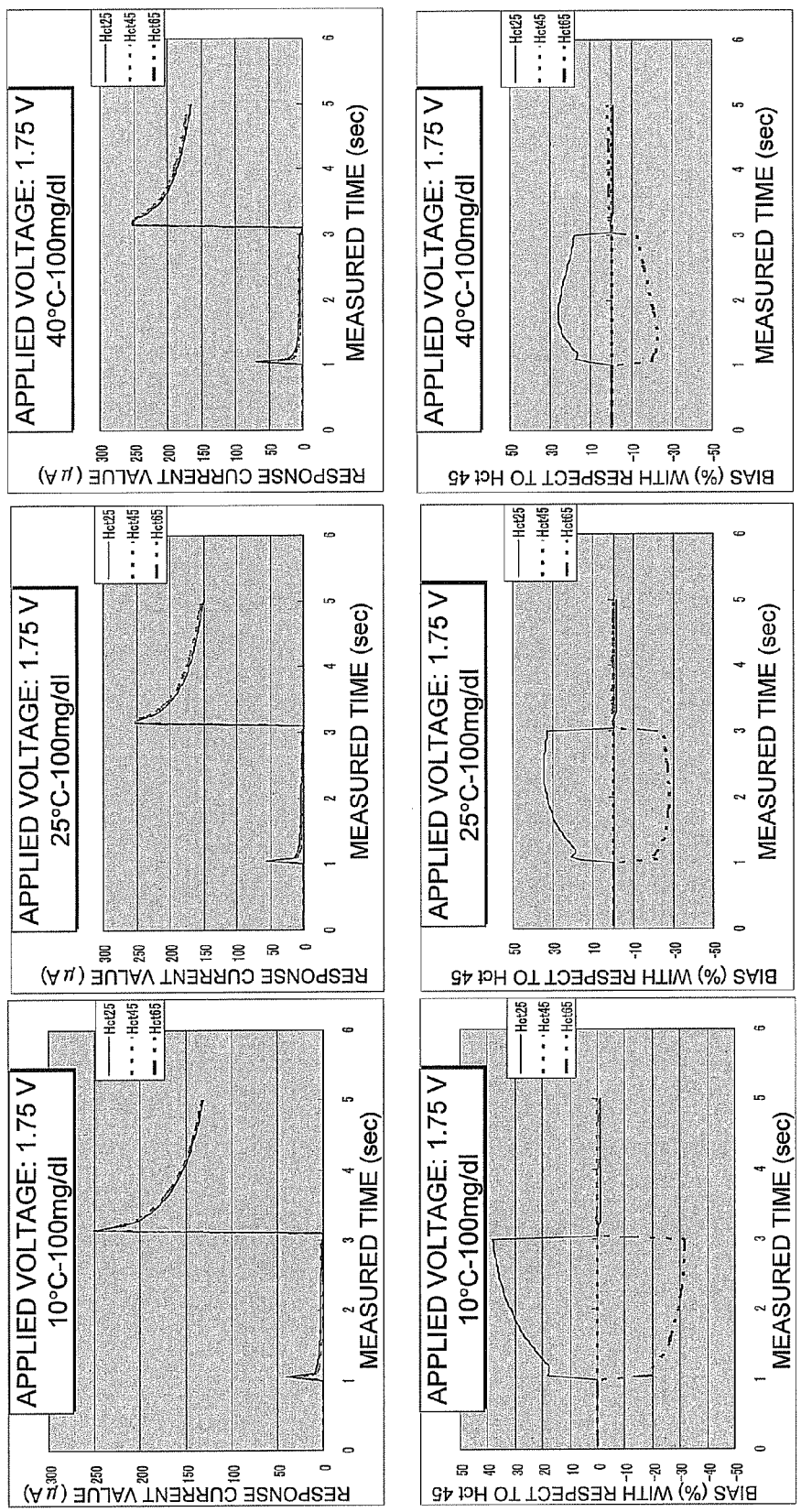
FIG. 51 includes charts representing the results of examining the effect of variation in the temperature and variation in the Hct value on the response current value in applying a voltage of 1.75 V in the exemplary embodiment 2.

In FIG. 51, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 51, each of the lower charts represents deviations of response current values corresponding to Hct values of 25 and 65 from a response current value corresponding to an Hct value of 45 in a corresponding one of the upper charts represented above the lower charts.

As represented in the charts of FIG. 51, it was consequently found that the response current value widely varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature, similarly to the aforementioned result of an applied voltage of 1.5 V.

Figure 52:
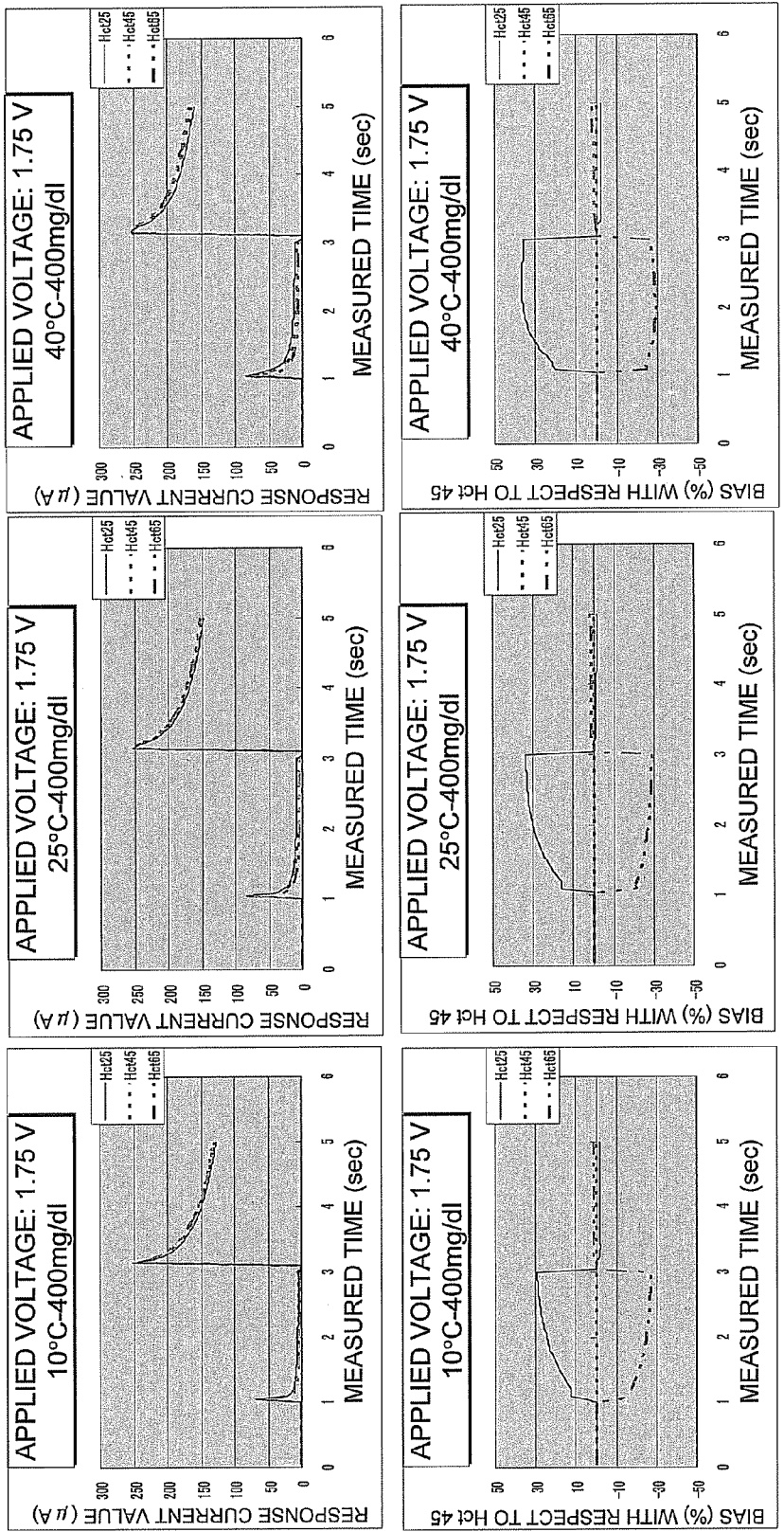
FIG. 52 includes charts representing the results of examining the effect of variation in the temperature and variation in the Hct value on the response current value in applying a voltage of 1.75 V in the exemplary embodiment 2.

FIG. 52 represents the measured results when the glucose concentration in FIG. 51 was changed from 100 mg/dl to 400 mg/dl.

Similarly to the aforementioned results, it was also found that the response current value varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature, similarly to the aforementioned result of a glucose concentration of 100 mg/dl represented in FIG. 51.

Figure 53:
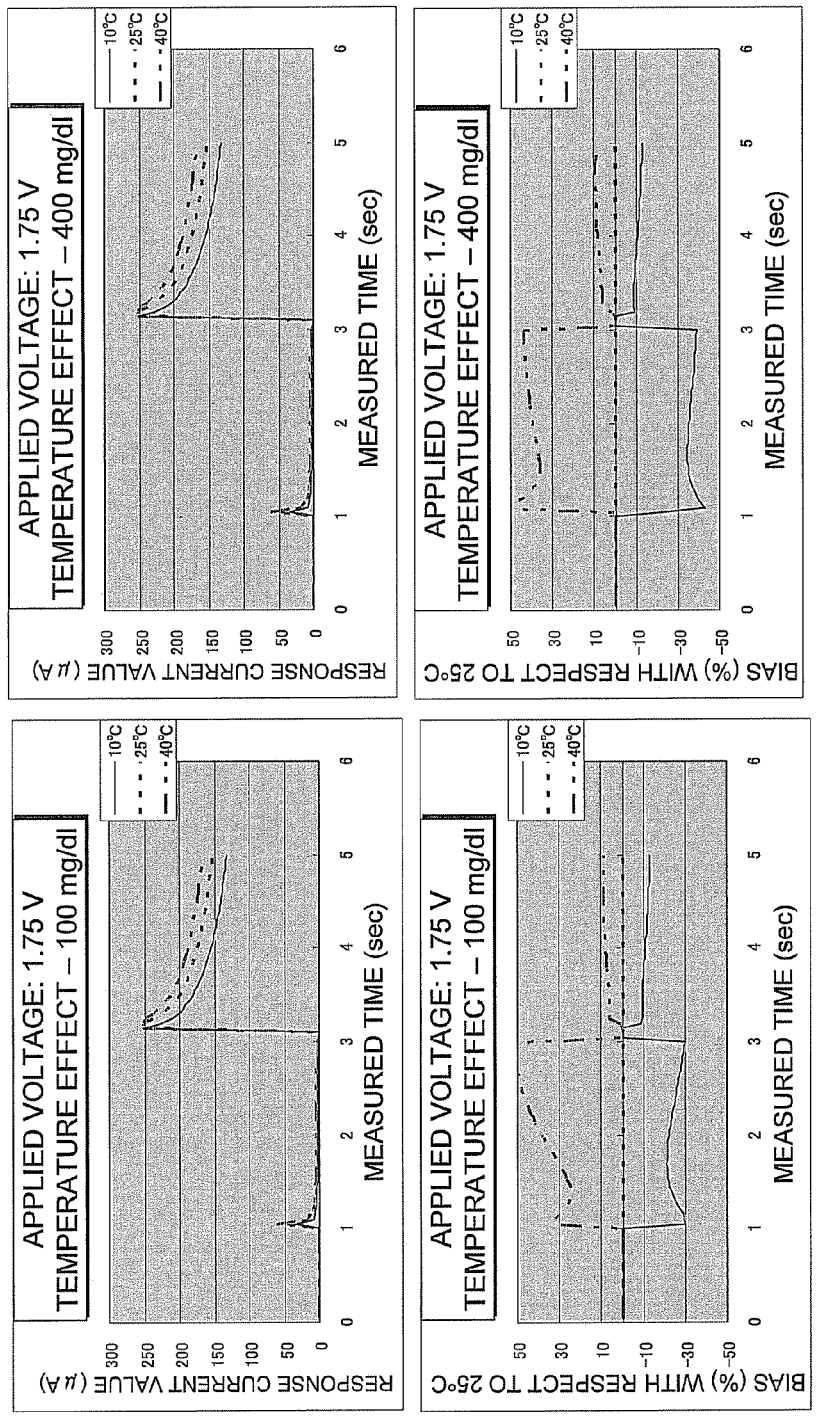
FIG. 53 includes charts representing a comprehensive result of examining the effect of variation in the temperature on the response current value in applying a voltage of 1.75 V in the exemplary embodiment 2.

FIG. 53 represents the measured results when the temperature conditions (10° C., 25° C. and 40° C.) were changed within each chart for easily understanding the effect of the blood sample temperature. It should be noted that the left upper and lower charts of FIG. 53 represent the measured results of response current values when the glucose concentration was set to be 100 mg/dl, whereas the right upper and lower charts of FIG. 53 represent the measured results of response current values when the glucose concentration was set to be 400 mg/dl.

It was consequently found that the response current value varied at both glucose concentrations of 100 mg/dl and 400 mg/dl in both measuring the temperature and measuring the glucose concentration when the blood sample temperature was changed. It was herein found that the temperature could be measured at a sensitivity of roughly 1° C./1%, similarly to the aforementioned result of an applied voltage of 1.5 V.

Figure 54:
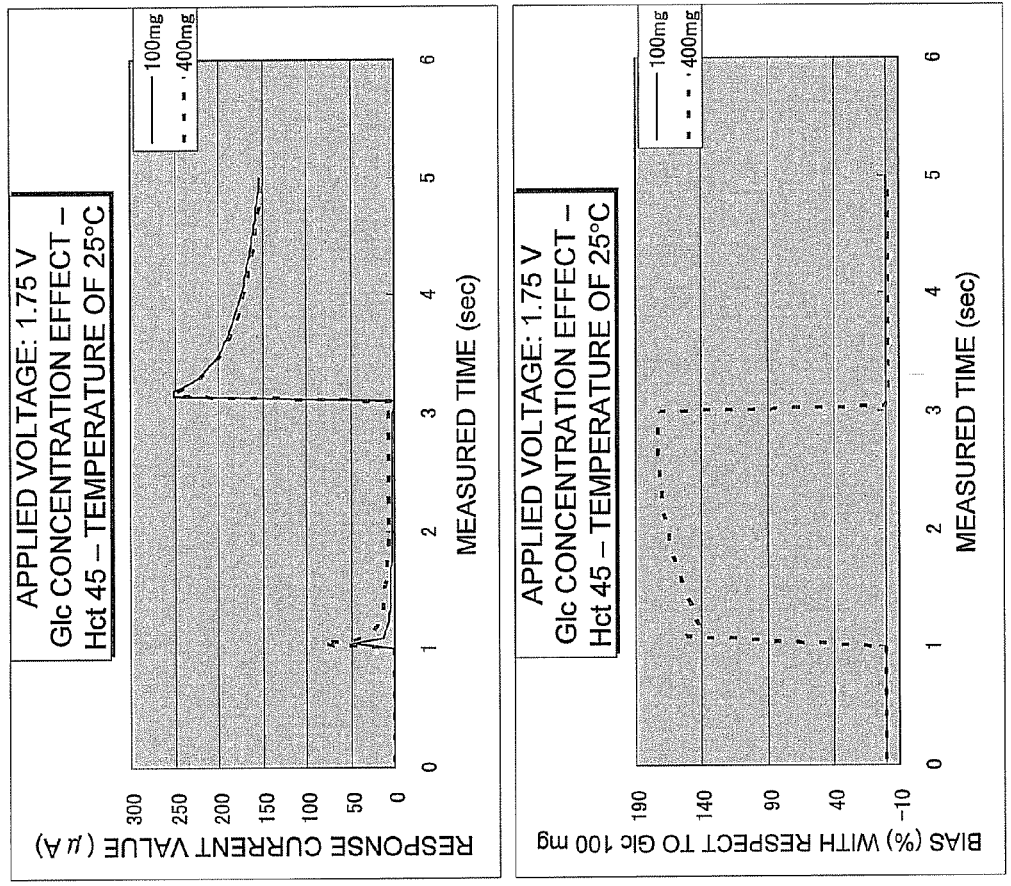
FIG. 54 includes charts representing a comprehensive result of examining the effect of variation in the glucose concentration on the response current value in applying a voltage of 1.75 V in the exemplary embodiment 2.

FIG. 54 represents the measured results when the glucose concentration was changed and set to be 100 mg/dl and 400 mg/dl in each chart for easily understanding the effect of the glucose concentration. It should be noted that the upper chart of FIG. 54 represents the measured results of response current values when the glucose concentration was set to be 100 mg/dl and 400 mg/dl, whereas the lower chart of FIG. 54 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature, similarly to the aforementioned results of applied voltages of 1.0 V to 1.5 V.

It was found from the aforementioned results that the response current value was not affected by variation in the glucose concentration and variation in the Hct value when the response current value was measured by applying a voltage of 1.75 V between the electrode A and the electrodes B and C and it was thereby possible to extract only the effect of variation in the temperature, similarly to the aforementioned result of an applied voltage of 1.5 V.

In the present exemplary embodiment, it is possible to exclude the effects of increase and reduction in the glucose concentration and increase and reduction in the Hct value by measuring the response current value through the application of a voltage of 1.5 V or greater between the electrode A and the electrodes B and C. It is thereby possible to use the present sensor chip as a temperature sensor.

<Applied Voltage of 2.0 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 2.0 V.

Figure 55:
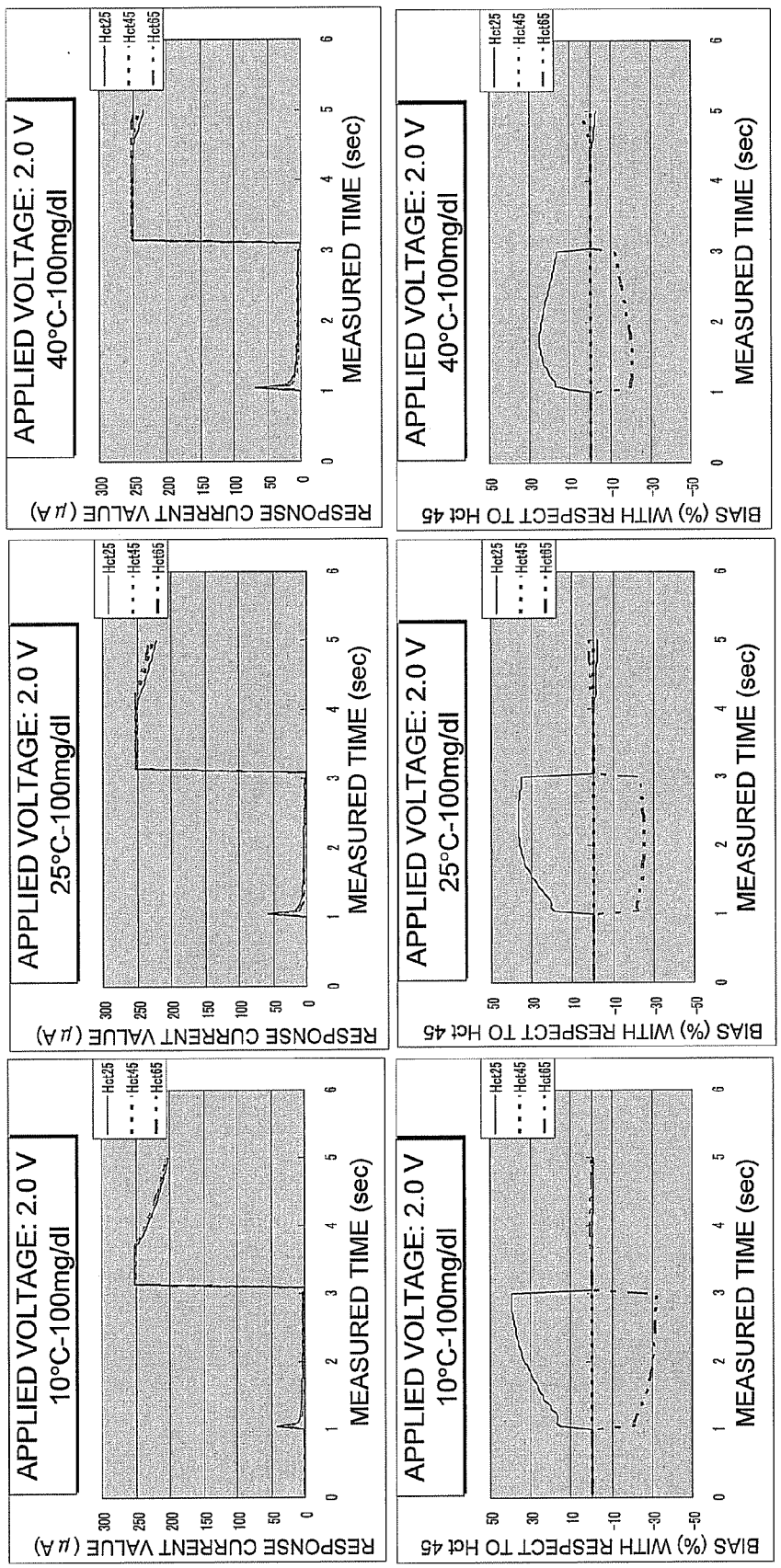
FIG. 55 includes charts representing the results of examining the effect of variation in the temperature and variation in the Hct value on the response current value in applying a voltage of 2.0 V in the exemplary embodiment 2.

In FIG. 55, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 55, each of the lower charts represents deviations of response current values corresponding to Hct values of 25 and 65 from a response current value corresponding to an Hct value of 45 in a corresponding one of the upper charts represented above the lower charts.

As represented in the charts of FIG. 55, it was consequently found that the response current value widely varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature, similarly to the aforementioned result of an applied voltage of 1.5 V.

Figure 56:
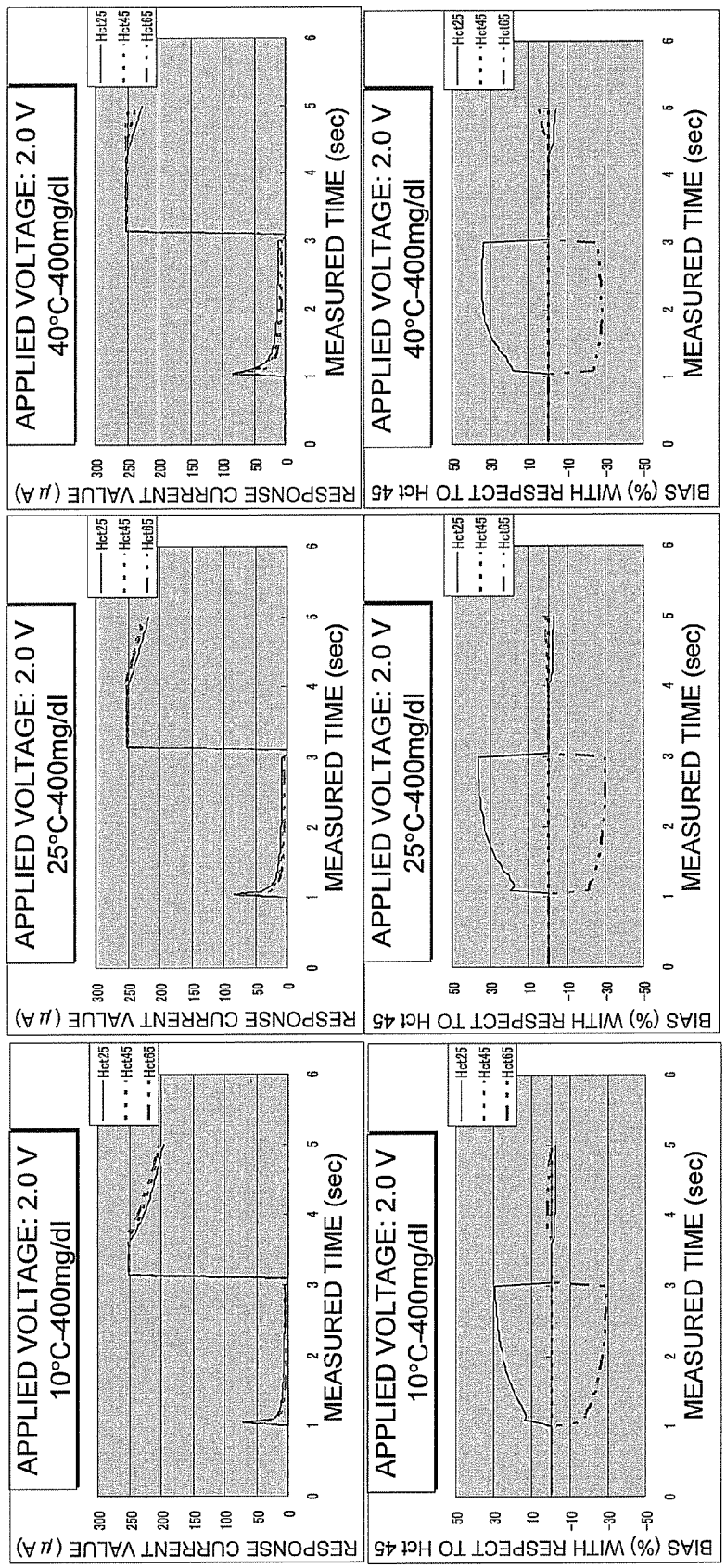
FIG. 56 includes charts representing the results of examining the effect of variation in the temperature and variation in the Hct value on the response current value in applying a voltage of 2.0 V in the exemplary embodiment 2.

FIG. 56 represents the measured results when the glucose concentration in FIG. 55 was changed from 100 mg/dl to 400 mg/dl.

Similarly to the aforementioned results, it was also found that the response current value varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature, similarly to the aforementioned result of a glucose concentration of 100 mg/dl represented in FIG. 55.

Figure 57:
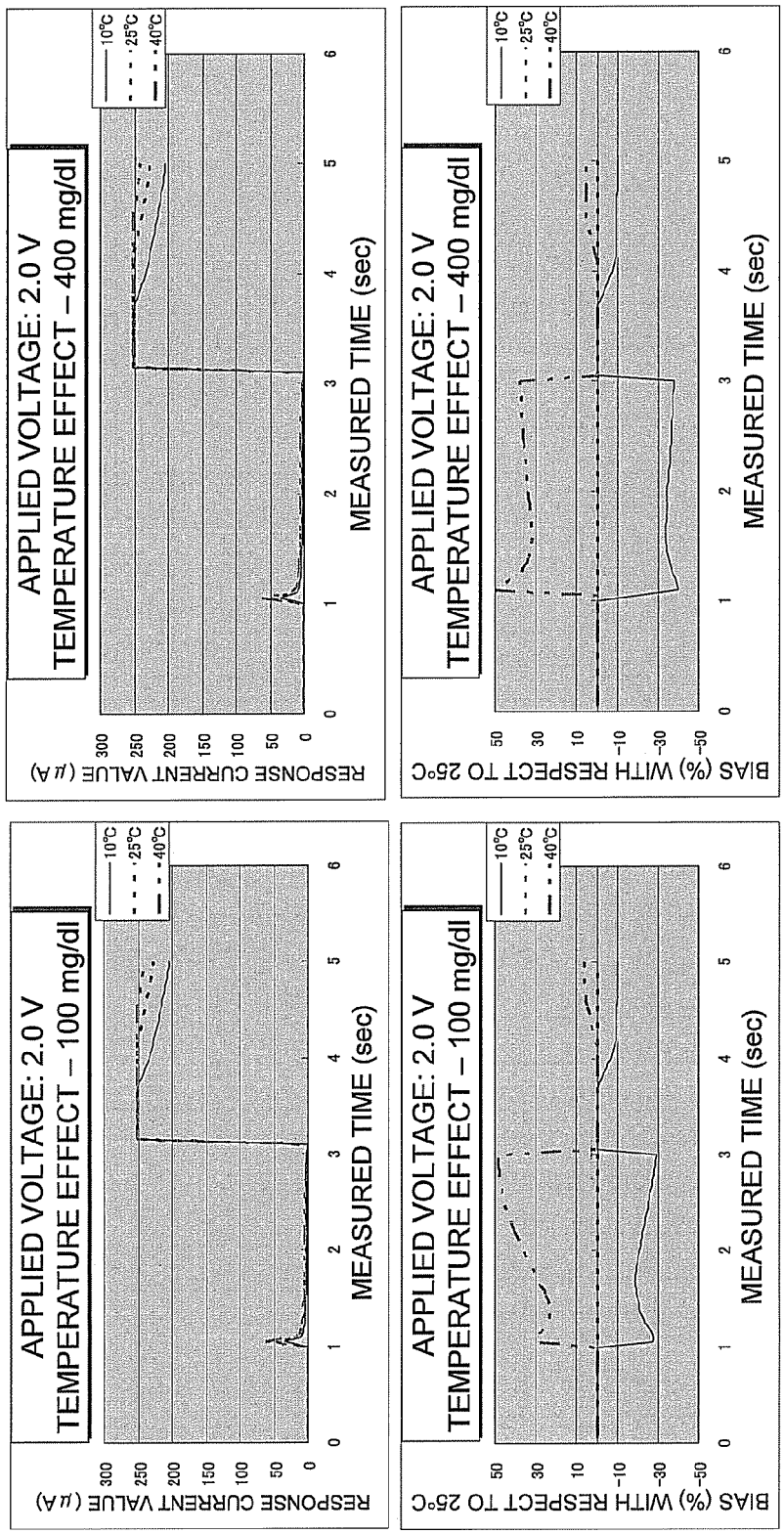
FIG. 57 includes charts representing a comprehensive result of examining the effect of variation in the temperature on the response current value in applying a voltage of 2.0 V in the exemplary embodiment 2.

FIG. 57 represents the measured results when the temperature conditions (10° C., 25° C. and 40° C.) were changed within each chart for easily understanding the effect of the blood sample temperature. It should be noted that the left upper and lower charts of FIG. 57 represent the measured results of response current values when the glucose concentration was set to be 100 mg/dl, whereas the right upper and lower charts of FIG. 57 represent the measured results of response current values when the glucose concentration was set to be 400 mg/dl.

It was consequently found that the response current value varied at both glucose concentrations of 100 mg/dl and 400 mg/dl in both measuring the temperature and measuring the glucose concentration when the blood sample temperature was changed. It was herein found that the temperature could be measured at a sensitivity of roughly 1° C./1%, similarly to the aforementioned result of an applied voltage of 1.5 V.

Figure 58:
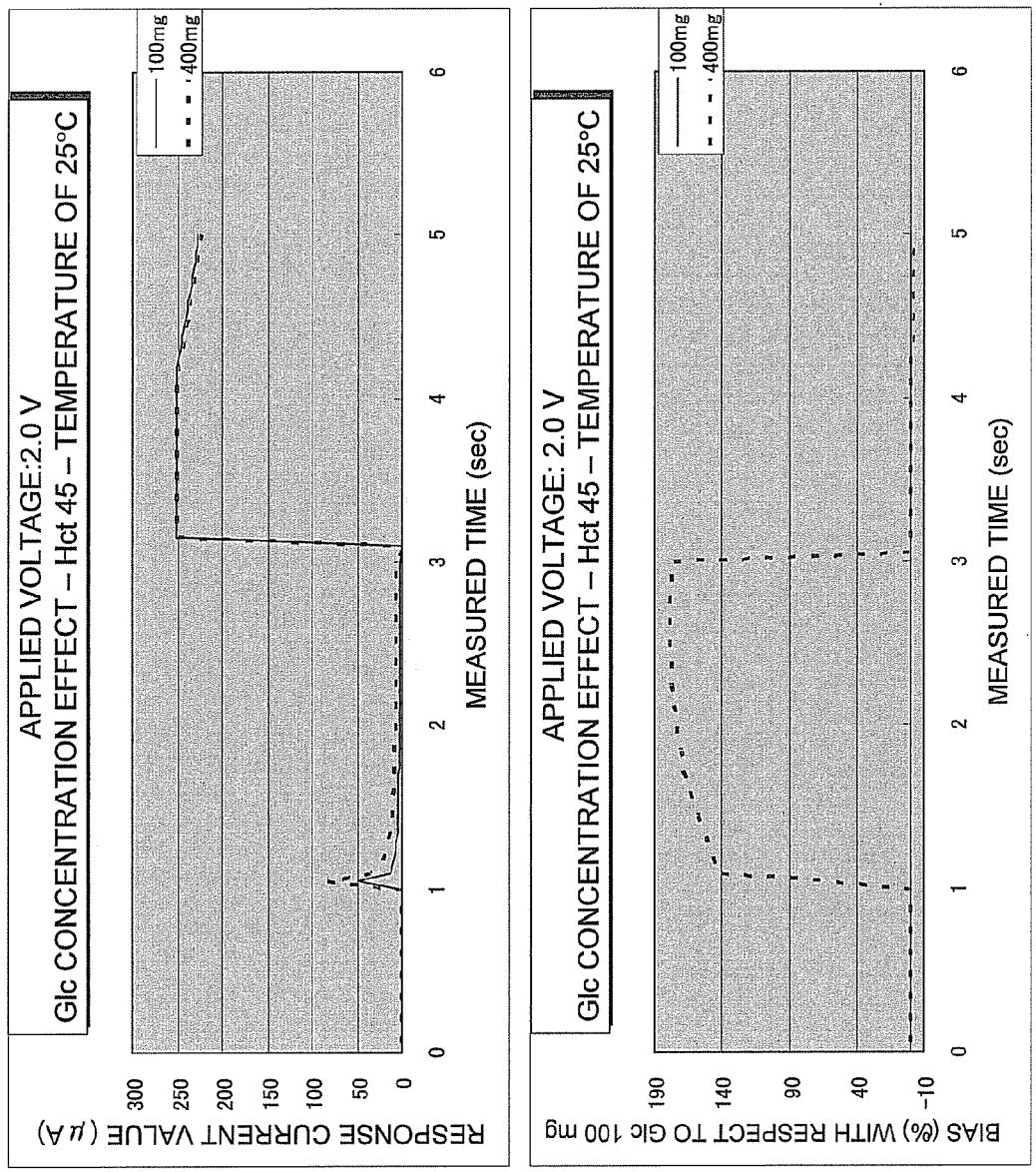
FIG. 58 includes charts representing a comprehensive result of examining the effect of variation in the glucose concentration on the response current value in applying a voltage of 2.0 V in the exemplary embodiment 2.

FIG. 58 represents the measured results when the glucose concentration was changed and set to be 100 mg/dl and 400 mg/dl in each chart for easily understanding the effect of the glucose concentration. It should be noted that the upper chart of FIG. 58 represents the measured results of response current values when the glucose concentration was set to be 100 mg/dl and 400 mg/dl, whereas the lower chart of FIG. 58 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature, similarly to the aforementioned results of applied voltages of 1.0 V to 1.75 V.

It was found from the aforementioned results that the response current value was not affected by variation in the glucose concentration and variation in the Hct value when the response current value was measured by applying a voltage of 2.0 V between the electrode A and the electrodes B and C and it was thereby possible to extract only the effect of variation in the temperature, similarly to the aforementioned results of applied voltages of 1.5 V and 1.75 V.

In the present exemplary embodiment, it is possible to exclude the effects of increase and reduction in the glucose concentration and increase and reduction in the Hct value by measuring the response current value through the application of a voltage of 1.5 V or greater between the electrode A and the electrodes B and C. It is thereby possible to use the present sensor chip as a temperature sensor.

<Applied Voltage of 2.5 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 2.5 V.

Figure 59:
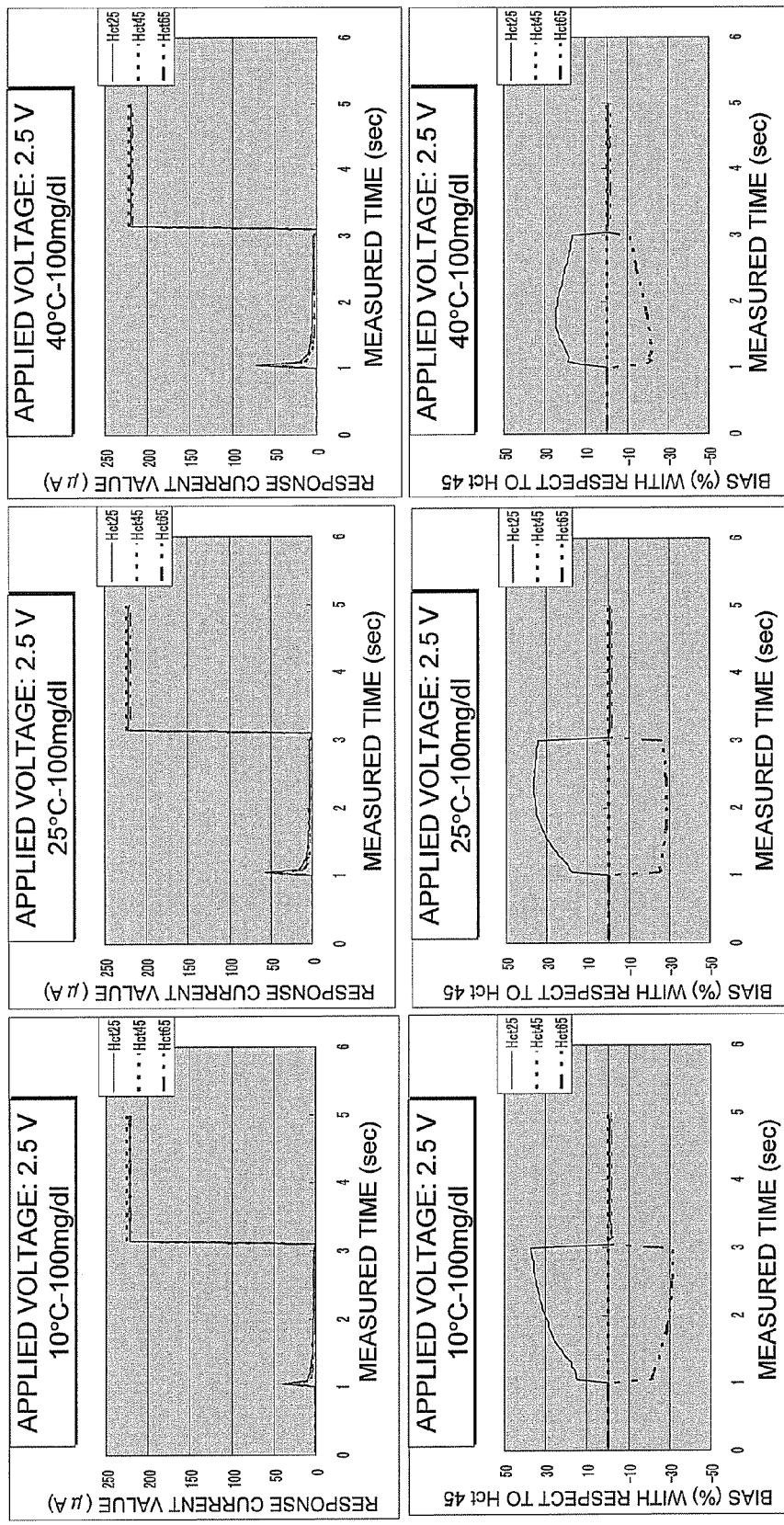
FIG. 59 includes charts representing the results of examining the effect of variation in the temperature and variation in the Hct value on the response current value in applying a voltage of 2.5 V in the exemplary embodiment 2.

In FIG. 59, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 59, each of the lower charts represents deviations of response current values corresponding to Hct values of 25 and 65 from a response current value corresponding to an Hct value of 45 in a corresponding one of the upper charts represented above the lower charts.

As represented in the charts of FIG. 59, it was consequently found that the response current value widely varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature, similarly to the aforementioned results of applied voltages of 1.5 V to 2.0 V.

Figure 60:
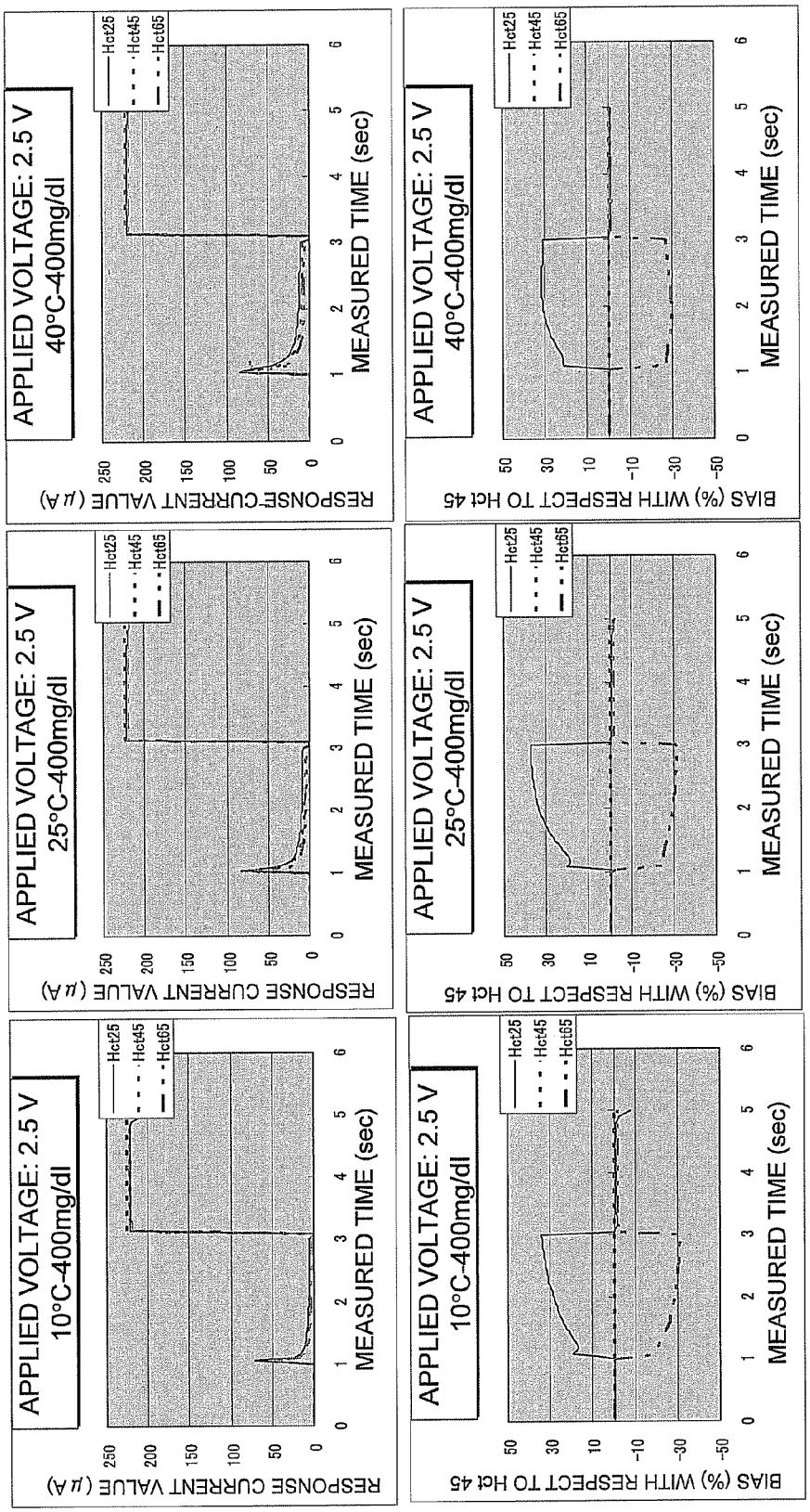
FIG. 60 includes charts representing the results of examining the effect of variation in the temperature and variation in the Hct value on the response current value in applying a voltage of 2.5 V in the exemplary embodiment 2.

FIG. 60 represents the measured results when the glucose concentration in FIG. 59 was changed from 100 mg/dl to 400 mg/dl.

Similarly to the aforementioned results, it was also found that the response current value varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature, similarly to the aforementioned result of a glucose concentration of 100 mg/dl represented in FIG. 59.

Figure 61:
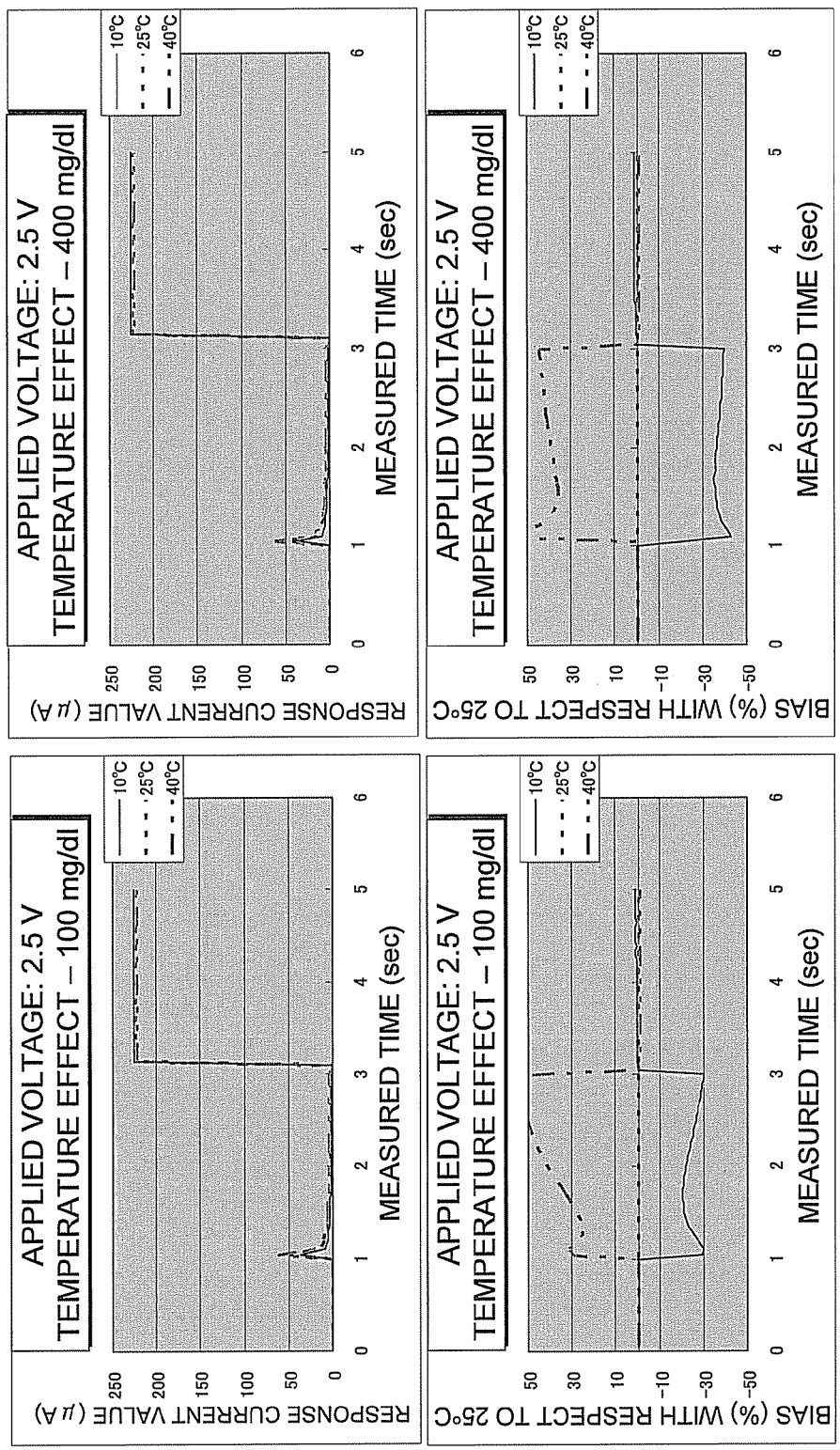
FIG. 61 includes charts representing a comprehensive result of examining the effect of variation in the temperature on the response current value in applying a voltage of 2.5 V in the exemplary embodiment 2.

FIG. 61 represents the measured results when the temperature conditions (10° C., 25° C. and 40° C.) were changed within each chart for easily understanding the effect of the blood sample temperature. It should be noted that the left upper and lower charts of FIG. 61 represent the measured results of response current values when the glucose concentration was set to be 100 mg/dl, whereas the right upper and lower charts of FIG. 61 represent the measured results of response current values when the glucose concentration was set to be 400 mg/dl.

It was consequently found that the response current value varied at both glucose concentrations of 100 mg/dl and 400 mg/dl in measuring the glucose concentration when the blood sample temperature was changed. However, it was herein found that the response current value hardly varied in measuring the temperature even through the blood sample temperature was changed.

Figure 62:
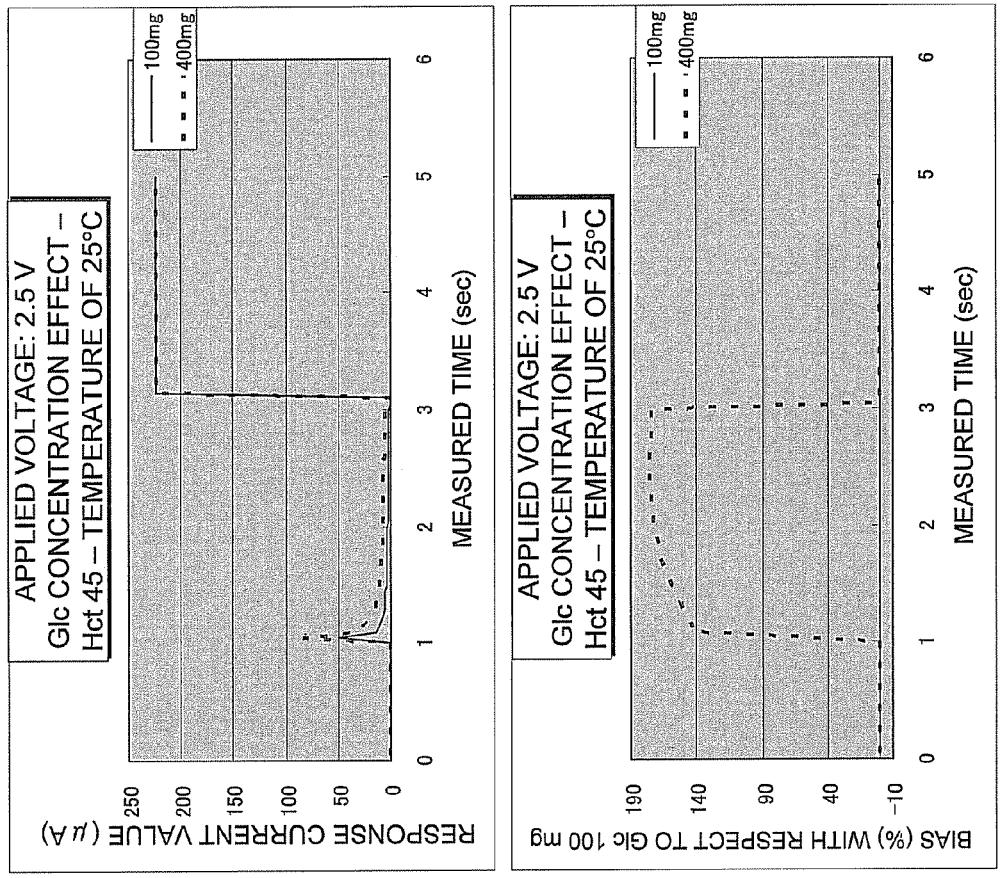
FIG. 62 includes charts representing a comprehensive result of examining the effect of variation in the glucose concentration on the response current value in applying a voltage of 2.5 V in the exemplary embodiment 2.

FIG. 62 represents the measured results when the glucose concentration was changed and set to be 100 mg/dl and 400 mg/dl in each chart for easily understanding the effect of the glucose concentration. It should be noted that the upper chart of FIG. 62 represents the measured results of response current values when the glucose concentration was set to be 100 mg/dl and 400 mg/dl, whereas the lower chart of FIG. 62 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature, similarly to the aforementioned results of applied voltages of 1.0 V to 1.75 V.

It was found from the aforementioned results that the response current value was not affected by variation in the temperature as well as by variation in the glucose concentration and variation in the Hct value when the response current value was measured by applying a voltage of 2.5 V between the electrode A and the electrodes B and C, similarly to the aforementioned results of applied voltages of 1.5 V and 2.0 V.

In the present exemplary embodiment, it is possible to exclude the effects of increase and reduction in the glucose concentration and increase and reduction in the Hct value by measuring the response current value through the application of a voltage of 2.5 V between the electrode A and the electrodes B and C. However, the applied voltage was herein too high, and a sensitivity as a temperature sensor was reduced. It was consequently found that the present sensor chip could not be used as a temperature sensor.

<Applied Voltage of 3.0 V>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 3.0 V.

Figure 63:
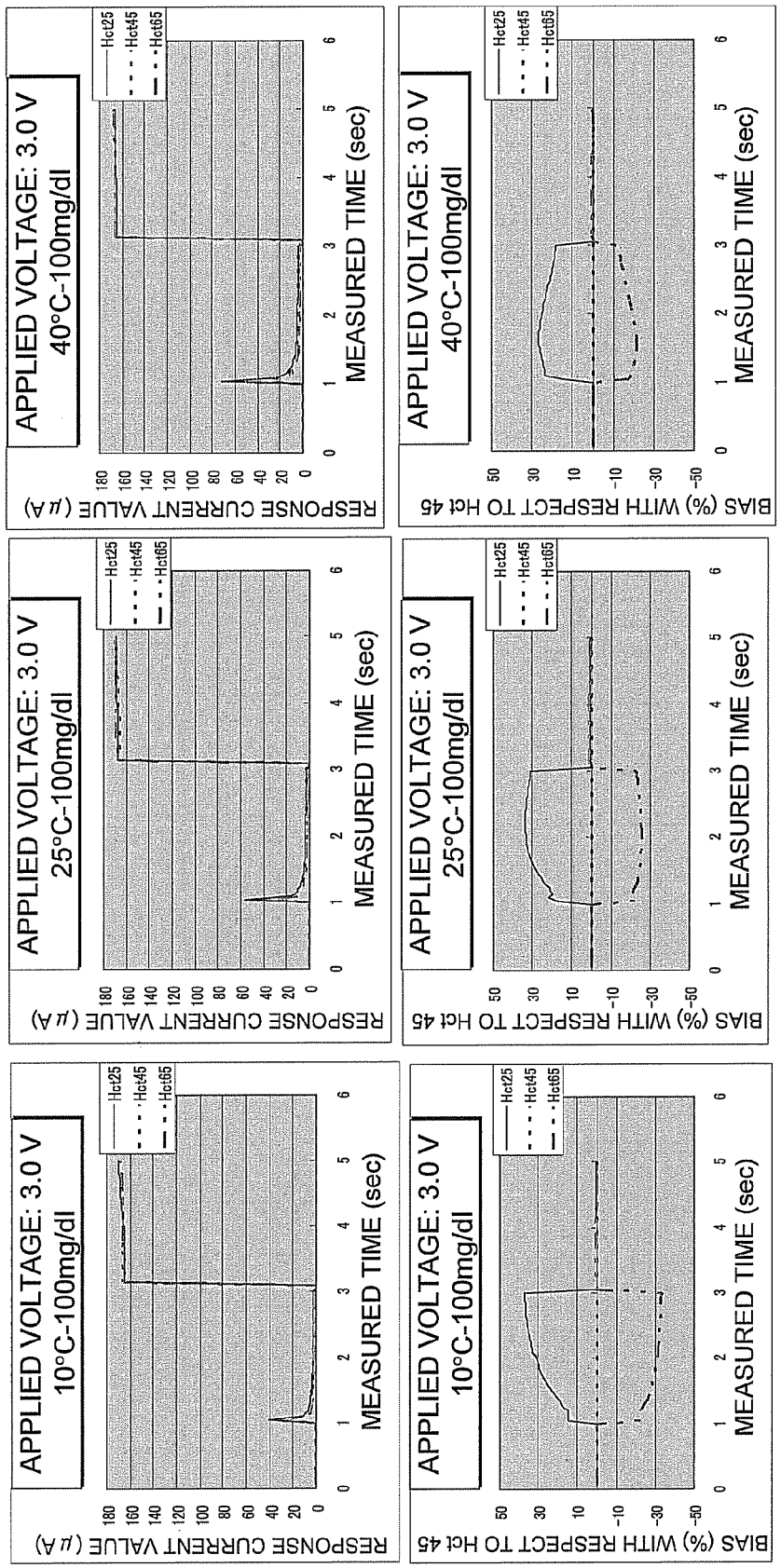
FIG. 63 includes charts representing the results of examining the effect of variation in the temperature and variation in the Hct value on the response current value in applying a voltage of 3.0 V in the exemplary embodiment 2.

In FIG. 63, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 63, each of the lower charts represents deviations of response current values corresponding to Hct values of 25 and 65 from a response current value corresponding to an Hct value of 45 in a corresponding one of the upper charts represented above the lower charts.

As represented in the charts of FIG. 63, it was consequently found that the response current value widely varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature, similarly to the aforementioned results of applied voltages of 1.5 V to 2.5 V.

Figure 64:
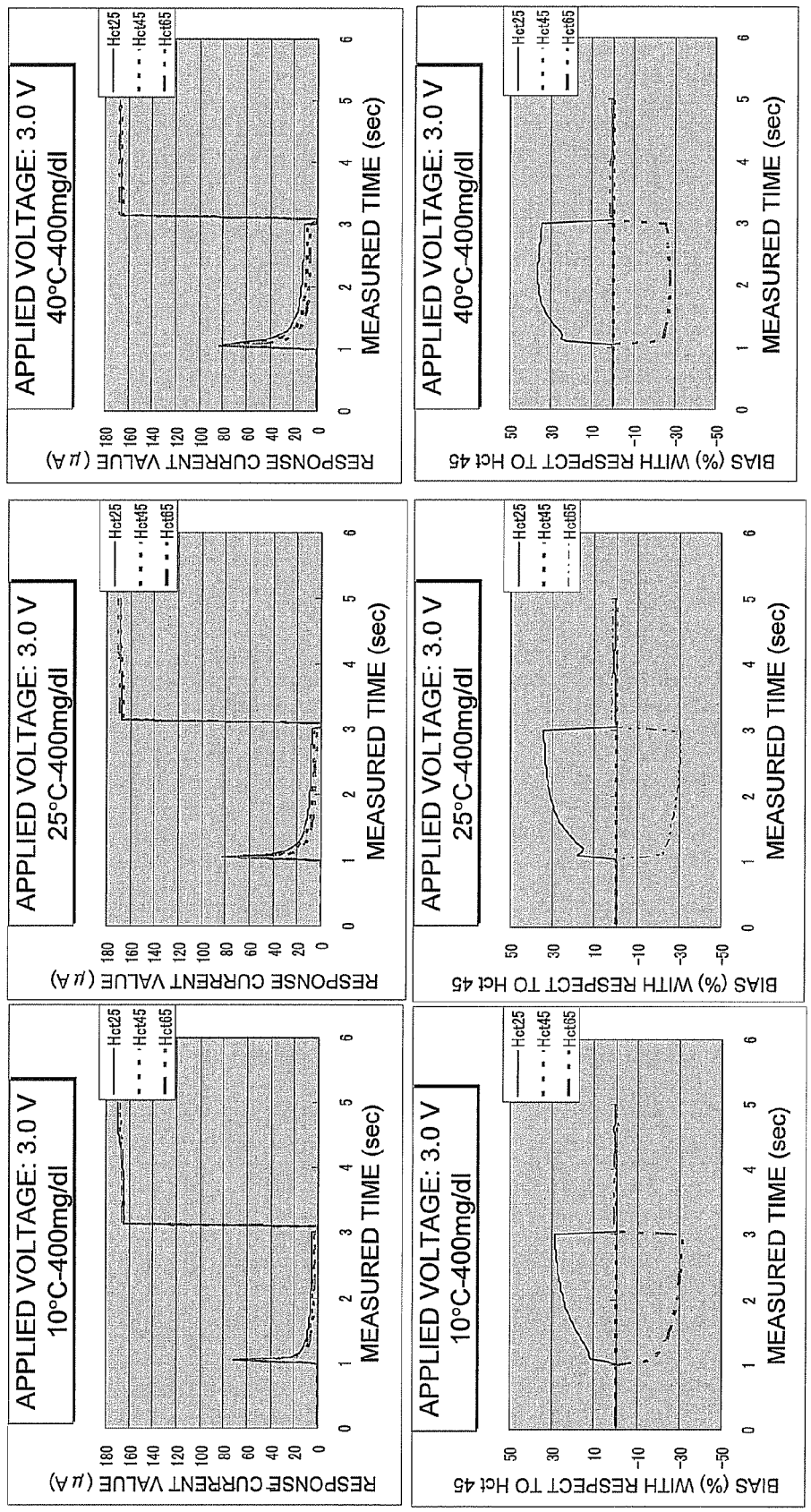
FIG. 64 includes charts representing the results of examining the effect of variation in the temperature and variation in the Hct value on the response current value in applying a voltage of 3.0 V in the exemplary embodiment 2.

FIG. 64 represents the measured results when the glucose concentration in FIG. 63 was changed from 100 mg/dl to 400 mg/dl.

Similarly to the aforementioned results, it was also found that the response current value varied due to increase and reduction in the Hct value at the respective blood sample temperatures of 10° C., 25° C. and 40° C. in measuring the glucose concentration. On the other hand, it was found that the response current value hardly varied due to increase and reduction in the Hct value in measuring the temperature, similarly to the aforementioned result of a glucose concentration of 100 mg/dl represented in FIG. 63.

Figure 65:
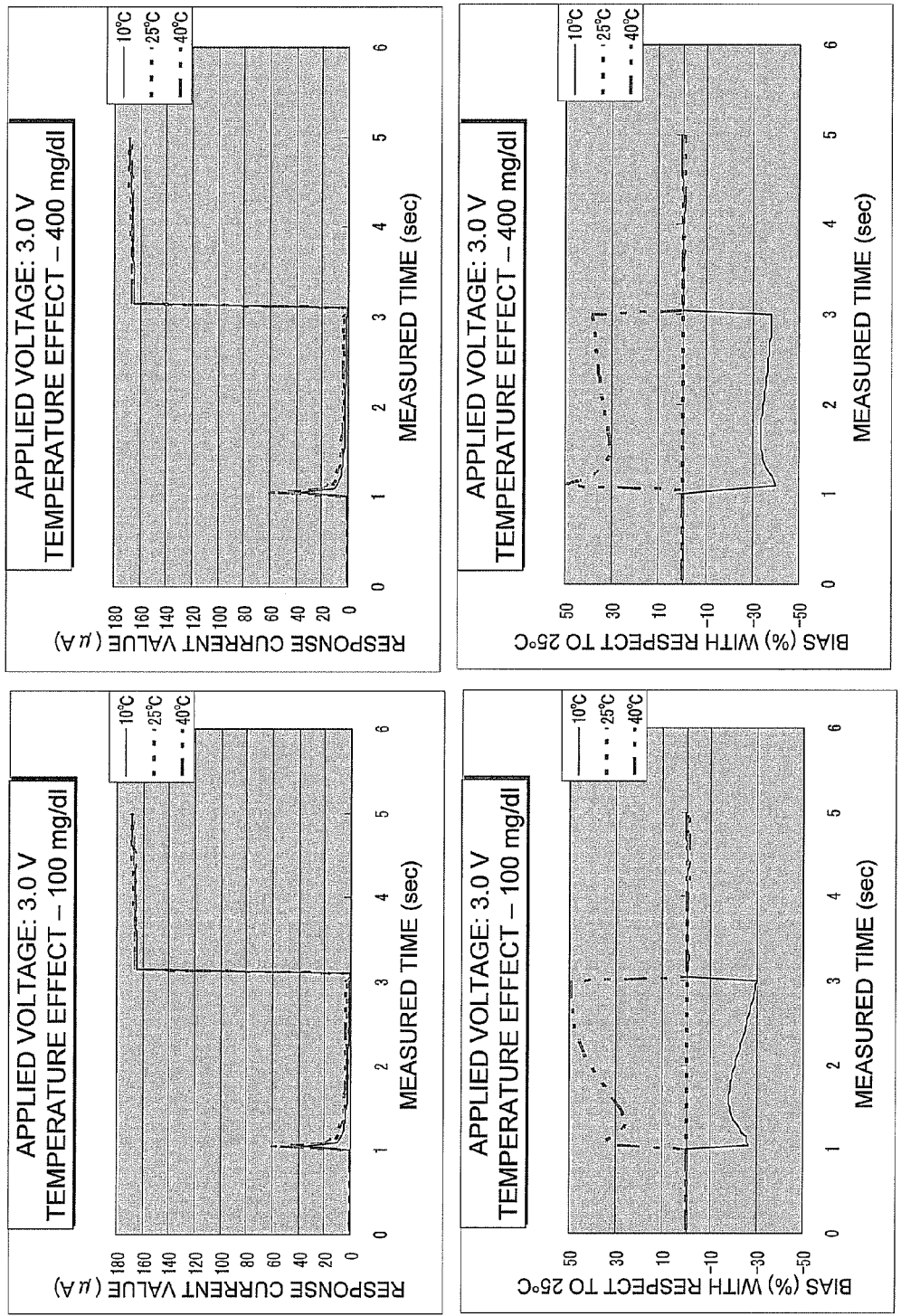
FIG. 65 includes charts representing a comprehensive result of examining the effect of variation in the temperature on the response current value in applying a voltage of 3.0 V in the exemplary embodiment 2.

FIG. 65 represents the measured results when the temperature conditions (10° C., 25° C. and 40° C.) were changed within each chart for easily understanding the effect of the blood sample temperature. It should be noted that the left upper and lower charts of FIG. 65 represent the measured results of response current values when the glucose concentration was set to be 100 mg/dl, whereas the right upper and lower charts of FIG. 65 represent the measured results of response current values when the glucose concentration was set to be 400 mg/dl.

It was consequently found that the response current value varied at both glucose concentrations of 100 mg/dl and 400 mg/dl in measuring the glucose concentration when the blood sample temperature was changed. However, it was herein found that the response current value hardly varied in measuring the temperature even through the blood sample temperature was changed.

Figure 66:
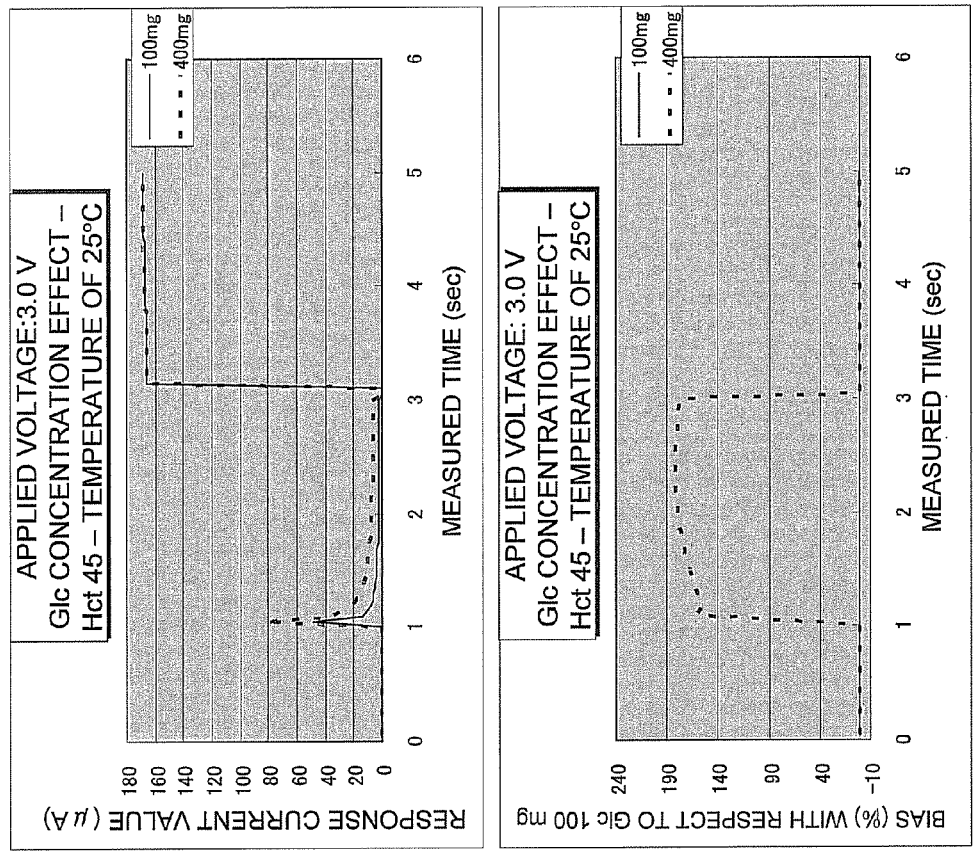
FIG. 66 includes charts representing a comprehensive result of examining the effect of variation in the glucose concentration on the response current value in applying a voltage of 3.0 V in the exemplary embodiment 2.

FIG. 66 represents the measured results when the glucose concentration was changed and set to be 100 mg/dl and 400 mg/dl in each chart for easily understanding the effect of the glucose concentration. It should be noted that the upper chart of FIG. 66 represents the measured results of response current values when the glucose concentration was set to be 100 mg/dl and 400 mg/dl, whereas the lower chart of FIG. 66 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature, similarly to the aforementioned results of applied voltages of 1.0 V to 2.5 V.

It was found from the aforementioned results that the response current value was not affected by variation in the temperature as well as by variation in the glucose concentration and variation in the Hct value when the response current value was measured by applying a voltage of 3.0 V between the electrode A and the electrodes B and C, similarly to the aforementioned results of applied voltages of 1.5 V and 2.5 V.

In the present exemplary embodiment, it is possible to exclude the effects of increase and reduction in the glucose concentration and increase and reduction in the Hct value by measuring the response current value through the application of a voltage of 3.0 V between the electrode A and the electrodes B and C. However, the applied voltage was herein too high, and a sensitivity as a temperature sensor was reduced. It was consequently found that the present sensor chip could not be used as a temperature sensor.

<Reagent Amount of 1.5 Times>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 1.0 V under the condition that the amount of the reagent was multiplied by 1.5 times in the reaction reagent layers respectively disposed on the electrodes A, B and C.

Specifically, the reagent herein used was obtained by changing weight percent of the compositions dissolved in $H_2O$ (water) in the reaction reagent layer 20 of the aforementioned exemplary embodiment represented in FIG. 4 as follows. The weight percent of potassium ferricyanide in $H_2O$ was changed from 1.7 wt % to 2.55 wt %. The weight percent of taurine in $H_2O$ was changed from 1.0 wt % to 1.5 wt %. The weight percent of maltitol in $H_2O$ was changed from 0.1 wt % to 0.2 wt %.

Figure 67:
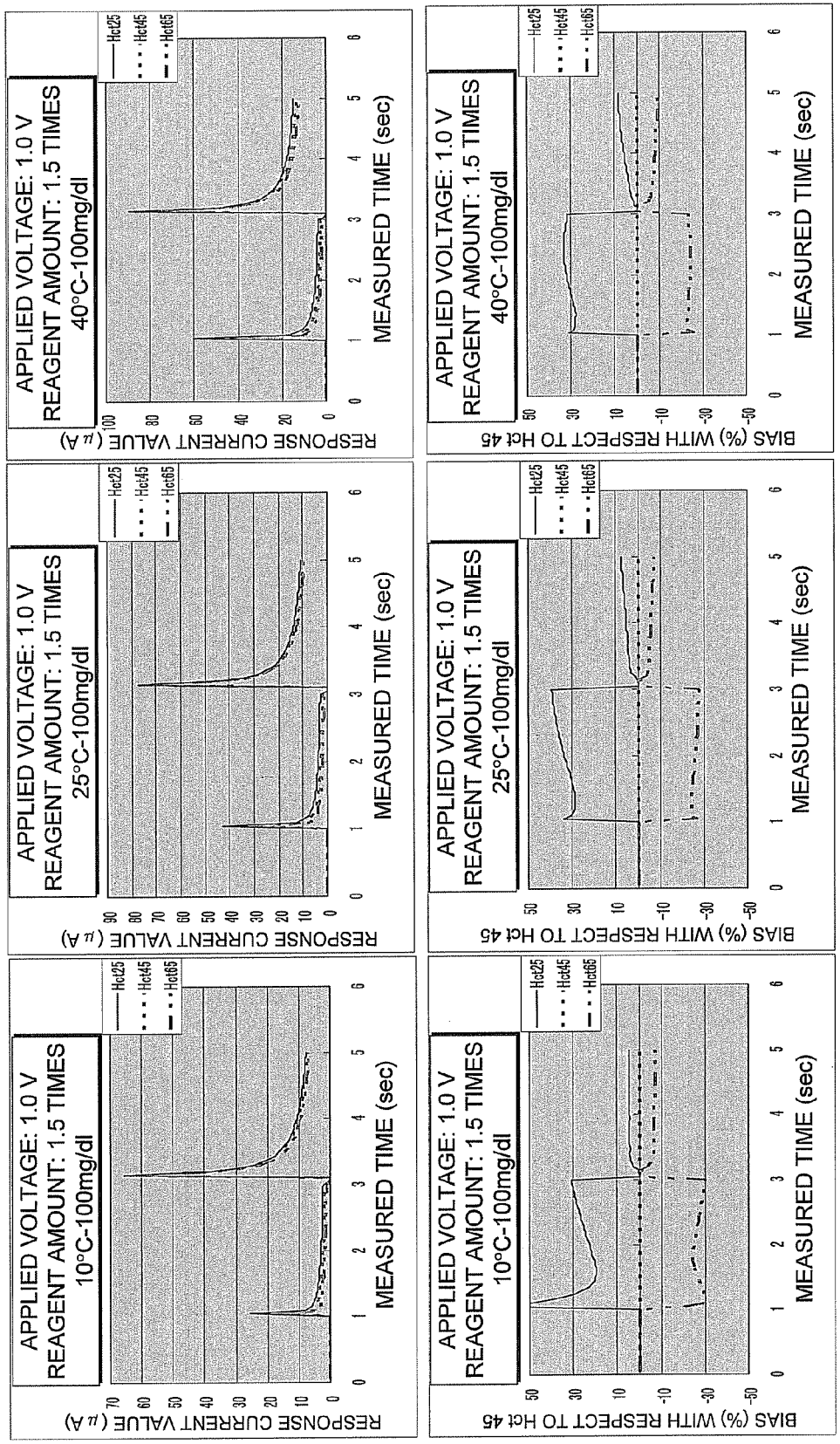
FIG. 67 includes charts representing the results of examining the effect of variation in the temperature and variation in the Hct value on the response current value in multiplying the amount of a reagent by 1.5 times and applying a voltage of 1.0 V in the exemplary embodiment 2.

In FIG. 67, the left to right upper charts respectively represent variation in the response current value when the temperature was changed and set to be 10° C., 25° C. and 40° C. Each chart represents variation in the response current value when the Hct value was changed and set to be 25, 45 and 65.

Further in FIG. 67, each of the lower charts represents deviations of response current values corresponding to Hct values of 25 and 65 from a response current value corresponding to an Hct value of 45 in a corresponding one of the upper charts represented above the lower charts.

As represented in the charts of FIG. 67, it was consequently found that the response current value widely varied due to increase and reduction in the Hct value at the respective blood sample temperatures of 10° C., 25° C. and 40° C. in both measuring the glucose concentration and measuring the temperature.

Figure 68:
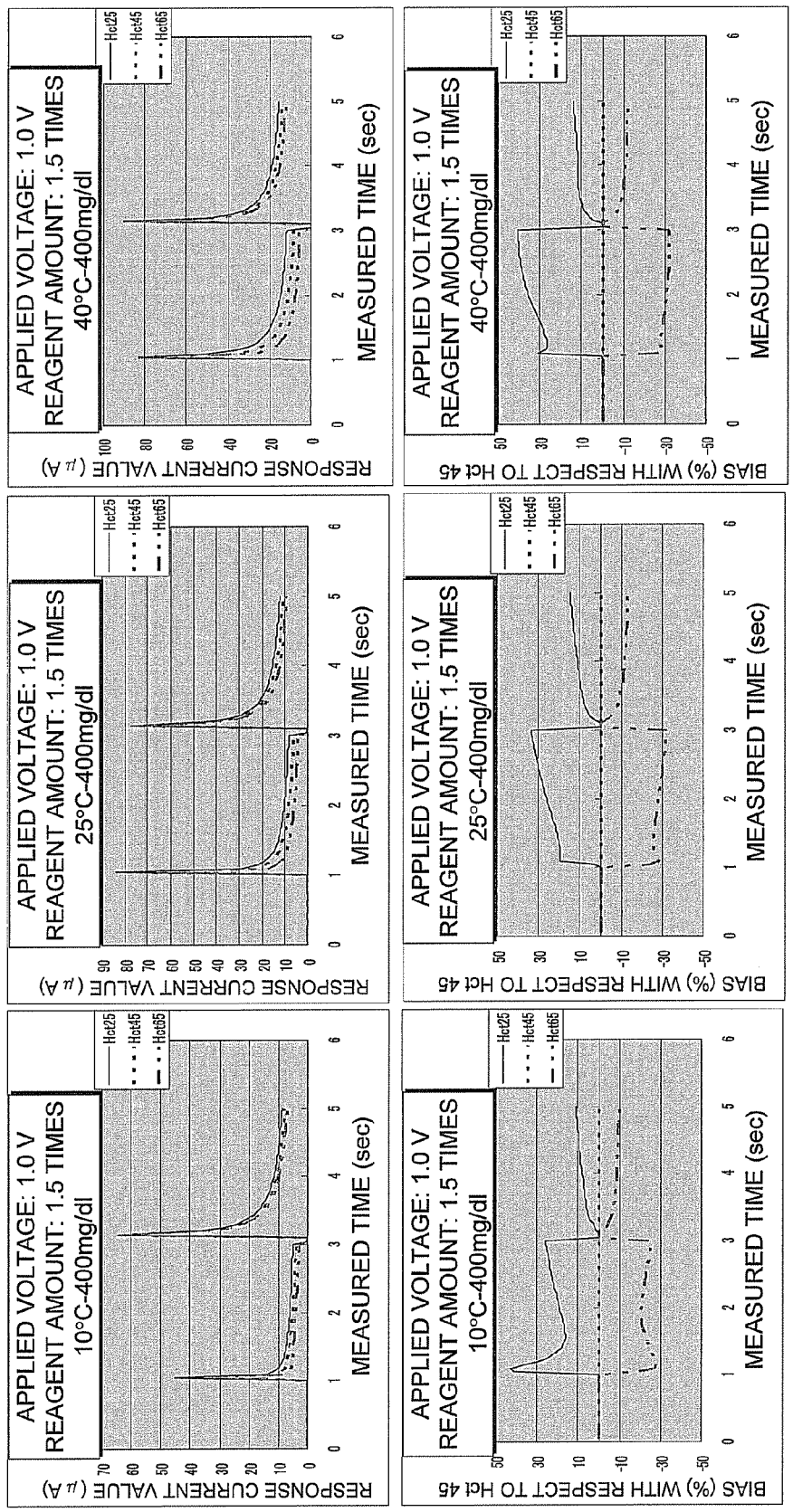
FIG. 68 includes charts representing the results of examining the effect of variation in the temperature and variation in the Hct value on the response current value in multiplying the amount of a reagent by 1.5 times and applying a voltage of 1.0 V in the exemplary embodiment 2.

FIG. 68 represents the measured results when the glucose concentration in FIG. 67 was changed from 100 mg/dl to 400 mg/dl.

Similarly to the aforementioned results, it was also found that the response current value widely varied due to increase and reduction in the Hct value at the respective blood sample temperatures of 10° C., 25° C. and 40° C. in both measuring the glucose concentration and measuring the temperature.

Figure 69:
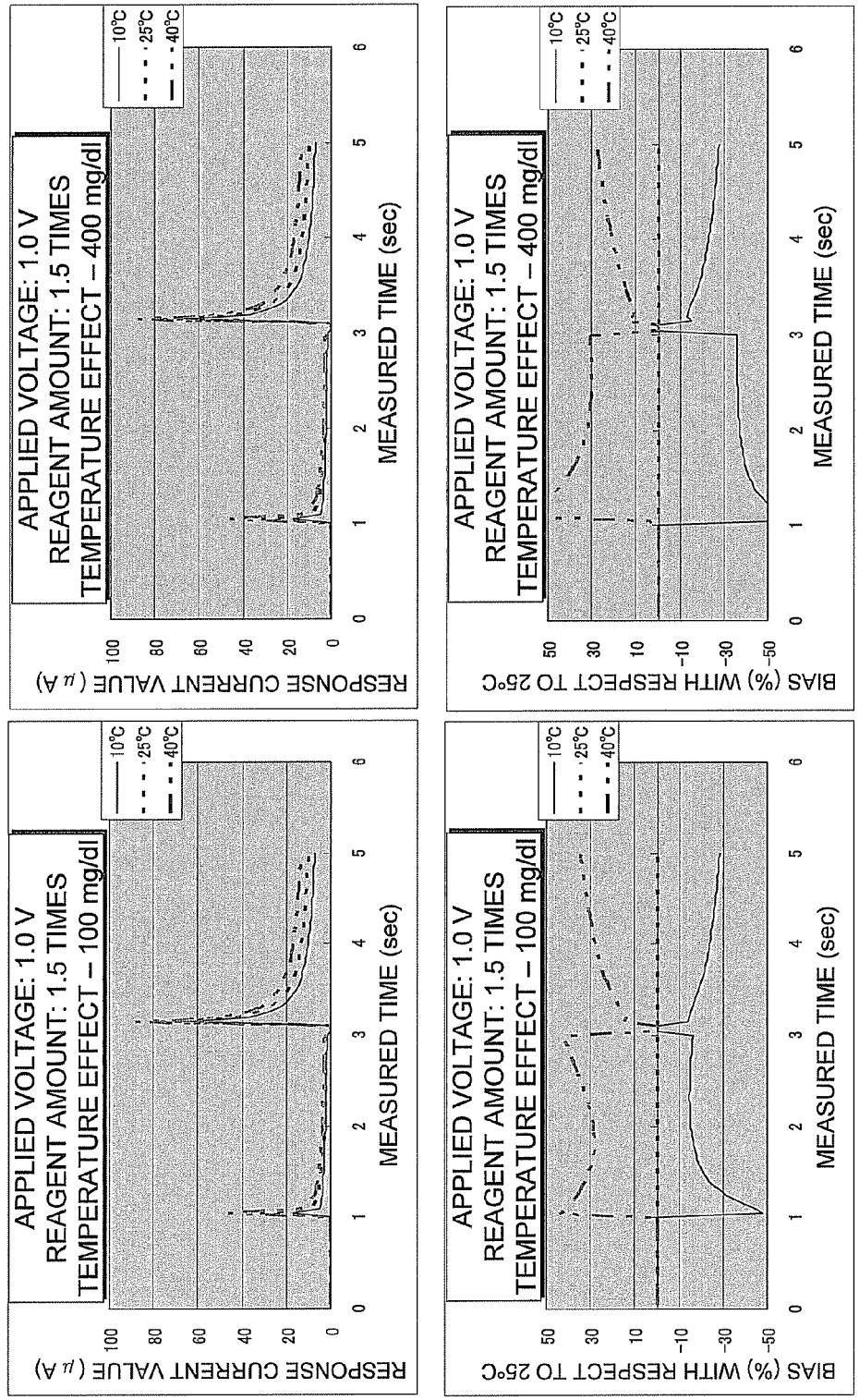
FIG. 69 includes charts representing a comprehensive result of examining the effect of variation in the temperature on the response current value in multiplying the amount of a reagent by 1.5 times and applying a voltage of 1.0 V in the exemplary embodiment 2.

FIG. 69 represents the measured results when the temperature conditions (10° C., 25° C. and 40° C.) were changed within each chart for easily understanding the effect of the blood sample temperature. It should be noted that the left upper and lower charts of FIG. 69 represent the measured results of response current values when the glucose concentration was set to be 100 mg/dl, whereas the right upper and lower charts of FIG. 69 represent the measured results of response current values when the glucose concentration was set to be 400 mg/dl.

It was consequently found that the response current value widely varied at both glucose concentrations of 100 mg/dl and 400 mg/dl in both measuring the temperature and measuring the glucose concentration when the blood sample temperature was changed.

Figure 70:
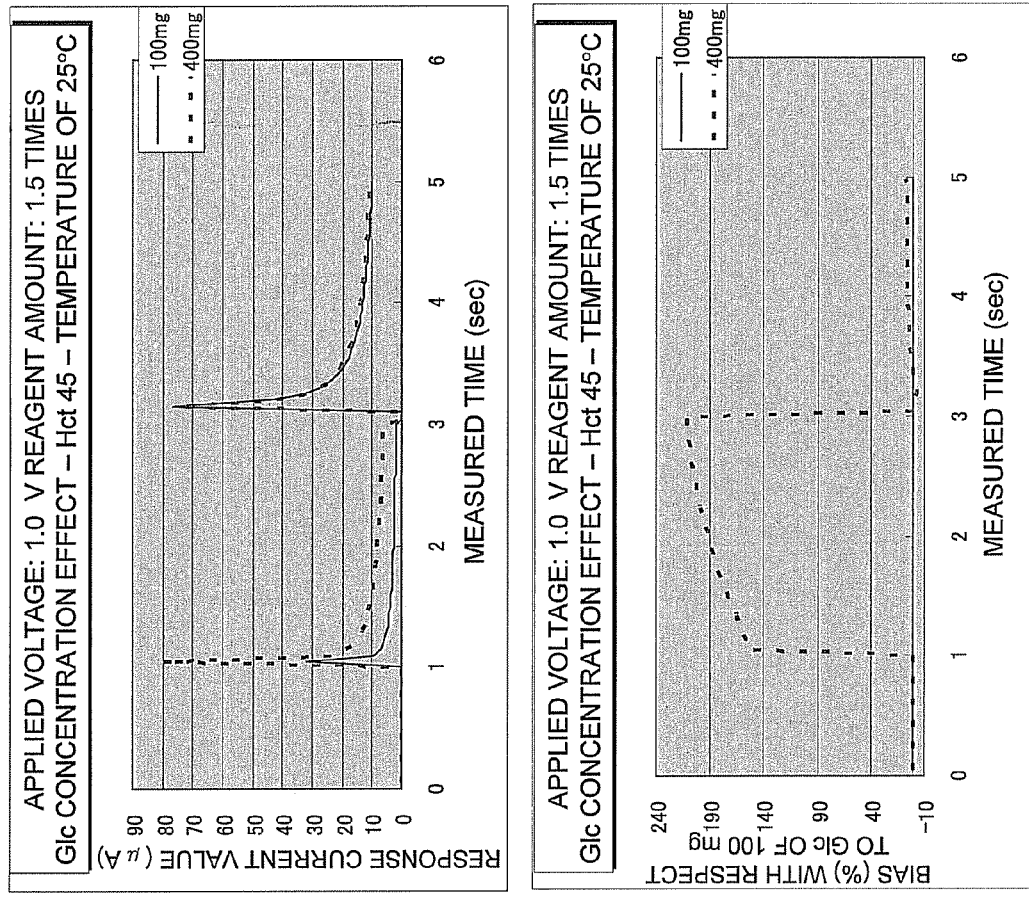
FIG. 70 includes charts representing a comprehensive result of examining the effect of variation in the glucose concentration on the response current value in multiplying the amount of a reagent by 1.5 times and applying a voltage of 1.0 V in the exemplary embodiment 2.

FIG. 70 represents the measured results when the glucose concentration was changed and set to be 100 mg/dl and 400 mg/dl in each chart for easily understanding the effect of the glucose concentration. It should be noted that the upper chart of FIG. 70 represents the measured results of response current values when the glucose concentration was set to be 100 mg/dl and 400 mg/dl, whereas the lower chart of FIG. 70 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature when the glucose concentration was changed and set to be 100 mg/dl and 400 mg/dl.

It was found from the aforementioned results that the response current value was affected by variation in the Hct value and variation in the temperature when the response current value was measured by applying a voltage of 1.0 V between the electrode A and the electrodes B and C under the condition that the amount of the reagent is multiplied by 1.5 times in the reaction reagent layers respectively disposed on the electrodes, and it was thereby impossible to extract only the effect of variation in the temperature. However, it was found from the results represented in FIG. 70 that the response current value was hardly affected by increase and reduction in the glucose concentration in measuring the temperature (i.e., in a measured time period from 3.0 second to 5.0 second) when a voltage of 1.0 V was applied between the electrode A and the electrodes B and C, similarly to the measured results of the amount of the reagent in the normal conditions.

<Reagent Amount of 0.5 Times>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 1.0 V under the condition that the amount of the reagent was multiplied by 0.5 times in the reaction reagent layers respectively disposed on the electrodes A, B and C.

Specifically, the reagent herein used was obtained by changing weight percent of the compositions dissolved in $H_2O$ (water) in the reaction reagent layer 20 of the aforementioned exemplary embodiment represented in FIG. 4 as follows. The weight percent of potassium ferricyanide in $H_2O$ was changed from 1.7 wt % to 0.85 wt %. The weight percent of taurine in $H_2O$ was changed from 1.0 wt % to 0.5 wt %. The weight percent of maltitol in $H_2O$ was changed from 0.1 wt % to 0.05 wt %.

Figure 71:
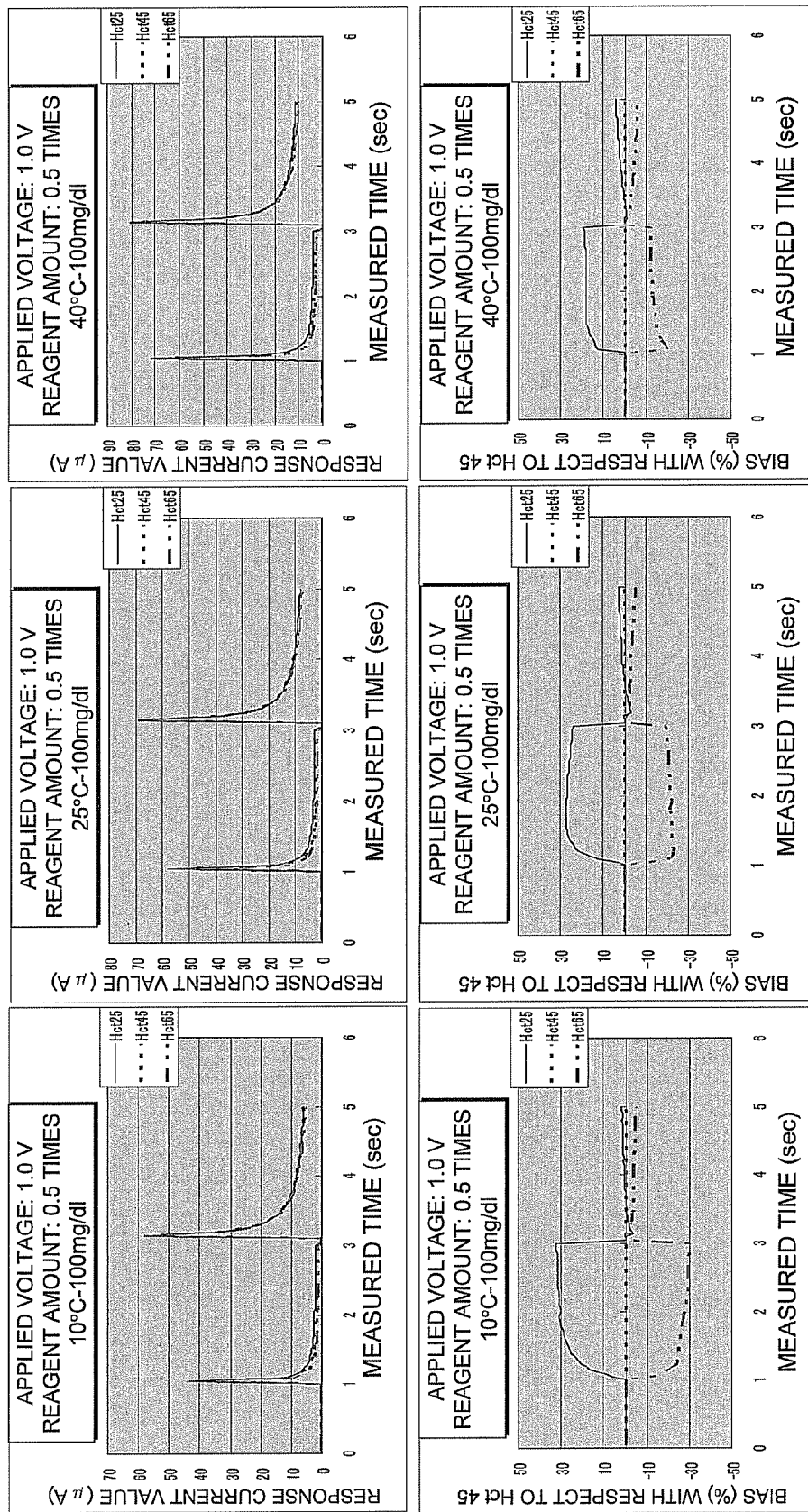
FIG. 71 includes charts representing the results of examining the effect of variation in the temperature and variation in the Hct value on the response current value in multiplying the amount of a reagent by 0.5 times and applying a voltage of 1.0 V in the exemplary embodiment 2.

In FIG. 71, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 71, each of the lower charts represents deviations of response current values corresponding to Hct values of 25 and 65 from a response current value corresponding to an Hct value of 45 in a corresponding one of the upper charts represented above the lower charts.

As represented in the charts of FIG. 71, it was consequently found that the response current value varied due to increase and reduction in the Hct value at the respective blood sample temperatures of 10° C., 25° C. and 40° C. in both measuring the glucose concentration and measuring the temperature.

Figure 72:
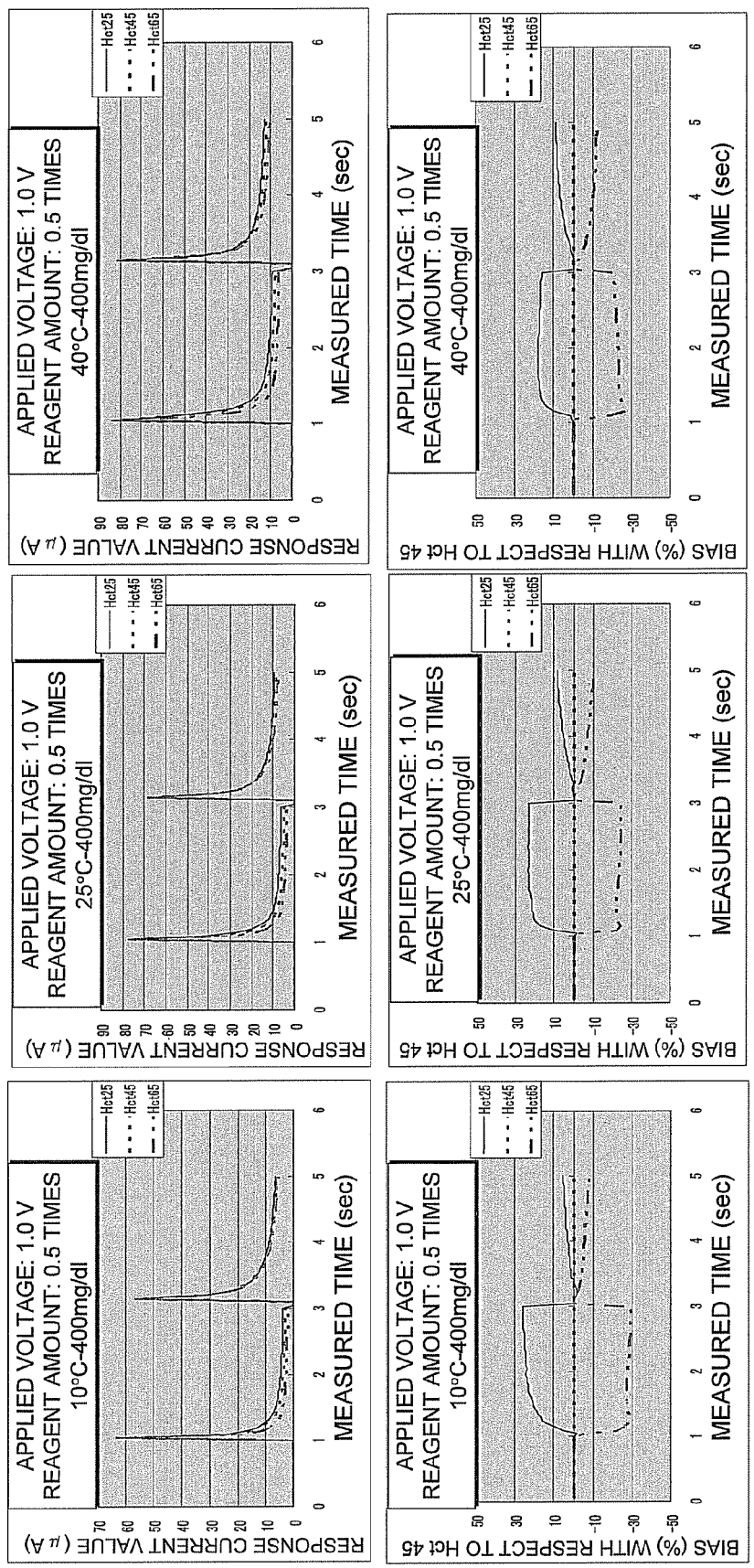
FIG. 72 includes charts representing the results of examining the effect of variation in the temperature and variation in the Hct value on the response current value in multiplying the amount of a reagent by 0.5 times and applying a voltage of 1.0 V in the exemplary embodiment 2.

FIG. 72 represents the measured results when the glucose concentration in FIG. 71 was changed from 100 mg/dl to 400 mg/dl.

Similarly to the aforementioned results, it was also found that the response current value varied due to increase and reduction in the Hct value at the respective blood sample temperatures of 10° C., 25° C. and 40° C. in both measuring the glucose concentration and measuring the temperature.

Figure 73:
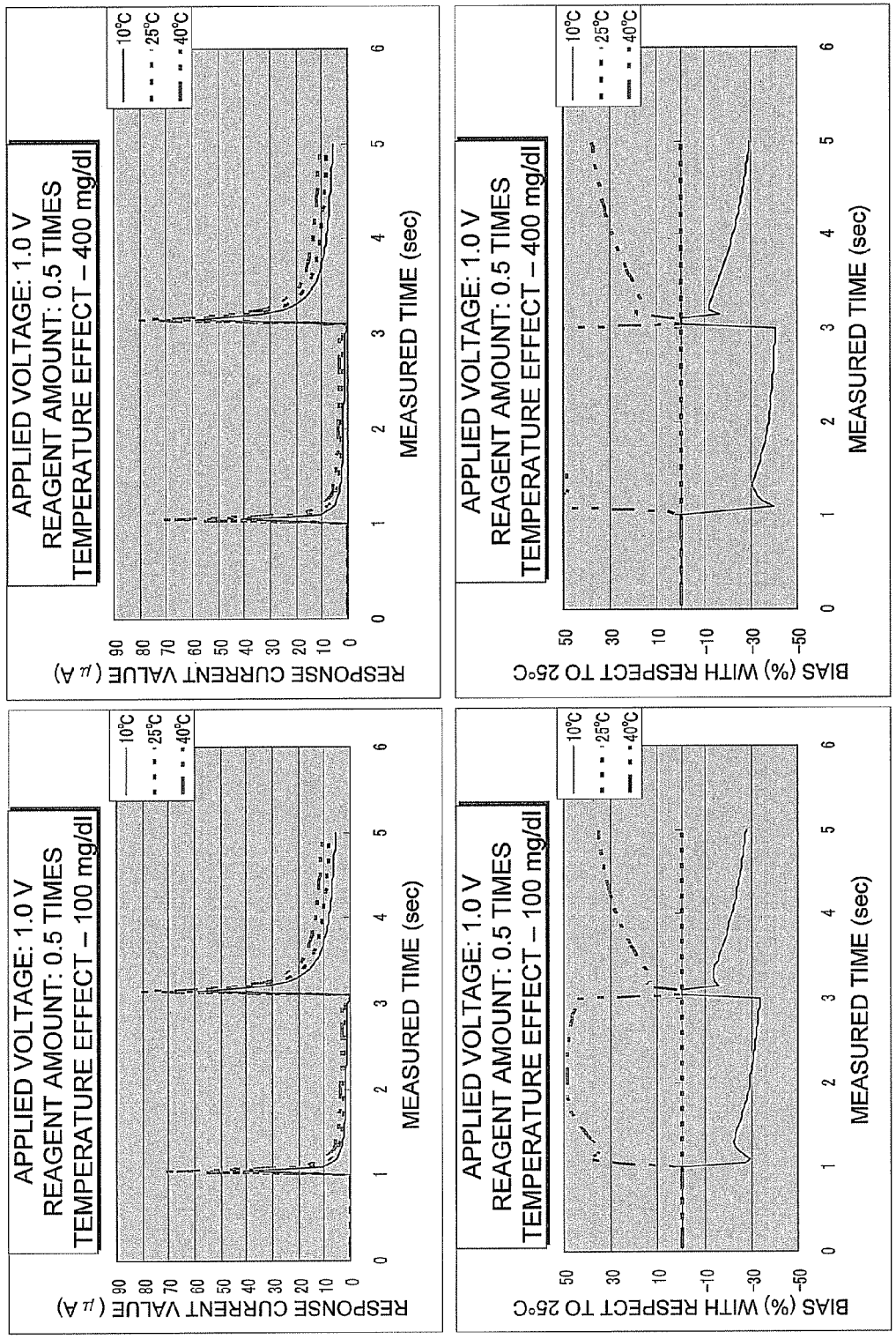
FIG. 73 includes charts representing a comprehensive result of examining the effect of variation in the temperature on the response current value in multiplying the amount of a reagent by 0.5 times and applying a voltage of 1.0 V in the exemplary embodiment 2.

FIG. 73 represents the measured results when the temperature conditions (10° C., 25° C. and 40° C.) were changed within each chart for easily understanding the effect of the blood sample temperature. It should be noted that the left upper and lower charts of FIG. 73 represent the measured results of response current values when the glucose concentration was set to be 100 mg/dl, whereas the right upper and lower charts of FIG. 73 represent the measured results of response current values when the glucose concentration was set to be 400 mg/dl.

It was consequently found that the response current value widely varied at both glucose concentrations of 100 mg/dl and 400 mg/dl in both measuring the temperature and measuring the glucose concentration when the blood sample temperature was changed.

Figure 74:
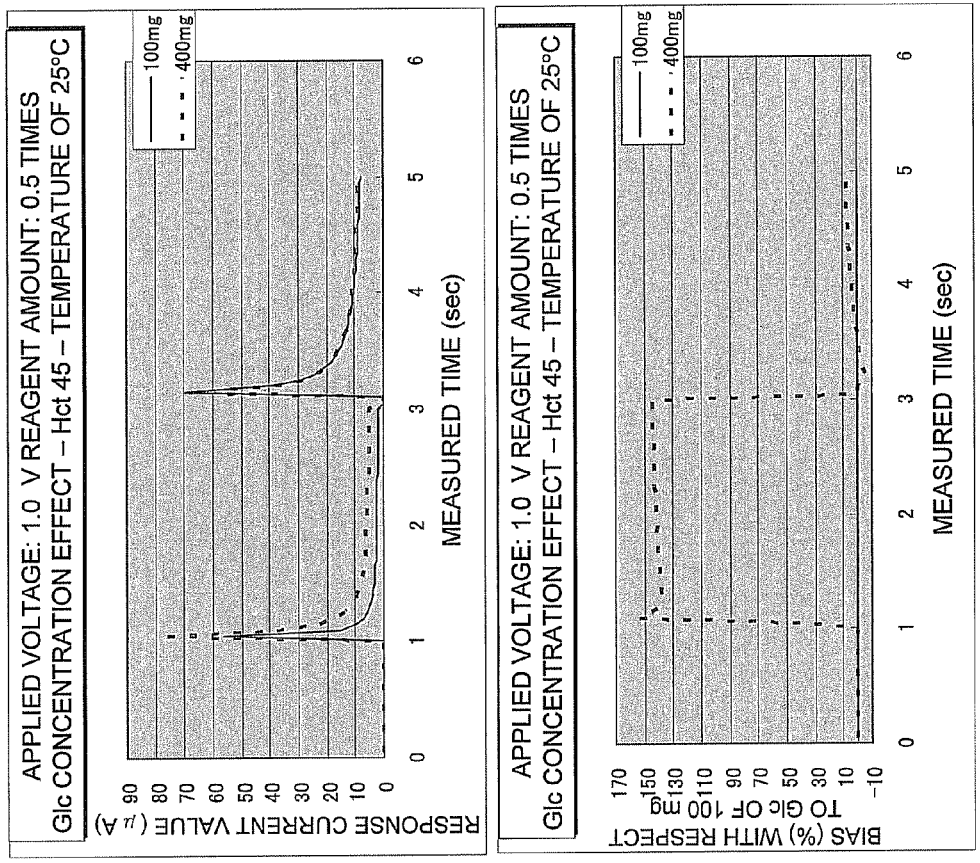
FIG. 74 includes charts representing a comprehensive result of examining the effect of variation in the glucose concentration on the response current value in multiplying the amount of a reagent by 0.5 times and applying a voltage of 1.0 V in the exemplary embodiment 2.

FIG. 74 represents the measured results when the glucose concentration was changed and set to be 100 mg/dl and 400 mg/dl in each chart for easily understanding the effect of the glucose concentration. It should be noted that the upper chart of FIG. 74 represents the measured results of response current values when the glucose concentration was set to be 100 mg/dl and 400 mg/dl, whereas the lower chart of FIG. 74 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature when the glucose concentration was changed and set to be 100 mg/dl and 400 mg/dl.

It was found from the aforementioned results that the response current value was affected by variation in the Hct value and variation in the temperature when the response current value was measured by applying a voltage of 1.0 V between the electrode A and the electrodes B and C under the condition that the amount of the reagent is multiplied by 0.5 times in the reaction reagent layers respectively disposed on the electrodes, and it was thereby impossible to extract only the effect of variation in the temperature. However, it was found from the results represented in FIG. 74 that the response current value was hardly affected by increase and reduction in the glucose concentration in measuring the temperature (i.e., in a measured time period from 3.0 second to 5.0 second) when a voltage of 1.0 V was applied between the electrode A and the electrodes B and C, similarly to the measured results of the amount of the reagent in the normal condition.

Therefore, it was found that the response current value was hardly affected by the amounts of the reagent multiplied by 0.5 times, 1.0 times and 1.5 times when a voltage of 1.0 V was applied between the electrode A and the electrodes B and C. It was consequently found that the response current value was hardly affected by increase and reduction in the amount of the reagent.

<Spacer Thickness of 50 μm>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 1.5 V under the condition that the thickness of the spacer interposed between the substrate and the upper cover was changed from 100 μm to 50 μm.

Figure 75:
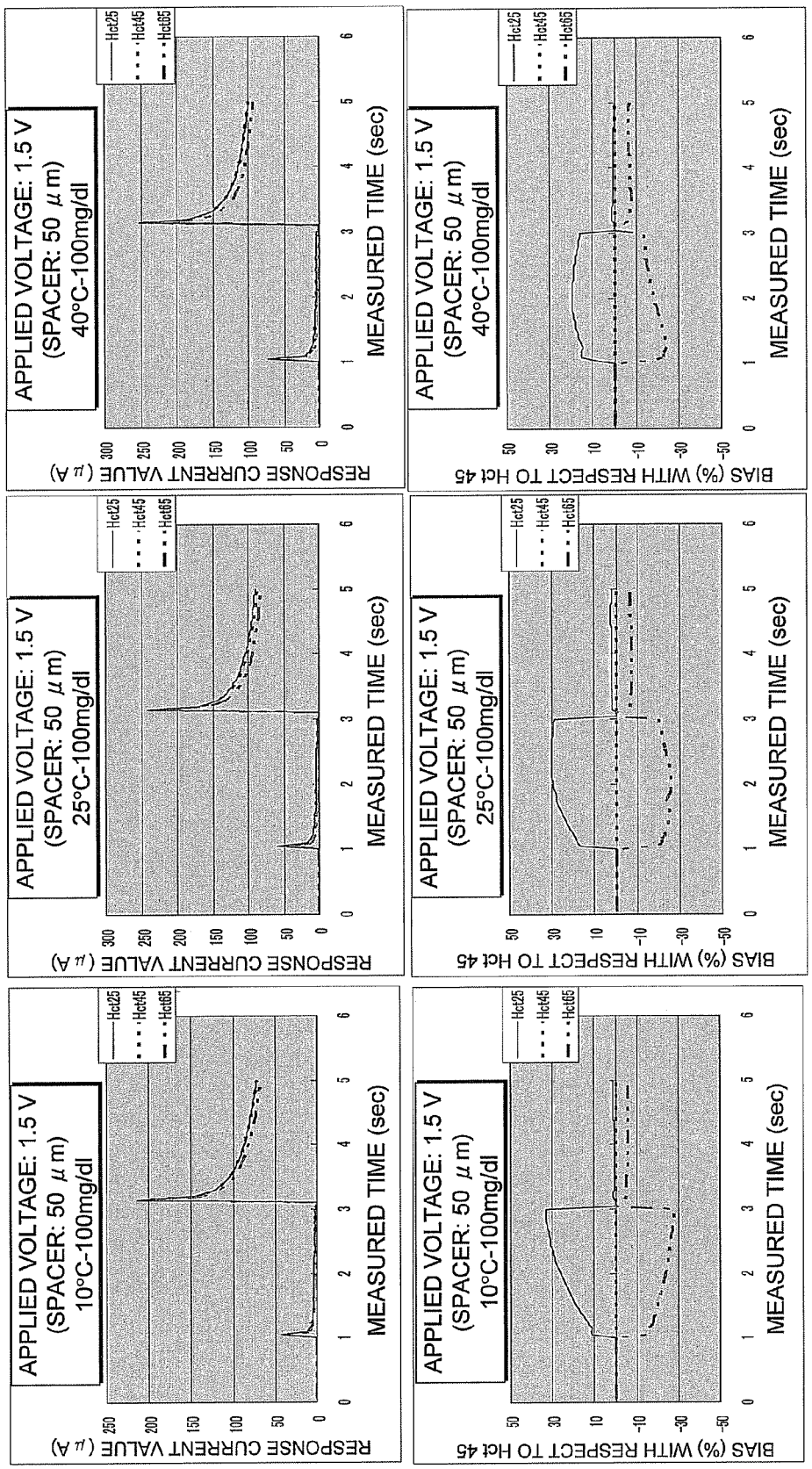
FIG. 75 includes charts representing the results of examining the effect of variation in the temperature and variation in the Hct value on the response current value in setting the thickness of a spacer to be 50 μm and applying a voltage of 1.5 V in the exemplary embodiment 2.

In FIG. 75, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 75, each of the lower charts represents deviations of response current values corresponding to Hct values of 25 and 65 from a response current value corresponding to an Hct value of 45 in a corresponding one of the upper charts represented above the lower charts.

As represented in the charts of FIG. 75, it was consequently found that the response current value widely varied due to increase and reduction in the Hct value at the respective blood sample temperatures of 10° C., 25° C. and 40° C. in measuring the glucose concentration. On the other hand, it was found that deviations among response current values due to increase and reduction in the Hct value was inhibited to be in a range of minus several % in measuring the temperature.

Figure 76:
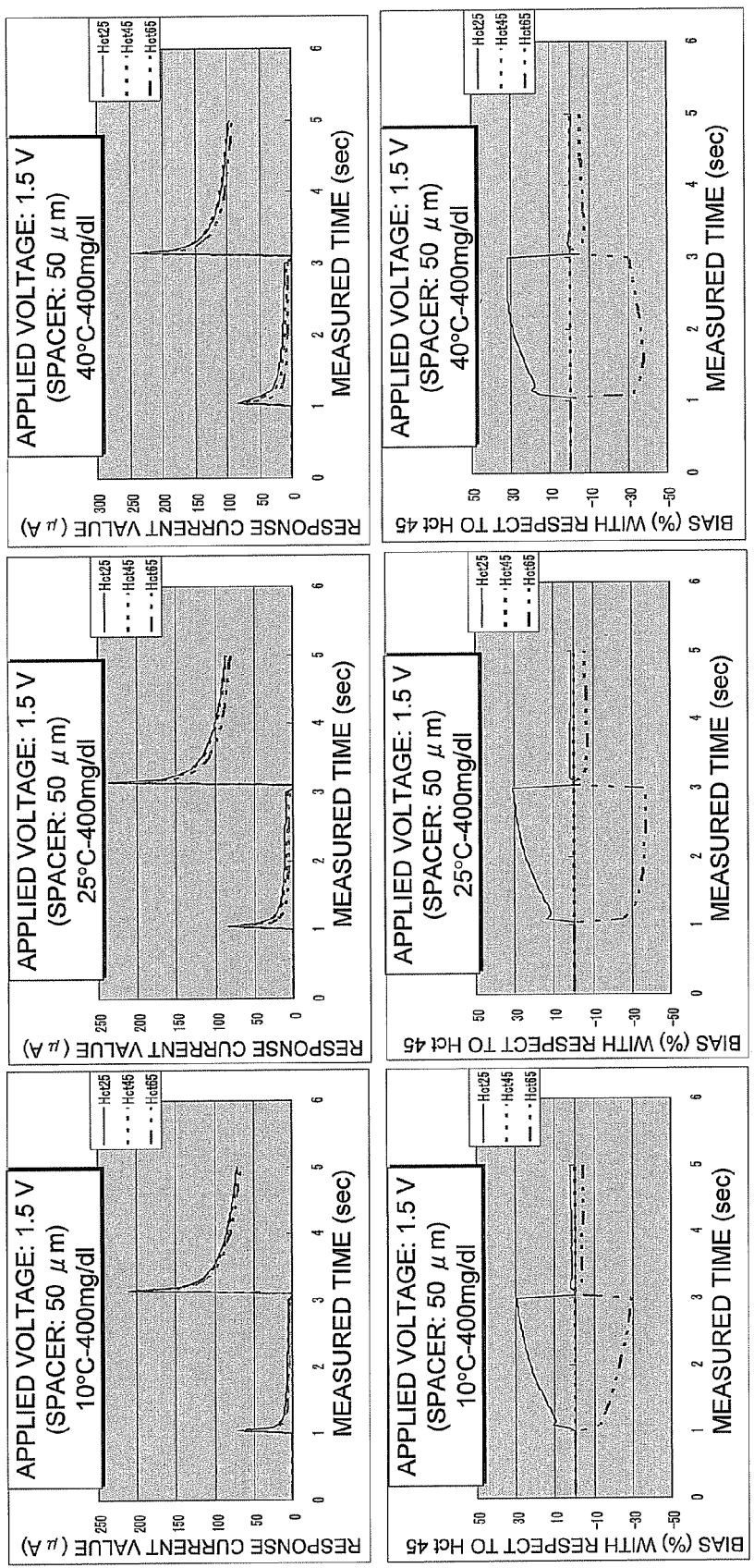
FIG. 76 includes charts representing the results of examining the effect of variation in the temperature and variation in the Hct value on the response current value in setting the thickness of a spacer to be 50 μm and applying a voltage of 1.5 V in the exemplary embodiment 2.

FIG. 76 represents the measured results when the glucose concentration in FIG. 75 was changed from 100 mg/dl to 400 mg/dl.

Similarly to the aforementioned results, it was also found that the response current value varied due to increase and reduction in the Hct value at the respective blood sample temperatures of 10° C., 25° C. and 40° C. in measuring the glucose concentration. On the other hand, it was found that deviations among response current values due to increase and reduction in the Hct value was inhibited in measuring the temperature, similarly to the aforementioned result of a glucose concentration of 100 mg/dl represented in FIG. 75.

Figure 77:
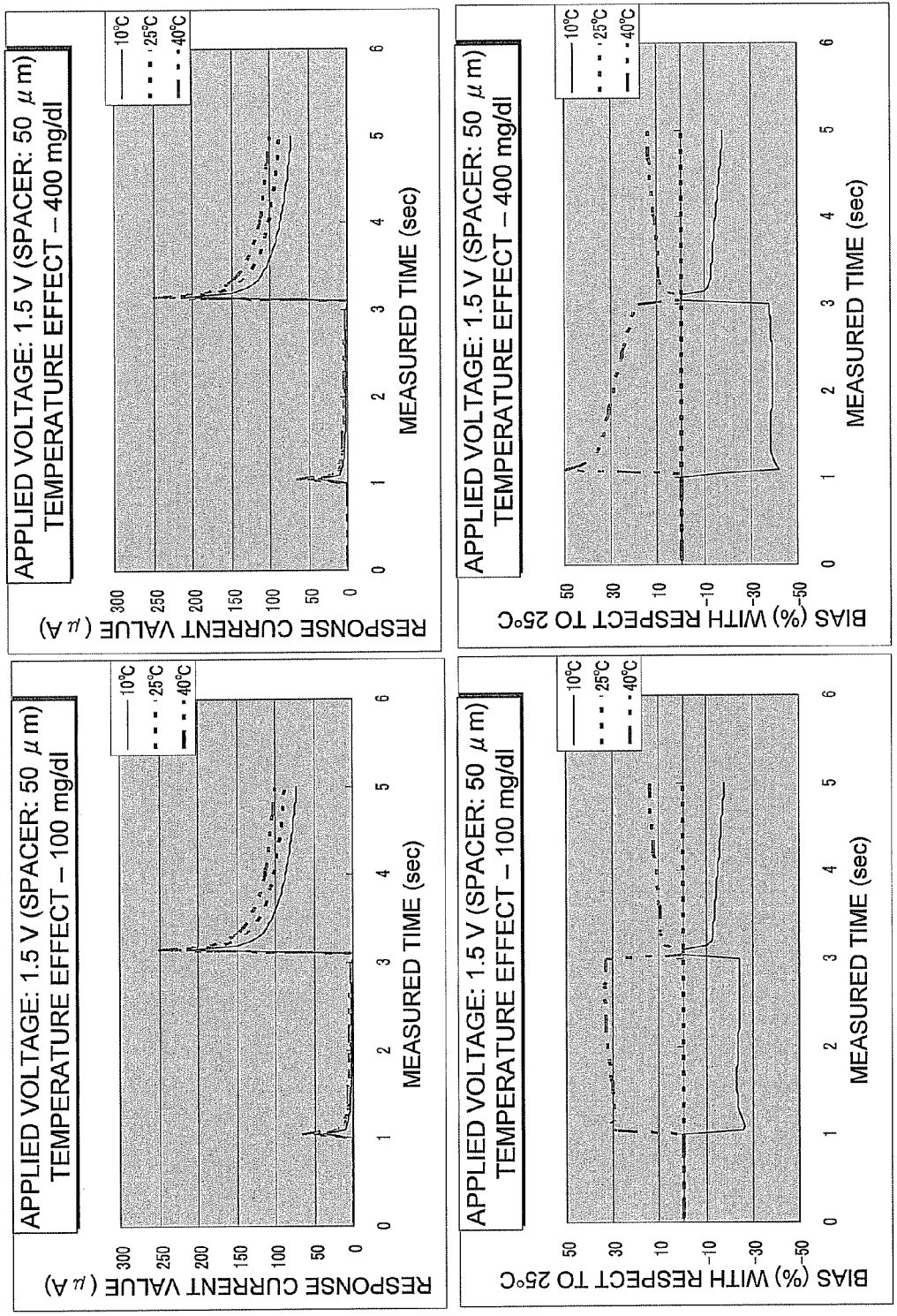
FIG. 77 includes charts representing a comprehensive result of examining the effect of variation in the temperature on the response current value in setting the thickness of a spacer to be 50 μm and applying a voltage of 1.5 V in the exemplary embodiment 2.

FIG. 77 represents the measured results when the temperature conditions (10° C., 25° C. and 40° C.) were changed within each chart for easily understanding the effect of the blood sample temperature. It should be noted that the left upper and lower charts of FIG. 77 represent the measured results of response current values when the glucose concentration was set to be 100 mg/dl, whereas the right upper and lower charts of FIG. 77 represent the measured results of response current values when the glucose concentration was set to be 400 mg/dl.

It was consequently found that the response current value varied at both glucose concentrations of 100 mg/dl and 400 mg/dl in both measuring the temperature and measuring the glucose concentration when the blood sample temperature was changed. It was herein found that the response current value was changed at a sensitivity of roughly 1° C./1% when the blood sample temperature was changed. This indicates that the sensor chip of the present exemplary embodiment functions as a temperature sensor.

Figure 78:
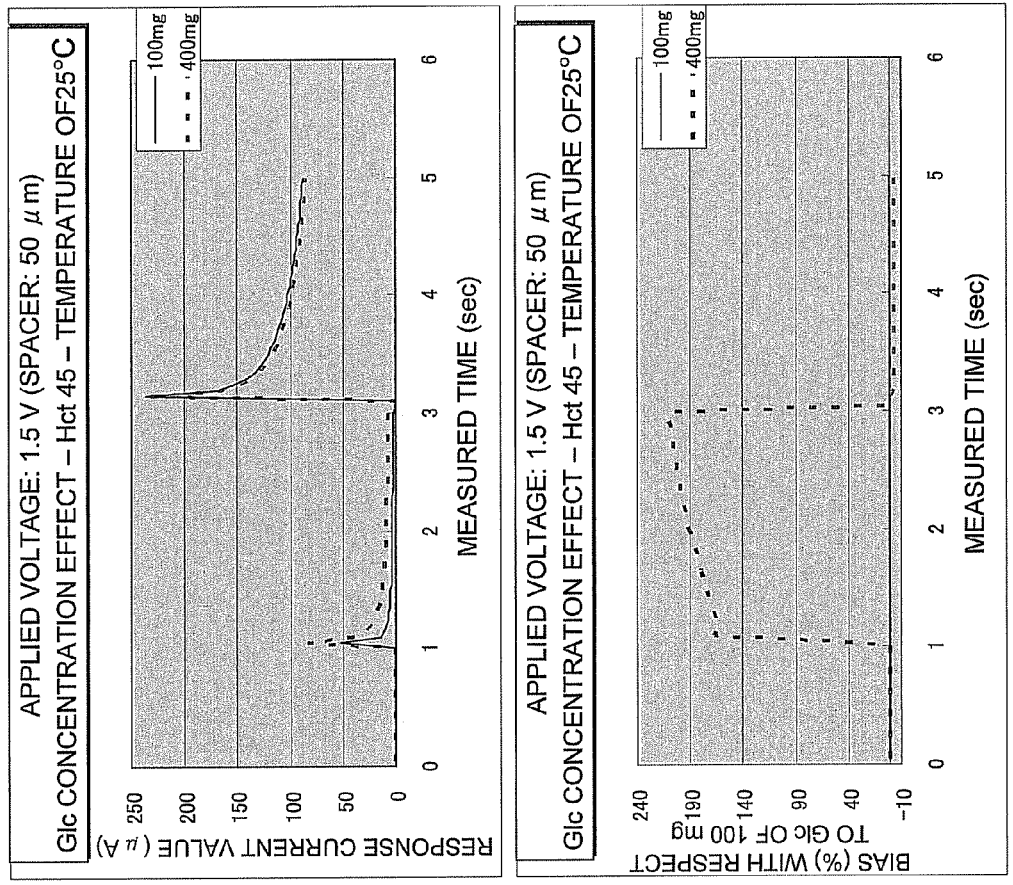
FIG. 78 includes charts representing a comprehensive result of examining the effect of variation in the glucose concentration on the response current value in setting the thickness of a spacer to be 50 μm and applying a voltage of 1.5 V in the exemplary embodiment 2.

FIG. 78 represents the measured results when the glucose concentration was changed and set to be 100 mg/dl and 400 mg/dl in each chart for easily understanding the effect of the glucose concentration. It should be noted that the upper chart of FIG. 78 represents the measured results of response current values when the glucose concentration was set to be 100 mg/dl and 400 mg/dl, whereas the lower chart of FIG. 78 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature.

It was found from the aforementioned results that the response current value was not affected by variation in the glucose concentration and variation in the Hct value regardless of reduction in the spacer thickness when the response current value was measured by applying a voltage of 1.5 V between the electrode A and the electrodes B and C and it was thereby possible to extract only the effect of variation in the temperature.

In the present exemplary embodiment, it is possible to exclude not only the effects of increase and reduction in the glucose concentration and increase and reduction in the Hct value but also the effect of the spacer thickness by measuring the response current value through the application of a voltage of 1.5 V between the electrode A and the electrodes B and C. It is thereby possible to use the present sensor chip as a temperature sensor.

<Spacer Thickness of 150 μm>

Measurements were herein executed for examining the effects of variation in the temperature (10° C., 25° C. and 40° C.), variation in the Hct value (25, 45 and 65) and variation in the glucose concentration (100 mg/dl, 400 mg/dl) on the response current value when a voltage to be applied between the electrode A and the electrodes B and C was set to be 1.5 V under the condition that the thickness of the spacer interposed between the substrate and the upper cover was changed from 100 µm to 150 µm.

Figure 79:
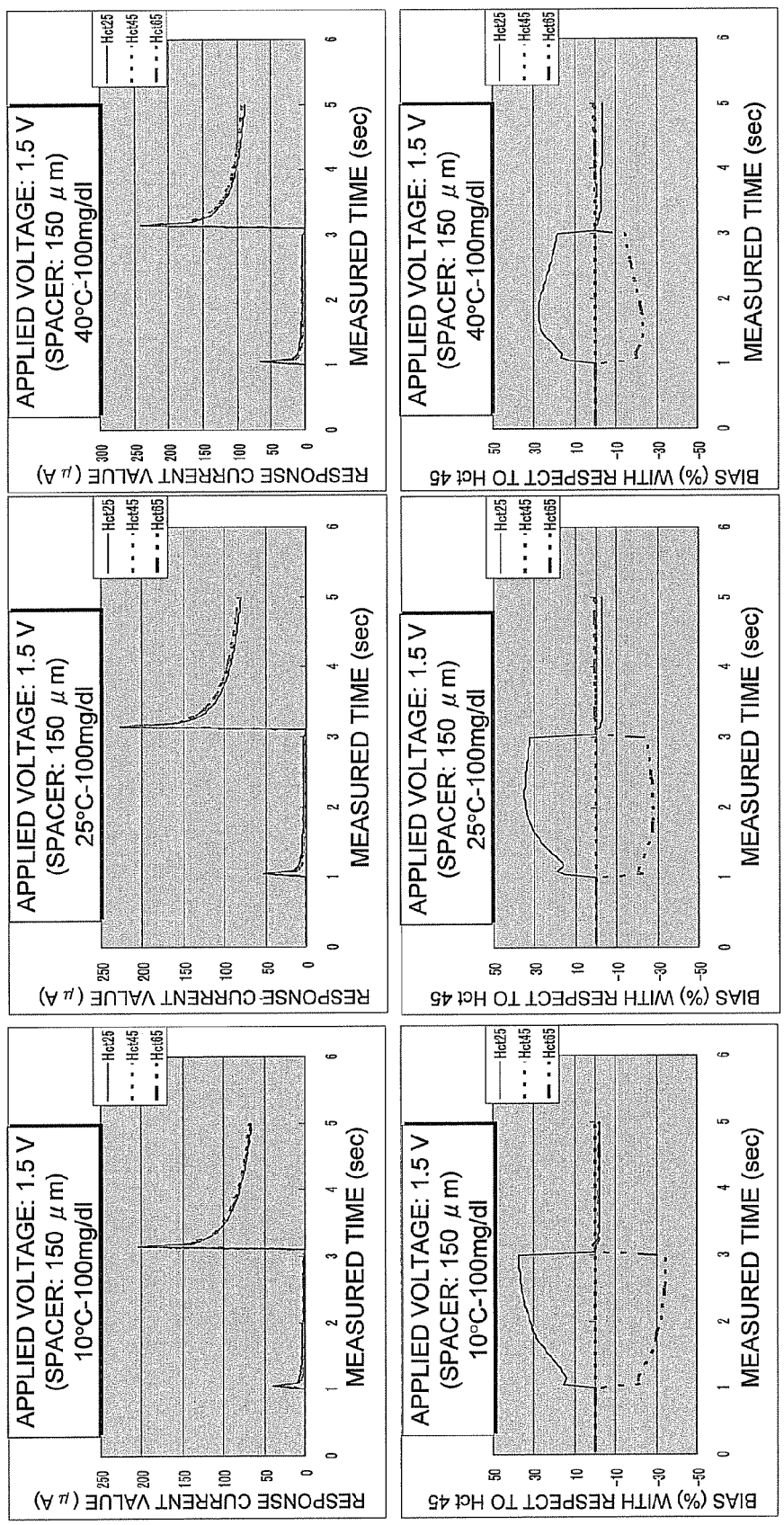
FIG. 79 includes charts representing the results of examining the effect of variation in the temperature and variation in the Hct value on the response current value in setting the thickness of a spacer to be 150 μm and applying a voltage of 1.5 V in the exemplary embodiment 2.

In FIG. 79, the left to right upper charts respectively represent variation in the response current value when the temperature was changed and set to be 10° C., 25° C. and 40° C. Each chart represents variation in the response current value when the Hct value was changed and set to be 25, 45 and 65. Further in FIG. 79, each of the lower charts represents deviations of response current values corresponding to Hct values of 25 and 65 from a response current value corresponding to an Hct value of 45 in a corresponding one of the upper charts represented above the lower charts.

As represented in the charts of FIG. 79, it was consequently found that the response current value widely varied due to increase and reduction in the Hct value at the respective blood sample temperatures of 10° C., 25° C. and 40° C. in measuring the glucose concentration. On the other hand, it was found that the response current value hardly varied dur to increase and reduction in the Hct value in measuring the temperature.

Figure 80:
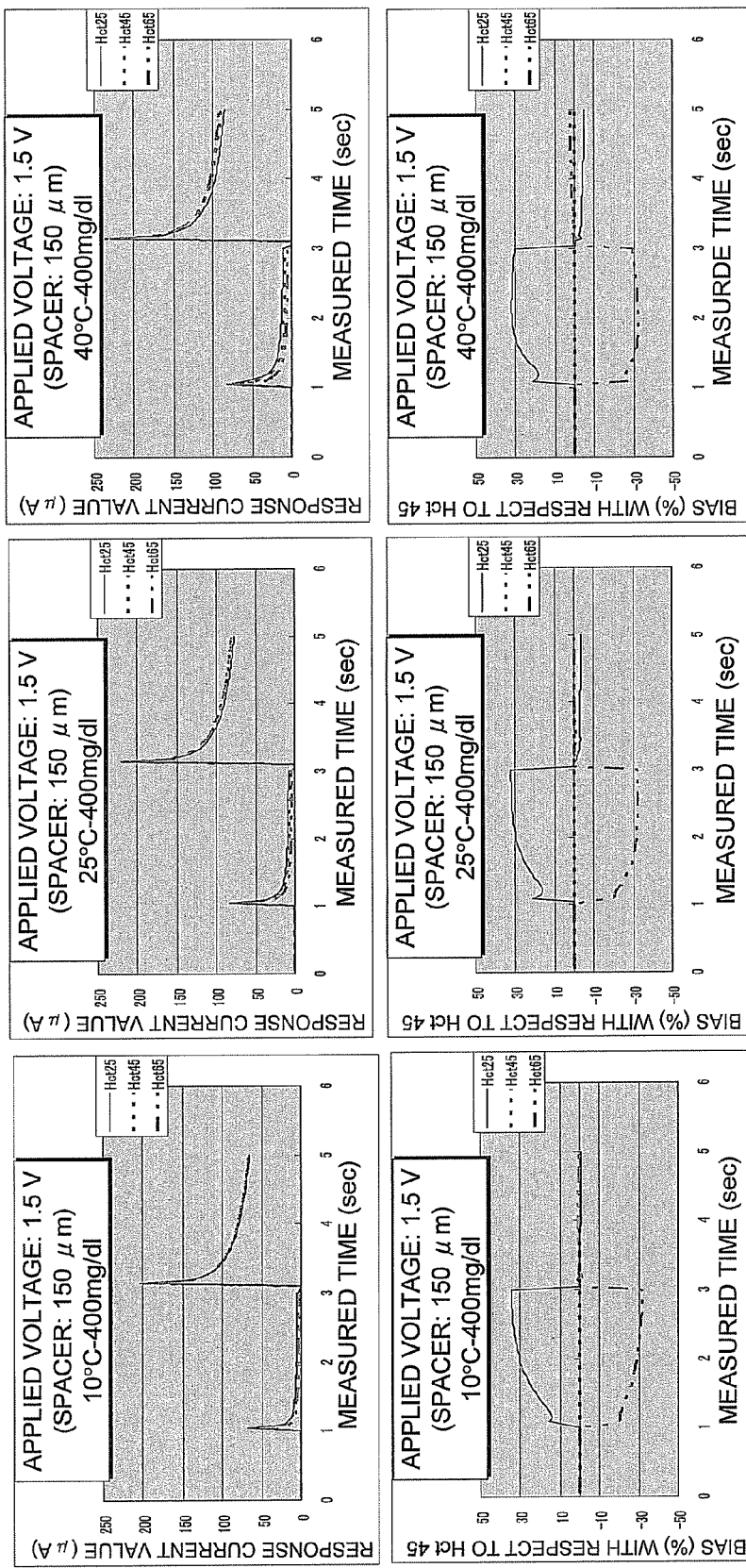
FIG. 80 includes charts representing the results of examining the effect of variation in the temperature and variation in the Hct value on the response current value in setting the thickness of a spacer to be 150 μm and applying a voltage of 1.5 V in the exemplary embodiment 2.

FIG. 80 represents the measured results when the glucose concentration in FIG. 79 was changed from 100 mg/dl to 400 mg/dl.

Similarly to the aforementioned results, it was also found that the response current value varied due to increase and reduction in the Hct value at the respective blood sample temperatures of 10° C., 25° C. and 40° C. in measuring the glucose concentration. On the other hand, it was found that deviations among response current values due to increase and reduction in the Hct value was inhibited in measuring the temperature, similarly to the aforementioned result of a glucose concentration of 100 mg/dl represented in FIG. 79.

Figure 81:
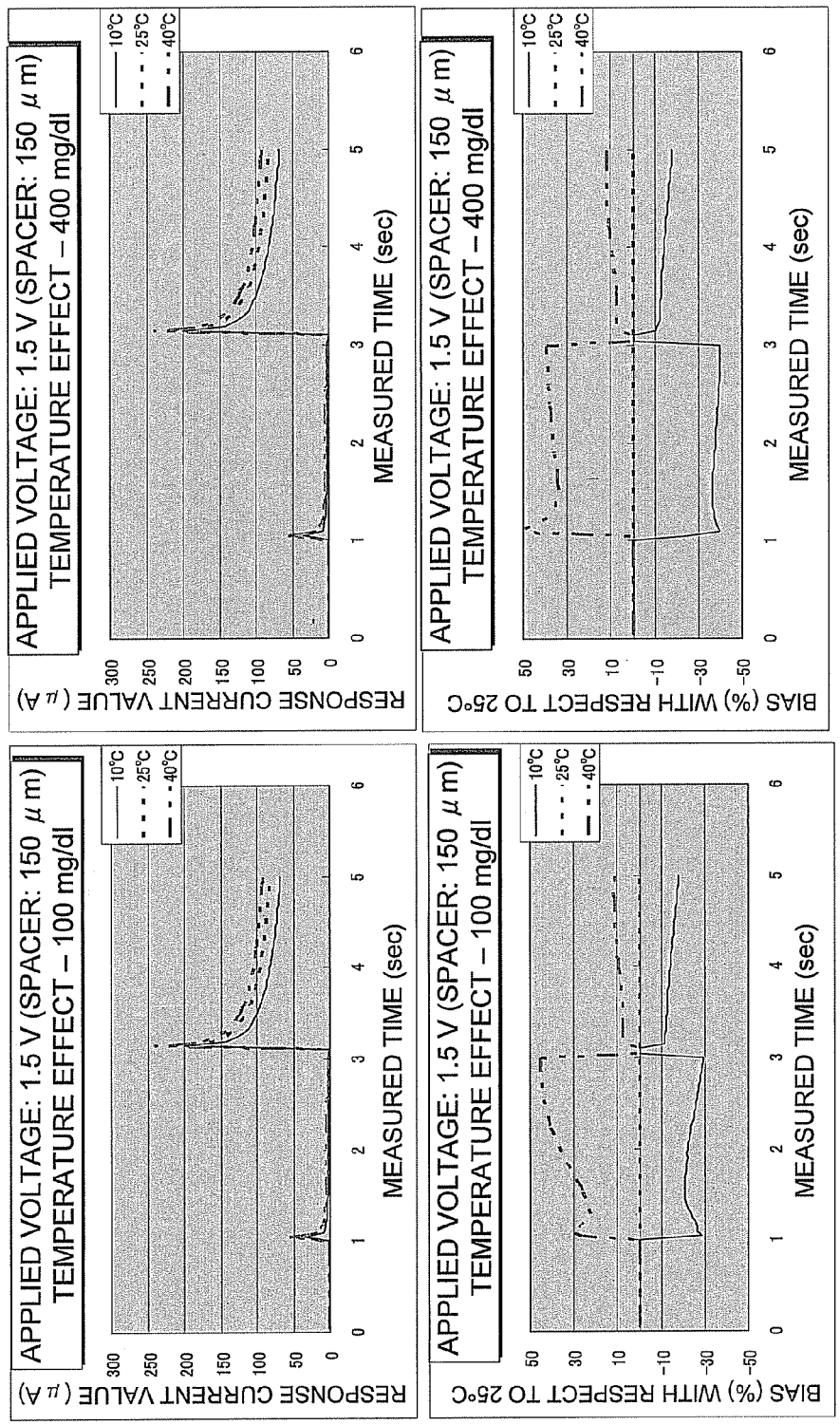
FIG. 81 includes charts representing a comprehensive result of examining the effect of variation in the temperature on the response current value in setting the thickness of a spacer to be 150 μm and applying a voltage of 1.5 V in the exemplary embodiment 2.

FIG. 81 represents the measured results when the temperature conditions (10° C., 25° C. and 40° C.) were changed within each chart for easily understanding the effect of the blood sample temperature. It should be noted that the left upper and lower charts of FIG. 81 represent the measured results of response current values when the glucose concentration was set to be 100 mg/dl, whereas the right upper and lower charts of FIG. 81 represent the measured results of response current values when the glucose concentration was set to be 400 mg/dl.

It was consequently found that the response current value varied at both glucose concentrations of 100 mg/dl and 400 mg/dl in both measuring the temperature and measuring the glucose concentration when the blood sample temperature was changed. It was herein found that the response current value was changed at a sensitivity of roughly 1° C./1% when the blood sample temperature was changed. This indicates that the sensor chip of the present exemplary embodiment functions as a temperature sensor.

Figure 82:
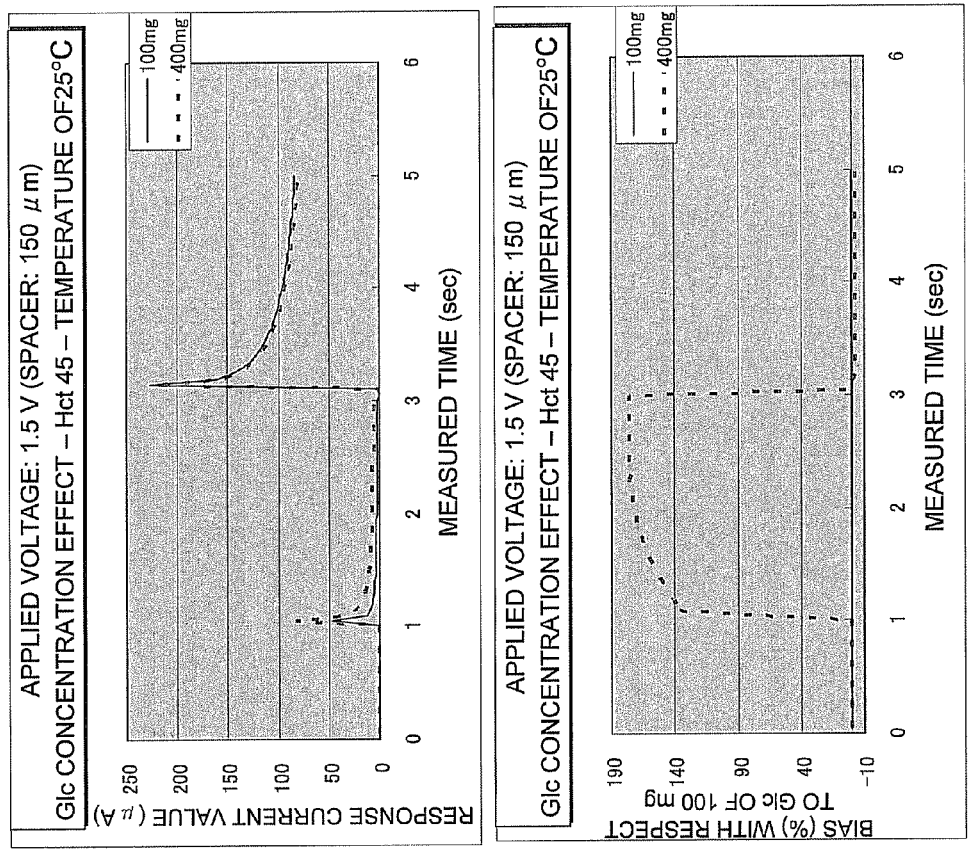
FIG. 82 includes charts representing a comprehensive result of examining the effect of variation in the glucose concentration on the response current value in setting the thickness of a spacer to be 150 μm and applying a voltage of 1.5 V in the exemplary embodiment 2.

FIG. 82 represents the measured results when the glucose concentration was changed and set to be 100 mg/dl and 400 mg/dl in each chart for easily understanding the effect of the glucose concentration. It should be noted that the upper chart of FIG. 82 represents the measured results of response current values when the glucose concentration was set to be 100 mg/dl and 400 mg/dl, whereas the lower chart of FIG. 82 represents a deviation between response current values corresponding to glucose concentrations of 100 mg/dl and 400 mg/dl.

It was consequently found that the response current value certainly varied in measuring the glucose concentration when the glucose concentration was changed and set to be 100 mg/dl and 400 mg/dl. On the other hand, it was found that the response current value hardly varied in measuring the temperature.

It was found from the aforementioned results that the response current value was not affected by variation in the glucose concentration and variation in the Hct value regardless of increase in the spacer thickness when the response current value was measured by applying a voltage of 1.5 V between the electrode A and the electrodes B and C and it was thereby possible to extract only the effect of variation in the temperature.

In the present exemplary embodiment, it is possible to exclude not only the effects of increase and reduction in the glucose concentration and increase and reduction in the Hct value but also the effect of the spacer thickness by measuring the response current value through the application of a voltage of 1.5 V between the electrode A and the electrodes B and C. It is thereby possible to use the present sensor chip as a temperature sensor.

<Comprehensive Results>

Figure 83:
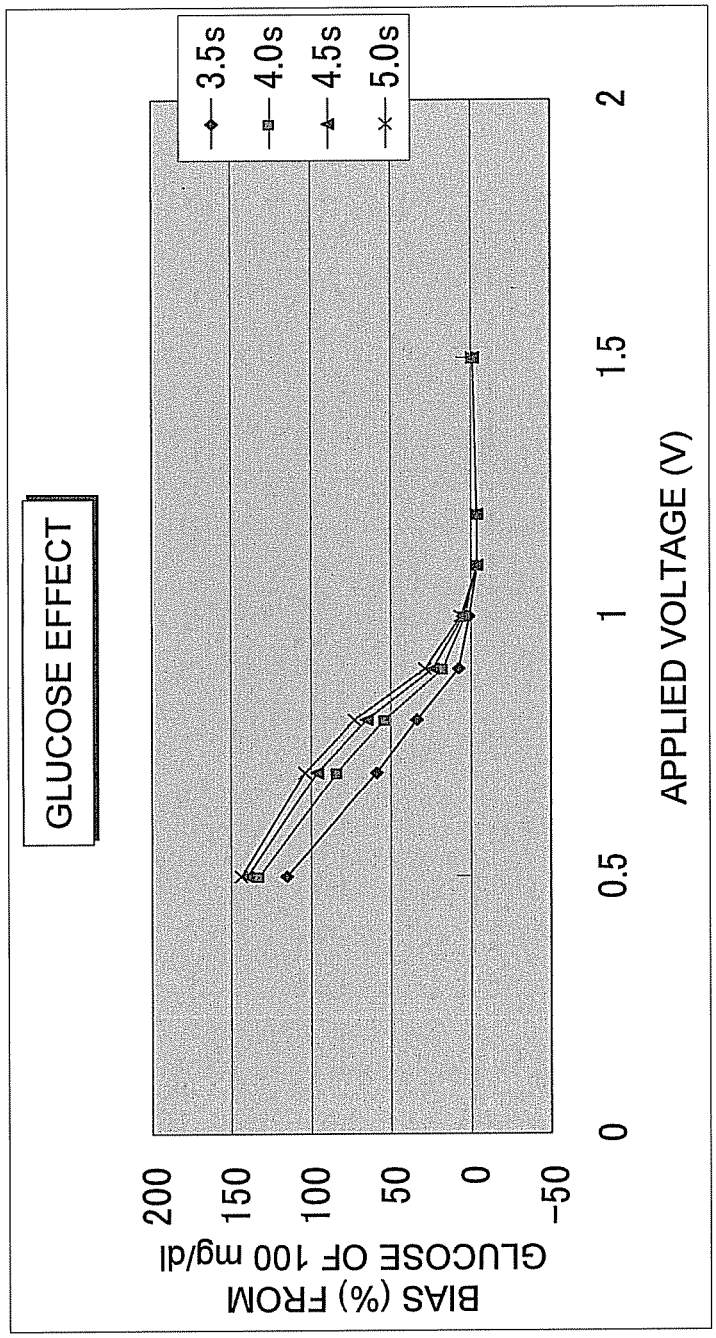
FIG. 83 is a chart produced by integrating the measured results in the exemplary embodiment 2 and comprehensively represents the effect of the glucose concentration on the response current value in applying a voltage of respective levels.
Figure 84:
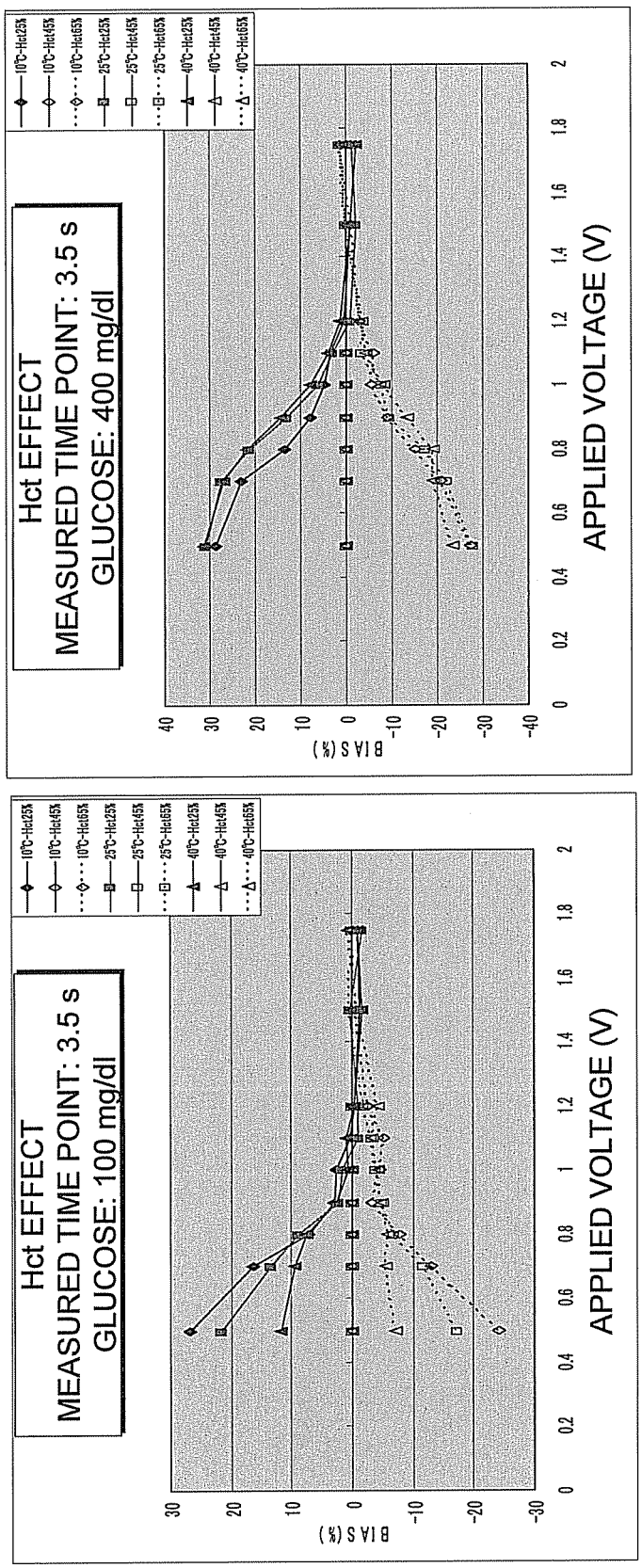
FIG. 84 includes charts produced by integrating the measured results in the exemplary embodiment 2 and comprehensively represents the effect of the Hct value on the response current value in applying a voltage of respective levels.

FIGS. 83 and 84 represent comprehensive data of the aforementioned measured results of the response current value.

FIG. 83 is a chart comprehensively representing the effect of increase and reduction in the glucose concentration on a response current value at the aforementioned respective applied voltages based on a glucose concentration of 100 mg/dl. It should be noted that each plot in the chart corresponds to a datum obtained every 0.5 seconds in a measured time period from 3.5 second to 5.0 second included in the measured time period for temperature measurement.

As represented in FIG. 83, it was consequently found that the response current value was affected by increase and reduction in the glucose concentration in an applied voltage range of 0.5 V to 1.0 V whereas the response current value was hardly affected by increase and reduction in the glucose concentration in an applied voltage range of 1.0 V to 1.5 V.

FIG. 84 includes charts comprehensively representing variation in the response current value with respect to applied voltages in various conditions of the temperature and the Hct value set in the aforementioned exemplary embodiment 2. It should be noted that the left chart of FIG. 84 represents the measured results at the timing of 3.5 second as a measured time point under the condition of a glucose concentration of 100 mg/dl, whereas the right chart of FIG. 84 represents the measured results at the timing of 3.5 second as a measured time point under the condition of a glucose concentration of 400 mg/dl.

As represented in FIG. 84, it was consequently found that variation in the response concentration started converging at an applied voltage of roughly 1.2 V and almost disappeared at an applied voltage of roughly 1.5 V in both conditions of a glucose concentration of 100 mg/dl and a glucose concentration of 400 mg/dl.

It was found from the aforementioned results that a voltage (of 1.5 V or greater), which is higher than a voltage (of roughly 0.25 V) to be normally applied in measuring the glucose concentration, is required for accurately measuring the blood sample temperature in the sensor chip configuration of the present exemplary embodiment as an applied voltage range for excluding both of the effects of the glucose concentration and the Hct value.

(Exemplary Embodiment 3)

Yet another exemplary embodiment of the present invention will be hereinafter explained with reference to FIGS. 98 to 103.

In the present exemplary embodiment, the response current value was measured using the sensor chip with a configuration (see FIG. 98) from that of the sensor chip in the aforementioned exemplary embodiment 1 by applying voltages of 0.5 V to 2.0 V similarly to the aforementioned exemplary embodiment 1.

Figure 98:
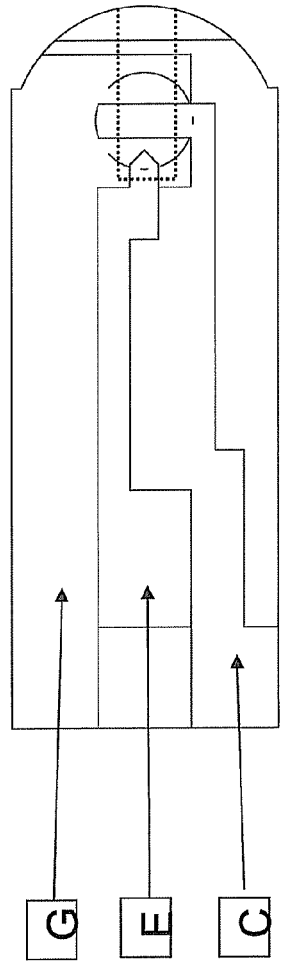
FIG. 98 includes an explanatory diagram representing a configuration of a sensor chip according to yet another exemplary embodiment of the present invention and an en explanatory table representing an exemplary pattern of applying a voltage to the sensor chip.

As represented in FIG. 98, the sensor chip used in the present exemplary embodiment includes the working electrode, the counter electrode and the detection electrode, while Pd as an electrode material, glucose dehydrogenase as an enzyme, and potassium ferricyanide as a mediator were used.

Further, the sensor chip used in the present exemplary embodiment includes three electrodes G, E and C. As represented in the lower table of FIG. 98, the magnitude and the application time period of a voltage to be applied to the electrodes G, E and C were set as follows. Firstly, the measurement was started at the timing when increase in an electricity of 0.05 μA was detected during application of a voltage of 0.5 V (500 mV) between the electrode E and the electrode G. Next, a voltage of 0.5 V was applied between the electrode C and the electrodes G and E for about 2 seconds in order to measure the glucose concentration. Subsequently, a voltage varying from 0.5 V to 2.0 V was applied between the electrode C and the electrodes G and E for about 3.0 seconds in order to measure the temperature.

The following explanation relates to results of examining the effect of increase and reduction in the glucose concentration on the temperature measurement when the applied voltage was changed from 0.5 V to 2.0 V.

<Applied Voltage of 0.5 V>

Measurements were herein executed for examining the effects of variation in the glucose concentration (100 mg/dl, 400 mg/dl) and variation in the temperature (10° C., 25° C. and 40° C.) on the response current value when a voltage to be applied among the electrodes was set to be 0.5 V.

Figure 99:
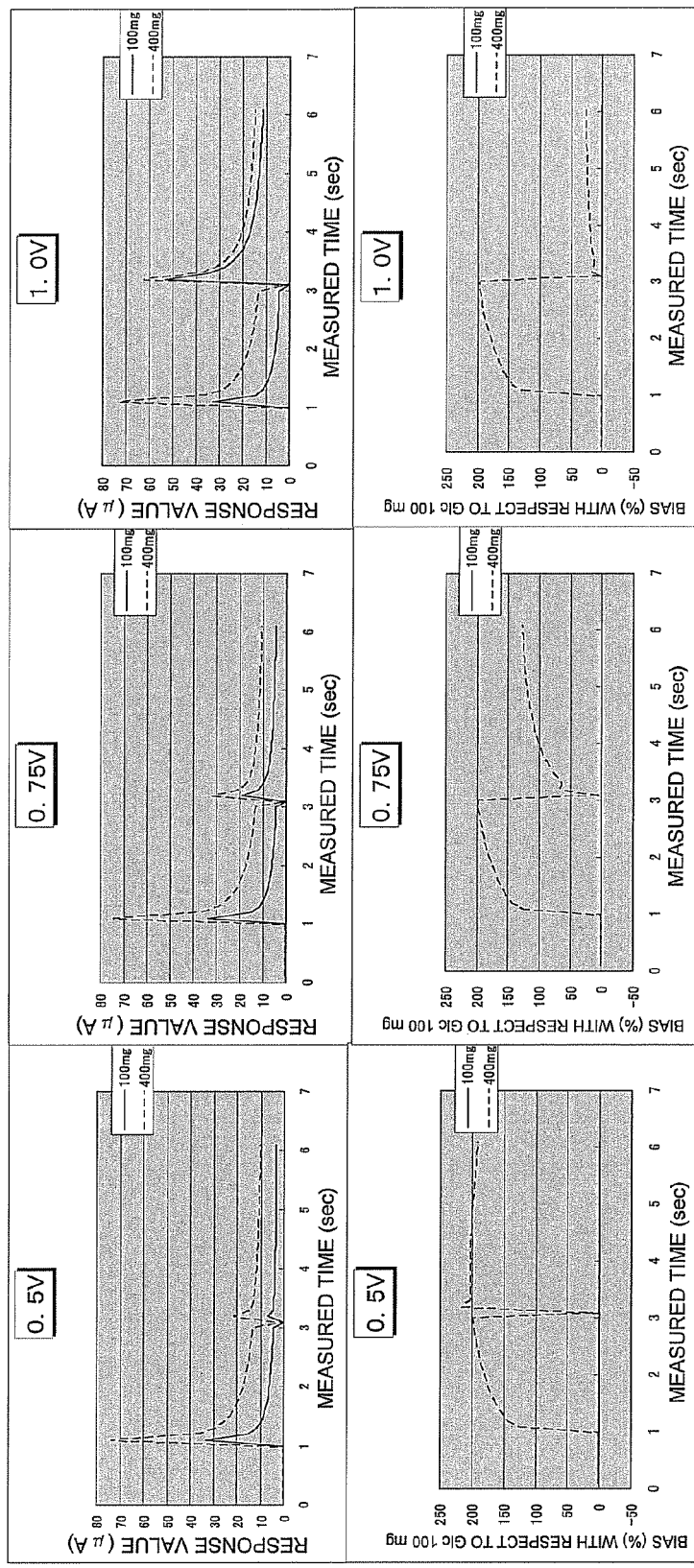
FIG. 99 includes charts representing the results of examining the effect of variation in the glucose concentration on the response current value in applying voltages of 0.5 to 1.0 V to the sensor chip illustrated in FIG. 98.

In FIG. 99, the left charts represent the measured results when the glucose concentration was changed and set to be 100 mg/dl and 400 mg/dl within each chart for easily understanding the effect of the glucose concentration. It should be noted that the left upper chart in FIG. 99 represents the measured results of response current values when the glucose concentration was set to be 100 mg/dl and 400 mg/dl, whereas the left lower chart in FIG. 99 represents a deviation between response current values corresponding to glucose concentrations of 100 mg/dl and 400 mg/dl.

It was consequently found that the response current value widely varied not only in measuring the glucose concentration but also in measuring the temperature when the glucose concentration is changed and set to be 100 mg/dl and 400 mg/dl.

Figure 101:
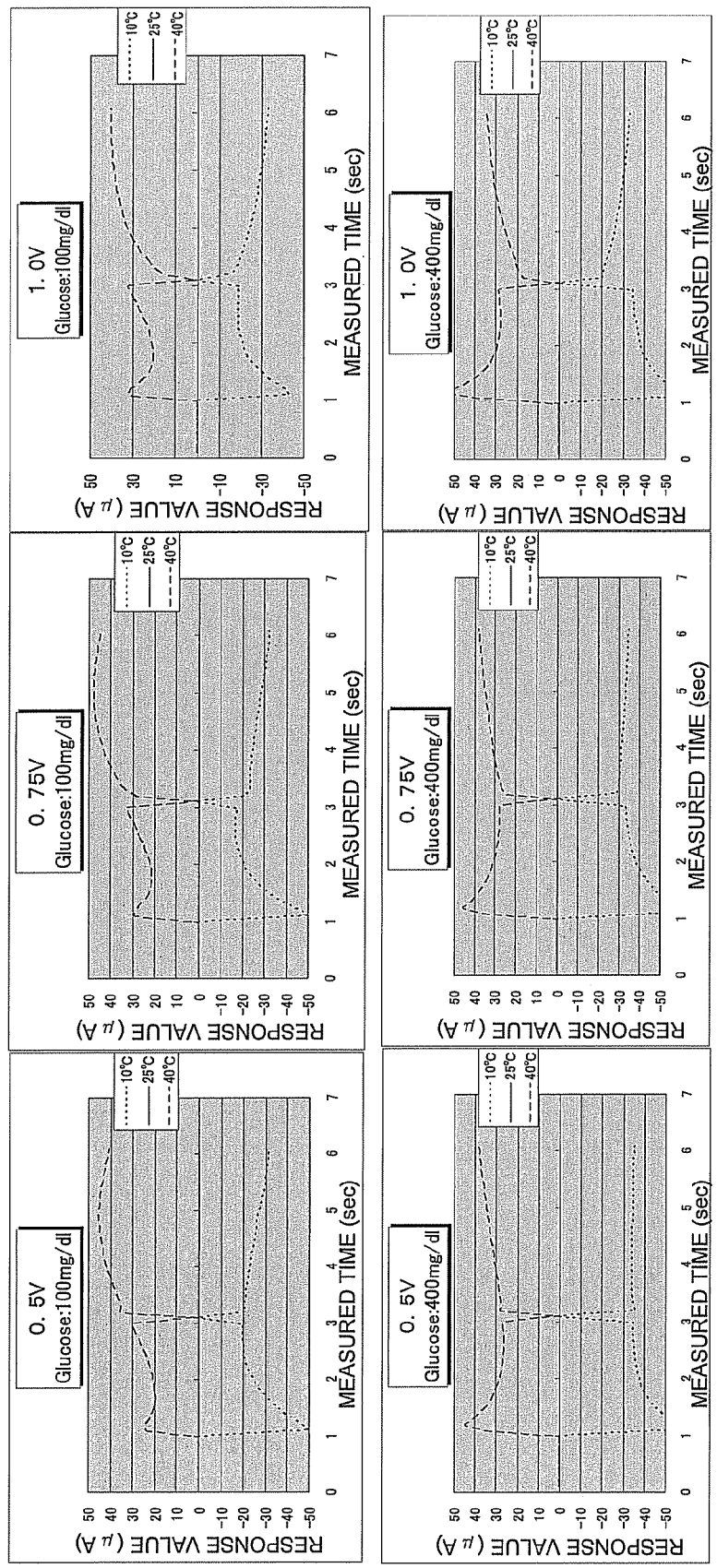
FIG. 101 includes charts representing a comprehensive result of examining the effect of variation in the temperature on the response current value in applying voltage of 0.5 to 1.0 V to the sensor chip illustrated in FIG. 98.

Further in FIG. 101, the left charts represent the measured results when the temperature conditions (10° C., 25° C. and 40° C.) were changed within each chart for easily understanding the effect of the blood sample temperature. It should be noted that the left upper chart of FIG. 101 represents the measured results of variation in the response current value when the glucose concentration was set to be 100 mg/dl, whereas the left lower chart of FIG. 101 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the glucose concentration and variation in the temperature when the response current value was measured by applying a voltage of 0.5 V among the electrodes and it was thereby impossible to extract only the effect of variation in the temperature.

<Applied Voltage of 0.75 V>

Measurements were herein executed for examining the effects of variation in the glucose concentration (100 mg/dl, 400 mg/dl) and variation in the temperature (10° C., 25° C. and 40° C.) on the response current value when a voltage to be applied among the electrodes was set to be 0.75 V.

In FIG. 99, the center charts represent the measured results when the glucose concentration was changed and set to be 100 mg/dl and 400 mg/dl within each chart for easily understanding the effect of the glucose concentration. It should be noted that the center upper chart in FIG. 99 represents the measured results of response current values when the glucose concentration was set to be 100 mg/dl and 400 mg/dl, whereas the center lower chart in FIG. 99 represents a deviation between response current values corresponding to glucose concentrations of 100 mg/dl and 400 mg/dl.

It was consequently found that the response current value widely varied not only in measuring the glucose concentration but also in measuring the temperature when the glucose concentration is changed and set to be 100 mg/dl and 400 mg/dl.

Further in FIG. 101, the center charts represent the measured results when the temperature conditions (10° C., 25° C. and 40° C.) were changed within each chart for easily understanding the effect of the blood sample temperature. It should be noted that the center upper chart of FIG. 101 represents the measured results of variation in the response current value when the glucose concentration was set to be 100 mg/dl, whereas the center lower chart of FIG. 101 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the glucose concentration and variation in the temperature when the response current value was measured by applying a voltage of 0.75 V among the electrodes and it was thereby impossible to extract only the effect of variation in the temperature.

<Applied Voltage of 1.0 V>

Measurements were herein executed for examining the effect of variation in the glucose concentration (100 mg/dl, 400 mg/dl) on the response current value when a voltage to be applied among the electrodes was set to be 1.0 V.

In FIG. 99, the right charts represent the measured results when the glucose concentration was changed and set to be 100 mg/dl and 400 mg/dl within each chart for easily understanding the effect of the glucose concentration. It should be noted that the right upper chart in FIG. 99 represents the measured results of response current values when the glucose concentration was set to be 100 mg/dl and 400 mg/dl, whereas the right lower chart in FIG. 99 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the deviation between response current values was inhibited to be in a range of roughly 30% in measuring the temperature.

Further in FIG. 101, the right charts represent the measured results when the temperature conditions (10° C., 25° C. and 40° C.) were changed within each chart for easily understanding the effect of the blood sample temperature. It should be noted that the right upper chart of FIG. 101 represents the measured results of variation in the response current value when the glucose concentration was set to be 100 mg/dl, whereas the right lower chart of FIG. 101 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.0 V among the electrodes. It should be noted that the effect of increase and reduction in the glucose concentration was likely to be inhibited in measuring the temperature when a voltage of 1.0 V was applied among the electrodes as represented in the right lower chart of FIG. 99.

<Applied Voltage of 1.25 V>

Measurements were herein executed for examining the effect of variation in the glucose concentration (100 mg/dl, 400 mg/dl) on the response current value when a voltage to be applied among the electrodes was set to be 1.25 V.

Figure 100:
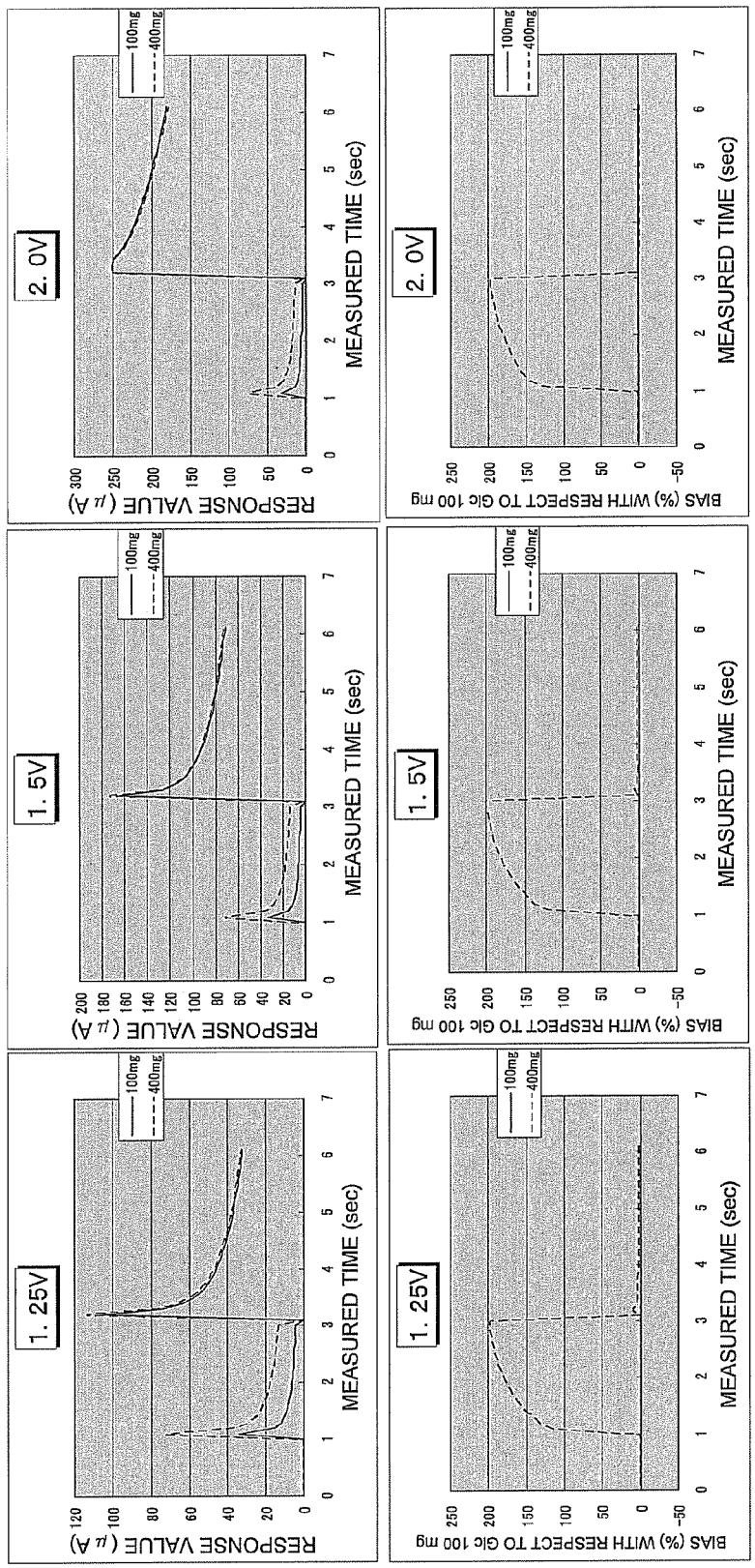
FIG. 100 includes charts representing the results of examining the effect of variation in the glucose concentration on the response current value in applying voltages of 1.25 to 2.0 V to the sensor chip illustrated in FIG. 98.

In FIG. 100, the left charts represent the measured results when the glucose concentration was changed and set to be 100 mg/dl and 400 mg/dl within each chart for easily understanding the effect of the glucose concentration. It should be noted that the left upper chart in FIG. 100 represents the measured results of response current values when the glucose concentration was set to be 100 mg/dl and 400 mg/dl, whereas the left lower chart in FIG. 100 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the response current value hardly varied in measuring the temperature.

Figure 102:
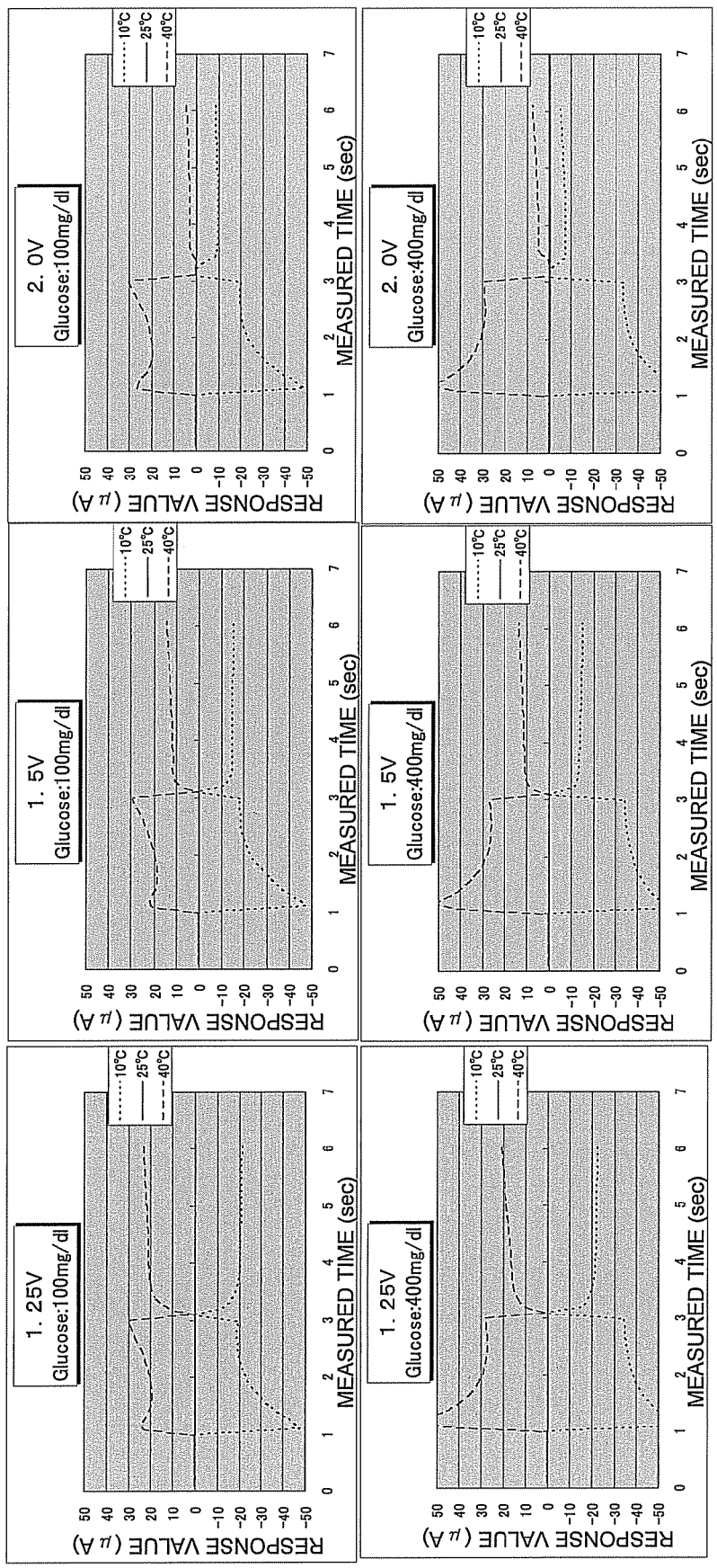
FIG. 102 includes charts representing a comprehensive result of examining the effect of variation in the temperature on the response current value in applying voltage of 1.25 to 2.0 V to the sensor chip illustrated in FIG. 98.

Further in FIG. 102, the left charts represent the measured results when the temperature conditions (10° C., 25° C. and 40° C.) were changed within each chart for easily understanding the effect of the blood sample temperature. It should be noted that the left upper chart of FIG. 102 represents the measured results of variation in the response current value when the glucose concentration was set to be 100 mg/dl, whereas the left lower chart of FIG. 102 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.25 V among the electrodes. It should be noted that the effect of increase and reduction in the glucose concentration was hardly produced in measuring the temperature when a voltage of 1.25 V was applied among the electrodes as represented in the left lower chart of FIG. 100.

<Applied Voltage of 1.5 V>

Measurements were herein executed for examining the effect of variation in the glucose concentration (100 mg/dl, 400 mg/dl) on the response current value when a voltage to be applied among the electrodes was set to be 1.5 V.

In FIG. 100, the center charts represent the measured results when the glucose concentration was changed and set to be 100 mg/dl and 400 mg/dl within each chart for easily understanding the effect of the glucose concentration. It should be noted that the center upper chart in FIG. 100 represents the measured results of response current values when the glucose concentration was set to be 100 mg/dl and 400 mg/dl, whereas the center lower chart in FIG. 100 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the response current value hardly varied in measuring the temperature.

Further in FIG. 102, the center charts represent the measured results when the temperature conditions (10° C., 25° C. and 40° C.) were changed within each chart for easily understanding the effect of the blood sample temperature. It should be noted that the center upper chart of FIG. 102 represents the measured results of variation in the response current value when the glucose concentration was set to be 100 mg/dl, whereas the center lower chart of FIG. 102 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.5 V among the electrodes. It should be noted that the effect of increase and reduction in the glucose concentration was hardly produced in measuring the temperature when a voltage of 1.5 V was applied among the electrodes as represented in the center lower chart of FIG. 100.

<Applied Voltage of 2.0 V>

Measurements were herein executed for examining the effect of variation in the glucose concentration (100 mg/dl, 400 mg/dl) on the response current value when a voltage to be applied among the electrodes was set to be 2.0 V.

In FIG. 100, the right charts represent the measured results when the glucose concentration was changed and set to be 100 mg/dl and 400 mg/dl within each chart for easily understanding the effect of the glucose concentration. It should be noted that the right upper chart in FIG. 100 represents the measured results of response current values when the glucose concentration was set to be 100 mg/dl and 400 mg/dl, whereas the right lower chart in FIG. 100 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the response current value hardly varied in measuring the temperature.

Further in FIG. 102, the right charts represent the measured results when the temperature conditions (10° C., 25° C. and 40° C.) were changed within each chart for easily understanding the effect of the blood sample temperature. It should be noted that the right upper chart of FIG. 102 represents the measured results of variation in the response current value when the glucose concentration was set to be 100 mg/dl, whereas the right lower chart of FIG. 102 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 2.0 V among the electrodes. It should be noted that the effect of increase and reduction in the glucose concentration was hardly produced in measuring the temperature when a voltage of 2.0 V was applied among the electrodes as represented in the right lower chart of FIG. 100.

<Comprehensive Results>

Figure 103:
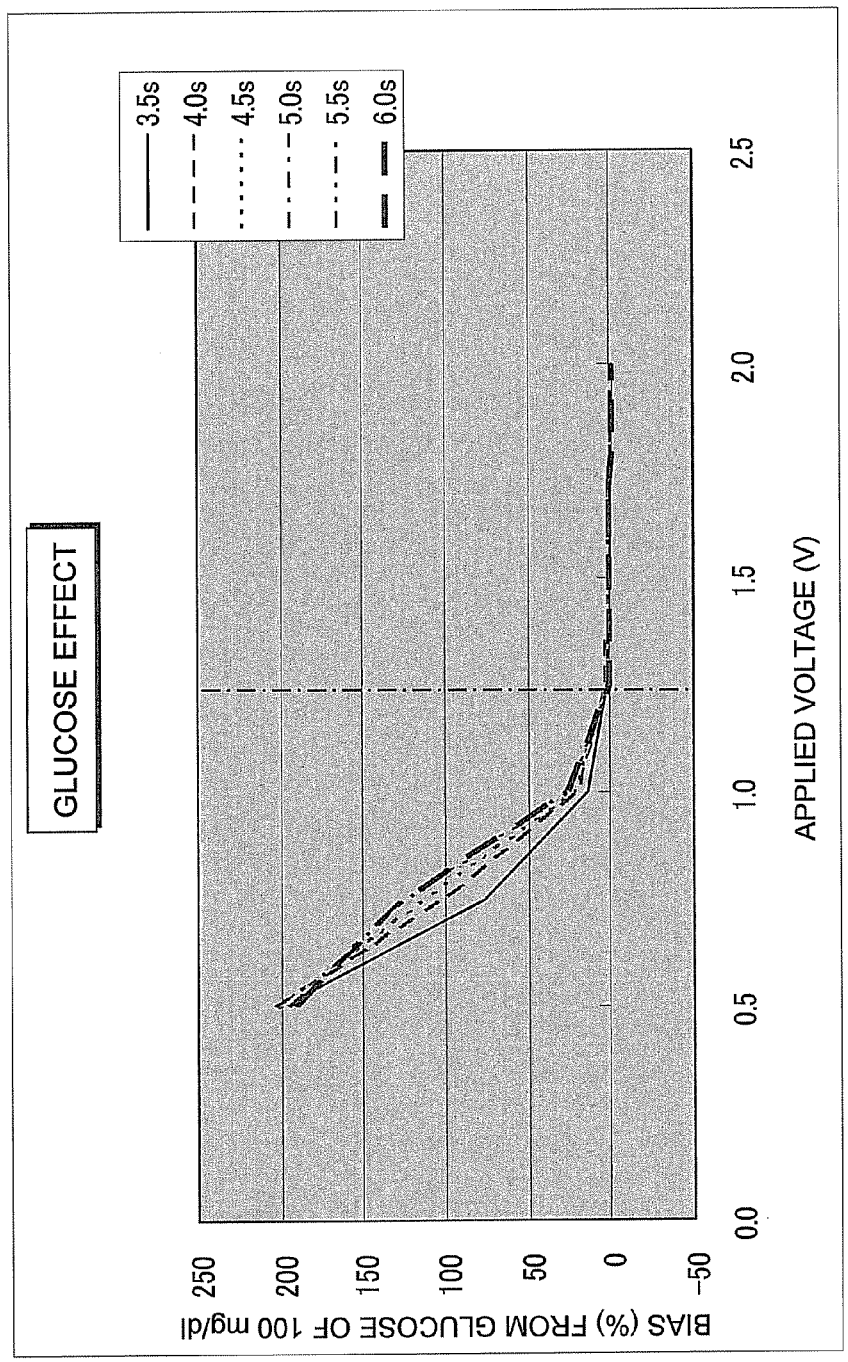
FIG. 103 is an explanatory chart comprehensively representing the magnitude of the applied voltage and the effect of the glucose concentration in the sensor chip illustrated in FIG. 98.

In the sensor chip configuration of the present exemplary embodiment, the following was found based on the aforementioned results obtained by measuring the glucose concentration and the temperature under the aforementioned respective conditions. Simply put, it was found that the temperature measurement could be accurately executed without being affected by the glucose concentration when a voltage of 1.25 or greater was applied in measuring the temperature as represented in FIG. 103.

(Exemplary Embodiment 4)

Yet another exemplary embodiment of the present invention will be hereinafter explained with reference to FIGS. 104 to 109.

Simply put, in the present exemplary embodiment, the response current value was measured using the sensor chip with a configuration (see FIG. 104) from that of the sensor chip in the aforementioned exemplary embodiment 1 by applying voltages of 0.5 V to 2.0 V similarly to the aforementioned exemplary embodiment 1.

As represented in FIG. 104, the sensor chip used in the present exemplary embodiment includes the working electrode, the counter electrode and the detection electrode, while carbon as an electrode material, glucose oxidase as an enzyme, and potassium ferricyanide as a mediator were used.

Further, the sensor chip used in the present exemplary embodiment includes three electrodes B, C and D. As represented in the lower table of FIG. 104, the magnitude and the application time period of a voltage to be applied to the electrodes B, C and D were set as follows. Firstly, the measurement was started at the timing when increase in an electricity of 0.05 µA was detected during application of a voltage of 0.5 V (500 mV) between the electrode C and the electrode D. Next, a voltage of 0.5 V was applied between the electrode B and the electrodes D and E for about 2 seconds in order to measure the glucose concentration. Subsequently, a voltage varying from 0.5 V to 2.0 V was applied between the electrode B and the electrode D for about 3.0 seconds in order to measure the temperature.

The following explanation relates to results of examining the effect of increase and reduction in the glucose concentration on the temperature measurement when the applied voltage was changed from 0.5 V to 2.0 V.

<Applied Voltage of 0.5 V>

Measurements were herein executed for examining the effect of variation in the glucose concentration (100 mg/dl, 400 mg/dl) on the response current value when a voltage to be applied among the electrodes was set to be 0.5 V.

Figure 105:
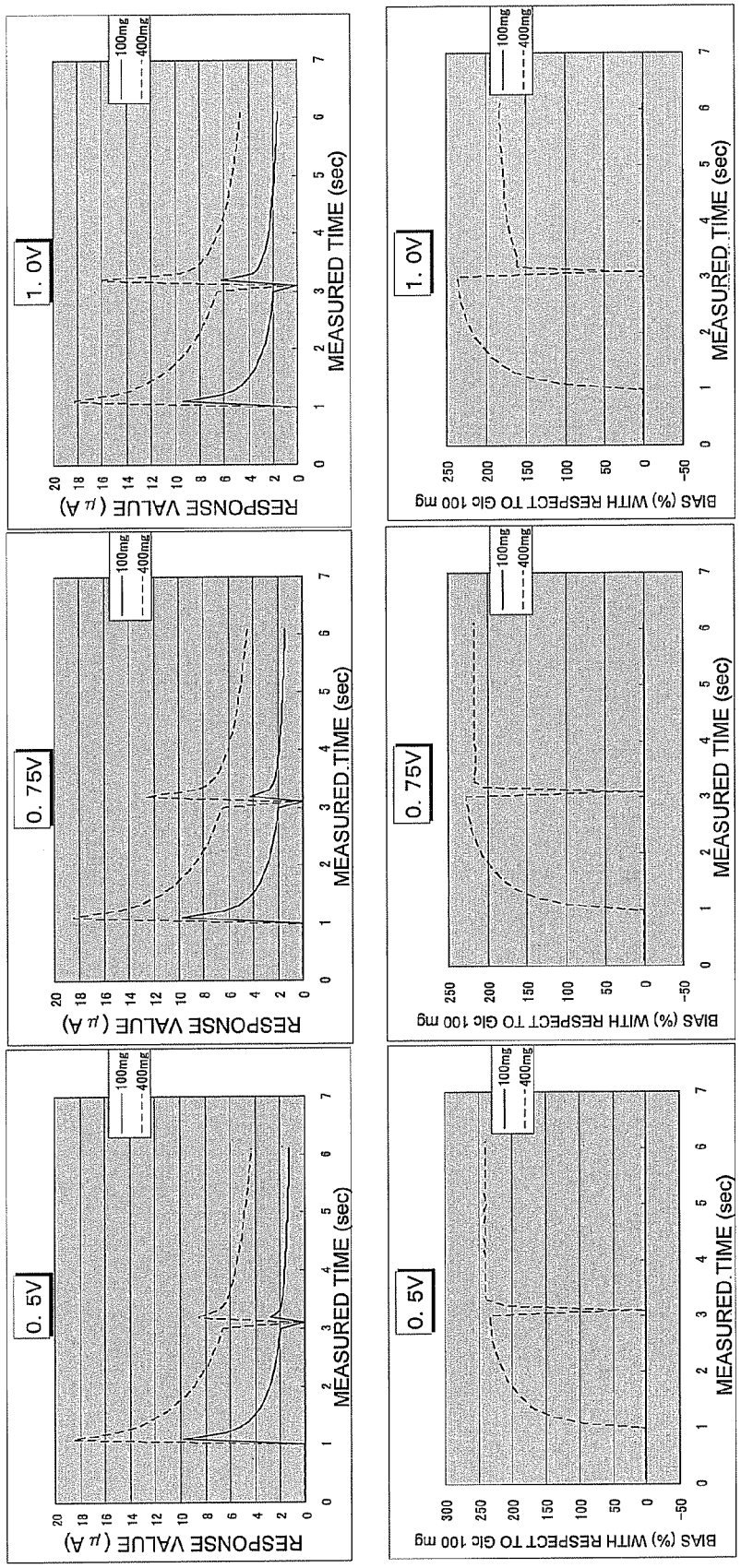
FIG. 105 includes charts representing the results of examining the effect of variation in the glucose concentration on the response current value in applying voltages of 0.5 to 1.0 V to the sensor chip illustrated in FIG. 104.

In FIG. 105, the left charts represent the measured results when the glucose concentration was changed and set to be 100 mg/dl and 400 mg/dl within each chart for easily understanding the effect of the glucose concentration. It should be noted that the left upper chart in FIG. 105 represents the measured results of response current values when the glucose concentration was set to be 100 mg/dl and 400 mg/dl, whereas the left lower chart in FIG. 105 represents a deviation between response current values corresponding to glucose concentrations of 100 mg/dl and 400 mg/dl.

It was consequently found that the response current value widely varied not only in measuring the glucose concentration but also in measuring the temperature when the glucose concentration is changed and set to be 100 mg/dl and 400 mg/dl.

Figure 107:
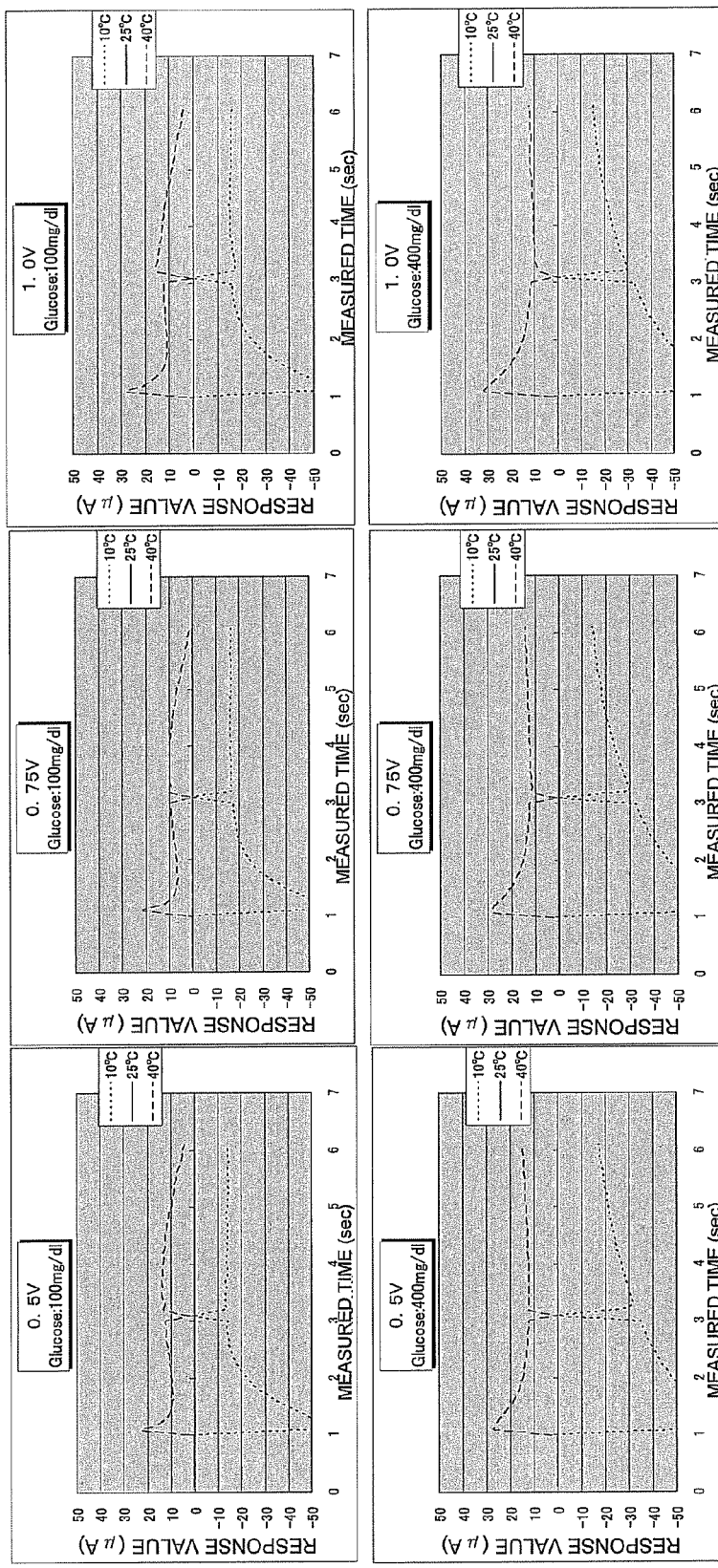
FIG. 107 includes charts representing a comprehensive result of examining the effect of variation in the temperature on the response current value in applying voltage of 0.5 to 1.0 V to the sensor chip illustrated in FIG. 104.

Further in FIG. 107, the left charts represent the measured results when the temperature conditions (10° C., 25° C. and 40° C.) were changed within each chart for easily understanding the effect of the blood sample temperature. It should be noted that the left upper chart of FIG. 107 represents the measured results of variation in the response current value when the glucose concentration was set to be 100 mg/dl, whereas the left lower chart of FIG. 107 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the glucose concentration and variation in the temperature when the response current value was measured by applying a voltage of 0.5 V among the electrodes and it was thereby impossible to extract only the effect of variation in the temperature.

<Applied Voltage of 0.75 V>

Measurements were herein executed for examining the effect of variation in the glucose concentration (100 mg/dl, 400 mg/dl) on the response current value when a voltage to be applied among the electrodes was set to be 0.75 V.

In FIG. 105, the center charts represent the measured results when the glucose concentration was changed and set to be 100 mg/dl and 400 mg/dl within each chart for easily understanding the effect of the glucose concentration. It should be noted that the center upper chart in FIG. 105 represents the measured results of response current values when the glucose concentration was set to be 100 mg/dl and 400 mg/dl, whereas the center lower chart in FIG. 105 represents a deviation between response current values corresponding to glucose concentrations of 100 mg/dl and 400 mg/dl.

It was consequently found that the response current value widely varied not only in measuring the glucose concentration but also in measuring the temperature when the glucose concentration is changed and set to be 100 mg/dl and 400 mg/dl.

Further in FIG. 107, the center charts represent the measured results when the temperature conditions (10° C., 25° C. and 40° C.) were changed within each chart for easily understanding the effect of the blood sample temperature. It should be noted that the center upper chart of FIG. 107 represents the measured results of variation in the response current value when the glucose concentration was set to be 100 mg/dl, whereas the center lower chart of FIG. 107 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the glucose concentration and variation in the temperature when the response current value was measured by applying a voltage of 0.75 V among the electrodes and it was thereby impossible to extract only the effect of variation in the temperature.

<Applied Voltage of 1.0 V>

Measurements were herein executed for examining the effect of variation in the glucose concentration (100 mg/dl, 400 mg/dl) on the response current value when a voltage to be applied among the electrodes was set to be 1.0 V.

In FIG. 105, the right charts represent the measured results when the glucose concentration was changed and set to be 100 mg/dl and 400 mg/dl within each chart for easily understanding the effect of the glucose concentration. It should be noted that the right upper chart in FIG. 105 represents the measured results of response current values when the glucose concentration was set to be 100 mg/dl and 400 mg/dl, whereas the right lower chart in FIG. 105 represents a deviation between response current values corresponding to glucose concentrations of 100 mg/dl and 400 mg/dl.

It was consequently found that the response current value widely varied in both measuring the glucose concentration and measuring the temperature when the glucose concentration is changed and set to be 100 mg/dl and 400 mg/dl.

Further in FIG. 107, the right charts represent the measured results when the temperature conditions (10° C., 25° C. and 40° C.) were changed within each chart for easily understanding the effect of the blood sample temperature. It should be noted that the right upper chart of FIG. 107 represents the measured results of variation in the response current value when the glucose concentration was set to be 100 mg/dl, whereas the right lower chart of FIG. 107 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature when the response current value was measured by applying a voltage of 1.0 V among the electrodes and it was thereby difficult to extract only the effect of variation in the temperature.

<Applied Voltage of 1.25 V>

Measurements were herein executed for examining the effect of variation in the glucose concentration (100 mg/dl, 400 mg/dl) on the response current value when a voltage to be applied among the electrodes was set to be 1.25 V.

Figure 106:
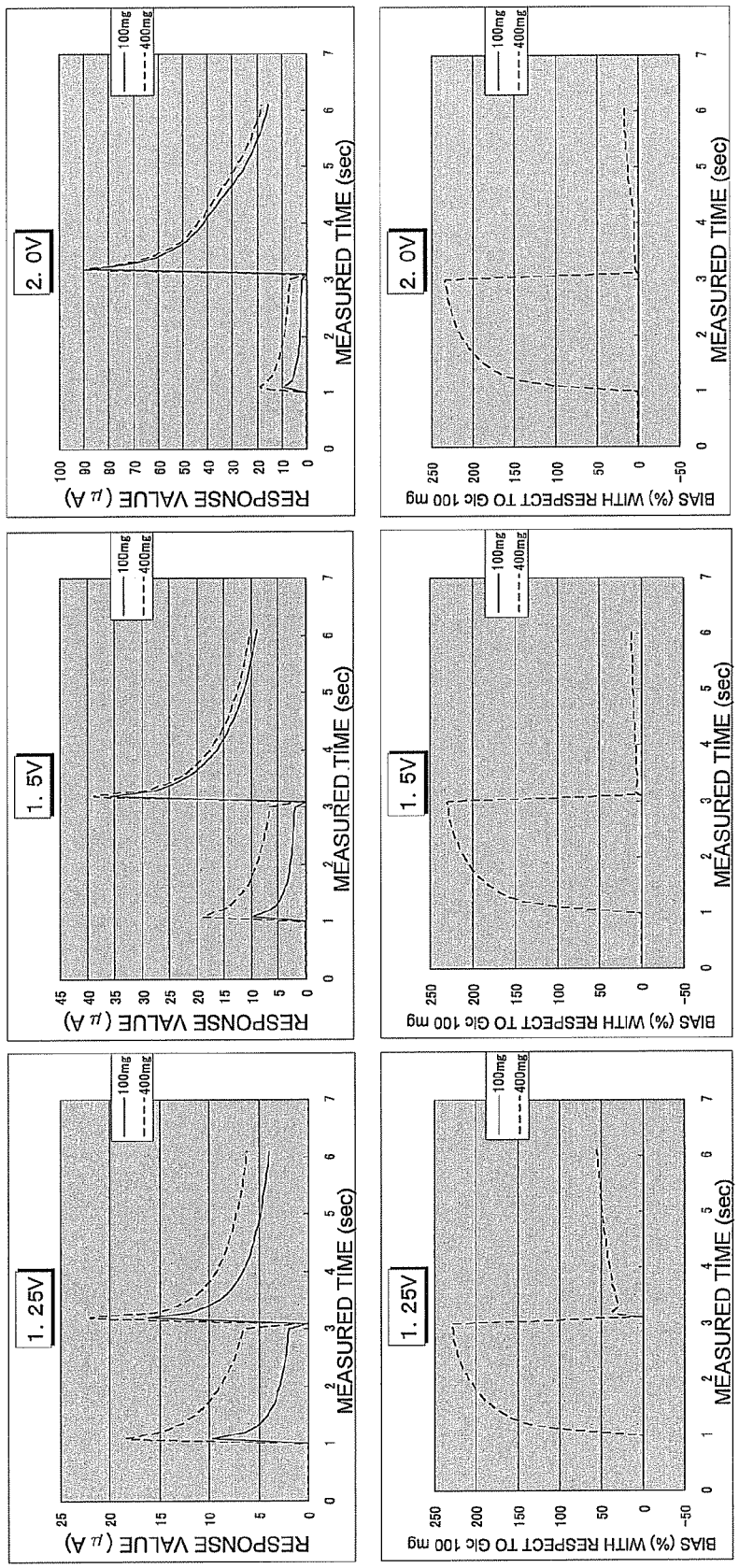
FIG. 106 includes charts representing the results of examining the effect of variation in the glucose concentration on the response current value in applying voltages of 1.25 to 2.0 V to the sensor chip illustrated in FIG. 104.

In FIG. 106, the left charts represent the measured results when the glucose concentration was changed and set to be 100 mg/dl and 400 mg/dl within each chart for easily understanding the effect of the glucose concentration. It should be noted that the left upper chart in FIG. 106 represents the measured results of response current values when the glucose concentration was set to be 100 mg/dl and 400 mg/dl, whereas the left lower chart in FIG. 106 represents a deviation between response current values corresponding to glucose concentrations of 100 mg/dl and 400 mg/dl.

It was consequently found that the response current value widely varied in both measuring the glucose concentration and measuring the temperature when the glucose concentration is changed and set to be 100 mg/dl and 400 mg/dl.

Figure 108:
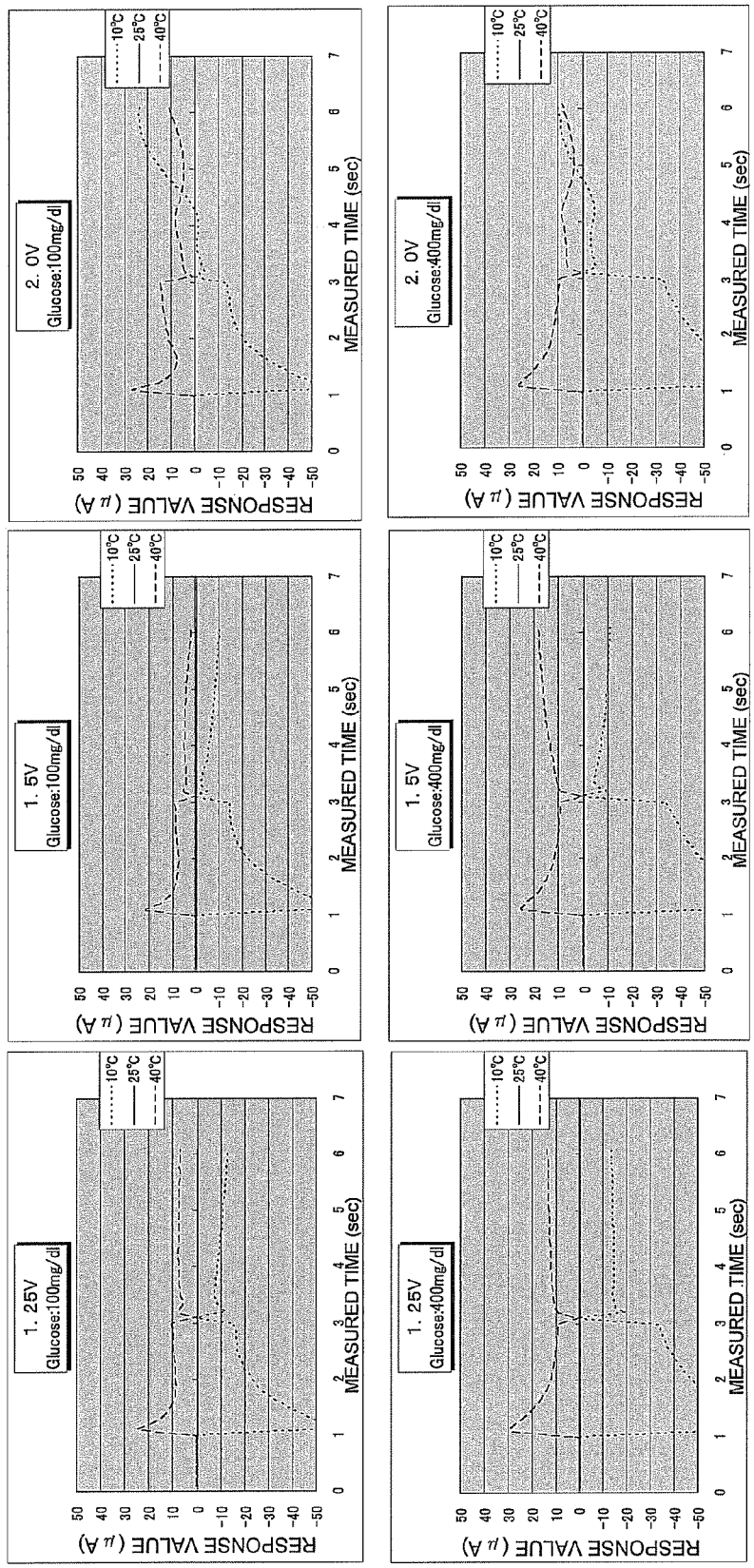
FIG. 108 includes charts representing a comprehensive result of examining the effect of variation in the temperature on the response current value in applying voltage of 1.25 to 2.0 V to the sensor chip illustrated in FIG. 104.

Further in FIG. 108, the left charts represent the measured results when the temperature conditions (10° C., 25° C. and 40° C.) were changed within each chart for easily understanding the effect of the blood sample temperature. It should be noted that the left upper chart of FIG. 108 represents the measured results of variation in the response current value when the glucose concentration was set to be 100 mg/dl, whereas the left lower chart of FIG. 108 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature when the response current value was measured by applying a voltage of 1.25 V among the electrodes and it was thereby difficult to extract only the effect of variation in the temperature.

<Applied Voltage of 1.5 V>

Measurements were herein executed for examining the effect of variation in the glucose concentration (100 mg/dl, 400 mg/dl) on the response current value when a voltage to be applied among the electrodes was set to be 1.5 V.

In FIG. 106, the center charts represent the measured results when the glucose concentration was changed and set to be 100 mg/dl and 400 mg/dl within each chart for easily understanding the effect of the glucose concentration. It should be noted that the center upper chart in FIG. 106 represents the measured results of response current values when the glucose concentration was set to be 100 mg/dl and 400 mg/dl, whereas the center lower chart in FIG. 106 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the response current value hardly varied in measuring the temperature when the glucose concentration is changed and set to be 100 mg/dl and 400 mg/dl.

Further in FIG. 108, the center charts represent the measured results when the temperature conditions (10° C., 25° C. and 40° C.) were changed within each chart for easily understanding the effect of the blood sample temperature. It should be noted that the center upper chart of FIG. 108 represents the measured results of variation in the response current value when the glucose concentration was set to be 100 mg/dl, whereas the center lower chart of FIG. 108 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.5 V among the electrodes. As represented in the center lower chart of FIG. 106, however, it was found that the response current value was hardly affected by increase and reduction in the glucose concentration in measuring the temperature when a voltage of 1.5 V was applied among the electrodes.

<Applied Voltage of 2.0 V>

Measurements were herein executed for examining the effect of variation in the glucose concentration (100 mg/dl, 400 mg/dl) on the response current value when a voltage to be applied among the electrodes was set to be 2.0 V.

In FIG. 106, the right charts represent the measured results when the glucose concentration was changed and set to be 100 mg/dl and 400 mg/dl within each chart for easily understanding the effect of the glucose concentration. It should be noted that the right upper chart in FIG. 106 represents the measured results of response current values when the glucose concentration was set to be 100 mg/dl and 400 mg/dl, whereas the right lower chart in FIG. 106 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the response current value hardly varied in measuring the temperature when the glucose concentration is changed and set to be 100 mg/dl and 400 mg/dl.

Further in FIG. 108, the right charts represent the measured results when the temperature conditions (10° C., 25° C. and 40° C.) were changed within each chart for easily understanding the effect of the blood sample temperature. It should be noted that the right upper chart of FIG. 108 represents the measured results of variation in the response current value when the glucose concentration was set to be 100 mg/dl, whereas the right lower chart of FIG. 108 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 2.0 V among the electrodes. As represented in the right lower chart of FIG. 106, however, it was found that the response current value was hardly affected by increase and reduction in the glucose concentration in measuring the temperature when a voltage of 2.0 V was applied among the electrodes.

<Comprehensive Results>

Figure 109:
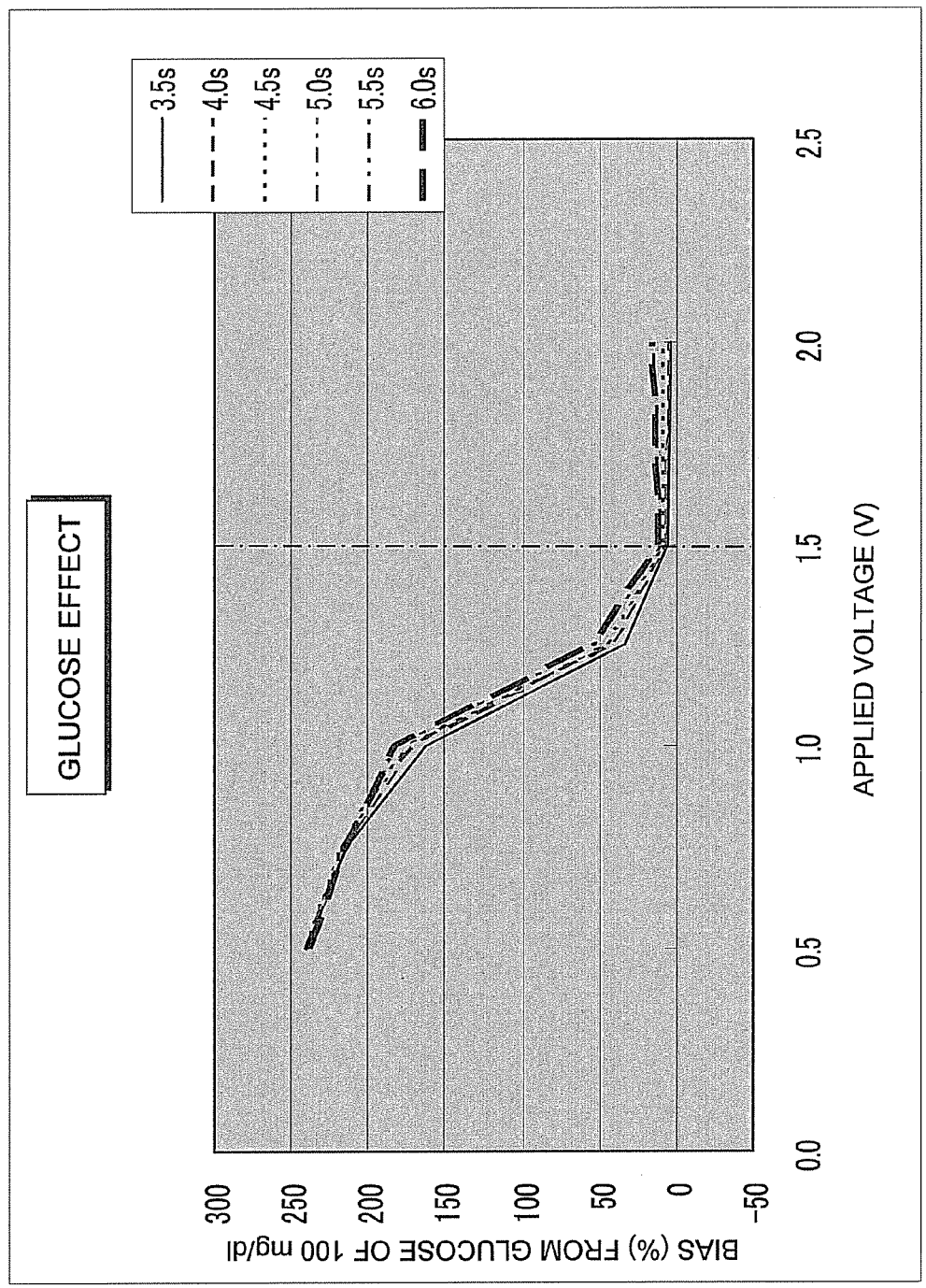
FIG. 109 is an explanatory chart comprehensively representing the magnitude of the applied voltage and the effect of the glucose concentration in the sensor chip illustrated in FIG. 104.

In the sensor chip configuration of the present exemplary embodiment, the following was found based on the aforementioned results obtained by measuring the glucose concentration and the temperature under the aforementioned respective conditions. Simply put, it was found that the temperature measurement could be accurately executed without being affected by the glucose concentration when a voltage of 1.5 or greater was applied in measuring the temperature as represented in FIG. 109.

(Exemplary Embodiment 5)

Yet another exemplary embodiment of the present invention will be hereinafter explained with reference to FIGS. 110 to 115.

Simply put, in the present exemplary embodiment, the response current value was measured using the sensor chip with a configuration (see FIG. 110) from that of the sensor chip in the aforementioned exemplary embodiment 1 under the same conditions (of applying voltages of 0.5 V to 2.0 V) as the aforementioned exemplary embodiment 1.

As represented in FIG. 110, the sensor chip used in the present exemplary embodiment includes the working electrode, the counter electrode and two detection electrodes, while Au as an electrode material, glucose dehydrogenase as an enzyme, and N,N-bis-(hydroxyethyl)-3-methoxy-p-nitroaniline as a mediator were used.

Further, the sensor chip used in the present exemplary embodiment includes four electrodes G, F, E and B. As represented in the lower table of FIG. 110, the magnitude and the application time period of a voltage to be applied to the electrodes G, F, E and B were set as follows. Firstly, the measurement was started at the timing when increase in an electricity of 0.05 µA was detected during application of a voltage of 0.5 V (500 mV) between the electrode E and the electrode F. Next, a voltage of 0.5 V was applied between the electrode G and the electrode B for about 2 seconds in order to measure the glucose concentration. Subsequently, a voltage varying from 0.5 V to 2.0 V was applied between the electrode G and the electrode B for about 3.0 seconds in order to measure the temperature.

The following explanation relates to results of examining the effect of increase and reduction in the glucose concentration on the temperature measurement when the applied voltage was changed from 0.5 V to 2.0 V.

<Applied Voltage of 0.5 V>

Measurements were herein executed for examining the effect of variation in the glucose concentration (100 mg/dl, 400 mg/dl) on the response current value when a voltage to be applied among the electrodes was set to be 0.5 V.

Figure 111:
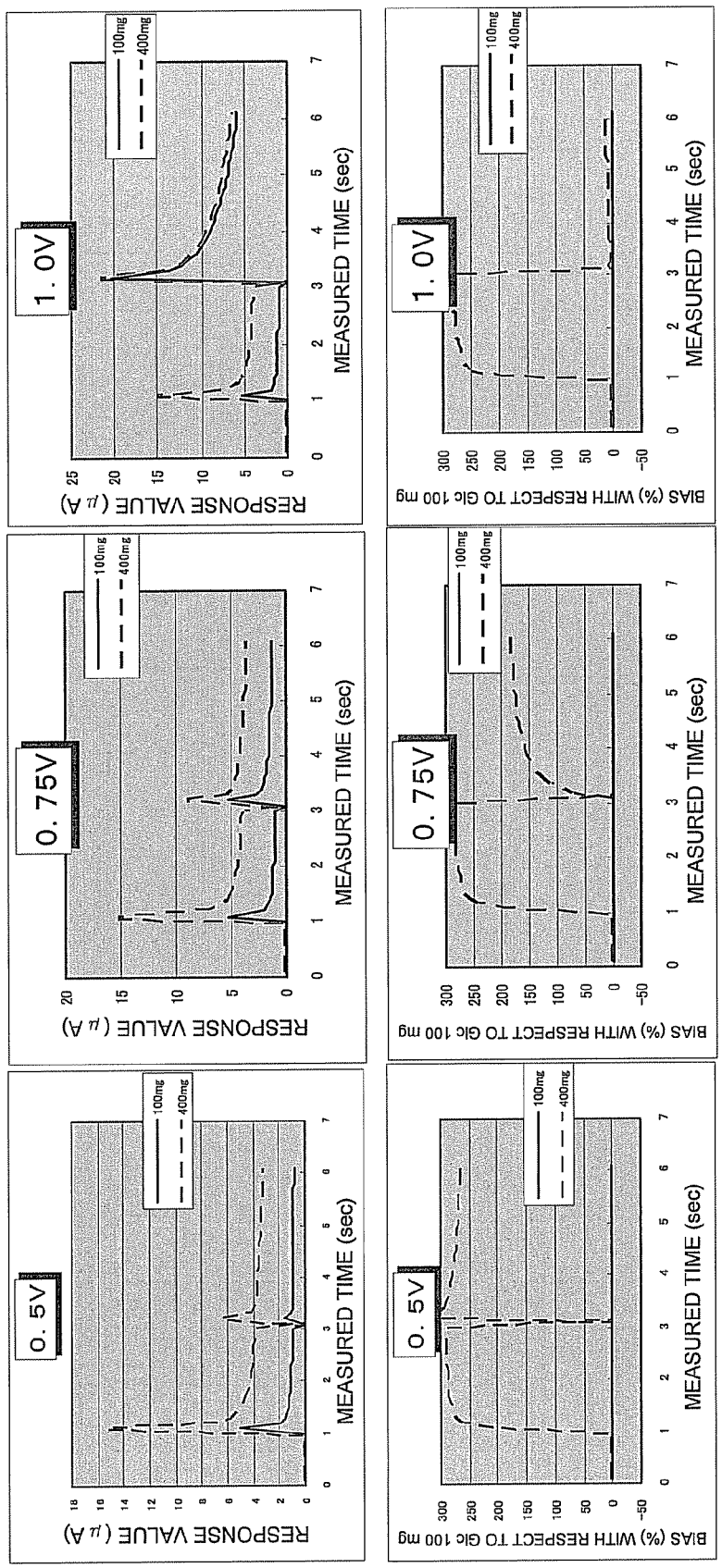
FIG. 111 includes charts representing the results of examining the effect of variation in the glucose concentration on the response current value in applying voltages of 0.5 to 1.0 V to the sensor chip illustrated in FIG. 110.

In FIG. 111, the left charts represent the measured results when the glucose concentration was changed and set to be 100 mg/dl and 400 mg/dl within each chart for easily understanding the effect of the glucose concentration. It should be noted that the left upper chart in FIG. 111 represents the measured results of response current values when the glucose concentration was set to be 100 mg/dl and 400 mg/dl, whereas the left lower chart in FIG. 111 represents a deviation between response current values corresponding to glucose concentrations of 100 mg/dl and 400 mg/dl.

It was consequently found that the response current value widely varied not only in measuring the glucose concentration but also in measuring the temperature when the glucose concentration is changed and set to be 100 mg/dl and 400 mg/dl.

Figure 113:
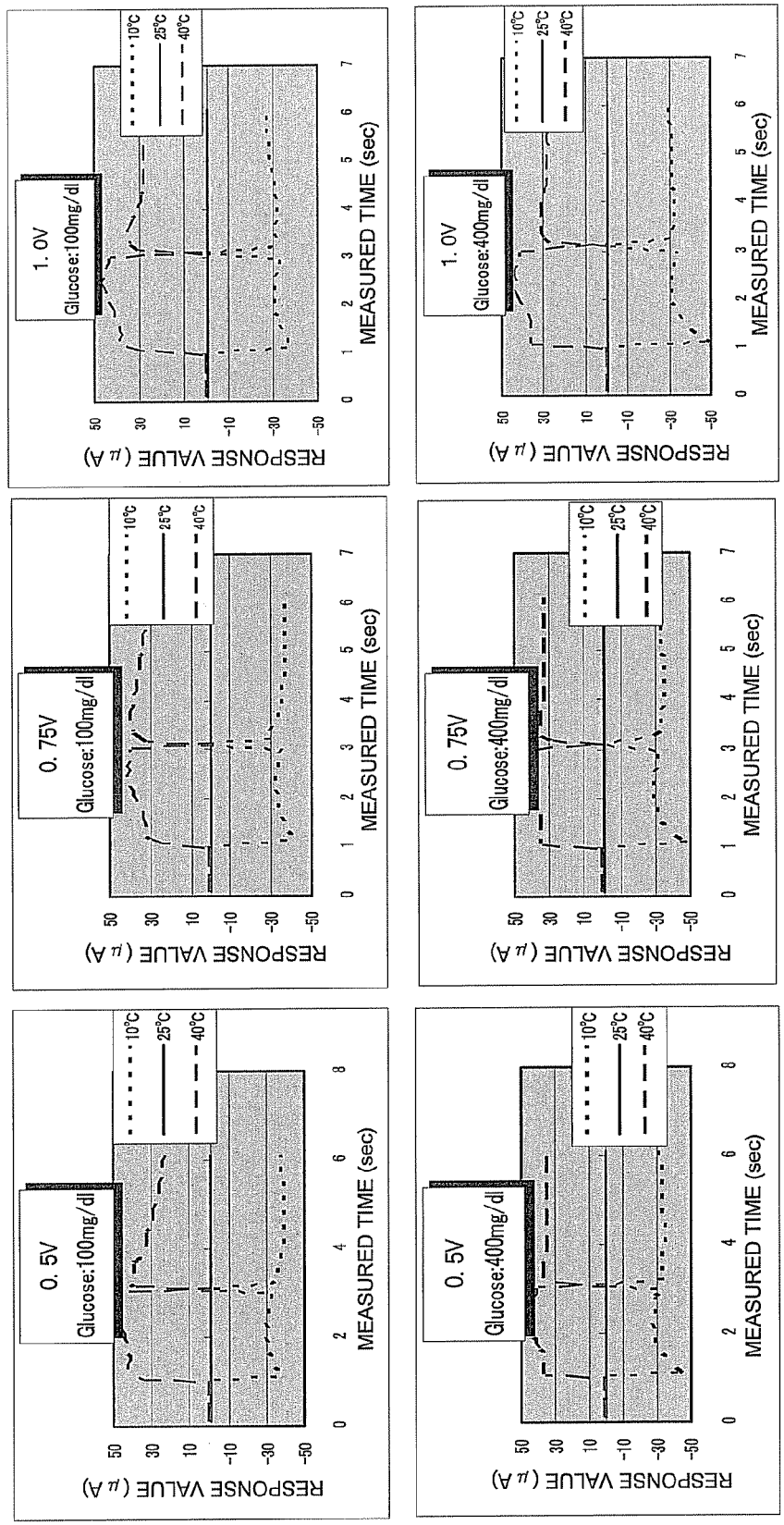
FIG. 113 includes charts representing a comprehensive result of examining the effect of variation in the temperature on the response current value in applying voltage of 0.5 to 1.0 V to the sensor chip illustrated in FIG. 110.

Further in FIG. 113, the left charts represent the measured results when the temperature conditions (10° C., 25° C. and 40° C.) were changed within each chart for easily understanding the effect of the blood sample temperature. It should be noted that the left upper chart of FIG. 113 represents the measured results of variation in the response current value when the glucose concentration was set to be 100 mg/dl, whereas the left lower chart of FIG. 113 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the glucose concentration and variation in the temperature when the response current value was measured by applying a voltage of 0.5 V among the electrodes and it was thereby impossible to extract only the effect of variation in the temperature.

<Applied Voltage of 0.75 V>

Measurements were herein executed for examining the effect of variation in the glucose concentration (100 mg/dl, 400 mg/dl) on the response current value when a voltage to be applied among the electrodes was set to be 0.75 V.

In FIG. 111, the center charts represent the measured results when the glucose concentration was changed and set to be 100 mg/dl and 400 mg/dl within each chart for easily understanding the effect of the glucose concentration. It should be noted that the center upper chart in FIG. 111 represents the measured results of response current values when the glucose concentration was set to be 100 mg/dl and 400 mg/dl, whereas the center lower chart in FIG. 111 represents a deviation between response current values corresponding to glucose concentrations of 100 mg/dl and 400 mg/dl.

It was consequently found that the response current value widely varied not only in measuring the glucose concentration but also in measuring the temperature when the glucose concentration is changed and set to be 100 mg/dl and 400 mg/dl.

Further in FIG. 113, the center charts represent the measured results when the temperature conditions (10° C., 25° C. and 40° C.) were changed within each chart for easily understanding the effect of the blood sample temperature. It should be noted that the center upper chart of FIG. 113 represents the measured results of variation in the response current value when the glucose concentration was set to be 100 mg/dl, whereas the center lower chart of FIG. 113 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the glucose concentration and variation in the temperature when the response current value was measured by applying a voltage of 0.75 V among the electrodes and it was thereby impossible to extract only the effect of variation in the temperature.

<Applied Voltage of 1.0 V>

Measurements were herein executed for examining the effect of variation in the glucose concentration (100 mg/dl, 400 mg/dl) on the response current value when a voltage to be applied among the electrodes was set to be 1.0 V.

In FIG. 111, the right charts represent the measured results when the glucose concentration was changed and set to be 100 mg/dl and 400 mg/dl within each chart for easily understanding the effect of the glucose concentration. It should be noted that the right upper chart in FIG. 111 represents the measured results of response current values when the glucose concentration was set to be 100 mg/dl and 400 mg/dl, whereas the right lower chart in FIG. 111 represents a deviation between response current values corresponding to glucose concentrations of 100 mg/dl and 400 mg/dl.

It was consequently found that the response current value certainly varied in measuring the glucose concentration but hardly varied in measuring the temperature when the glucose concentration is changed and set to be 100 mg/dl and 400 mg/dl.

Further in FIG. 113, the right charts represent the measured results when the temperature conditions (10° C., 25° C. and 40° C.) were changed within each chart for easily understanding the effect of the blood sample temperature. It should be noted that the right upper chart of FIG. 113 represents the measured results of variation in the response current value when the glucose concentration was set to be 100 mg/dl, whereas the right lower chart of FIG. 113 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.0 V among the electrodes. As represented in the right lower chart of FIG. 111, however, it was found that the response current value was hardly affected by increase and reduction in the glucose concentration in measuring the temperature when a voltage of 1.0 V was applied among the electrodes.

<Applied Voltage of 1.25 V>

Measurements were herein executed for examining the effect of variation in the glucose concentration (100 mg/dl, 400 mg/dl) on the response current value when a voltage to be applied among the electrodes was set to be 1.25 V.

Figure 112:
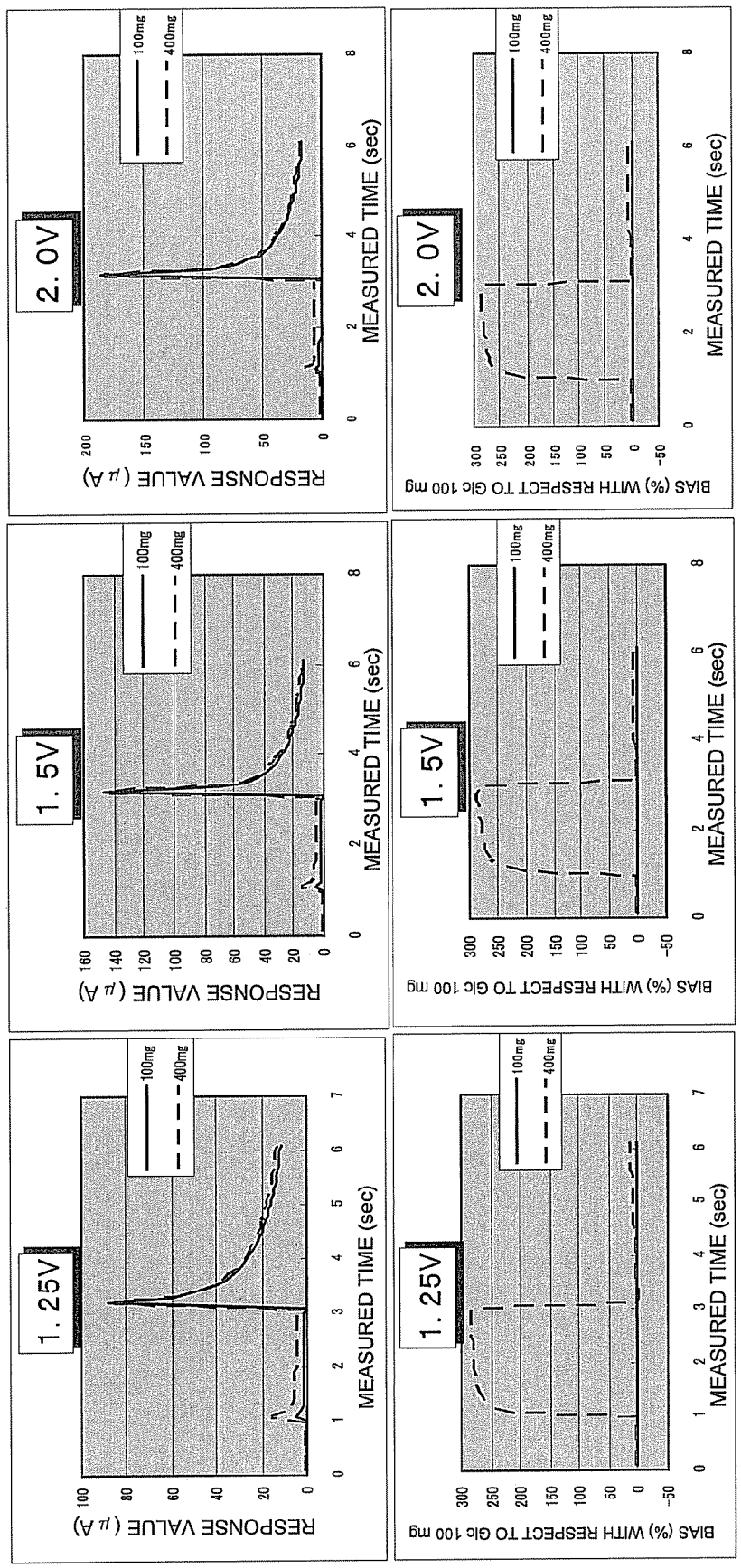
FIG. 112 includes charts representing the results of examining the effect of variation in the glucose concentration on the response current value in applying voltages of 1.25 to 2.0 V to the sensor chip illustrated in FIG. 110.

In FIG. 112, the left charts represent the measured results when the glucose concentration was changed and set to be 100 mg/dl and 400 mg/dl within each chart for easily understanding the effect of the glucose concentration. It should be noted that the left upper chart in FIG. 112 represents the measured results of response current values when the glucose concentration was set to be 100 mg/dl and 400 mg/dl, whereas the left lower chart in FIG. 112 represents a deviation between response current values corresponding to glucose concentrations of 100 mg/dl and 400 mg/dl.

It was consequently found that the response current value certainly varied in measuring the glucose concentration and but hardly varied in measuring the temperature when the glucose concentration is changed and set to be 100 mg/dl and 400 mg/dl.

Figure 114:
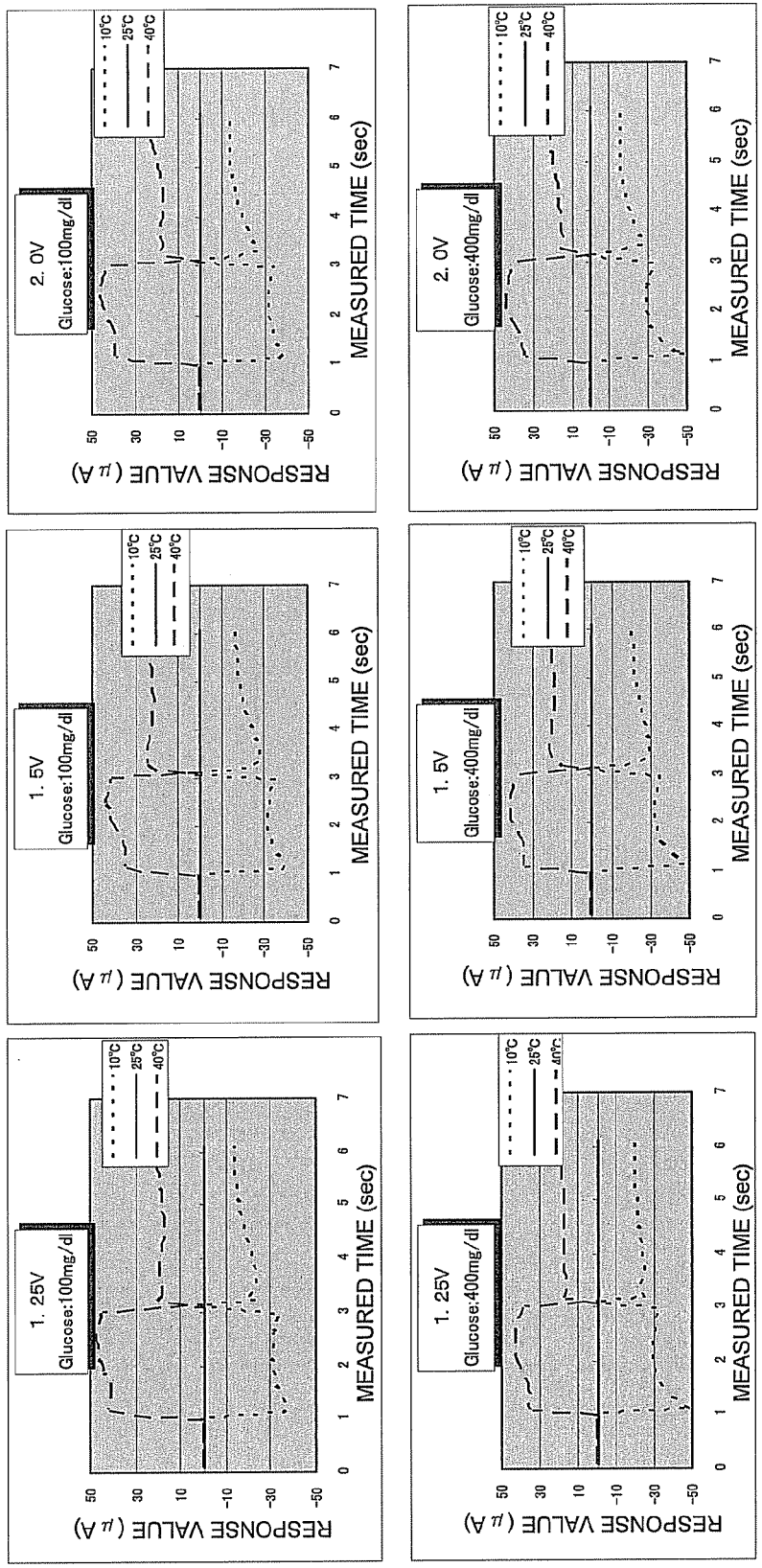
FIG. 114 includes charts representing a comprehensive result of examining the effect of variation in the temperature on the response current value in applying voltage of 1.25 to 2.0 V to the sensor chip illustrated in FIG. 110.

Further in FIG. 114, the left charts represent the measured results when the temperature conditions (10° C., 25° C. and 40° C.) were changed within each chart for easily understanding the effect of the blood sample temperature. It should be noted that the left upper chart of FIG. 114 represents the measured results of variation in the response current value when the glucose concentration was set to be 100 mg/dl, whereas the left lower chart of FIG. 114 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.25 V among the electrodes. As represented in the left lower chart of FIG. 112, however, it was found that the response current value was hardly affected by increase and reduction in the glucose concentration when a voltage of 1.25 V was applied among the electrodes.

<Applied Voltage of 1.5 V>

Measurements were herein executed for examining the effect of variation in the glucose concentration (100 mg/dl, 400 mg/dl) on the response current value when a voltage to be applied among the electrodes was set to be 1.5 V.

In FIG. 112, the center charts represent the measured results when the glucose concentration was changed and set to be 100 mg/dl and 400 mg/dl within each chart for easily understanding the effect of the glucose concentration. It should be noted that the center upper chart in FIG. 112 represents the measured results of response current values when the glucose concentration was set to be 100 mg/dl and 400 mg/dl, whereas the center lower chart in FIG. 112 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the response current value hardly varied in measuring the temperature when the glucose concentration is changed and set to be 100 mg/dl and 400 mg/dl.

Further in FIG. 114, the center charts represent the measured results when the temperature conditions (10° C., 25° C. and 40° C.) were changed within each chart for easily understanding the effect of the blood sample temperature. It should be noted that the center upper chart of FIG. 114 represents the measured results of variation in the response current value when the glucose concentration was set to be 100 mg/dl, whereas the center lower chart of FIG. 114 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.5 V among the electrodes. As represented in the center lower chart of FIG. 112, however, it was found that the response current value was hardly affected by increase and reduction in the glucose concentration in measuring the temperature when a voltage of 1.5 V was applied among the electrodes.

<Applied Voltage of 2.0 V>

Measurements were herein executed for examining the effect of variation in the glucose concentration (100 mg/dl, 400 mg/dl) on the response current value when a voltage to be applied among the electrodes was set to be 2.0 V.

In FIG. 112, the right charts represent the measured results when the glucose concentration was changed and set to be 100 mg/dl and 400 mg/dl within each chart for easily understanding the effect of the glucose concentration. It should be noted that the right upper chart in FIG. 112 represents the measured results of response current values when the glucose concentration was set to be 100 mg/dl and 400 mg/dl, whereas the right lower chart in FIG. 112 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the response current value hardly varied in measuring the temperature when the glucose concentration is changed and set to be 100 mg/dl and 400 mg/dl.

Further in FIG. 114, the right charts represent the measured results when the temperature conditions (10° C., 25° C. and 40° C.) were changed within each chart for easily understanding the effect of the blood sample temperature. It should be noted that the right upper chart of FIG. 114 represents the measured results of variation in the response current value when the glucose concentration was set to be 100 mg/dl, whereas the right lower chart of FIG. 114 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 2.0 V among the electrodes. As represented in the right lower chart of FIG. 112, however, it was found that the response current value was hardly affected by increase and reduction in the glucose concentration in measuring the temperature when a voltage of 2.0 V was applied among the electrodes.

<Comprehensive Results>

Figure 115:
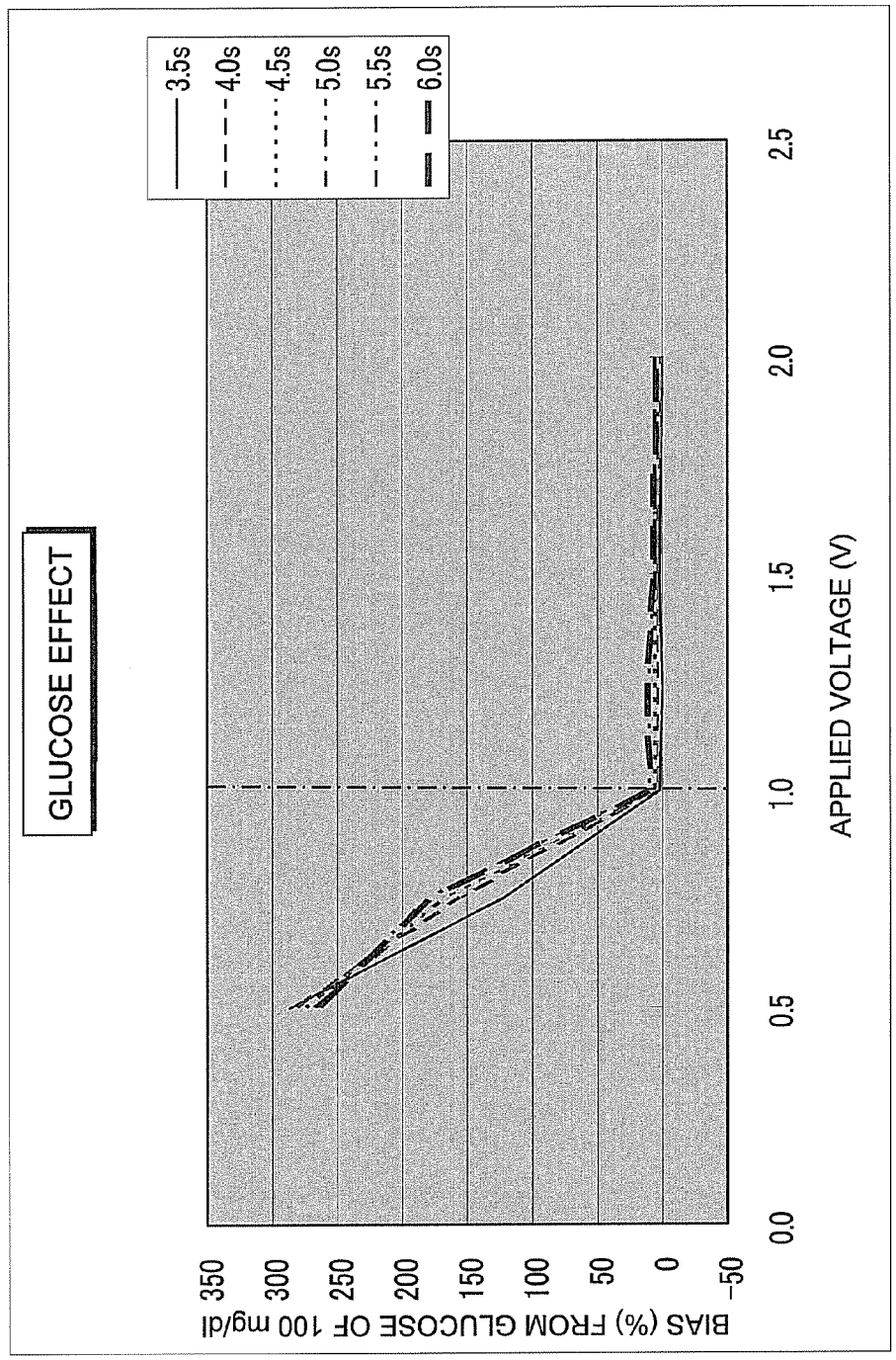
FIG. 115 is an explanatory chart comprehensively representing the magnitude of an applied voltage and the effect of the glucose concentration in the sensor chip illustrated in FIG. 110.

In the sensor chip configuration of the present exemplary embodiment, the following was found based on the aforementioned results obtained by measuring the glucose concentration and the temperature under the aforementioned respective conditions. Simply put, it was found that the temperature measurement could be accurately executed without being affected by the glucose concentration when a voltage of 1.0 or greater was applied in measuring the temperature as represented in FIG. 115.

(Exemplary Embodiment 6)

Yet another exemplary embodiment of the present invention will be hereinafter explained with reference to FIGS. 116 to 121.

Simply put, in the present exemplary embodiment, the response current value was measured using the sensor chip with a configuration (see FIG. 116) from that of the sensor chip in the aforementioned exemplary embodiment 1 by applying voltages of 0.5 V to 2.0 V similarly to the aforementioned exemplary embodiment 1.

As represented in FIG. 116, the sensor chip used in the present exemplary embodiment includes the working electrode, the counter electrode and the detection electrode, while carbon/Ag as an electrode material and glucose dehydrogenase as an enzyme were used. It should be noted that the reagent was knead into the electrode material and was thereby supported.

Further, the sensor chip used in the present exemplary embodiment includes three electrodes A, B and C. As represented in the lower table of FIG. 116, the magnitude and the application time period of a voltage to be applied to the electrodes A, B and C were set as follows. Firstly, the measurement was started at the timing when increase in an electricity of 0.05 µA was detected during application of a voltage of 0.5 V (500 mV) between the electrode C and the electrode B. Next, a voltage of 0.5 V was applied between the electrode A and the electrode B for about 2 seconds in order to measure the glucose concentration. Subsequently, a voltage varying from 0.5 V to 2.0 V was applied between the electrode A and the electrode B for about 3.0 seconds in order to measure the temperature.

The following explanation relates to results of examining the effect of increase and reduction in the glucose concentration on the temperature measurement when the applied voltage was changed from 0.5 V to 2.0 V.

<Applied Voltage of 0.5 V>

Measurements were herein executed for examining the effect of variation in the glucose concentration (100 mg/dl, 400 mg/dl) on the response current value when a voltage to be applied among the electrodes was set to be 0.5 V.

Figure 117:
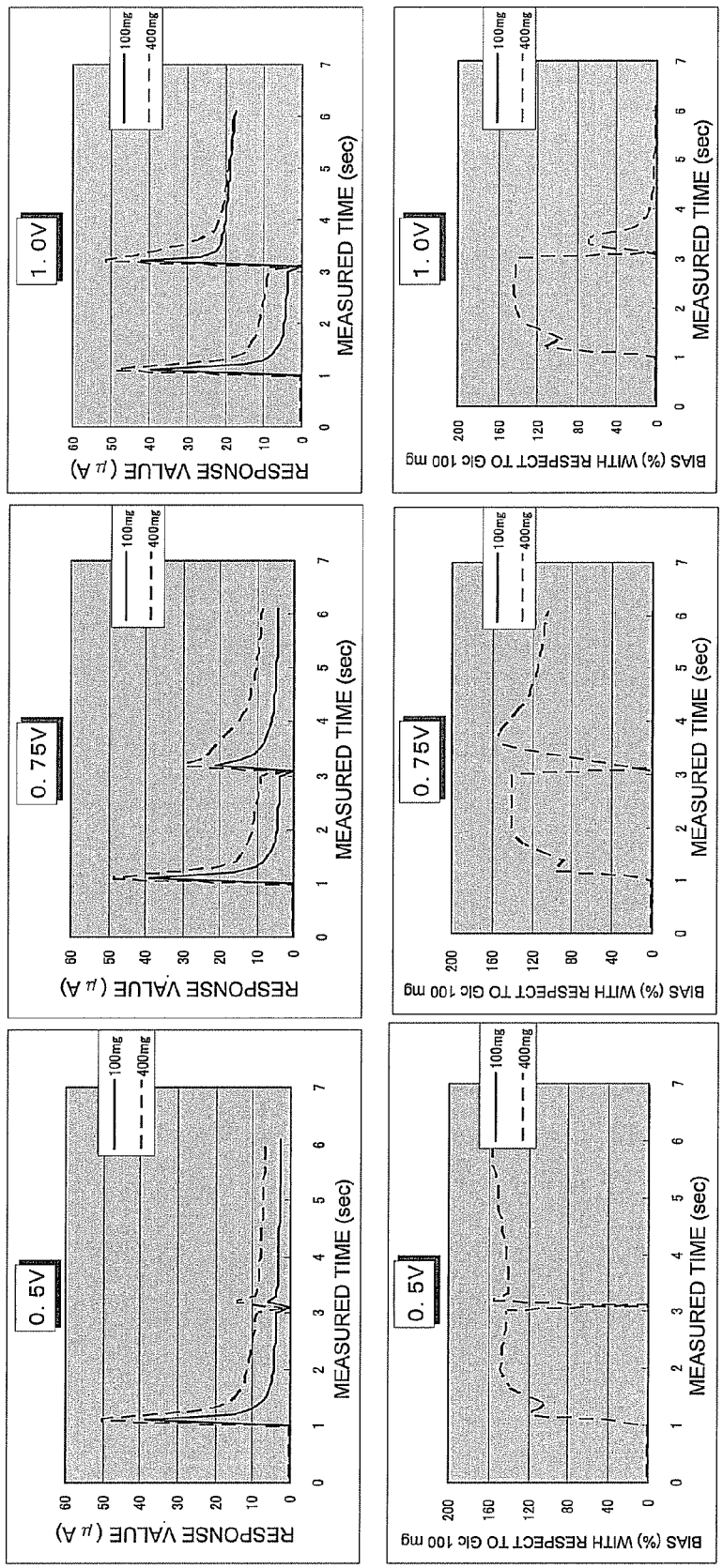
FIG. 117 includes charts representing the results of examining the effect of variation in the glucose concentration on the response current value in applying voltages of 0.5 to 1.0 V to the sensor chip illustrated in FIG. 116.

In FIG. 117, the left charts represent the measured results when the glucose concentration was changed and set to be 100 mg/dl and 400 mg/dl within each chart for easily understanding the effect of the glucose concentration. It should be noted that the left upper chart in FIG. 117 represents the measured results of response current values when the glucose concentration was set to be 100 mg/dl and 400 mg/dl, whereas the left lower chart in FIG. 117 represents a deviation between response current values corresponding to glucose concentrations of 100 mg/dl and 400 mg/dl.

It was consequently found that the response current value widely varied not only in measuring the glucose concentration but also in measuring the temperature when the glucose concentration is changed and set to be 100 mg/dl and 400 mg/dl.

Figure 119:
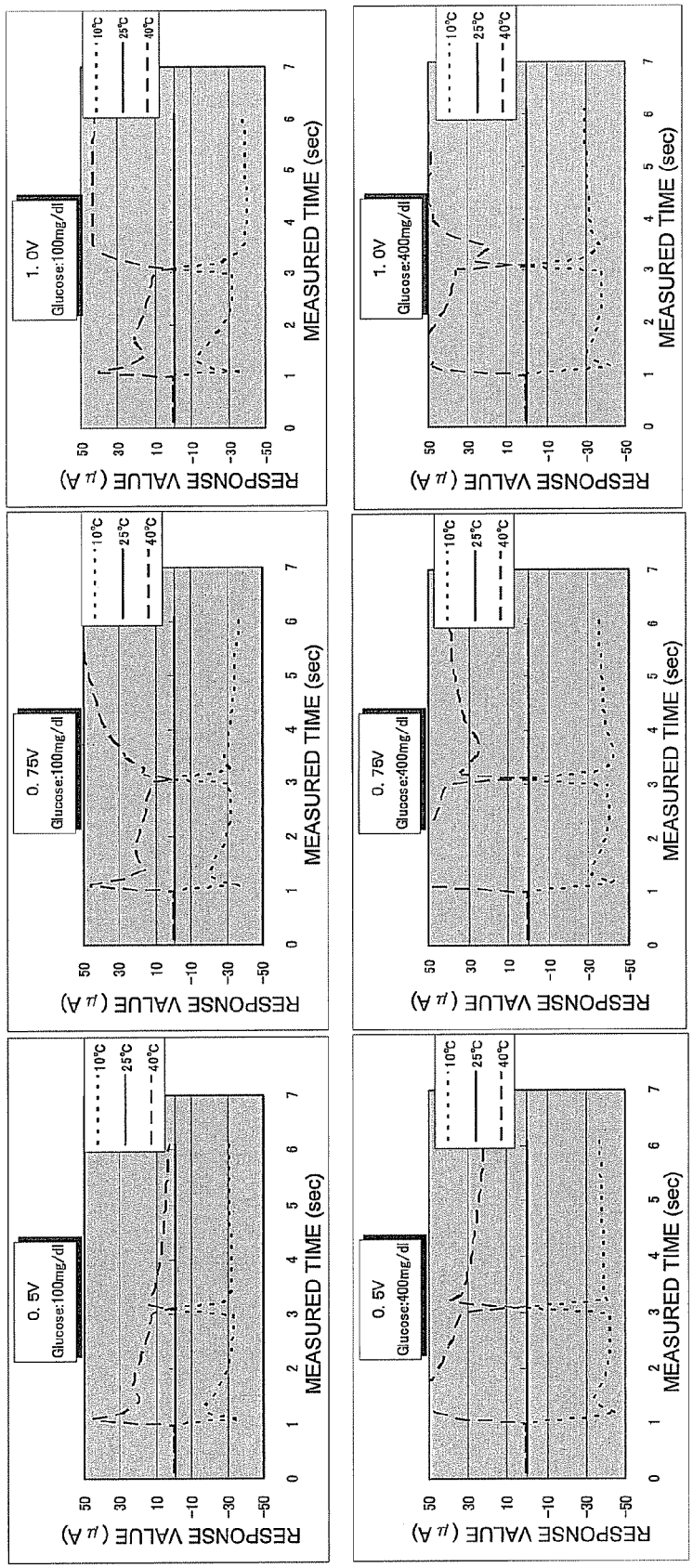
FIG. 119 includes charts representing a comprehensive result of examining the effect of variation in the temperature on the response current value in applying voltage of 0.5 to 1.0 V to the sensor chip illustrated in FIG. 116.

Further in FIG. 119, the left charts represent the measured results when the temperature conditions (10° C., 25° C. and 40° C.) were changed within each chart for easily understanding the effect of the blood sample temperature. It should be noted that the left upper chart of FIG. 119 represents the measured results of variation in the response current value when the glucose concentration was set to be 100 mg/dl, whereas the left lower chart of FIG. 119 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the glucose concentration and variation in the temperature when the response current value was measured by applying a voltage of 0.5 V among the electrodes and it was thereby impossible to extract only the effect of variation in the temperature.

<Applied Voltage of 0.75 V>

Measurements were herein executed for examining the effect of variation in the glucose concentration (100 mg/dl, 400 mg/dl) on the response current value when a voltage to be applied among the electrodes was set to be 0.75 V.

In FIG. 117, the center charts represent the measured results when the glucose concentration was changed and set to be 100 mg/dl and 400 mg/dl within each chart for easily understanding the effect of the glucose concentration. It should be noted that the center upper chart in FIG. 117 represents the measured results of response current values when the glucose concentration was set to be 100 mg/dl and 400 mg/dl, whereas the center lower chart in FIG. 117 represents a deviation between response current values corresponding to glucose concentrations of 100 mg/dl and 400 mg/dl.

It was consequently found that the response current value widely varied not only in measuring the glucose concentration but also in measuring the temperature when the glucose concentration is changed and set to be 100 mg/dl and 400 mg/dl.

Further in FIG. 119, the center charts represent the measured results when the temperature conditions (10° C., 25° C. and 40° C.) were changed within each chart for easily understanding the effect of the blood sample temperature. It should be noted that the center upper chart of FIG. 119 represents the measured results of variation in the response current value when the glucose concentration was set to be 100 mg/dl, whereas the center lower chart of FIG. 119 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the glucose concentration and variation in the temperature when the response current value was measured by applying a voltage of 0.75 V among the electrodes and it was thereby impossible to extract only the effect of variation in the temperature.

<Applied Voltage of 1.0 V>

Measurements were herein executed for examining the effect of variation in the glucose concentration (100 mg/dl, 400 mg/dl) on the response current value when a voltage to be applied among the electrodes was set to be 1.0 V.

In FIG. 117, the right charts represent the measured results when the glucose concentration was changed and set to be 100 mg/dl and 400 mg/dl within each chart for easily understanding the effect of the glucose concentration. It should be noted that the right upper chart in FIG. 117 represents the measured results of response current values when the glucose concentration was set to be 100 mg/dl and 400 mg/dl, whereas the right lower chart in FIG. 117 represents a deviation between response current values corresponding to glucose concentrations of 100 mg/dl and 400 mg/dl.

It was consequently found that the response current value certainly varied in measuring the glucose concentration but hardly varied at a measure time point of 4.0 second or thereafter in measuring the temperature when the glucose concentration is changed and set to be 100 mg/dl and 400 mg/dl.

Further in FIG. 119, the right charts represent the measured results when the temperature conditions (10° C., 25° C. and 40° C.) were changed within each chart for easily understanding the effect of the blood sample temperature. It should be noted that the right upper chart of FIG. 119 represents the measured results of variation in the response current value when the glucose concentration was set to be 100 mg/dl, whereas the right lower chart of FIG. 119 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.0 V among the electrodes. As represented in the right lower chart of FIG. 117, however, it was found that the response current value was hardly affected by increase and reduction in the glucose concentration at a measured time point of 4.0 second or thereafter in measuring the temperature when a voltage of 1.0 V was applied among the electrodes.

<Applied Voltage of 1.25 V>

Measurements were herein executed for examining the effect of variation in the glucose concentration (100 mg/dl, 400 mg/dl) on the response current value when a voltage to be applied among the electrodes was set to be 1.25 V.

Figure 118:
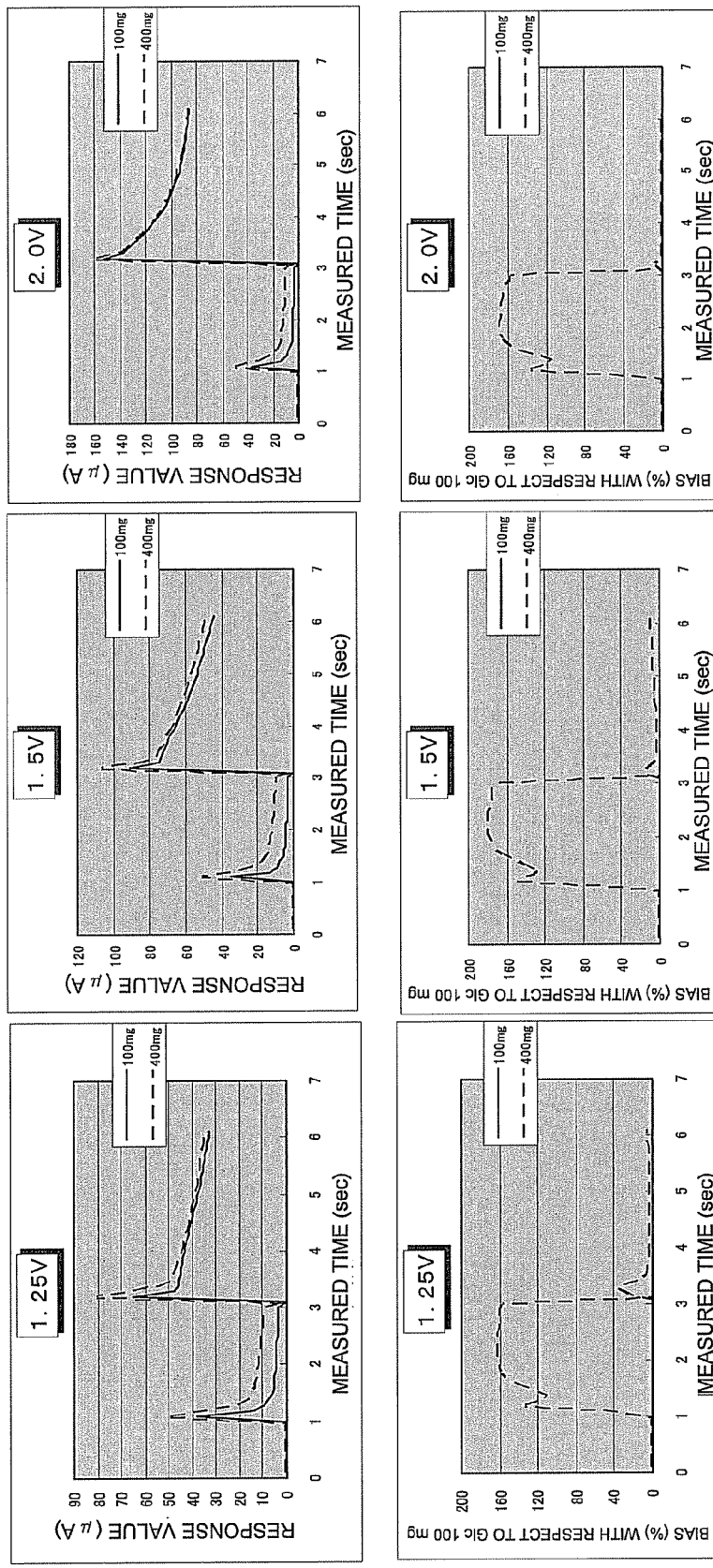
FIG. 118 includes charts representing the results of examining the effect of variation in the glucose concentration on the response current value in applying voltages of 1.25 to 2.0 V to the sensor chip illustrated in FIG. 116.

In FIG. 118, the left charts represent the measured results when the glucose concentration was changed and set to be 100 mg/dl and 400 mg/dl within each chart for easily understanding the effect of the glucose concentration. It should be noted that the left upper chart in FIG. 118 represents the measured results of response current values when the glucose concentration was set to be 100 mg/dl and 400 mg/dl, whereas the left lower chart in FIG. 118 represents a deviation between response current values corresponding to glucose concentrations of 100 mg/dl and 400 mg/dl.

It was consequently found that the response current value certainly varied in measuring the glucose concentration and but hardly varied in measuring the temperature when the glucose concentration is changed and set to be 100 mg/dl and 400 mg/dl.

Further in FIG. 120, the left charts represent the measured results when the temperature conditions (10° C., 25° C. and 40° C.) were changed within each chart for easily understanding the effect of the blood sample temperature. It should be noted that the left upper chart of FIG. 120 represents the measured results of variation in the response current value when the glucose concentration was set to be 100 mg/dl, whereas the left lower chart of FIG. 120 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.25 V among the electrodes. As represented in the left lower chart of FIG. 118, however, it was found that the response current value was hardly affected by increase and reduction in the glucose concentration when a voltage of 1.25 V was applied among the electrodes.

<Applied Voltage of 1.5 V>

Measurements were herein executed for examining the effect of variation in the glucose concentration (100 mg/dl, 400 mg/dl) on the response current value when a voltage to be applied among the electrodes was set to be 1.5 V.

In FIG. 118, the center charts represent the measured results when the glucose concentration was changed and set to be 100 mg/dl and 400 mg/dl within each chart for easily understanding the effect of the glucose concentration. It should be noted that the center upper chart in FIG. 118 represents the measured results of response current values when the glucose concentration was set to be 100 mg/dl and 400 mg/dl, whereas the center lower chart in FIG. 118 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the response current value hardly varied in measuring the temperature when the glucose concentration is changed and set to be 100 mg/dl and 400 mg/dl.

Further in FIG. 120, the center charts represent the measured results when the temperature conditions (10° C., 25° C. and 40° C.) were changed within each chart for easily understanding the effect of the blood sample temperature. It should be noted that the center upper chart of FIG. 120 represents the measured results of variation in the response current value when the glucose concentration was set to be 100 mg/dl, whereas the center lower chart of FIG. 120 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 1.5 V among the electrodes. As represented in the center lower chart of FIG. 118, however, it was found that the response current value was hardly affected by increase and reduction in the glucose concentration in measuring the temperature when a voltage of 1.5 V was applied among the electrodes.

<Applied Voltage of 2.0 V>

Measurements were herein executed for examining the effect of variation in the glucose concentration (100 mg/dl, 400 mg/dl) on the response current value when a voltage to be applied among the electrodes was set to be 2.0 V.

In FIG. 118, the right charts represent the measured results when the glucose concentration was changed and set to be 100 mg/dl and 400 mg/dl within each chart for easily understanding the effect of the glucose concentration. It should be noted that the right upper chart in FIG. 118 represents the measured results of response current values when the glucose concentration was set to be 100 mg/dl and 400 mg/dl, whereas the right lower chart in FIG. 118 represents a deviation between response current values corresponding to glucose concentrations of 100 mg/dl and 400 mg/dl.

It was consequently found that the response current value certainly varied in measuring the glucose concentration when the glucose concentration is changed and set to be 100 mg/dl and 400 mg/dl. On the other hand, it was found that the response current value hardly varied in measuring the temperature when the glucose concentration is changed and set to be 100 mg/dl and 400 mg/dl.

Further in FIG. 120, the right charts represent the measured results when the temperature conditions (10° C., 25° C. and 40° C.) were changed within each chart for easily understanding the effect of the blood sample temperature. It should be noted that the right upper chart of FIG. 120 represents the measured results of variation in the response current value when the glucose concentration was set to be 100 mg/dl, whereas the right lower chart of FIG. 120 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature in both measuring the glucose concentration and measuring the temperature when the response current value was measured by applying a voltage of 2.0 V among the electrodes. As represented in the right lower chart of FIG. 118, however, it was found that the response current value was hardly affected by increase and reduction in the glucose concentration in measuring the temperature when a voltage of 2.0 V was applied among the electrodes.

<Comprehensive Results>

In the sensor chip configuration of the present exemplary embodiment, the following was found based on the aforementioned results obtained by measuring the glucose concentration and the temperature under the aforementioned respective conditions. Simply put, it was found that the temperature measurement could be accurately executed without being approximately affected by the glucose concentration when a voltage of 1.0 or greater was applied in measuring the temperature as represented in FIG. 125.

However, it was found that the temperature measurement could be executed without being affected by the glucose concentration only at a measured time point of 4.0 second or thereafter when a voltage of 1.0 V was applied.

(Exemplary Embodiment 7)

Yet another exemplary embodiment of the present invention will be hereinafter explained with reference to FIGS. 122 to 133.

In the present exemplary embodiment, the glucose concentration was firstly measured and the temperature was secondly measured by applying a voltage optimal for each measurement to the respective electrodes using a sensor chip with the configuration explained in the aforementioned exemplary embodiments. Simply put, the following description relates to results of tests executed to prove that both of the temperature and the glucose concentration can be appropriately measured even if the order of measuring the temperature and the glucose concentration represented in FIGS. 96 (b) to 96 (e) is reversed.

<Blood Sample at 10° C.>
<Condition 1 (P3)>

As represented in left charts of FIG. 122, the response current value was herein measured using a blood sample at 10° C. in two glucose concentration conditions of 100 mg/l and 400 mg/l. The response current value was measured by firstly applying a voltage of 0.25 V to the respective electrodes in measuring the glucose concentration and secondly applying a voltage of 1.25 V to the respective electrodes in measuring the temperature. Further, a voltage was applied only for 0.5 seconds in measuring the temperature, and the interval between the glucose concentration measurement and the temperature measurement was set to be 2.0 seconds.

It should be noted that the left upper chart of FIG. 122 represents a relation between an elapsed time and a response current value in executing the measurements. Further, the left lower chart in FIG. 122 represents an elapsed time and a ratio of a response current value at a glucose concentration of 400 mg/l with respect to a response current value at a glucose concentration of 100 mg/l in executing the measurements. The configuration will be hereinafter applied to left charts in FIG. 123 and thereafter.

As represented in the left charts of FIG. 122, it was consequently found that the response current value hardly varied due to the glucose concentration (100 mg/l and 400 mg/l) in measuring the temperature by applying a voltage of 1.25 V.

Further, a response current value at a glucose concentration of 400 mg/l was detected to be higher than a response current value at a glucose condition of 100 mg/l in measuring the glucose concentration by applying a voltage of 0.25 V.

It was consequently found that the response current value did not vary due to the glucose concentration in measuring the temperature but variation in the response current value due to the glucose concentration could be distinctly detected only in measuring the glucose concentration. It was accordingly found that the temperature and the glucose concentration could be accurately detected under the aforementioned condition.

<Condition 2 (P4)>

As represented in right charts of FIG. 122, the response current value was herein measured using a blood sample at 10° C. in two glucose concentration conditions of 100 mg/l and 400 mg/l. The response current value was measured by firstly applying a voltage of 0.5 V to the respective electrodes in measuring the glucose concentration and secondly applying a voltage of 1.25 V to the respective electrodes in measuring the temperature. Further, a voltage was applied only for 0.5 seconds in measuring the temperature, and the interval between the glucose concentration measurement and the temperature measurement was set to be 2.0 seconds. In other words, the condition 2 is different from the condition 1 only in that a voltage to be applied in measuring the glucose concentration was changed from 0.25 V to 0.5 V.

It should be noted that the right upper chart of FIG. 122 represents a relation between an elapsed time and a response current value in executing the measurements. Further, the right lower chart in FIG. 122 represents an elapsed time and a ratio of a response current value at a glucose concentration of 400 mg/l with respect to a response current value at a glucose concentration of 100 mg/l in executing the measurements. The configuration will be hereinafter applied to right charts in FIG. 123 and thereafter.

As represented in the right charts of FIG. 122, it was consequently found that the response current value hardly varied due to the glucose concentration (100 mg/l and 400 mg/l) in measuring the temperature by applying a voltage of 1.25 V.

Further, a response current value at a glucose concentration of 400 mg/l was detected to be higher than a response current value at a glucose condition of 100 mg/l in measuring the glucose concentration by applying a voltage of 0.5 V.

It was consequently found that the response current value did not vary due to the glucose concentration in measuring the temperature but variation in the response current value due to the glucose concentration could be distinctly detected only in measuring the glucose concentration. It was accordingly found that the temperature and the glucose concentration could be accurately detected under the aforementioned condition.

<Condition 3 (P5)>

As represented in left charts of FIG. 123, the response current value was herein measured using a blood sample at 10° C. in two glucose concentration conditions of 100 mg/l and 400 mg/l. The response current value was measured by firstly applying a voltage of 0.25 V to the respective electrodes in measuring the glucose concentration and secondly applying a voltage of 1.25 V to the respective electrodes in measuring the temperature. Further, a voltage was applied only for 1.0 seconds in measuring the temperature, and the interval between the glucose concentration measurement and the temperature measurement was set to be 2.0 seconds. In other words, the condition 3 is different from the condition 1 only in that a period of time for applying a voltage in measuring the temperature was changed from 0.5 second to 1.0 seconds.

As represented in the left charts of FIG. 123, it was consequently found that the response current value hardly varied due to the glucose concentration (100 mg/l and 400 mg/l) in measuring the temperature by applying a voltage of 1.25 V.

Further, a response current value at a glucose concentration of 400 mg/l was detected to be higher than a response current value at a glucose condition of 100 mg/l in measuring the glucose concentration by applying a voltage of 0.25 V.

It was consequently found that the response current value did not vary due to the glucose concentration in measuring the temperature but variation in the response current value due to the glucose concentration could be distinctly detected only in measuring the glucose concentration. It was accordingly found that the temperature and the glucose concentration could be accurately detected under the aforementioned condition.

<Condition 4 (P6)>

As represented in right charts of FIG. 123, the response current value was herein measured using a blood sample at 10° C. in two glucose concentration conditions of 100 mg/l and 400 mg/l. The response current value was measured by firstly applying a voltage of 0.5 V to the respective electrodes in measuring the glucose concentration and secondly applying a voltage of 1.25 V to the respective electrodes in measuring the temperature. Further, a voltage was applied only for 0.5 seconds in measuring the temperature, and the interval between the glucose concentration measurement and the temperature measurement was set to be 2.0 seconds. In other words, the condition 4 is different from the condition 3 only in that a voltage to be applied in measuring the glucose concentration was changed from 0.25 V to 0.5 V.

It should be noted that the right upper chart of FIG. 123 represents a relation between an elapsed time and a response current value in executing the measurements. Further, the right lower chart in FIG. 123 represents an elapsed time and a ratio of a response current value at a glucose concentration of 400 mg/l with respect to a response current value at a glucose concentration of 100 mg/l in executing the measurements.

As represented in the right charts of FIG. 123, it was consequently found that the response current value hardly varied due to the glucose concentration (100 mg/l and 400 mg/l) in measuring the temperature by applying a voltage of 1.25 V.

Further, a response current value at a glucose concentration of 400 mg/l was detected to be higher than a response current value at a glucose condition of 100 mg/l in measuring the glucose concentration by applying a voltage of 0.5 V.

It was consequently found that the response current value did not vary due to the glucose concentration in measuring the temperature but variation in the response current value due to the glucose concentration could be distinctly detected only in measuring the glucose concentration. It was accordingly found that the temperature and the glucose concentration could be accurately detected under the aforementioned condition.

<Condition 5 (P7)>

As represented in left charts of FIG. 124, the response current value was herein measured using a blood sample at 10° C. in two glucose concentration conditions of 100 mg/l and 400 mg/l. The response current value was measured by firstly applying a voltage of 0.25 V to the respective electrodes in measuring the glucose concentration and secondly applying a voltage of 1.25 V to the respective electrodes in measuring the temperature. Further, a voltage was applied only for 1.0 seconds in measuring the temperature, and the interval between the glucose concentration measurement and the temperature measurement was set to be 4.0 seconds. In other words, the condition 5 is different from the condition 3 only in that the interval between the temperature measurement and the glucose concentration measurement was changed from 2.0 seconds to 4.0 seconds.

As represented in the left charts of FIG. 124, it was consequently found that the response current value hardly varied due to the glucose concentration (100 mg/l and 400 mg/l) in measuring the temperature by applying a voltage of 1.25 V.

Further, a response current value at a glucose concentration of 400 mg/l was detected to be higher than a response current value at a glucose condition of 100 mg/l in measuring the glucose concentration by applying a voltage of 0.25 V.

It was consequently found that the response current value did not vary due to the glucose concentration in measuring the temperature but variation in the response current value due to the glucose concentration could be distinctly detected only in measuring the glucose concentration. It was accordingly found that the temperature and the glucose concentration could be accurately detected under the aforementioned condition.

<Condition 6 (P8)>

As represented in right charts of FIG. 124, the response current value was herein measured using a blood sample at 10° C. in two glucose concentration conditions of 100 mg/l and 400 mg/l. The response current value was measured by firstly applying a voltage of 0.5 V to the respective electrodes in measuring the glucose concentration and secondly applying a voltage of 1.25 V to the respective electrodes in measuring the temperature. Further, a voltage was applied only for 0.5 seconds in measuring the temperature, and the interval between the glucose concentration measurement and the temperature measurement was set to be 4.0 seconds. In other words, the condition 6 is different from the condition 5 only in that a voltage to be applied in measuring the glucose concentration was changed from 0.25 V to 0.5 V.

It should be noted that the right upper chart of FIG. 124 represents a relation between an elapsed time and a response current value in executing the measurements. Further, the right lower chart in FIG. 124 represents an elapsed time and a ratio of a response current value at a glucose concentration of 400 mg/l with respect to a response current value at a glucose concentration of 100 mg/l in executing the measurements.

As represented in the right charts of FIG. 124, it was consequently found that the response current value hardly varied due to the glucose concentration (100 mg/l and 400 mg/l) in measuring the temperature by applying a voltage of 1.25 V.

Further, a response current value at a glucose concentration of 400 mg/l was detected to be higher than a response current value at a glucose condition of 100 mg/l in measuring the glucose concentration by applying a voltage of 0.5 V.

It was consequently found that the response current value did not vary due to the glucose concentration in measuring the temperature but variation in the response current value due to the glucose concentration could be distinctly detected only in measuring the glucose concentration. It was accordingly found that the temperature and the glucose concentration could be accurately detected under the aforementioned condition.

<Condition 7 (P9)>

As represented in left charts of FIG. 125, the response current value was herein measured using a blood sample at 10° C. in two glucose concentration conditions of 100 mg/l and 400 mg/l. The response current value was measured by firstly applying a voltage of 0.25 V to the respective electrodes in measuring the glucose concentration and secondly applying a voltage of 1.5 V to the respective electrodes in measuring the temperature. Further, a voltage was applied only for 1.0 seconds in measuring the temperature, and the interval between the glucose concentration measurement and the temperature measurement was set to be 2.0 seconds. In other words, the condition 7 is different from the condition 3 only in that a voltage to be applied in measuring the temperature was changed from 1.25 V to 1.5 V.

As represented in the left charts of FIG. 125, it was consequently found that the response current value hardly varied due to the glucose concentration (100 mg/l and 400 mg/l) in measuring the temperature by applying a voltage of 1.5 V.

Further, a response current value at a glucose concentration of 400 mg/l was detected to be higher than a response current value at a glucose condition of 100 mg/l in measuring the glucose concentration by applying a voltage of 0.25 V.

It was consequently found that the response current value did not vary due to the glucose concentration in measuring the temperature but variation in the response current value due to the glucose concentration could be distinctly detected only in measuring the glucose concentration. It was accordingly found that the temperature and the glucose concentration could be accurately detected under the aforementioned condition.

<Condition 8 (P10)>

As represented in right charts of FIG. 125, the response current value was herein measured using a blood sample at 10° C. in two glucose concentration conditions of 100 mg/l and 400 mg/l. The response current value was measured by firstly applying a voltage of 0.5 V to the respective electrodes in measuring the glucose concentration and secondly applying a voltage of 1.5 V to the respective electrodes in measuring the temperature. Further, a voltage was applied only for 1.0 seconds in measuring the temperature, and the interval between the glucose concentration measurement and the temperature measurement was set to be 2.0 seconds. In other words, the condition 8 is different from the condition 7 only in that a voltage to be applied in measuring the glucose concentration was changed from 0.25 V to 0.5 V.

It should be noted that the right upper chart of FIG. 125 represents a relation between an elapsed time and a response current value in executing the measurements. Further, the right lower chart in FIG. 125 represents an elapsed time and a ratio of a response current value at a glucose concentration of 400 mg/l with respect to a response current value at a glucose concentration of 100 mg/l in executing the measurements.

As represented in the right charts of FIG. 125, it was consequently found that the response current value hardly varied due to the glucose concentration (100 mg/l and 400 mg/l) in measuring the temperature by applying a voltage of 1.5 V.

Further, a response current value at a glucose concentration of 400 mg/l was detected to be higher than a response current value at a glucose condition of 100 mg/l in measuring the glucose concentration by applying a voltage of 0.5 V.

It was consequently found that the response current value did not vary due to the glucose concentration in measuring the temperature but variation in the response current value due to the glucose concentration could be distinctly detected only in measuring the glucose concentration. It was accordingly found that the temperature and the glucose concentration could be accurately detected under the aforementioned condition.

<Blood Sample at 25° C.>

The following description relates to results of executing the aforementioned measurements under the conditions 1 to 8 using a blood sample at 25° C. with reference to FIGS. 126 to 129.

Similarly to the aforementioned FIGS. 122 to 125, it was consequently found that the response current value did not vary due to the glucose concentration in measuring the temperature under the respective conditions but variation in the response current value due to the glucose concentration could be distinctly detected only in measuring the glucose concentration under the respective conditions. It was accordingly found that the temperature and the glucose concentration could be accurately detected under the aforementioned conditions.

<Blood Sample at 40° C.>

The following description relates to results of executing the aforementioned measurements under the conditions 1 to 8 using a blood sample at 40° C. with reference to FIGS. 130 to 133.

Similarly to the aforementioned FIGS. 122 to 125, it was consequently found that the response current value did not vary due to the glucose concentration in measuring the temperature under the respective conditions but variation in the response current value due to the glucose concentration could be distinctly detected only in measuring the glucose concentration under the respective conditions. It was accordingly found that the temperature and the glucose concentration could be accurately detected under the aforementioned conditions.

<Comprehensive Results>

It was found from the aforementioned results that the temperature and the glucose concentration could be accurately measured regardless of the order of the temperature measurement and the glucose concentration measurement in measuring the temperature by applying a voltage of 1.25 V or 1.5 V optimal for the temperature measurement, which was verified in the aforementioned exemplary embodiments 1 and 2, and in measuring the glucose concentration by applying a voltage of 0.25 V or 0.5 V optimal for the glucose concentration measurement, which was verified in the aforementioned exemplary embodiments 1 and 2.

(Exemplary Embodiment 8)

Yet another exemplary embodiment of the present invention will be hereinafter explained with reference to FIGS. 134 to 138.

In the present exemplary embodiment, measurements were executed by reducing a voltage to be applied in measuring the glucose concentration with use of a sensor chip (see FIG. 110) having the configuration explained in the aforementioned exemplary embodiment 5. Simply put, the following explanation relates to test results not for verifying the aforementioned optimal voltage range to be applied in measuring the temperature but for verifying an optimal voltage range to be applied in measuring the glucose concentration. In the following explanation, the measured results were obtained by changing a voltage to be applied in measuring the glucose concentration in the descending order of 0.5 V, 0.3 V, 0.2 V and 0.1 V.

<Applied Voltage of 0.5 V>

Measurements were herein executed for examining the effect of variation in the glucose concentration (100 mg/dl, 400 mg/dl) on the response current value when a voltage to be applied in measuring the glucose concentration was set to be 0.5 V and a voltage to be applied in measuring the temperature was set to be 1.0 V.

In FIG. 134, the left charts represent the measured results when the glucose concentration was changed and set to be 100 mg/dl and 400 mg/dl within each chart for easily understanding the effect of the glucose concentration. It should be noted that the left upper chart in FIG. 134 represents the measured results of response current values when the glucose concentration was set to be 100 mg/dl and 400 mg/dl, whereas the left lower chart in FIG. 134 represents a deviation between response current values corresponding to glucose concentrations of 100 mg/dl and 400 mg/dl.

It was consequently found that the response current value distinctly varied in measuring the glucose concentration but hardly varied in measuring the temperature when the glucose concentration is changed and set to be 100 mg/dl and 400 mg/dl.

Further in FIG. 136, the left charts represent the measured results when the temperature conditions (10° C., 25° C. and 40° C.) were changed within each chart for easily understanding the effect of the blood sample temperature. It should be noted that the left upper chart of FIG. 136 represents the measured results of variation in the response current value when the glucose concentration was set to be 100 mg/dl, whereas the left lower chart of FIG. 136 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature when the response current value was measured by applying a voltage of 0.5 V among the electrodes in measuring the glucose concentration, similarly to the aforementioned respective exemplary embodiments. However, it was also found that the glucose concentration could be accurately measured by executing correction and the like based on the result of measuring the temperature.

<Applied Voltage of 0.3 V>

Measurements were herein executed for examining the effect of variation in the glucose concentration (100 mg/dl, 400 mg/dl) on the response current value when a voltage to be applied in measuring the glucose concentration was set to be 0.3 V and a voltage to be applied in measuring the temperature was set to be 1.0 V.

In FIG. 134, the right charts represent the measured results when the glucose concentration was changed and set to be 100 mg/dl and 400 mg/dl within each chart for easily understanding the effect of the glucose concentration. It should be noted that the right upper chart in FIG. 134 represents the measured results of response current values when the glucose concentration was set to be 100 mg/dl and 400 mg/dl, whereas the right lower chart in FIG. 134 represents a deviation between response current values corresponding to glucose concentrations of 100 mg/dl and 400 mg/dl.

It was consequently found that the response current value distinctly varied in measuring the glucose concentration but hardly varied in measuring the temperature when the glucose concentration is changed and set to be 100 mg/dl and 400 mg/dl.

Further in FIG. 136, the right charts represent the measured results when the temperature conditions (10° C., 25° C. and 40° C.) were changed within each chart for easily understanding the effect of the blood sample temperature. It should be noted that the right upper chart of FIG. 136 represents the measured results of variation in the response current value when the glucose concentration was set to be 100 mg/dl, whereas the right lower chart of FIG. 136 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature when the response current value was measured by applying a voltage of 0.3 V among the electrodes in measuring the glucose concentration. However, it was also found that the glucose concentration could be accurately measured by executing correction and the like based on the result of measuring the temperature.

<Applied Voltage of 0.2 V>

Measurements were herein executed for examining the effect of variation in the glucose concentration (100 mg/dl, 400 mg/dl) on the response current value when a voltage to be applied in measuring the glucose concentration was set to be 0.2 V and a voltage to be applied in measuring the temperature was set to be 1.0 V.

In FIG. 135, the left charts represent the measured results when the glucose concentration was changed and set to be 100 mg/dl and 400 mg/dl within each chart for easily understanding the effect of the glucose concentration. It should be noted that the left upper chart in FIG. 135 represents the measured results of response current values when the glucose concentration was set to be 100 mg/dl and 400 mg/dl, whereas the left lower chart in FIG. 135 represents a deviation between response current values corresponding to glucose concentrations of 100 mg/dl and 400 mg/dl.

It was consequently found that the response current value distinctly varied in measuring the glucose concentration but hardly varied in measuring the temperature when the glucose concentration is changed and set to be 100 mg/dl and 400 mg/dl.

Further in FIG. 137, the left charts represent the measured results when the temperature conditions (10° C., 25° C. and 40° C.) were changed within each chart for easily understanding the effect of the blood sample temperature. It should be noted that the left upper chart of FIG. 137 represents the measured results of variation in the response current value when the glucose concentration was set to be 100 mg/dl, whereas the left lower chart of FIG. 137 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature even when the response current value was measured by applying a voltage of 0.2 V among the electrodes in measuring the glucose concentration. However, it was also found that the glucose concentration could be accurately measured by executing correction and the like based on the result of measuring the temperature.

<Applied Voltage of 0.1 V>

Measurements were herein executed for examining the effect of variation in the glucose concentration (100 mg/dl, 400 mg/dl) on the response current value when a voltage to be applied in measuring the glucose concentration was set to be 0.1 V and a voltage to be applied in measuring the temperature was set to be 1.0 V.

In FIG. 135, the right charts represent the measured results when the glucose concentration was changed and set to be 100 mg/dl and 400 mg/dl within each chart for easily understanding the effect of the glucose concentration. It should be noted that the right upper chart in FIG. 135 represents the measured results of response current values when the glucose concentration was set to be 100 mg/dl and 400 mg/dl, whereas the right lower chart in FIG. 135 represents a deviation between response current values corresponding to glucose concentrations of 100 mg/dl and 400 mg/dl.

It was consequently found that the response current value distinctly varied in measuring the glucose concentration but hardly varied in measuring the temperature when the glucose concentration is changed and set to be 100 mg/dl and 400 mg/dl.

Further in FIG. 137, the right charts represent the measured results when the temperature conditions (10° C., 25° C. and 40° C.) were changed within each chart for easily understanding the effect of the blood sample temperature. It should be noted that the right upper chart of FIG. 137 represents the measured results of variation in the response current value when the glucose concentration was set to be 100 mg/dl, whereas the right lower chart of FIG. 137 represents the measured results of variation in the response current value when the glucose concentration was set to be 400 mg/dl.

It was consequently found that the response current value widely varied not only in measuring the temperature but also in measuring the glucose concentration under the both conditions of a glucose concentration of 100 mg/dl and a glucose concentration of 400 mg/dl when the blood sample temperature is changed.

It was found from the aforementioned results that the response current value was affected by variation in the temperature even when the response current value was measured by applying a voltage of 0.1 V among the electrodes in measuring the glucose concentration. However, it was also found that the glucose concentration could be accurately measured by executing correction and the like based on the result of measuring the temperature.

<Comprehensive Results>

It was found from the aforementioned results that the glucose concentration could be measured at the respective applied voltages even when the voltage to be applied in measuring the glucose concentration was reduced from 0.5 V to 0.1 V.

As represented in FIG. 138, a voltage to be applied in measuring the glucose concentration is herein set to be 0.1 V, whereas a voltage to be applied in measuring the temperature is set to be 1.0. Under the condition, "A" is set as a sensitivity difference between a response current value at a glucose concentration of 100 mg/dl and a response current value at a glucose concentration of 400 mg/dl in measuring the glucose concentration, whereas "B" is set as a sensitivity difference between a response current value at a glucose concentration of 100 mg/dl and a response current value at a glucose concentration of 400 mg/dl in measuring the temperature. A voltage to be applied in measuring the temperature will be specified based on an optimal range of B/A as follows.

For example, B/A is calculated as 10%/150% (=6.7%) where the lower limit of an applied voltage for enabling measurement of the glucose concentration is set to be 0.1 V whereas the lower limit of an applied voltage for enabling measurement of the temperature is set to be 1.0 V.

The value of A is increased in proportion to increase in an applied voltage from 0.1 V in measuring the glucose concentration, whereas the value of B is reduced in proportion to increase in an applied voltage from 1.0 V in measuring the temperature.

It is consequently concluded that a satisfactory measured result can be obtained by setting a voltage to be applied in measuring the glucose concentration and a voltage to be applied in measuring the temperature for satisfying a condition of "B/A<6.7%".

(Reference Example 1)

A reference example will be hereinafter explained with reference to charts of FIGS. 85 to 90 for further easily understanding the advantageous effects of the present invention.

Specifically in the present reference example, measurements were executed by applying a voltage under conditions roughly the same as those of FIG. 10 except for one different condition with use of the same sensor chip configuration as that of FIG. 9 explained in the aforementioned exemplary embodiment 1. Specifically, the present reference example is different from the aforementioned exemplary embodiment 1 in that a voltage to be applied in measuring the temperature (i.e., a measured time period from 3.5 second to 5.0 second) represented in FIG. 10 is changed from 1.5 V to be 0.5 V.

Figure 85:
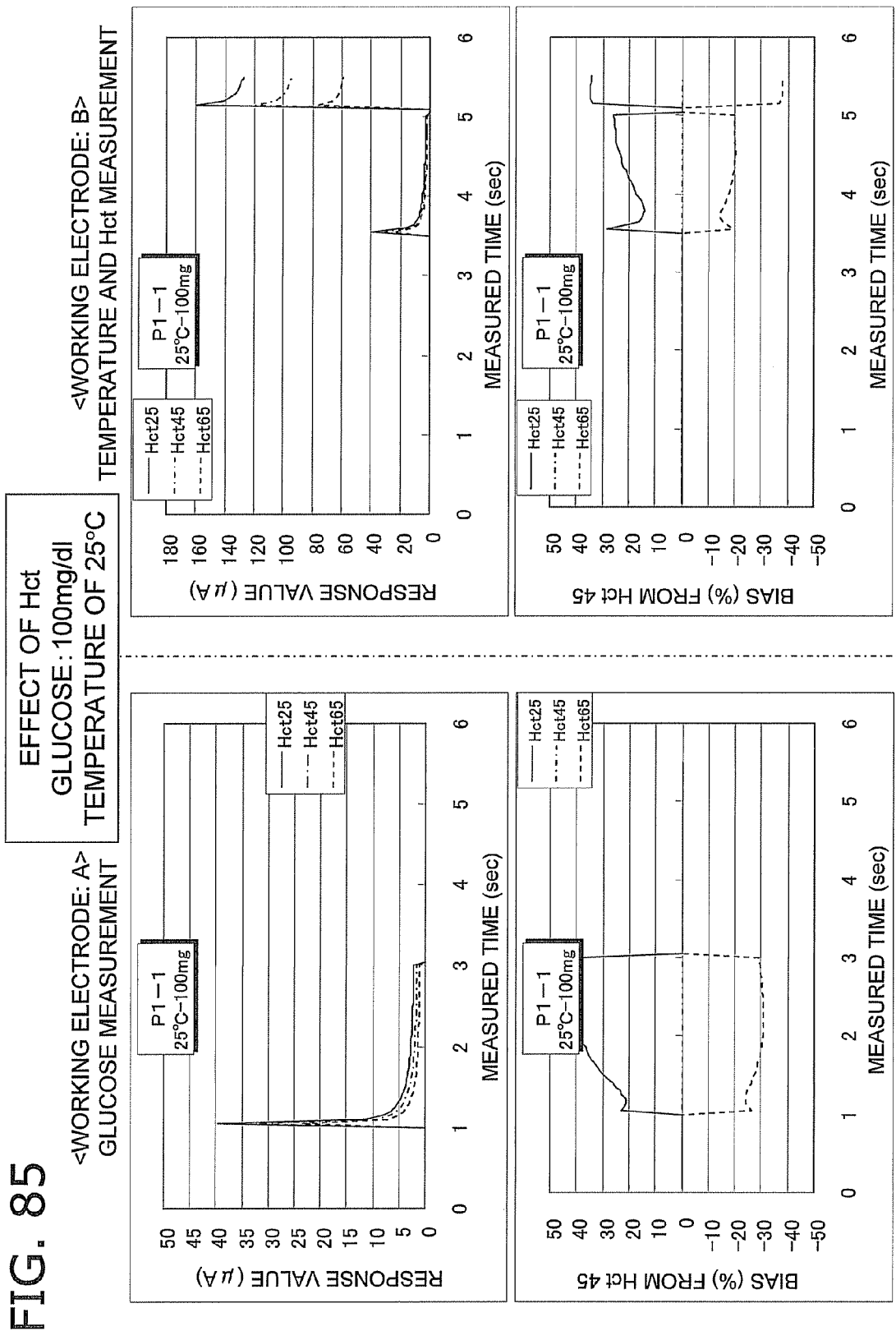
FIG. 85 includes charts representing the results of examining the effect of variation in the Hct value on the response current value in a reference example 1.
Figure 86:
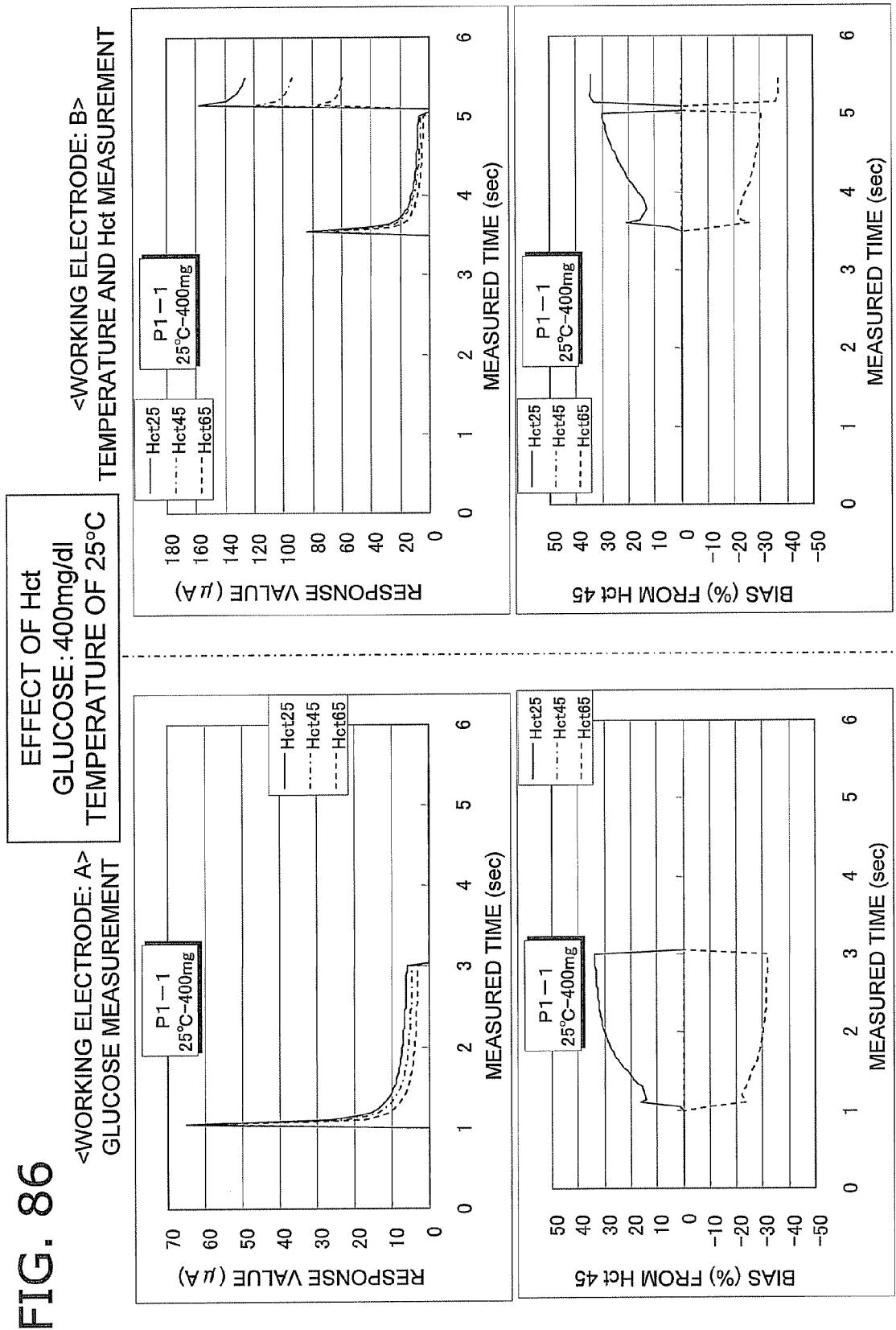
FIG. 86 includes charts representing the results of examining the effect of variation in the Hct value on the response current value in the reference example 1.

FIGS. 85 and 86 represent the measured results of response current values in the respective electrodes when the glucose concentration and the temperature were set to be constant for examining the effect of increase and reduction in the Hct value on the response current value.

Specifically in FIG. 85, variation in the response current value was examined when the glucose concentration was set to be constant as 100 mg/dl and the temperature was set to be constant as 25° C. whereas the Hct value was set to be 25, 45 and 65. In FIG. 86, on the other hand, variation in the response current value was examined when the glucose concentration was set to be constant as 400 mg/dl and the and temperature was set to be constant as 25° C. whereas the Hct value was set to be 25, 45 and 65 similarly to the above.

As represented in the left upper chart of FIG. 85, it was consequently found that the response current value varied among the conditions of the Hct value in measuring the glucose concentration even when the glucose concentration was constant. Further, as represented in the left lower chart in FIG. 85, it was found that deviations of response current values corresponding to Hct values of 24 and 65 from a response current value corresponding to an Hct value of 45 were plus/minus 30% or greater.

Further, as represented in the right upper chart of FIG. 85, it was found that the measured results of the response current value varied among three conditions of the Hct value in a measured time period from 3.5 second to 5.0 second for temperature measurement in measuring the blood sample temperature and the Hct value. Yet further, as represented in the right lower chart of FIG. 85, it was found that deviations of response current values corresponding to Hct values of 24 and 65 from a response current value corresponding to an Hct value of 45 was roughly plus/minus 20%.

Likewise, as represented in the left upper and lower charts of FIG. 86 where the glucose concentration was set to be 400 mg/dl, it was found that deviations among response current values were plus/minus 30% or greater in both measuring the glucose concentration and measuring the temperature.

In the present reference example, it was found from the measured results of response current values represented in FIGS. 85 and 86 that the response current value varied due to increase and reduction in the Hct value at an applied voltage in measuring the glucose concentration even when the glucose concentration is set to be constant. It was also found that the response current value varied due to increase and reduction in the Hct value in measuring the temperature as well.

Figure 87:
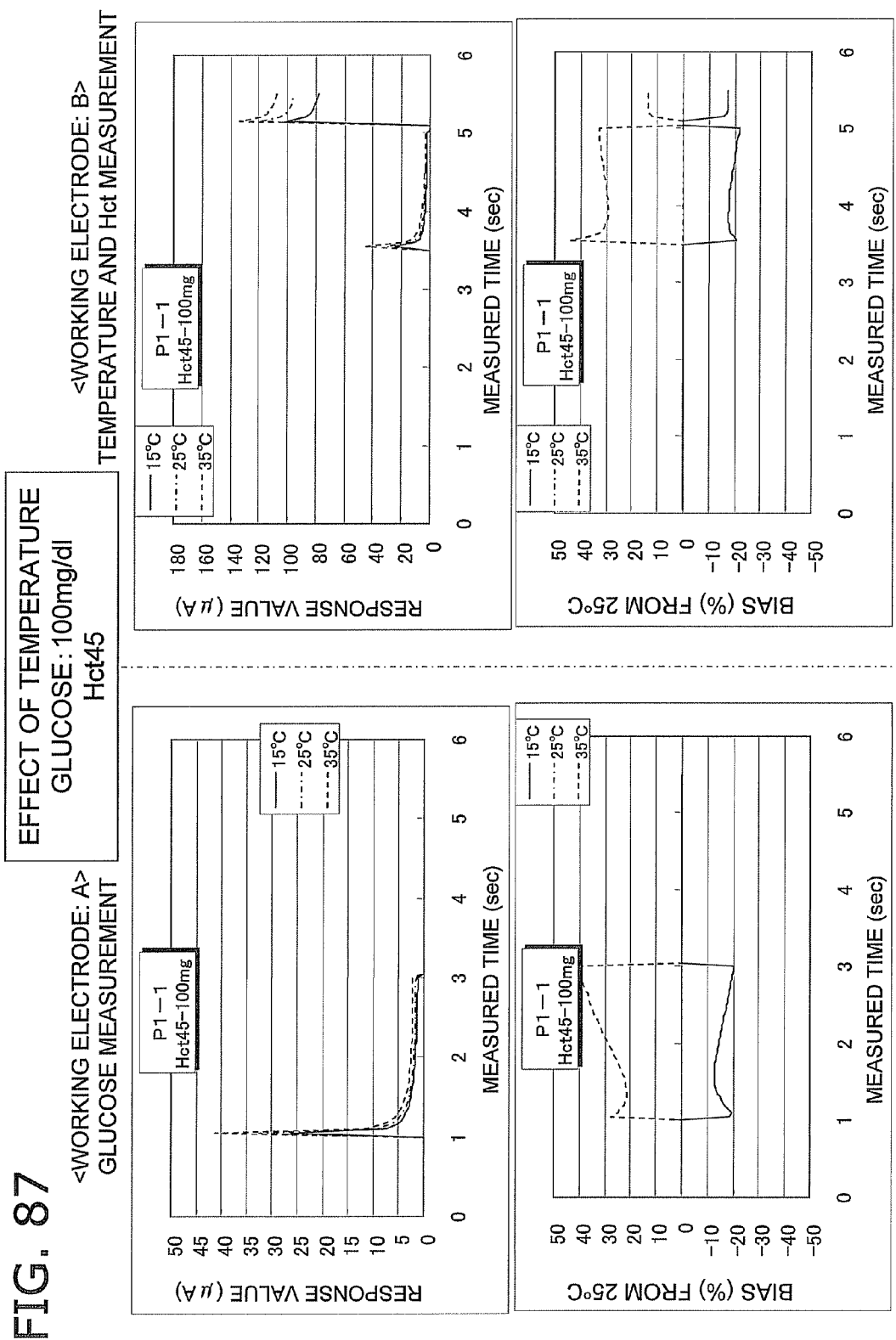
FIG. 87 includes charts representing the results of examining the effect of variation in the blood sample temperature on the response current value in the reference example 1.
Figure 88:
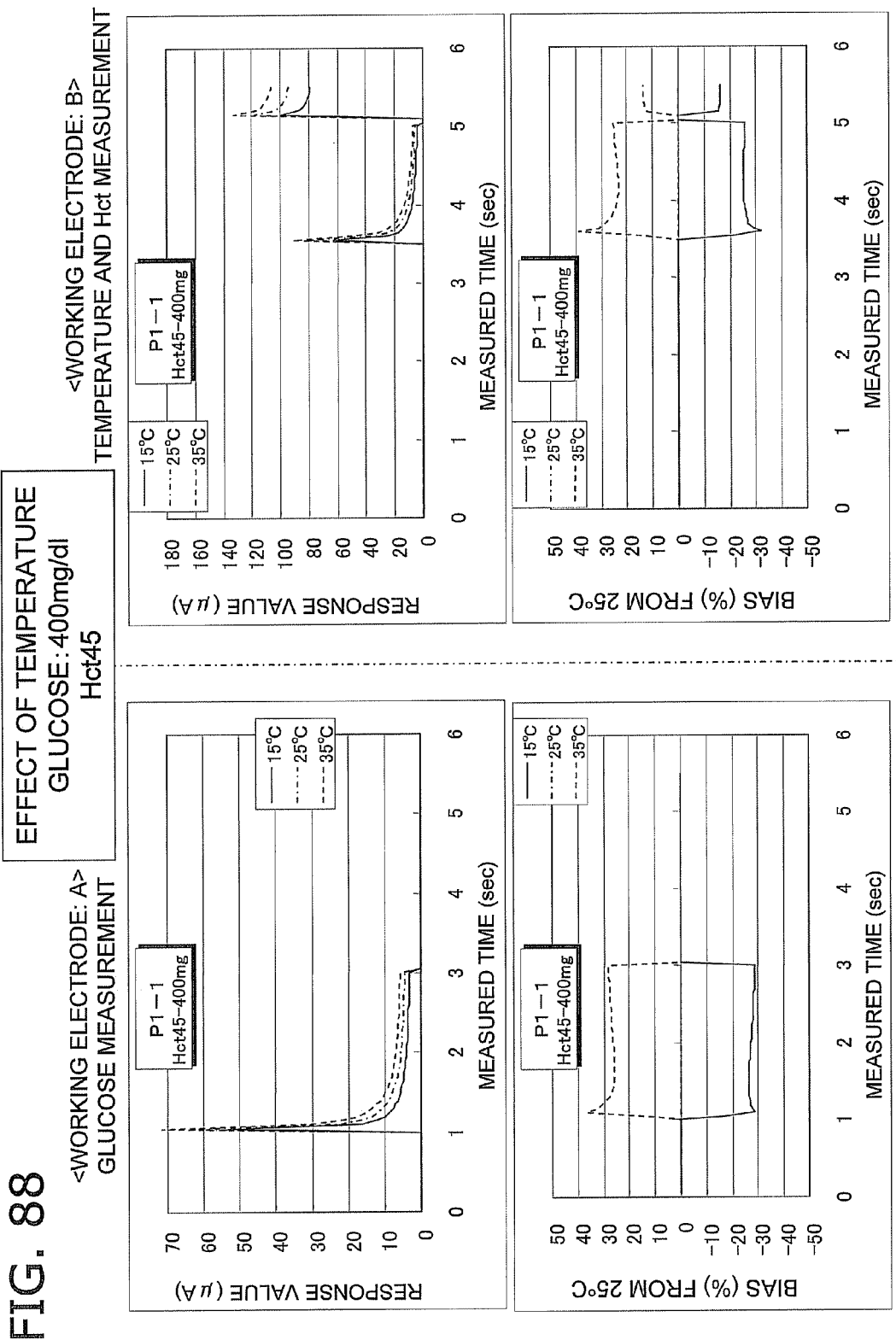
FIG. 88 includes charts representing the results of examining the effect of variation in the blood sample temperature on the response current value in the reference example 1.

Next, FIGS. 87 and 88 represent the measured results of response current values in the respective electrodes when the glucose concentration was set to be 100 mg/dl and 400 mg/dl whereas the Hct value was set to be constant as 45 for examining the effect of increase and reduction in the temperature on the detected current value.

Specifically in FIG. 87, variation in the response current value was examined when the glucose concentration was set to be constant as 100 mg/dl and the Hct value was set to be constant as 45 whereas the temperature was set to be 15° C., 25° C. and 35° C. In FIG. 88, on the other hand, variation in the response current value was examined when the glucose concentration was set to be constant as 400 mg/dl and the Hct value was set to be constant as 45 whereas the temperature was set to be 15° C., 25° C. and 35° C. similarly to the above.

As represented in the left upper chart of FIG. 87, it was consequently found that the response current value varied among the conditions of the temperature in measuring the glucose concentration even when the glucose concentration was set to be constant. As represented in the left lower chart of FIG. 87, it was found that deviations of response current values corresponding to temperatures of 15° C. and 35° C. from a response current value corresponding to a temperature of 25° C. were roughly plus/minus 20%.

Further, as represented in the right upper chart of FIG. 87, it was found that the response current value varied among three conditions of the temperature in a measured time period from 3.5 second to 5.0 second for temperature measurement in measuring the temperature and the Hct value. As represented in the right lower chart of FIG. 87, it was found that deviations of response current values corresponding to temperatures of 15° C. and 35° C. from a response current value corresponding to a temperature of 25° C. were plus/minus 20% or greater.

Likewise, as represented in the left upper and lower charts of FIG. 88 where the glucose concentration was set to be 400 mg/dl, it was found that deviations among response current values were roughly plus/minus 28% in measuring the glucose concentration. As represented in the right upper and lower charts of FIG. 88, on the other hand, it was found that deviations among response current values were roughly plus/minus 30% in measuring the temperature and the Hct value.

In the present reference example, it was found from the measured results of response current values represented in FIGS. 87 and 88 that the response current value was affected by increase and reduction in the Hct value when a voltage of 0.5 V was applied in measuring the temperature and it was thereby difficult to extract the response current value as the effect of increase and reduction in the temperature.

Figure 89:
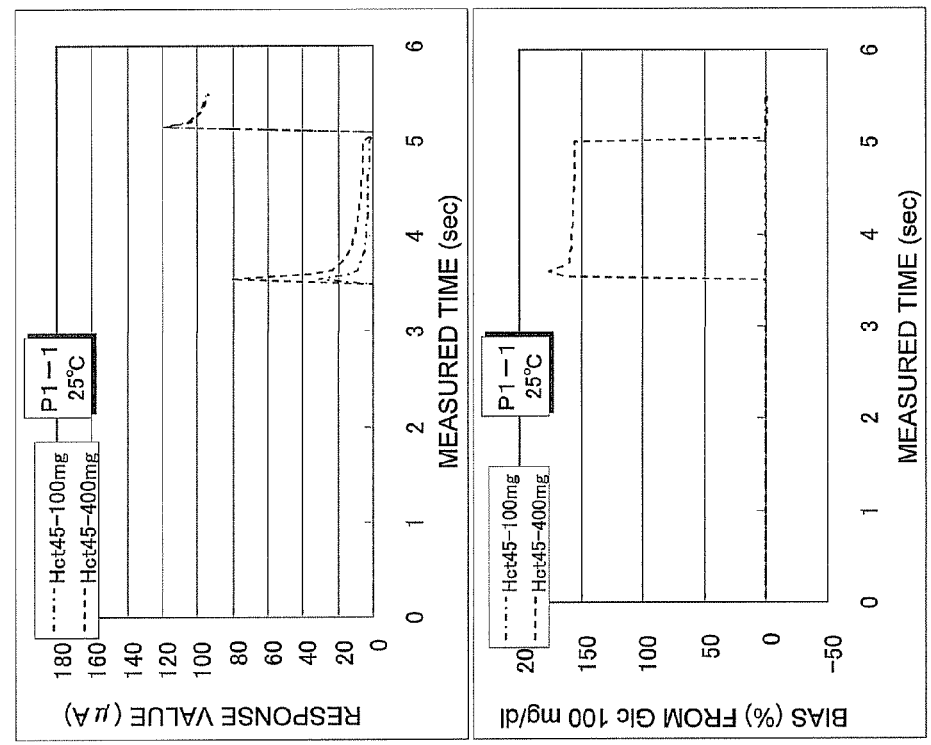
FIG. 89 includes charts representing the results of examining the effect of variation in the glucose concentration on the response current value in the reference example 1.

FIG. 89 represents the measured results of response current values in the respective electrodes when the Hct value and the temperature were set to be constant for examining the effect of the glucose concentration.

Specifically in FIG. 89, variation in the response current value was examined when the Hct value was set to be constant as 45 and the temperature was set to be constant as 25° C. whereas the glucose concentration was set to be 100 and 400 mg/dl.

As represented in the left upper chart of FIG. 89, it was consequently found that the response current value was detected as a difference between glucose concentration conditions when the glucose concentration was changed and set to be 100 mg/dl and 400 mg/dl in measuring the glucose concentration. As represented in the left lower chart of FIG. 89, it was found that a deviation of a response current value at a glucose concentration of 400 mg/dl from a response current value at a glucose concentration of 100 mg/dl could be detected to be roughly plus 150 to 200%.

As represented in the right upper chart of FIG. 89, on the other hand, it was found that the response current value widely varied between two glucose concentration conditions in a measured time period from 3.5 second to 5.0 second for temperature measurement in measuring the temperature and the Hct value. As represented in the right lower chart of FIG. 89, it was found that a deviation of a response current value at a glucose concentration of 100 mg/dl from a response current value at a glucose concentration of 400 mg/dl varied to a great extent.

In the present reference example, it was found from the measured results of response current values represented in FIG. 89 that the response current value, corresponding to the glucose concentration, could be detected in accordance with increase and reduction in the glucose concentration. On the other hand, it was also found that the response current value was affected by increase and reduction in the glucose concentration in measuring the temperature even when a voltage of 0.5 V was applied in measuring the temperature.

Figure 90:
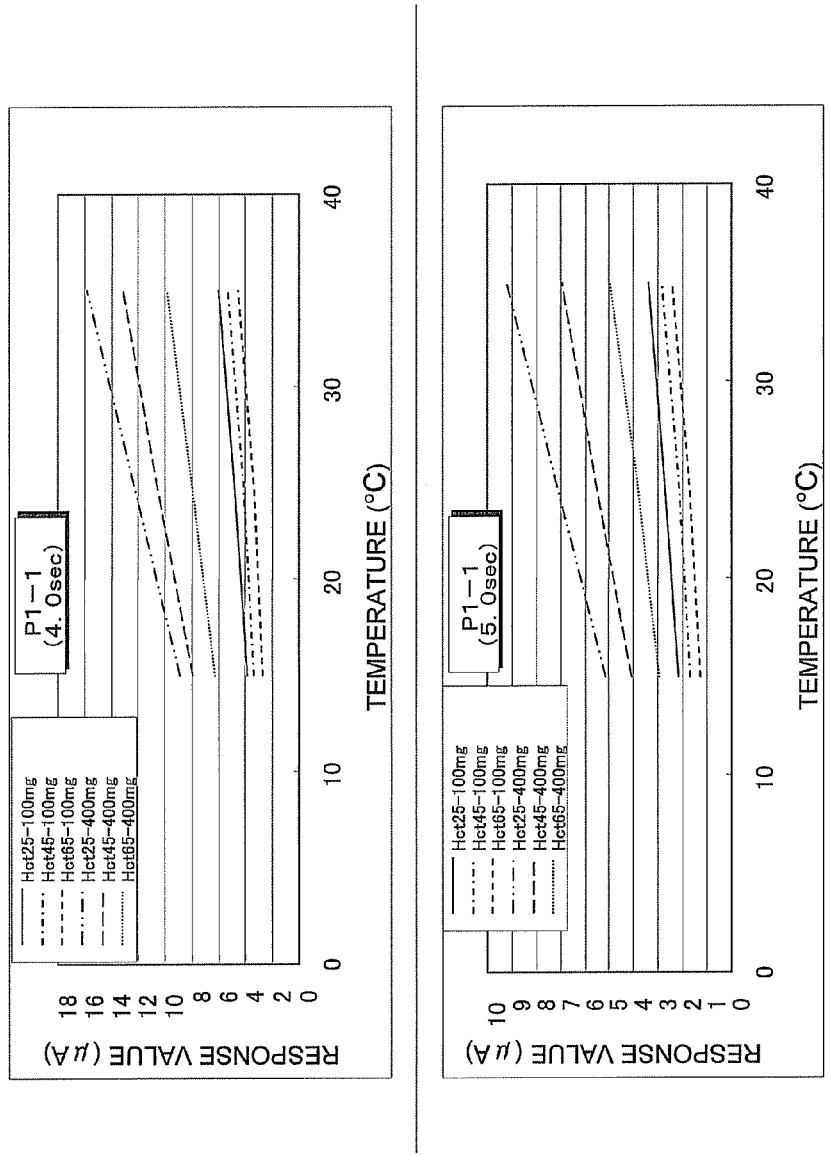
FIG. 90 includes charts representing a relation between variation in the blood sample temperature and variation in the response current value in the reference example 1.

FIG. 90 includes charts comprehensively representing the measured results of response current values represented in FIGS. 85 to 89, and represents variation in the response current value (Y-axis) with respect to the temperature (X-axis) when the Hct value and the glucose concentration were changed.

Specifically, as represented in the upper chart of FIG. 90, it was found that the response current value roughly linearly varied in accordance with variation in the temperature when the response current value was measured at the timing of 4.0 second as a measured time point included in a voltage application time period from 3.5 second to 5.0 second for temperature measurement. Further, it was found that variation thereof was wide enough not to measure measurement accuracy regardless of response current values.

Further, as represented in the lower chart of FIG. 90, it was found that the response current value roughly linearly varied in accordance with variation in the temperature when the response current value was measured at the timing of 5.0 second as a measured time point. Yet further, it was found that variation thereof was wide enough not to measure measurement accuracy, for instance, regardless of response current values.

It was found from the aforementioned measured results that the response current value was affected by increase and reduction in the glucose concentration and increase and reduction in the Hct value even when a voltage of roughly 0.5 V, which is roughly the same level as a voltage of 2.5 V to 0.50 V to be applied in measuring the glucose concentration, was applied in measuring the temperature as configured in the present reference example and it was thereby difficult to detect the response current value only by focusing on the effect of variation in the temperature. Further, the response current value is at a low level and an SN (signal/noise) ratio will be relatively small. Accuracy will be thereby worse. It was consequently found that the sensor chip of the present reference example could not be used as a temperature sensor for directly measuring the blood sample temperature.

<Working Effects>

A biological sample temperature measurement method according to an aspect of the present invention is a method of measuring the temperature of a biological sample in a sensor chip including: a temperature electrode unit formed by a working electrode and a counter electrode, each of which includes a regent containing an electrolyte; and a capillary allowing the biological sample to be introduced therein. The biological sample temperature measurement method includes a taking-in step and a temperature measurement step. In the taking-in step, a predetermined amount of the biological sample is taken in from the entirety of the biological sample introduced into the capillary. In the temperature measurement step, the temperature of the biological sample is measured by applying a predetermined voltage to the temperature electrode when the temperature of the biological sample is measured. The predetermined voltage herein allows the temperature measurement to be less affected by increase and reduction in the analyte contained in the biological sample.

In the biological sample temperature measurement method, the reagent containing the electrolyte herein exists in the working electrode and the counter electrode. Simultaneously, the predetermined voltage is applied when the temperature of the biological sample is measured. The predetermined voltage allows the temperature measurement to be less affected by increase and reduction in the amount of the analyte contained in the biological sample.

The analyte contained in the biological sample herein includes, for instance, hematocrit, glucose and reducing substance. Further, a relatively high voltage of 1 V or greater, for instance, is included in the predetermined voltage allowing a result of the measurement to be less affected by increase and reduction in the amount of the analyte contained in the biological sample.

Accordingly, it is possible to highly accurately measure the temperature of the biological sample for preventing a result of the measurement from depending on the amount of the analyte contained in the biological sample such as the hematocrit value or the glucose concentration. Consequently, it is also possible to enhance accuracy of a variety of corrections using the temperature of the biological sample based on the highly accurately calculated temperature measurement result.

A biological sample temperature measurement method according to an aspect of the present invention relates to the aforementioned biological sample temperature measurement method. Here, the amount of the taken-in biological sample in the taking-in step is less than or equal to 5 μL, and a period of time for applying the voltage in the temperature measurement step is less than or equal to 15 seconds.

Accordingly, it is possible to execute the temperature measurement in a short period of time under the condition that the amount of the taken-in biological sample is reduced.

A biological sample temperature measurement method according to an aspect of the present invention relates to the aforementioned biological sample temperature measurement method. Here, the predetermined voltage is a direct-current voltage falling in a voltage range allowing a solvent in the biological sample to be electrolyzed.

Accordingly, it is possible to accurately measure the temperature by applying, for instance, a relatively high voltage of 1 V or greater to the temperature electrode unit for allowing the solvent in the biological sample to be decomposed.

A biological sample temperature measurement method according to an aspect of the present invention relates to the aforementioned biological sample temperature measurement method. Here, the analyte contained in the biological sample is one of glucose, hematocrit and reducing substance. Further, the voltage to be applied in the temperature measurement step is a direct-current voltage allowing the temperature measurement to be less affected by increase and reduction in a preliminarily measured analyte amount.

Accordingly, it is possible to respectively measure the glucose concentration, the hematocrit value, the reducing substance concentration and the like in the biological sample.

Further, when the concentration of glucose contained in the biological sample is measured, for instance, it is possible to measure the biological sample temperature and the reducing substance concentration as well as the glucose concentration. Therefore, it is possible to accurately execute glucose measurement by correcting the measured result of the glucose concentration based on the measured results of the temperature and the reducing substance accurately measured by applying a voltage allowing the measurements to be less affected by increase and reduction in the amount of hematocrit or the like.

A biological sample temperature measurement method according to an aspect of the present invention relates to the aforementioned biological sample temperature measurement method. Here, a voltage with a potential difference of 1.0 V or greater is applied in the temperature measurement step.

Accordingly, it is possible to accurately execute the temperature measurement without depending on the concentration of the analyte contained in the biological sample by applying to the electrode unit a voltage with a potential difference optimal for the temperature measurement, which is higher than the voltage to be generally applied in measuring the concentration of the analyte contained in the biological sample.

A biological sample concentration measurement method according to an aspect of the present invention is a method of measuring the concentration of an analyte contained in a biological sample in a sensor chip including: an electrode unit formed by a working electrode and a counter electrode, each of which includes a reagent containing an electrolyte; and a capillary allowing the biological sample to be introduced therein. The biological sample concentration measurement method includes a taking-in step, a temperature measurement step and a concentration measurement step. In the taking-in step, a predetermined amount of the biological sample is taken in from the entirety of the biological sample introduced into the capillary. In the temperature measurement step, the temperature of the biological sample is measured by applying a predetermined voltage to the electrode unit when the temperature of the biological sample is measured. The predetermined voltage allows the temperature measurement to be less effected by increase and reduction in the amount of the analyte contained in the biological sample. In the concentration measurement step, the concentration of the analyte contained in the biological sample is measured by applying a predetermined voltage to the electrode unit.

In the biological sample concentration measurement method, the reagent containing the electrolyte herein exists on the working electrode and the counter electrode. Further, the predetermined voltage is applied when the temperature of the biological sample is measured. The predetermined voltage allows the temperature measurement to be less affected by increase and reduction in the amount of the analyte contained in the biological sample. Yet further, the concentration of the analyte contained in the biological sample is measured by applying the predetermined voltage to the aforementioned electrode unit on the sensor chip.

Examples of the analyte contained in the biological sample are herein hematocrit, glucose, reducing substance and the like.

It is possible to highly accurately measure the temperature of the biological sample by applying the predetermined voltage preventing the measurement from depending on the amount of the analyte contained in the biological sample such as the hematocrit value and the glucose concentration. It is also possible to measure the concentration of the analyte contained in the biological sample as well as the temperature of the biological sample. As a result, it is also possible to enhance accuracy of a variety of corrections using the temperature of the biological sample based on the highly accurately calculated temperature measurement result.

A biological sample concentration measurement method according to an aspect of the present invention relates to the aforementioned biological sample concentration measurement method. Here, at least one of the concentrations of glucose, hematocrit and reducing substance is measured as the concentration of the analyte contained in the biological sample in the concentration measurement step.

Accordingly, it is possible to respectively measure the glucose concentration, the hematocrit value, the reducing substance concentration and the like in the biological sample.

Further, when the concentration of glucose contained in the blood sample is measured, for instance, it is possible to measure the blood sample temperature and the reducing substance concentration as well as the glucose concentration. Therefore, it is possible to accurately measure the glucose concentration, for instance, by correcting the measured result of the glucose concentration based on the measured results of the temperature and the reducing substance.

A biological sample concentration measurement method according to an aspect of the present invention relates to the aforementioned biological sample concentration measurement method. Here, the voltage to be applied in the temperature measurement step has a potential difference greater than that of the voltage to be applied in measuring the concentration of the analyte in the concentration measurement step.

Accordingly, it is possible to highly accurately execute the temperature measurement without depending on the concentration of the analyte contained in the biological sample by applying to the electrode unit a voltage higher than the voltage to be generally applied in measuring the concentration of the analyte contained in the biological sample.

A biological sample concentration measurement method according to an aspect of the present invention relates to the aforementioned biological sample concentration measurement method. Here, a voltage with a potential difference of 1.0 V or greater is applied in the temperature measurement step.

Accordingly, it is possible to highly accurately execute the temperature measurement without depending on the concentration of the analyte contained in the biological sample by applying to the electrode unit a voltage with a potential difference optimal for the temperature measurement, which is higher than the voltage to be generally applied in measuring the concentration of the analyte contained in the biological sample.

A biological sample concentration measurement method according to an aspect of the present invention relates to the aforementioned biological sample concentration measurement method. Here, the biological sample concentration method further includes a correction step of correcting the concentration of the analyte contained in the biological sample measured in the concentration measurement step based on the temperature of the biological sample measured in the temperature measurement step.

Accordingly, it is possible to accurately correct the measured result of the concentration of the analyte (e.g., glucose, hematocrit and reducing substance) contained in the biological sample using the measured result of the temperature of the biological sample accurately measured without being affected by the concentration of the analyte contained in the biological sample. Therefore, it is possible to highly accurately execute measurements of the glucose concentration and the like.

A biological sample concentration measurement method according to an aspect of the present invention relates to the aforementioned biological sample concentration measurement method. Here, a voltage is applied to a measurement electrode unit disposed as an individual electrode unit separately from the electrode unit in the concentration measurement step. Further, the temperature measurement step is executed independently from the concentration measurement step.

Accordingly, the biological sample temperature and the analyte concentration can be measured using different electrode units. Therefore, the temperature measurement step and the concentration measurement step can be executed independently from each other. In other words, the temperature measurement step and the concentration measurement step can be executed simultaneously or at different timings.

A biological sample concentration measurement method according to an aspect of the present invention relates to the aforementioned biological sample concentration measurement method. Here, an order and a timing of the voltage application in the temperature measurement step is arbitrarily determined with respect to the voltage application in the concentration measurement step.

Accordingly, the temperature measurement step can be executed based on the timing of the voltage application in the concentration measurement step.

For example, the timings of executing the temperature measurement step and the concentration measurement step can be partially or entirely overlapped with each other. Simultaneously, the measurement timings can be controlled by arbitrarily setting a period of time (e.g., an application time period) of the temperature measurement step and a period of time (e.g., an application time period) of the concentration measurement step. Further, actions of the temperature measurement step can be executed a plurality of times during execution of the concentration measurement step. Yet further, variation in the biological sample temperature can be measured during execution of the concentration measurement by respectively obtaining the temperature data immediately after the beginning of the concentration measurement step and immediately before the end of the concentration measurement step.

Therefore, it is possible to achieve a correction function more flexible for variation in the temperature.

A biological sample concentration measurement method according to an aspect of the present invention relates to the aforementioned biological sample concentration measurement method. Here, the temperature measurement step is executed after the concentration measurement step is completed.

The temperature measurement is thus executed after the concentration measurement of the analyte contained in the biological sample is completed. Therefore, it is possible to measure the concentration and the temperature by shifting a voltage to be applied to the electrode unit from a lower level to a higher level.

A biological sample concentration measurement method according to an aspect of the present invention relates to the aforementioned biological sample concentration measurement method. Here, the voltage application is deactivated after the temperature measurement is completed in the temperature measurement step and the concentration measurement is executed by re-applying a voltage after a predetermined period of time is elapsed in the concentration measurement step.

Accordingly, it is possible to reliably keep a reaction time for the biological sample and the reagent by the predetermined period of time elapsed after a relatively high voltage is applied in executing the temperature measurement. Under the condition, it is possible to measure the concentration of the analyte contained in the biological sample. Therefore, it is possible to highly accurately execute the concentration measurement.

A sensor chip according to an aspect of the present invention is configured to measure the temperature of a biological sample. The sensor chip includes a capillary and a temperature electrode unit. The capillary allows the biological sample to be introduced therein. The temperature electrode unit is configured to measure the temperature of the biological sample. The temperature electrode unit includes a working electrode and a counter electrode. The working and counter electrodes respectively includes a reagent containing an electrolyte. The temperature electrode unit is configured to receive a predetermined voltage to be applied in measuring the temperature of the biological sample. The predetermined voltage allows the temperature measurement to be less effected by an analyte contained in the biological sample.

In the sensor chip configured to measure the temperature of the biological sample, the reagent containing the electrolyte exists in the working electrode and the counter electrode, and the predetermined voltage is applied in measuring the temperature of the biological sample. The predetermined voltage herein allows the temperature measurement to be less affected by increase and reduction in the amount of the analyte contained in the biological sample.

Accordingly, it is possible to highly accurately measure the temperature of the biological sample without depending on the amount of the analyte contained in the biological sample. As a result, it is also possible to enhance accuracy of a variety of corrections using the temperature of the biological sample based on the highly accurately calculated temperature measurement result.

A sensor chip according to an aspect of the present invention relates to the aforementioned sensor chip. Here, the amount of the taken-in biological sample into the capillary is less than or equal to 5 µL, and a period of time for applying the predetermined voltage to the temperature electrode unit is less than or equal to 15 seconds.

Accordingly, it is possible to execute the temperature measurement in a short period of time under the condition that the amount of the taken-in biological sample is reduced.

A sensor chip according to an aspect of the present invention relates to the aforementioned sensor chip. Here, the predetermined voltage is a direct-current voltage falling in a voltage range allowing a solvent in the biological sample to be electrolyzed.

Accordingly, it is possible to accurately measure the temperature by applying, for instance, a relatively high voltage of 1 V or greater to the temperature electrode unit for allowing the solvent in the biological sample to be decomposed.

A sensor chip according to an aspect of the present invention relates to the aforementioned sensor chip. Here, the sensor chip is a disposable sensor chip.

Accordingly, it is possible to accurately measure the temperature of the biological sample using the disposable sensor chip.

A sensor chip according to an aspect of the present invention relates to the aforementioned sensor chip. Here, the sensor chip further includes an analysis electrode unit configured to measure a concentration of the analyte contained in the biological sample.

Accordingly, it is possible to measure the concentration of the analyte contained in the biological sample such as glucose simultaneously with the measurement of the biological sample temperature.

A sensor chip according to an aspect of the present invention relates to the aforementioned sensor chip. Here, the temperature electrode unit also functions as the analysis electrode unit.

Accordingly, the well-known analysis electrode unit can be used as the temperature electrode unit as it is, without being additionally provided with another electrode unit as the temperature electrode unit. Therefore, it is possible to accurately measure the temperature and the concentration of the analyte contained in the biological sample without changing the simple configuration.

A sensor chip according to an aspect of the present invention relates to the aforementioned sensor chip. Here, the analyte includes at least one of glucose, hematocrit and reducing substance.

Accordingly, it is possible to respectively measure the glucose concentration, the hematocrit value and the reducing substance concentration and the like in the biological sample.

Further, in measuring the concentration of glucose contained in the blood sample as the biological sample, for example, it is possible to simultaneously measure the blood sample temperature and the reducing substance concentration. Therefore, it is possible to accurately measure the glucose concentration by executing correction and the like with respect to the measured result of the glucose concentration based on the measured results of the blood sample temperature and the reducing substance concentration.

A sensor chip according to an aspect of the present invention relates to the aforementioned sensor chip. Here, the working electrode and the counter electrode are opposed to each other.

Accordingly, it is possible to execute measurements of the temperature and the like by effectively applying a voltage in the biological sample.

A sensor chip according to an aspect of the present invention relates to the aforementioned sensor chip. Here, the temperature electrode unit is formed by kneading the electrolyte therein.

Accordingly, it is possible to form the temperature electrode unit on a substrate of the sensor chip as an electrode unit containing an electrolyte without forming the temperature electrode unit by dripping and applying a reagent containing an electrolyte thereon and drying it out. Therefore, it is possible to simplify the manufacturing processing.

A measuring instrument according to an aspect of the present invention is configured to apply a voltage to a sensor chip including an electrode unit formed by a working electrode and a counter electrode, each of which includes a reagent containing an electrolyte. The measuring instrument includes an insertion section, a voltage application section and a temperature measurement section. The insertion section allows the sensor chip to be loaded therein. The voltage application section is configured to apply a predetermined voltage to the electrode unit of the sensor chip loaded into the insertion section. The predetermined voltage inhibits the effect of an analyte contained in the biological sample. The temperature measurement section is configured to measure a temperature of the biological sample based on an output value of the voltage applied by the voltage application section.

In measuring the temperature of the biological sample, the predetermined voltage is herein applied to the sensor chip loaded in the insertion section for measuring the temperature of the biological sample. The predetermined voltage herein allows the temperature measurement to be less affected by increase and reduction in the amount of the analyte contained in the biological sample.

For example, the predetermined voltage, allowing the temperature measurement to be less affected by increase and reduction in the amount of the analyte contained in the biological sample, herein refers to a voltage of 1.0 V or greater higher than the voltage to be applied in measuring the glucose concentration and the like.

Accordingly, the temperature of the biological sample can be highly accurately measured without depending on the amount of the analyte contained in the biological sample. As a result, it is also possible to enhance a variety of corrections using the temperature of the biological sample based on the highly accurately calculated temperature measurement result.

A measuring instrument according to an aspect of the present invention relates to the aforementioned measuring instrument. Here, the voltage application section is configured to apply a direct-current voltage falling in a voltage range allowing a solvent in the biological sample to be electrolyzed.

Accordingly, the solvent in the biological sample is decomposed. For example, it is possible to accurately execute the temperature measurement by applying a relatively high direct-current voltage of 1 V or greater to the temperature electrode unit.

A measuring instrument according to an aspect of the present invention relates to the aforementioned measuring instrument. Here, the measuring instrument further includes an analyte measurement section configured to measure the concentration of the analyte contained in the biological sample based on the output value of the predetermined voltage applied by the voltage application section.

Accordingly, it is possible to accurately measure the glucose concentration and the like.

A measuring instrument according to an aspect of the present invention relates to the aforementioned measuring instrument. Here, the analyte measurement section is configured to measure at least one of the concentrations of glucose, hematocrit and reducing substance as the concentration of the analyte contained in the biological sample.

Accordingly, it is possible to respectively measure the glucose concentration, the hematocrit value, the reducing substance concentration and the like in the biological sample.

Further, in measuring the concentration of glucose contained in the blood sample as the biological sample, for instance, it is possible to simultaneously measure the temperature of the biological sample and the concentration of the reducing substance. Therefore, it is possible to accurately measure the glucose concentration by executing correction and the like with respect to the measured result of the glucose concentration based on the measured results of the biological sample temperature and the reducing substance concentration.

A measuring instrument according to an aspect of the present invention relates to the aforementioned measuring instrument. In the temperature measurement, the voltage application section is herein configured to apply a voltage with a potential difference greater than a potential difference of the voltage to be applied when the concentration of the analyte is measured in the concentration measurement.

Accordingly, the temperature measurement can be highly accurately executed without depending on the concentration of the analyte contained in the biological sample by applying a voltage (e.g., 1 V or greater) higher than the voltage to be generally applied in measuring the concentration of the analyte contained in the biological sample.

A measuring instrument according to an aspect of the present invention relates to the aforementioned measuring instrument. Here, the voltage application section is configured to apply a voltage with a potential difference of 1.0 V or greater in the temperature measurement.

Accordingly, the temperature measurement can be highly accurately executed without depending on the concentration of the analyte contained in the biological sample by applying to the electrode unit a voltage with a potential difference optimal for the temperature measurement, which is higher than the voltage to be generally applied in measuring the concentration of the analyte contained in the biological sample.

A biosensor system according to an aspect of the present invention includes the aforementioned sensor chip, a measuring instrument, a voltage application section, a first temperature measurement section and an analyte measurement section. The measuring instrument includes a control circuit configured to control application of a predetermined voltage to the temperature electrode unit of the sensor chip for a predetermined period of time. The voltage application section is configured to apply the predetermined voltage to the temperature electrode unit for the predetermined period of time under the control of the control circuit. The first temperature measurement section is configured to measure the temperature of the biological sample based on a magnitude of an electric current flowing through the temperature electrode unit making contact with the biological sample. The analyte measurement section is configured to measure the concentration of the analyte based on a magnitude of an electric current to be generated in the biological sample as a result of an electrochemical reaction where the analyte contained in the biological sample serves as a substrate.

In the biosensor system including the aforementioned sensor chip configured to measure the temperature of the biological sample, the temperature of the biological sample is measured by applying the predetermined voltage to the temperature electrode unit of the sensor chip, and simultaneously, the concentration of the analyte contained in the biological sample is measured by detecting an electric current to be generated in the biological sample as a result of a reaction mediated by an oxidoreductase for which the analyte contained in the biological sample serves as a substrate. Further, examples of the aforementioned electrochemical reaction include a reaction mediated by an oxidoreductase.

For example, the analyte contained in the biological sample herein includes hematocrit, glucose, reducing substance and the like. Further, the aforementioned voltage to be applied in measuring the temperature of the biological sample includes, for instance, a relatively high voltage of 1 V or greater allowing the measurement result to be less affected by increase and reduction in the amount of the analyte.

Accordingly, the temperature of the biological sample can be highly accurately measured without depending on the amount of the analyte contained in the biological sample such as the hematocrit value and the glucose concentration. As a result, it is also possible to enhance accuracy of a variety of corrections using the temperature of the biological sample based on the highly accurately calculated temperature measurement result.

A biosensor system according to an aspect of the present invention relates to the aforementioned biosensor system. Here, the biosensor system further includes a concentration correction section configured to correct the concentration of the analyte contained in the biological sample based on the temperature measured by the first temperature measurement section.

Accordingly, it is possible to accurately measure the concentration of the analyte contained in the biological sample based on the accurately measured result of the biological sample temperature.

A biosensor system according to an aspect of the present invention relates to the aforementioned biosensor system. Here, the measuring instrument includes a second temperature measurement section configured to measure one of an internal environmental temperature, a surface environmental temperature and a surrounding environmental temperature. Further, the concentration correction section is configured to compare a temperature datum measured by the first temperature measurement section and a temperature datum measured by the second temperature measurement section and is configured to correct the analyte concentration with a selected one of the measured temperature data.

In the biosensor system including the sensor ship embedded with a thermister, it is accordingly possible to correct the concentration of the analyte selectively using the measured results of temperatures including the temperature on the measuring instrument and the temperature in the periphery of the measuring instrument. Therefore, it is possible to more accurately measure the concentration of the analyte.

A biosensor system according to an aspect of the present invention relates to the aforementioned biosensor system. Here, the concentration correction section is configured to determine a predetermined coefficient depending on a difference between the temperature datum measured by the first temperature measurement section and the temperature datum measured by the second temperature measurement section and is configured to correct the concentration of the analyte contained in the biological sample based on a result obtained by executing a calculation for the coefficient and the respective temperature data.

Accordingly, it is possible to more accurately measure the concentration of the analyte by correcting the concentration of the analyte based on the coefficient calculated based on the results of temperatures measured by the first and second temperature measurement sections.

A biosensor system according to an aspect of the present invention relates to the aforementioned biosensor system. Here, the voltage application section is configured to apply a direct-current voltage falling in a voltage range allowing a solvent in the biological sample to be electrolyzed.

Accordingly, it is possible to accurately measure the temperature, for instance, by applying to the temperature electrode unit a relatively high direct-current voltage of 1 V or greater allowing the solvent in the biological sample to be decomposed.

A biosensor system according to an aspect of the present invention relates to the aforementioned biosensor system. Here, the analyte measurement section is configured to measure at least one of the concentrations of glucose, hematocrit and reducing substance as the concentration of the analyte contained in the biological sample.

Accordingly, it is possible to respectively measure the glucose concentration, the hematocrit value, the reducing substance concentration and the like in the biological sample.

Further, in measuring the concentration of glucose contained in the blood sample as the biological sample, for instance, it is possible to simultaneously measure the biological sample temperature and the reducing substance concentration. Therefore, it is possible to accurately measure the glucose concentration by executing correction and the like for the measured result of the glucose concentration based on the measured results of the biological sample temperature and the reducing substance concentration.

A biosensor system according to an aspect of the present invention relates to the aforementioned biosensor system. In the temperature measurement, the voltage application section is herein configured to apply a voltage with a potential difference greater than that of the voltage to be applied when the concentration of the analyte is measured in the concentration measurement.

Accordingly, the temperature measurement can be highly accurately executed without depending on the concentration of the analyte contained in the biological sample by applying to the electrode unit a voltage (e.g., 1 V or greater) higher than the voltage to be generally applied in measuring the concentration of the analyte contained in the biological sample.

A biosensor system according to an aspect of the present invention relates to the aforementioned biosensor system. Here, the voltage application section is configured to apply a voltage with a potential difference of 1.0 V or greater in the temperature measurement.

Accordingly, the temperature measurement can be highly accurately executed without depending on the concentration of the analyte contained in the biological sample by applying the electrode unit a voltage with a potential difference optimal for the temperature measurement, which is higher than the voltage to be generally applied in measuring the concentration of the analyte contained in the biological sample.

<Other Exemplary Embodiments>

Exemplary embodiments of the present invention have been described above. However, the present invention is not limited to the aforementioned exemplary embodiments. A variety of changes can be herein made without departing from the scope of the present invention.

(A)

The biosensor system 100 of the aforementioned exemplary embodiments can directly measure the blood sample temperature using the electrodes 11 and 12 of the sensor chip 200 even when temperature is rapidly changed in the sensor usage environment. Therefore, the concentration of the analyte contained in the blood sample can be highly accurately measured by accurately measuring the temperature and further executing correction based on the temperature. An environment temperature measurement section, typified by a thermister, is not thereby basically required to be disposed in the measuring instrument. However, the environment temperature measurement section such as the thermister may be required to be disposed in the measuring instrument when the measurement section measures an electric current amount at a low accuracy.

For example, when the volume of the capillary section 40 is reduced for reducing the volume of the blood sample, it is also required to reduce the area of the temperature electrode of the measurement section. Accordingly, the current amount to be obtained by the measurement section is reduced. Consequently, the measurement section reduces its accuracy of obtaining the current amount. In this case, it is preferable to compare a temperature t to be obtained by the measurement section and a temperature t1 (Step S43 in the flowchart (a) of FIG. 8) to be obtained by the environment temperature measurement section (i.e., the second temperature measurement section) and select the temperature t to be obtained by the measurement section only when a difference is produced between the temperature t and the temperature t1.

Specifically, it is preferable to execute the following processing represented in the flowchart (a) of FIG. 8. In Step S41, the temperature t is calculated based on the datum a (see Step S2 in FIG. 6). In Step S42, a concentration x is calculated based on the datum b (see Step S3 in FIG. 6). In Step S43, the environment temperature t1 is measured. In Step S46, when no difference is produced between the outside environment temperature and the blood sample temperature, the temperature t1 to be obtained by the environment temperature measurement section of the measuring instrument is selected. In Step S45, when a difference is produced between the outside environment temperature and the blood sample temperature due to rapid temperature change or the like, the temperature t to be obtained by the measurement section is selected because the environment temperature measurement section of the measuring instrument cannot cope with the situation.

More specifically, a temperature threshold Z is preliminarily set and a value of |t−t1| is compared with the temperature threshold Z in Step S44. When the value of |t−t1| is greater than or equal to the temperature threshold Z, the concentration x is corrected based on the temperature t in Step S45. When the value of |t−t1| is less than the temperature threshold Z, the concentration x is corrected based on the environment temperature t1 in Step S46. The range of the temperature threshold Z is set in consideration of accuracy of the environment temperature measurement section of the measuring instrument and accuracy of the measurement section of the sensor chip. The temperature threshold Z falls in a range of 0.01 to 5.0° C., preferably falls in a range of 0.1 to 2.0° C., and more preferably falls in a range of 0.2 to 1.0° C.

As represented in the diagram (b) of FIG. 8, the computation unit (concentration determination unit) 306 (see FIG. 5) in the biosensor system 100 herein includes a temperature calculation section 310, a concentration calculation section 311, an environment temperature measurement section 312, a comparison section 313 and a correction section 314. The temperature calculation section 310 is configured to calculate the temperature t of the blood sample based on the datum a. The concentration calculation section 311 is configured to calculate the concentration x of the analyte contained in the blood sample based on the datum b. The environment temperature measurement section 312 is configured to measure the environment temperature t1 in the surrounding of the blood sample. The comparison section 313 is configured to compare a difference between the temperature t and the environment temperature t1 with the temperature threshold Z. The correction section (i.e., an analyte correction section) 314 is configured to correct the concentration x based on the temperature t when "|t−t1|≥Z" is satisfied and correct the concentration x based on the environment temperature t1 when "|t−t1|<Z" is satisfied.

(B)

In the aforementioned exemplary embodiments, the sensor chip 200 has been exemplified as a sensor chip of the present invention. The sensor chip 200 is configured to measure the temperature of the blood sample and the concentration of glucose and the like using the electrodes 11 and 12 in common. In the present invention, however, the sensor chip is not limited to the above.

As illustrated in the diagram (a) of FIG. 91, for instance, the sensor chip of the present invention may be a sensor chip 210 including four electrodes A to D forming two electrode systems, i.e., a glucose measurement system (formed by the electrodes A and B) and a temperature measurement system (formed by the electrodes C and D).

In this case, as represented in the chart (b) of FIG. 91, a voltage of 0.25 V is applied to the electrodes A and B in the glucose measurement system. As represented in the chart (c) of FIG. 91, on the other hand, a voltage of 0.25 V is applied to the electrodes C and D in the temperature measurement system in measuring the concentration of interfering substances (i.e., substances excluding glucose and Hct, such as vitamin C, ascorbic acid and the like), whereas a voltage of 1.5 V is applied to the electrodes C and D in the temperature measurement system in measuring the temperature.

Further, it is preferable to use an enzyme and a mediator as a reagent to be applied onto the electrodes A and B in the glucose measurement system and use a substance functioning as an electrolyte after being dissolved (preferably the same mediator as that applied onto the electrodes A and B in the glucose measurement system) as a reagent to be applied onto the electrodes C and D in the temperature measurement system.

Accordingly, it is possible to obtain a current value due to enzyme and glucose at the electrodes A and B in the glucose measurement system, whereas it is possible to obtain a current value due to the temperature at the electrodes C and D in the temperature measurement system.

(C)

In the aforementioned exemplary embodiments, examples have been explained that the glucose measurement system and the temperature measurement system respectively execute measurements using the sensor chip 200 in common. However, the sensor chip of the present invention is not limited to the above.

Figure 92:
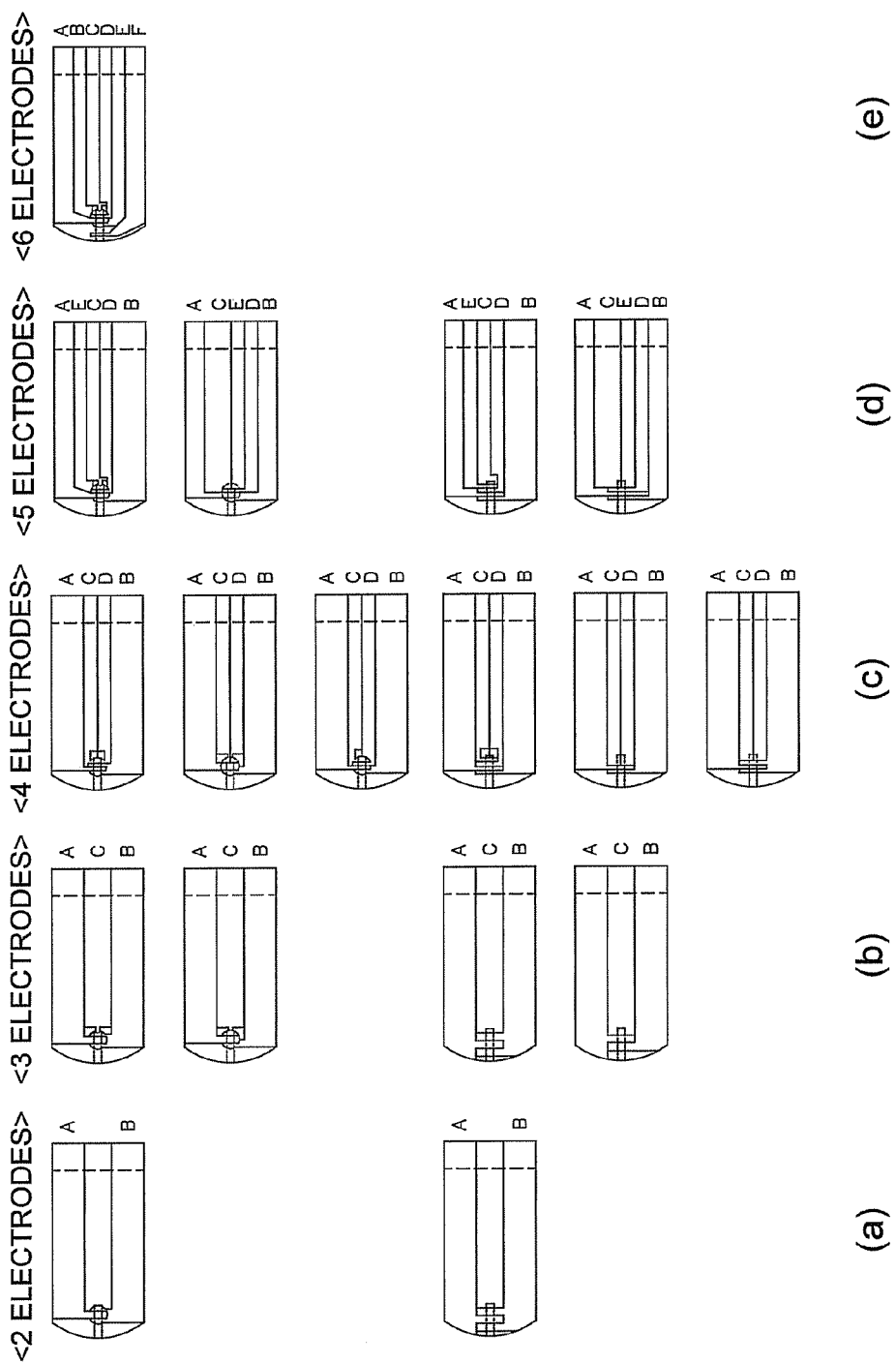
FIG. 92 includes plan views (a) to (e) illustrating configurations of sensor chips respectively provided with two to six electrodes according to yet another exemplary embodiment of the present invention.

For example, it is possible to use any one of the sensor chips formed by: an electrode pattern of two electrodes illustrated in the diagram (a) of FIG. 92; an electrode pattern of three electrodes illustrated in the diagram (b) of FIG. 92; an electrode pattern of four electrodes illustrated in the diagram (c) of FIG. 92; an electrode pattern of five electrodes illustrated in the diagram (d) of FIG. 92; and an electrode pattern of six electrodes illustrated in the diagram (e) of FIG. 92.

(D)

In the aforementioned exemplary embodiments, the sensor chip 200 has been exemplified as a sensor chip of the present invention and adopts a reagent arrangement that the reagent is applied on the working electrode in a roughly circular shape. However, the sensor chip of the present invention is not limited to the above.

Figure 93:
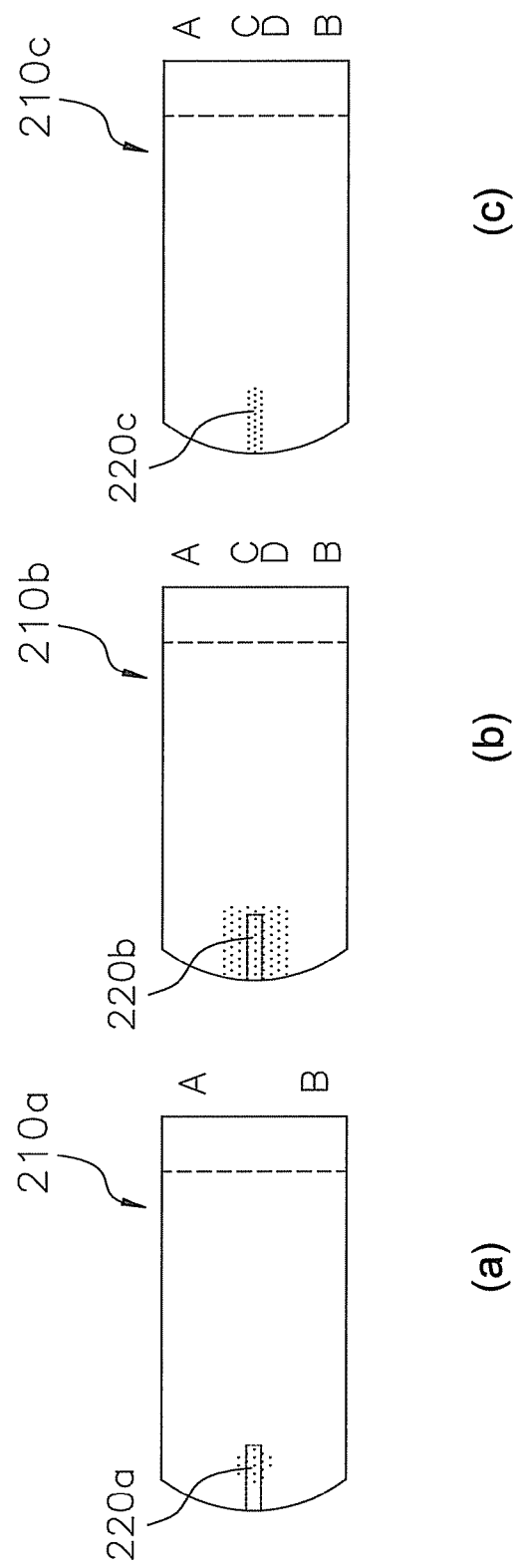
FIG. 93 includes plan views (a) to (c) illustrating exemplary arrangements of a reagent on a working electrode in a sensor chip according to yet another exemplary embodiment of the present invention.

For example, it is possible to use any one of: a sensor chip 210*a* including a reagent layer 220*a* dripped on the working electrode as illustrated in the diagram (a) of FIG. 93; a sensor chip 210*b* including a reagent layer 220*b*, which includes the capillary section and is entirely arranged by means of paste printing or the like, as illustrated in the diagram (b) of FIG. 93; and a sensor chip 210*c* including a reagent layer 220*c* formed along the capillary section as illustrated in the diagram (c) of FIG. 93.

(E)

In the aforementioned exemplary embodiments, the sensor chip 200, including three electrodes A, B and C disposed therein, has been exemplified as a sensor chip of the present invention. However, the sensor chip of the present invention is not limited to the above.

Figure 94:
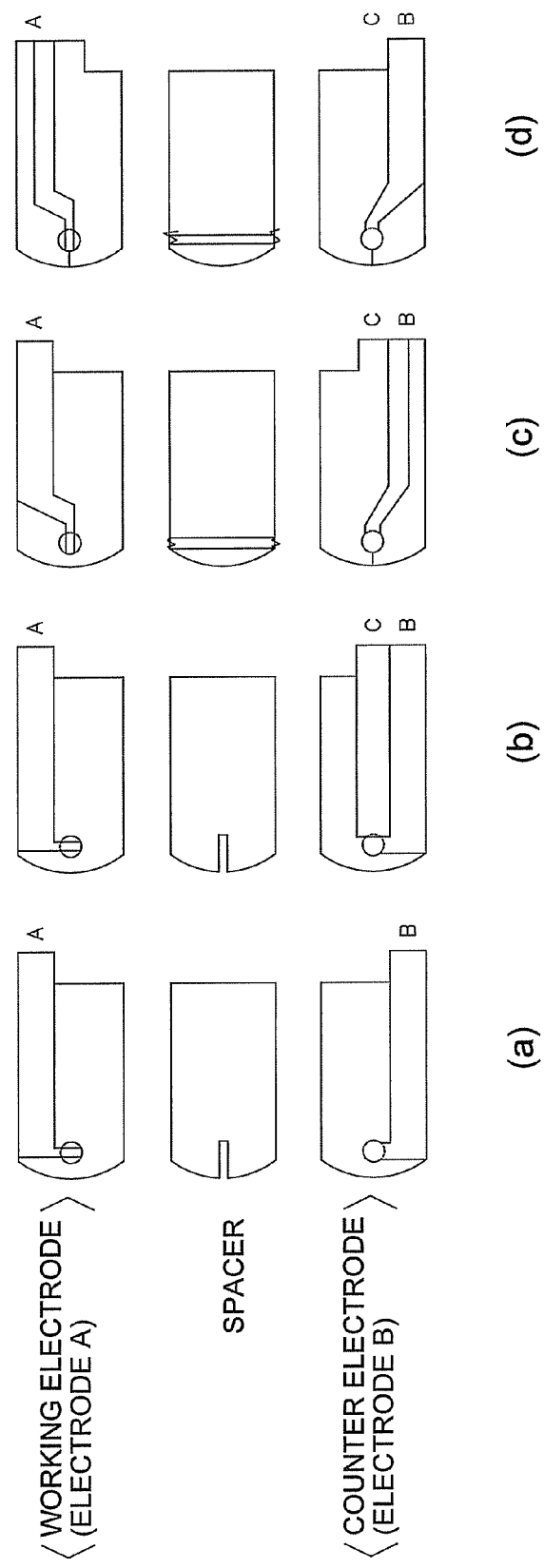
FIG. 94 includes plan views (a) to (d) illustrating exemplary configurations of the electrodes of the sensor chip according to yet another exemplary embodiment of the present invention.

For example, the sensor chip may be formed by the combination of two electrodes A and B as illustrated in the diagram (a) of FIG. 94. Alternatively, the sensor chip may be formed by the combination of three electrodes A, B and C differently shaped as illustrated in the diagrams (b) to (d) of FIG. 94.

(F)

In the aforementioned exemplary embodiments, the sensor chip 200 has been exemplified as a sensor chip of the present invention and has the structure that the reaction reagent layer 20 is disposed on three electrodes A, B and C. However, the sensor chip of the present invention is not limited to the above.

Figure 95:
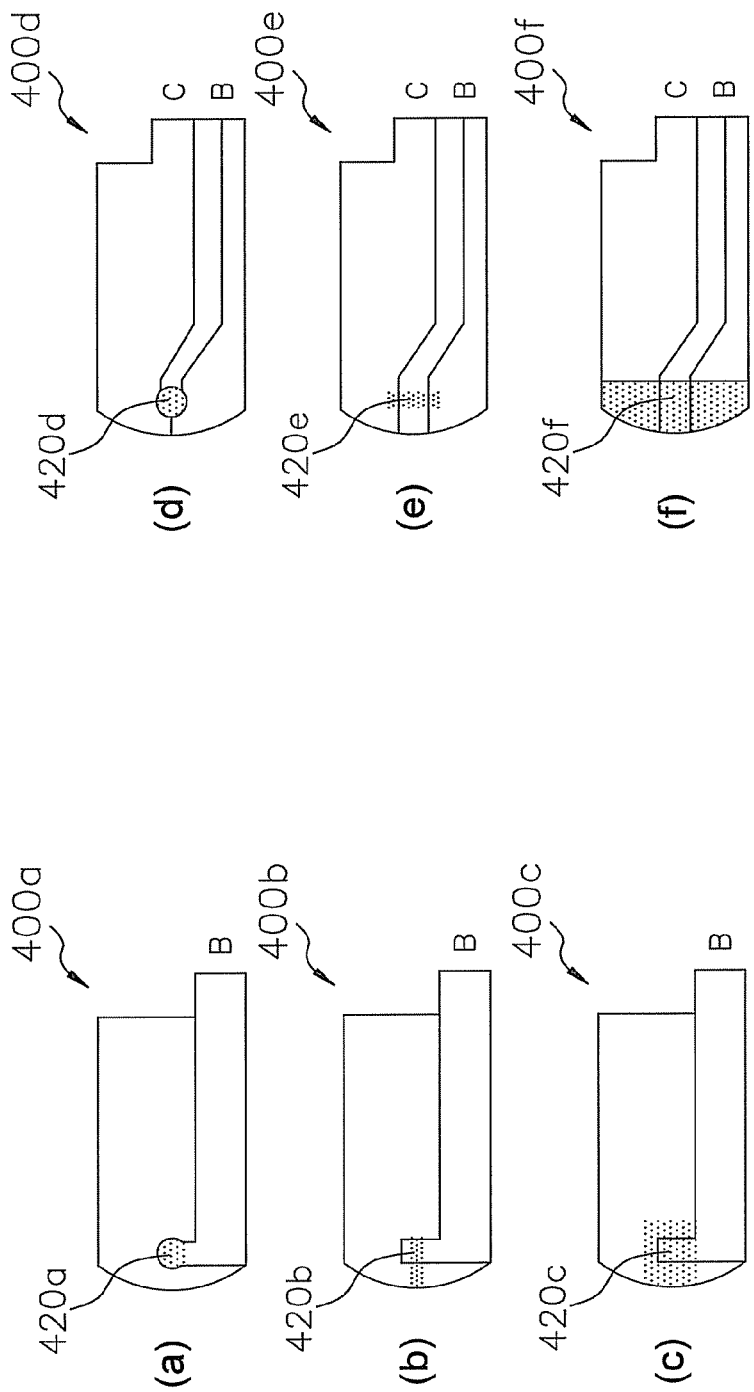
FIG. 95 includes plan views (a) to (f) illustrating exemplary arrangements of a reagent on a counter electrode in a sensor chip according to yet another exemplary embodiment of the present invention.

For example, when including two electrodes, the sensor chip may be any one of sensor chips 400*a* to 400*c* respectively including a reagent layer disposed on the counter electrode (electrode B) as follows. As illustrated in the diagram (a) of FIG. 95, the sensor chip 400*a* includes a reagent layer 420*a* applied onto the electrode B in a circular shape. As illustrated in the diagram (b) of FIG. 95, the sensor chip 400*b* includes a reagent layer 420*b* applied along the capillary as well as onto the electrode B in a rectangular shape. As illustrated in FIG. 95 (*c*), the sensor chip 400*c* includes a regent layer 420*c* applied onto the electrode B in a square shape.

Alternatively, when including three electrodes, the sensor chip may be any one of sensor chips 400*d* to 400*f* respectively including a reagent layer disposed on the counter electrode (electrode B) as follows. As illustrated in the diagram (d) of FIG. 95, the sensor chip 400*d* includes a reagent layer 420*d* applied onto the electrode B in a circular shape. As illustrated in the diagram (e) of FIG. 95, the sensor chip 400*e* includes a reagent layer 420*e* applied onto the capillary as well as onto the electrode B in a transversely elongated rectangular shape. As illustrated in the diagram (f) of FIG. 95, the sensor chip 400*f* includes a regent layer 420*f* applied to cover the tip of the sensor chip.

(G)

In the aforementioned exemplary embodiments, the case has been exemplified that the blood sample temperature, the glucose concentration and the like were measured by applying a predetermined voltage to the respective electrodes for a predetermined period of time with use of the sensor chip 200 including three electrodes A, B and C. However, the measurement related configurations of the present invention are not limited to the above.

For example, as illustrated in the diagram (a) of FIG. 96, a sensor chip 500*a* including two electrodes A and B may be used. In this case, the working electrode A may function as both a glucose measurement electrode and a temperature measurement electrode.

As represented in the chart (b) of FIG. 96, the glucose concentration may be herein measured by applying a voltage of 0.25 V between the electrodes A and B in a time period from 0 second to 3.5 second, and the temperature may be subsequently measured by applying a voltage of 1.5 V between the electrodes A and B in a time period from 3.5 second to 6.0 second.

Alternatively, as represented in the chart (c) of FIG. 96, the temperature may be firstly measured by applying a voltage of 1.5 V in a time period from 0 second to 1.5 second, and the glucose concentration may be subsequently measured by applying a voltage of 0.25 V.

Yet alternatively, as represented in the chart (d) of FIG. 96, a voltage may not be applied in a predetermined period (from 0 second to 1.5 second) for reliably keeping a reaction time of the blood sample and the reagent. Then, the glucose concentration may be measured by applying a voltage of 0.25 V in a time period from 1.5 second to 3.5 second, and the temperature may be subsequently measured by applying a voltage of 1.5 V in a time period from 3.5 second to 5.0 second.

Yet alternatively, as represented in the chart (e) of FIG. 96, the temperature may be firstly measured by applying a voltage of 1.5 V in a time period from 0 second to 1.5 second. Next, a voltage may not be applied in a predetermined period (from 1.5 second to 3.0 second) until reactions are completely done between the blood sample and the reagent. Subsequently, the glucose concentration may be measured by applying a voltage of 0.25 V in a time period from 3.0 second to 5.0 second.

It should be noted that the same electrode is preferably used as the working electrode when a high voltage (1.5 V) is firstly applied in measuring the temperature as illustrated in the charts (c) and (e) of FIG. 96. It is accordingly possible to reliably obtain sufficient detection ability in measuring the glucose concentration.

(H)

In the aforementioned exemplary embodiments, the case has been exemplified that the blood sample temperature, the glucose concentration and the like were measured by applying a predetermined voltage to the respective electrodes for a predetermined period of time with use of the sensor chip 200 including three electrodes A, B and C. However, the measurement related configurations of the present invention are not limited to the above.

Figure 97:
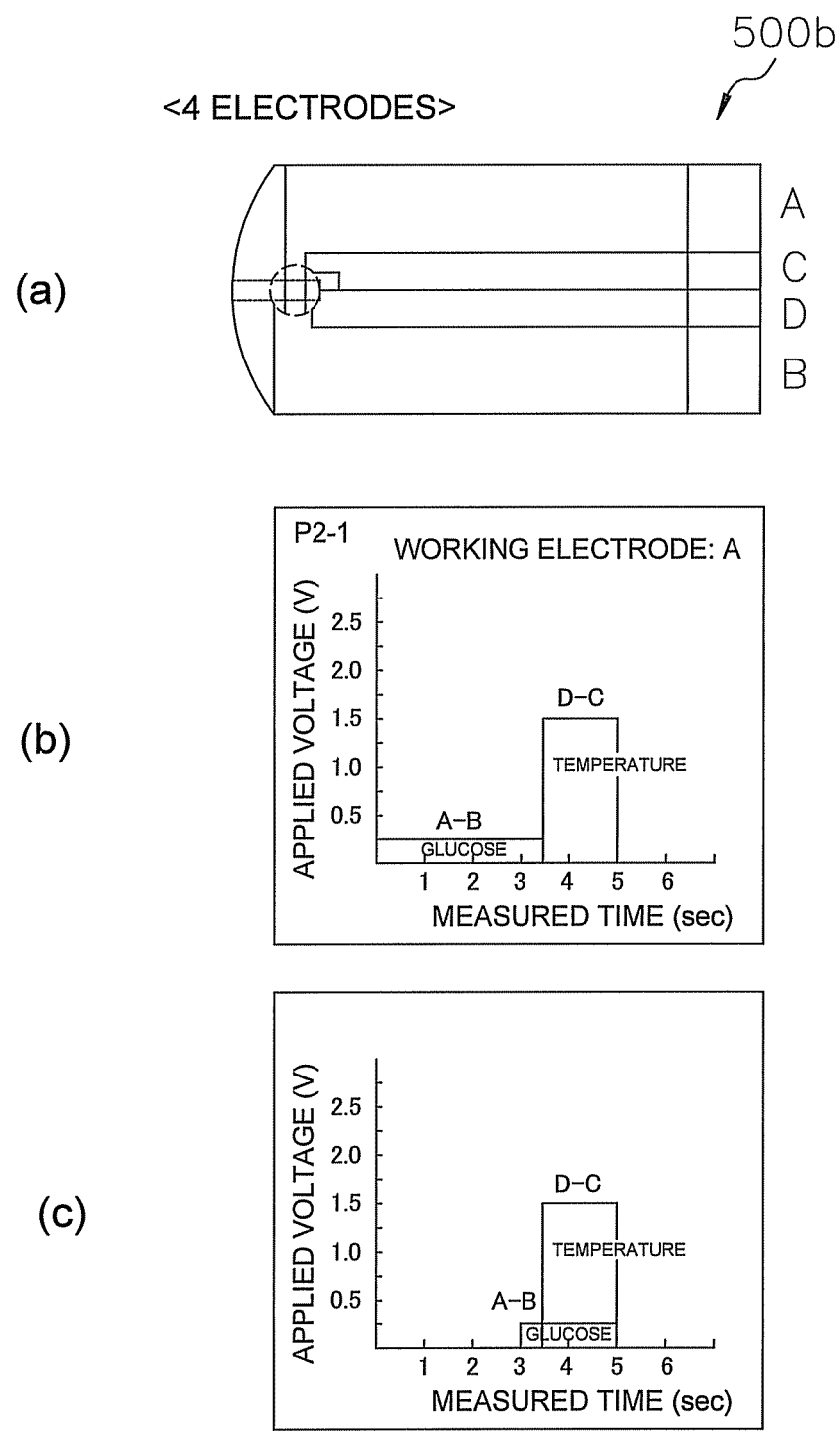
FIG. 97 includes a plan view (a) of a configuration of a sensor chip according to yet another exemplary embodiment of the present invention and charts (b) and (c) representing an exemplary pattern of applying a voltage to electrodes in a glucose measurement system and a temperature measurement system.

For example, as illustrated in the diagram (a) of FIG. 97, a sensor chip 500*b* including four electrodes A, B, C and D may be used. In this case, the electrode A may be used as a working electrode in measuring the glucose concentration (note either the electrode B or the electrodes B and C may be set as a counter electrode or counter electrodes), whereas the electrode D may be used as a working electrode in measuring the temperature (note either the electrode C or the electrodes C and B may be set as a counter electrode or counter electrodes before the glucose measurement whereas one or more of the electrodes A, B and C may be set as a counter electrode or counter electrodes after the glucose concentration measurement).

As represented in the chart (b) of FIG. 97, the glucose concentration may be herein measured by applying a voltage of 0.25 V in a time period from 0 second to 3.5 second, and the temperature may be measured by applying a voltage of 1.5 V in a time period from 3.5 second to 5.0 second, similarly to the aforementioned two-electrode configuration.

Alternatively, as represented in the chart (c) of FIG. 97, the glucose concentration may be measured by applying a voltage of 0.25 V in a time period from 3.0 second to 5.0 second, and the temperature may be measured by applying a voltage of 1.5 V in a time period from 3.5 second to 5.0 second for simultaneously executing the temperature measurement and the glucose concentration measurement in this period.

(I)

In the aforementioned exemplary embodiments, glucose, hematocrit, oxidation-reduction substance and the like, which are contained in the blood sample, have been exemplified as the analyte of the biological sample. However, the analyte of the present invention is not limited to the above.

For example, any substances other than glucose and the like may be set as the analyte when any biological sample other than the blood sample is set as an analysis target.

(J)

In the aforementioned exemplary embodiments, the case has been exemplified that a voltage with a positive potential was applied to the electrodes of the sensor chip 200 in measuring the temperature and measuring the concentration. However, the voltage potential in the present invention is not limited to the above.

For example, not only a voltage with a positive potential but also a voltage with a negative potential may be applied to the sensor chip in both measuring the temperature and measuring the concentration.

(K)

In the aforementioned exemplary embodiments, the sensor chip 200 has been exemplified as a sensor chip of the present invention and has the structure that the working and counter electrodes (the electrodes 11, 12 and 13) are disposed on the same plane as illustrated in FIG. 3. However, the sensor chip of the present invention is not limited to the above.

For example, the sensor chip of the present invention may have a structure that the working electrode and the counter electrode are opposed to each other.

(L)

In the aforementioned exemplary embodiments, a range of 1.0 V and greater has been exemplified as a preferable range of a voltage to be applied in measuring the temperature. However, the preferable applied voltage range in the present invention is not limited to the above.

For example, it is possible to express a preferable range of a voltage to be applied in measuring the temperature not only with a directly expressed numeric value but also with a numeric value, such as a ratio with respect to a voltage to be applied in measuring the glucose concentration or a potential difference.

Further, it is obviously possible to measure a voltage to be applied in measuring the glucose concentration within a range of 0.1 V to 0.5 V, as explained in the aforementioned exemplary embodiment 8. Yet further, it is similarly possible to specify a ratio with respect to a voltage to be applied in measuring the temperature, a potential difference, or the like as a preferable range for a voltage to be applied in measuring the glucose concentration.

INDUSTRIAL APPLICABILITY

A sensor chip, a biosensor system including the sensor chip, a temperature measurement method of a biological sample and a concentration measurement method of a biological sample according to the present invention can achieve an advantageous effect of effectively inhibiting occurrence of a concentration measurement error due to temperature, and can be thereby applied to a variety of fields requiring a high precision measurement.

REFERENCE SIGNS LIST 11, 12 Electrode (temperature electrode unit, analysis electrode unit, first temperature measurement section, analyte measurement section)
13 Electrode
16 Air vent aperture
17 Biological sample inlet
20 Reaction reagent layer
40 Capillary section
100 Biosensor system
101 Measuring instrument
102 Attachment port
103 Display unit
200 Sensor chip
201 Insulator substrate
202 Spacer
203 Cover
204 Notch
210 Sensor chip
201a, 210b, 210c Sensor chip
220a, 220b, 220c Reagent layer
300 Control circuit
301a, 301b, 301c Connector
302 Switching circuit
303 Current/voltage converter circuit
304 Analogue/digital (A/D) converter circuit
305 Reference voltage source (Voltage application section)
306 Computation unit (Concentration determination section)
307 Temperature measurement section
308 Computation section
309 Concentration calculation section
310 Temperature calculation section
311 Concentration calculation section
312 Environmental temperature measurement section
313 Comparison section
314 Correction section (Analyte correction section)
400a to 400f Sensor chip
420a to 420f Reagent Layer
500a, 500b Sensor chip

The invention claimed is:

1. A biological sample concentration measurement method of measuring a concentration of an analyte contained in a biological sample in a sensor chip including: an electrode unit formed by a working electrode and a counter electrode, the working and counter electrodes respectively including a reagent containing an electrolyte; and a capillary allowing the biological sample to be introduced therein, the biological sample concentration measurement method comprising:
a taking-in step of taking in a predetermined amount of the biological sample from an entirety of the biological sample introduced into the capillary;
a temperature measurement step of measuring a temperature of the biological sample by applying a first voltage to the electrode unit when the temperature of the biological sample is measured, the first voltage allowing the temperature measurement to be less affected by increase and reduction in an amount of the analyte contained in the biological sample; and
a concentration measurement step of measuring the concentration of the analyte in the biological sample by applying a second voltage to the electrode unit, wherein the first voltage has a potential difference greater than the second voltage.

2. The biological sample concentration measurement method recited in claim 1,
wherein the concentration measurement step includes measuring at least one of the concentrations of glucose, hematocrit and reducing substance as the concentration of the analyte in the biological sample.

3. The biological sample concentration measurement method recited in claim 1,
wherein the temperature measurement step includes applying the first voltage with a potential difference of 1.0V or greater.

4. The biological sample concentration measurement method recited in claim 1, further comprising:
a correction step of correcting the concentration of the analyte contained in the biological sample measured in the concentration measurement step based on the temperature of the biological sample measured in the temperature measurement step.

5. The biological sample concentration measurement method recited in claim 1,
wherein the sensor chip includes a plurality of electrode units, the plurality of electrode units including a measurement electrode unit,
the concentration measurement step includes applying the second voltage to the measurement electrode unit disposed as an individual electrode unit that the first voltage is applied to in the temperature measurement step, and
the temperature measurement step is executed independently from the concentration measurement step.

6. The biological sample concentration measurement method recited in claim 5,
wherein an order and a timing of the voltage application in the temperature measurement step is arbitrarily determined with respect to the voltage application in the concentration measurement step.

7. The biological sample concentration measurement method recited in claim 1,
wherein the temperature measurement step is executed after the concentration measurement step is completed.

8. The biological sample concentration measurement method recited in claim 1,
wherein the voltage application is deactivated after the temperature measurement is completed in the temperature measurement step and the concentration measurement is executed by re-applying the second voltage after a predetermined period of time is elapsed in the concentration measurement step.

9. A sensor chip comprising:
a capillary allowing a biological sample to be introduced therein;
a temperature electrode unit configured to measure the temperature of the biological sample, the temperature electrode unit including a working electrode and a counter electrode, the working and counter electrodes respectively including a reagent containing an electrolyte, the temperature electrode unit configured to receive a first voltage to be applied in measuring the temperature of the biological sample, the first voltage allowing the temperature measurement to be less affected by an analyte contained in the biological sample; and
an analysis electrode unit configured to receive a second voltage to be applied in measuring a concentration of the analyte in the biological sample,
wherein the first voltage has a potential difference greater than the second voltage.

10. The sensor chip recited in claim 9,
wherein an amount of the biological sample introduced into the capillary is less than or equal to 5 μL, and
a period of time for applying the first or second voltage is less than or equal to 15 seconds.

11. The sensor chip recited in claim 9,
wherein the sensor chip is a disposable sensor chip.

12. The sensor chip recited in claim 9,
wherein the temperature electrode unit also functions as the analysis electrode unit.

13. The sensor chip recited in claim 9,
wherein the analyte includes at least one of glucose, hematocrit and reducing substance.

14. The sensor chip recited in claim 9,
wherein the working electrode and the counter electrode are opposed to each other.

15. The sensor chip recited in claim 9,
wherein at least one of the temperature electrode unit and the analysis electrode unit is formed by kneading the electrolyte therein.

16. A biosensor system, comprising:
the sensor chip recited in claim 9;
a measuring instrument including a control circuit configured to control application of the first voltage to the temperature electrode unit of the sensor chip for a predetermined period of time;
a voltage application section configured to apply the first voltage to the temperature electrode unit for the predetermined period of time under the control of the control circuit;
a first temperature measurement section configured to measure the temperature of the biological sample based on a magnitude of an electric current flowing through the temperature electrode unit making contact with the biological sample; and
an analyte measurement section configured to measure the concentration of the analyte based on a magnitude of an electric current to be generated in the biological sample as a result of an electrochemical reaction where the analyte contained in the biological sample serves as a substrate.

17. The biosensor system recited in claim 16, further comprising:
a concentration correction section configured to correct the concentration of the analyte contained in the biological sample based on the temperature measured by the first temperature measurement section.

18. The biosensor system recited in claim 17,
wherein the measuring instrument includes a second temperature measurement section configured to measure one of an internal environmental temperature of the measuring instrument, a surface environmental temperature of the measuring instrument and a surrounding environmental temperature of the measuring instrument, and
the concentration correction section is configured to compare a temperature datum measured by the first temperature measurement section and a temperature datum measured by the second temperature measurement section and correct the analyte concentration with a selected one of the measured temperature data.

19. The biosensor system recited in claim 18,
wherein the concentration correction section is configured to determine a predetermined coefficient depending on a difference between the temperature datum measured by the first temperature measurement section and the temperature datum measured by the second temperature measurement section and correct the concentration of the analyte contained in the biological sample based on a result obtained by executing a calculation for the coefficient and the respective temperature data.

20. The biosensor system recited in claim 16, wherein the first is voltage a direct-current voltage falling in a voltage range allowing a solvent in the biological sample to be electrolyzed.

21. The biosensor system recited in claim 20, wherein the analyte measurement section is configured to measure at least one of concentrations of glucose, hematocrit and reducing substance as the concentration of the analyte contained in the biological sample.

22. The biosensor system recited in claim 16, wherein the voltage application section applies the second voltage to the analysis electrode unit of the sensor chip when the analyte measurement section measures the concentration of the analyte.

23. The biosensor system recited in claim 22, wherein the voltage application section is configured to apply the first voltage with a potential difference of 1.0 V or greater.

24. A measuring instrument configured to apply a voltage to a sensor chip including an electrode unit formed by a working electrode and a counter electrode, the working and counter electrodes respectively including a reagent containing an electrolyte, the measuring instrument comprising:
    an insertion section allowing the sensor chip to be loaded therein;
    a voltage application section configured to apply a first voltage and a second voltage to the electrode unit of the sensor chip loaded into the insertion section, the first voltage allowing a temperature measurement of a biological sample to be less affected by an analyte contained in the biological sample, the first voltage being different than the second voltage;
    a temperature measurement section configured to measure a temperature of the biological sample introduced into the sensor chip based on an output value of the first voltage; and
    an analyte measurement section configured to measure a concentration of the analyte in the biological sample based on an output value of the second voltage.

25. The measuring instrument recited in claim 24, wherein the analyte measurement section is configured to measure at least one of the concentrations of glucose, hematocrit and reducing substance as the concentration of the analyte contained in the biological sample.

26. The measuring instrument recited in claim 24, wherein the first voltage has a potential difference greater than the second voltage.

27. The measuring instrument recited in claim 26, wherein the voltage application section is configured to apply the first voltage with a potential difference of 1.0 V or greater.

* * * * *